(12) United States Patent
Pei et al.

(10) Patent No.: US 10,815,276 B2
(45) Date of Patent: *Oct. 27, 2020

(54) CELL PENETRATING PEPTIDES AND METHODS OF MAKING AND USING THEREOF

(71) Applicant: Entrada Therapeutics, Inc., Boston, MA (US)

(72) Inventors: Dehua Pei, Columbus, OH (US); Ziqing Qian, Columbus, OH (US)

(73) Assignee: Entrada Therapeutics, Inc., Boston, MA (US)

( * ) Notice: Subject to any disclaimer, the term of this patent is extended or adjusted under 35 U.S.C. 154(b) by 237 days.

This patent is subject to a terminal disclaimer.

(21) Appl. No.: 15/360,719

(22) Filed: Nov. 23, 2016

(65) Prior Publication Data

US 2017/0355730 A1   Dec. 14, 2017

Related U.S. Application Data

(63) Continuation-in-part of application No. 15/312,878, filed as application No. PCT/US2015/032043 on May 21, 2015, now Pat. No. 10,626,147.

(60) Provisional application No. 62/158,351, filed on May 7, 2015, provisional application No. 62/001,535, filed on May 21, 2014.

(51) Int. Cl.
| | |
|---|---|
| *C07K 7/64* | (2006.01) |
| *A61K 49/00* | (2006.01) |
| *A61K 38/46* | (2006.01) |
| *A61K 38/05* | (2006.01) |
| *A61K 47/64* | (2017.01) |
| *A61K 38/12* | (2006.01) |
| *C07K 7/06* | (2006.01) |

(52) U.S. Cl.
CPC ............ *C07K 7/64* (2013.01); *A61K 38/05* (2013.01); *A61K 38/12* (2013.01); *A61K 38/465* (2013.01); *A61K 47/64* (2017.08); *A61K 49/0039* (2013.01); *A61K 49/0041* (2013.01); *A61K 49/0043* (2013.01); *A61K 49/0047* (2013.01); *A61K 49/0056* (2013.01); *C07K 7/06* (2013.01); *C12Y 301/03048* (2013.01)

(58) Field of Classification Search
CPC . C07K 7/64; C07K 7/06; A61K 38/12; A61K 47/64; A61K 38/05; A61K 38/465; A61K 49/0039; A61K 49/0041; A61K 49/0056; A61K 49/0043; A61K 49/0047; C12Y 301/03048

See application file for complete search history.

(56) References Cited

U.S. PATENT DOCUMENTS

| | | |
|---|---|---|
| 5,965,536 A | 10/1999 | Cohen et al. |
| 6,110,889 A | 8/2000 | Miller et al. |
| 6,251,854 B1 | 6/2001 | Montal et al. |
| 6,355,619 B1 | 3/2002 | Miller et al. |
| 6,593,292 B1 | 7/2003 | Rothbard et al. |
| 6,605,115 B1 | 8/2003 | Cooke et al. |
| 6,649,587 B1 | 11/2003 | Frydman et al. |
| 6,669,951 B2 | 12/2003 | Rothbard et al. |
| 6,730,293 B1 | 5/2004 | Rothbard et al. |
| 6,759,387 B2 | 7/2004 | Rothbard et al. |
| 6,794,545 B1 | 9/2004 | Frydman et al. |
| 6,809,176 B2 | 10/2004 | Blokhin et al. |
| 6,960,648 B2 | 11/2005 | Bonny |
| 6,982,351 B2 | 1/2006 | Frydman et al. |
| 7,026,347 B2 | 4/2006 | Frydman et al. |
| 7,169,814 B2 | 1/2007 | Rothbard et al. |
| 7,186,825 B2 | 3/2007 | Frydman et al. |
| 7,229,961 B2 | 6/2007 | Rothbard et al. |
| 7,253,207 B2 | 8/2007 | Blokhin et al. |
| 7,279,502 B2 | 10/2007 | Clifford et al. |
| 7,312,244 B2 | 12/2007 | Clifford et al. |
| 7,585,834 B2 | 9/2009 | Wender et al. |
| 8,614,290 B2 | 12/2013 | Wester et al. |
| 8,628,750 B2 | 1/2014 | Wester et al. |
| 8,629,112 B2 | 1/2014 | Gombert et al. |
| 9,169,290 B2 | 10/2015 | O'Neil |

(Continued)

FOREIGN PATENT DOCUMENTS

| | | |
|---|---|---|
| CA | 2417064 A1 | 2/2002 |
| CA | 2455951 A1 | 2/2003 |

(Continued)

OTHER PUBLICATIONS

Lee et al, J.Peptide Res., 63, 69-84 (Year: 2004).*

(Continued)

*Primary Examiner* — Sudhakar Katakam
(74) *Attorney, Agent, or Firm* — Cooley, LLP

(57) ABSTRACT

Disclosed herein are compounds having activity as cell penetrating peptides. In some examples, the compounds can comprise a cell penetrating peptide moiety and a cargo moiety. The cargo moiety can comprise one or more detectable moieties, one or more therapeutic moieties, one or more targeting moieties, or any combination thereof. In some examples, the cell penetrating peptide moiety is cyclic. In some examples, the cell penetrating peptide moiety and cargo moiety together are cyclic. In some examples, the cell penetrating peptide moiety is cyclic and the cargo moiety is appended to the cyclic cell penetrating peptide moiety structure. In some examples, the cargo moiety is cyclic and the cell penetrating peptide moiety is cyclic, and together they form a fused bicyclic system.

40 Claims, 30 Drawing Sheets

Specification includes a Sequence Listing.

(56) References Cited

U.S. PATENT DOCUMENTS

| | | |
|---|---|---|
| 2002/0009491 A1 | 1/2002 | Rothbard et al. |
| 2002/0035243 A1 | 3/2002 | Imfeld et al. |
| 2002/0120100 A1 | 8/2002 | Bonny |
| 2002/0127198 A1 | 9/2002 | Rothbard et al. |
| 2003/0022831 A1 | 1/2003 | Rothbard et al. |
| 2003/0032593 A1 | 2/2003 | Wender et al. |
| 2003/0032594 A1 | 2/2003 | Bonny |
| 2003/0072715 A1 | 4/2003 | Frydman et al. |
| 2003/0130356 A1 | 7/2003 | Frydman et al. |
| 2003/0167129 A1 | 9/2003 | Nestor et al. |
| 2004/0152687 A1 | 8/2004 | Frydman et al. |
| 2004/0192665 A1 | 9/2004 | Frydman et al. |
| 2004/0248783 A1 | 12/2004 | Kawabe et al. |
| 2005/0192210 A1 | 9/2005 | Rothbard et al. |
| 2006/0128614 A1 | 6/2006 | Cheng et al. |
| 2006/0141514 A1 | 6/2006 | Rozzelle et al. |
| 2012/0045393 A1 | 2/2012 | Linder et al. |
| 2014/0303071 A1 | 10/2014 | O'Neil |
| 2015/0038671 A1 | 2/2015 | Parang et al. |
| 2016/0031941 A1 | 2/2016 | Eckert et al. |
| 2017/0112896 A1 | 4/2017 | Briesewitz |
| 2017/0190743 A1 | 7/2017 | Pei et al. |
| 2017/0304383 A1 | 10/2017 | Briesewitz et al. |

FOREIGN PATENT DOCUMENTS

| | | |
|---|---|---|
| CN | 105440105 A | 3/2016 |
| EP | 1185493 B1 | 7/2005 |
| EP | 1574507 A2 | 9/2005 |
| JP | 3791981 A | 6/2006 |
| JP | 3791981 B2 | 6/2006 |
| JP | 2016-065018 A | 4/2016 |
| WO | WO 1999/021877 | 5/1999 |
| WO | WO 2000/011022 | 3/2000 |
| WO | WO 2001/013957 | 3/2001 |
| WO | WO 2002/057313 | 7/2002 |
| WO | WO 2002/064091 | 8/2002 |
| WO | WO 2002/067917 | 9/2002 |
| WO | WO 2002/090503 | 11/2002 |
| WO | WO 2003/059942 | 7/2003 |
| WO | WO 2003/070755 | 8/2003 |
| WO | WO 2003/092631 | 11/2003 |
| WO | WO 2003/092632 | 11/2003 |
| WO | WO 2004/050685 | 6/2004 |
| WO | WO 2006/041805 A1 | 4/2006 |
| WO | WO 2006/058436 | 6/2006 |
| WO | WO 2006/086773 A2 | 8/2006 |
| WO | WO 2007/040535 A1 | 4/2007 |
| WO | WO 2007/055578 | 5/2007 |
| WO | WO 2007/070372 | 6/2007 |
| WO | WO 2007/072037 | 6/2007 |
| WO | WO 2007/096662 | 8/2007 |
| WO | WO 2007/106554 A2 | 9/2007 |
| WO | WO 2007/108749 A1 | 9/2007 |
| WO | WO 2007/111993 A2 | 10/2007 |
| WO | WO 2008/077194 | 7/2008 |
| WO | WO 2009/027706 | 3/2009 |
| WO | WO 2009/092062 | 7/2009 |
| WO | WO 2010/045335 | 4/2010 |
| WO | WO 2010/107832 | 9/2010 |
| WO | WO 2011/095218 | 8/2011 |
| WO | WO 2011/095607 | 8/2011 |
| WO | WO 2013/142184 | 9/2013 |
| WO | WO 2014/053629 A1 | 4/2014 |
| WO | WO 2015/179691 | 11/2015 |
| WO | WO 2016/033368 | 3/2016 |
| WO | WO 2016/044683 A1 | 3/2016 |

OTHER PUBLICATIONS

Kessler et al, Angew.Chem.Int.Ed.Engl., 21, 512-523 (Year: 1982).*
Lalonde, M. S. et al., "Inhibition of Both HIV-1 Reverse Transcription and Gene Expression by a Cyclic Peptide that Binds the Tat-Transactivating Response Element (TAR) RNA," (2011) PLoS Pathog 7(5):e1002038. doi:10.1371/journal.ppat.1002038.
Jang S. et al., "Cell-Penetrating, Dimeric α-Helical Peptides: Nanomolar Inhibitors of HIV-1 Transcription," Angew. Chem. Int. Ed. 2014, 53, 10086-10089.
Shirazi, A. N. et al., "Cyclic peptides containing tryptophan and arginine as Src kinase inhibitors," Bioorganic & Medicinal Chemistry Letters 23 (2013) 3230-3234.
Extended European Search Report in European Patent Application No. 15796259.8, dated Jan. 22, 2018, 6 pages.
Karpurapu, M. et al., "Inhibition of nuclear factor of activated T cells (NFAT) c3 activation attenuates acute lung injury and pulmonary edema in murine models of sepsis," Oncotarget. Jan. 25, 2018;9(12):10606-10620.
Liao, H. et al., "Cell-permeable bicyclic peptidyl inhibitors against T-cell protein tyrosine phosphatase from a combinatorial library," Org Biomol Chem. Nov. 22, 2017;15(45):9595-9598.
Qian, Z. et al., "Enhancing the Cell Permeability and Metabolic Stability of Peptidyl Drugs by Reversible Bicyclization," Angew Chem Int Ed Engl. Feb. 1, 2017;56(6):1525-1529.
Rhodes, C.A. et al., "Cell-Permeable Bicyclic Peptidyl Inhibitors against NEMO-IkB Kinase Interaction Directly from a Combinatorial Library," J Am Chem Soc. Sep. 26, 2018;140(38):12102-12110.
Verdurmen et al., "Preferential Uptake of L-versus D-Amino Acid Cell-Penetrating Peptides in a Cell Type-Dependent Manner," Chemistry & Biology, 2011, vol. 18, p. 1000-1010.
International Search Report and Written Opinion for International Application No. PCT/US2015/032043, dated Jan. 14, 2016, 11 pages.
International Preliminary Report on Patentability for International Application No. PCT/US2015/032043, dated Nov. 22, 2016, 8 pages.
Alonso, A. et al., Protein tyrosine phosphatases in the human genome, Cell, Jun. 2004, 117(6):699-711.
Andaloussi, S. E. L. et al., "Design of a peptide-based vector, PepFect6, for efficient delivery of siRNA in cell culture and systemically in vivo," Nucleic Acids Research, May 2011, 39(9):3972-3987.
Anderl, J. et al., "Chemical modification allows phallotoxins and amatoxins to be used as tools in cell biology," Beilstein Journal of Organic Chemistry, 2012, 8(233):2072-2084.
Appelbaum, J. S. et al., "Arginine Topology Controls Escape of Minimally Cationic Proteins from Early Endosomes to the Cytoplasm," Chemistry & Biology, Jul. 2012, 19:819-830.
Birts, C. N. et al., "A cyclic peptide inhibitor of C-terminal binding protein dimerization links metabolism with mitotic fidelity in breast cancer cells," Chem. Sci. 2013, 4, 3046-3057.
Bolte, S. et al., "A guided tour into subcellular colocalization analysis in light microscopy," J. Microsc., Dec. 2006, 224(Pt. 3), 213-232.
Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun,. Oct. 1994, 204(1):129-134.
Carpenter, A. E. et al., "CellProfiler: image analysis software for identifying and quantifying cell phenotypes," Genome Biology, 2006, 7:R100. 11 pages.
Cascales, L. et al., "Identification and Characterization of a New Family of Cell-Penetrating Peptides," J. Biol. Chem., Oct. 2011, 286(42):36932-36943.
Chatterjee, J. et al., "N-Methylation of Peptides: A New Perspective in Medicinal Chemistry," Acc. Chem. Res., 2008, 41(10):1331-1342.
Chen, X. et al., "On-Bead Screening of Combinatorial Libraries: Reduction of Nonspecific Binding by Decreasing Surface Ligand Density," J. Comb. Chem. 2009, 11(4):604-611.
Cheng, S. H. et al., "Defective intracellular transport and processing of CFTR is the molecular basis of most cystic fibrosis," Cell, Nov. 1990, 63(4):827-834.
Cooley, C. B. et al., "Oligocarbonate Molecular Transporters: Oligomerization-Based Syntheses and Cell-Penetrating Studies," J. Am. Chem. Soc., 2009, 131(45):16401-16403.

(56) References Cited

OTHER PUBLICATIONS

Cushing, P. R. et al., "The Relative Binding Affinities of PDZ Partners for CFTR: A Biochemical Basis for Efficient Endocytic Recycling," Biochemistry, 2008, 47(38):10084-10098.
Cushing, P. R. et al., "A Stabilizing Influence: CAL PDZ Inhibition Extends the Half-Life of ΔF508-CFTR," Angew. Chem. Int. Ed., Dec. 2010, 49(51):9907-9911.
Deshayes, S. et al., "Cell-penetrating peptides: tools for intracellular delivery of therapeutics," Cell. Mol. Life Sci., Aug. 2005, 62(16):1839-1849.
Dewan, V. et al., "Cyclic Peptide Inhibitors of HIV-1 Capsid-Human Lysyl-tRNA Synthetase Interaction," ACS Chem. Biol., 2012, 7(4):761-769.
Doyle, D. A. et al., "Crystal Structures of a Complexed and Peptide-Free Membrane Protein-Binding Domain: Molecular Basis of Peptide Recognition by PDZ," Cell, Jun. 1996, 85(7):1067-1076.
Driggers, E. M. et al., "The exploration of macrocycles for drug discovery—an underexploited structural class," Nat. Rev. Drug Discov., Jul. 2008, 7:608-624.
Duchardt, F. et al., "A Comprehensive Model for the Cellular Uptake of Cationic Cell-penetrating Peptides," Traffic, Jul. 2007, 8(7):848-866.
Duchardt, F. et al., "A Cell-penetrating Peptide Derived from Human Lactoferrin with Conformation-dependent Uptake Efficiency," J. Biol. Chem., Dec. 2009, 284(52):36099-36108.
Eguchi, A. et al., "Protein Transduction Domain of HIV-1 Tat Protein Promotes Efficient Delivery of DNA into Mammalian Cells," J. Biol. Chem., Jul. 2001, 276:26204-26210.
Eichler, J. et al., "Novel α-glucosidase inhibitors identified using multiple cyclic peptide combinatorial libraries," Molecular Diversity, Aug. 1996, 1(4):233-240.
Elchelby, M. et al., "Increased insulin sensitivity and obesity resistance in mice lacking the protein tyrosine phosphatase-1B gene," Science, Mar. 1999, 283(5407):1544-1548.
El-Sayed, A et al., "Delivery of Macromolecules Using Arginine-Rich Cell-Penetrating Peptides: Ways to Overcome Endosomal Entrapment," The AAPS Journal, Mar. 2009, 11(1):13-22.
Fernandez-Lopez, S. et al., "Antibacterial agents based on the cyclic D,L-α-peptide architecture," Nature, Jul. 2001, 412:452-455 and Correction page, Nature, Nov. 2001, 414:329.
Ferrari, A. et al., "Caveolae-Mediated Internalization of Extracellular HIV-1 Tat Fusion Proteins Visualized in Real Time," Molecular Therapy, 2003, 8:284-294.
Fittipaldi, A. et al., "Cell Membrane Lipid Rafts Mediate Caveolar Endocytosis of HIV-1 Tat Fusion Proteins," J. Biol. Chem., Sep. 2003, 278:34141-34149.
Frackenpohl, J. et al., "The Outstanding Biological Stability of β- and γ-Peptides toward Proteolytic Enzymes: An In Vitro Investigation with Fifteen Peptidases," Chembiochem, Jun. 2001, 2(6):445-455.
Frankel, A. D. et al., "Cellular uptake of the tat protein from human immunodeficiency virus," Cell, Dec. 1988, 55(6):1189-1193.
Frost, J. R. et al., "Macrocyclization of Organo-Peptide Hybrids through a Dual Bio-orthogonal Ligation: Insights from Structure—Reactivity Studies," ChemBioChem, Jan. 2013, 14(1):147-160.
Futaki, S., "Membrane-permeable arginine-rich peptides and the translocation mechanisms," Advanced Drug Delivery Reviews, Feb. 2005, 57(4): 547-558.
Futaki, S. et al., "Arginine-rich peptides. An abundant source of membrane-permeable peptides having potential as carriers for intracellular protein delivery." The Journal of Biological Chemistry, 2001, 276(8):5836-5840.
Giebel, L. B. et al., "Screening of cyclic peptide phage libraries identifies ligands that bind streptavidin with high affinities," Biochemistry, 1995, 34(47):15430-15435.
Gobbo, M. et al, "Synthesis and biological activity of some linear and cyclic kinin analogues," International Journal of Peptide & Protein Research, Jul. 1994, 44(1):1-9.

Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.
Goun, E. A. et al., "Molecular Transporters: Synthesis of Oligoguanidinium Transporters and Their Application to Drug Delivery and Real-Time Imaging," ChemBioChem, Oct. 2006, 7(10):1497-1515.
Green, M. et al., "Autonomous functional domains of chemically synthesized human immunodeficiency virus tat trans-activator protein," Cell, Dec. 1988, 55(6):1179-1188.
Gupta, B. et al., "Intracellular delivery of large molecules and small particles by cell-penetrating proteins and peptides," Advanced Drug Delivery Reviews, Feb. 2005, 57(4):637-651.
Hamill, K. M. et al., "Polymyxins facilitate entry into mammalian cells," Chem. Sci., 2016, 7:5059-5068.
Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34):11555-11566.
He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.
Heinis, C. et al., "Phage-encoded combinatorial chemical libraries based on bicyclic peptides," Nat. Chem. Biol., 2009, 5:502-507.
Herce, H. D. et al., "Molecular dynamics simulations suggest a mechanism for translocation of the HIV-1 TAT peptide across lipid membranes," Proc. Natl. Acad. Sci. U. S. A., Dec. 2007, 104(52):20805-20810.
Herce, H. D. et al., "Arginine-Rich Peptides Destabilize the Plasma Membrane, Consistent with a Pore Formation Translocation Mechanism of Cell-Penetrating Peptides," Biophys. J., Oct. 2009, 97(7):1917-1925.
Hili, R. et al., "Macrocyclization of Linear Peptides Enabled by Amphoteric Molecules," J. Am. Chem. Soc., 2010, 132(9):2889-2891.
Hirose, H. et al., "Transient Focal Membrane Deformation Induced by Arginine-rich Peptides Leads to Their Direct Penetration into Cells," Mol. Ther., 2012, 20(5):984-993.
Holub, J. M. et al., "Improved assays for determining the cytosolic access of peptides, proteins, and their mimetics," Biochemistry, Dec. 2013, 52(50):9036-9046.
Horn, M. et al., "Tuning the properties of a novel short cell-penetrating peptide by intramolecular cyclization with a triazole bridge," Chem. Commun. 2016, 52:2261-2264.
Hoyer, J. et al., "Peptide Vectors for the Nonviral Delivery of Nucleic Acids," Acc. Chem. Res., 2012, 45(7):1048-1056.
Illsley, N. P. et al., "Membrane chloride transport measured using a chloride-sensitive fluorescent probe," Biochemistry, 1987, 26(5):1215-1219.
Jeong, J. H. et al., "siRNA Conjugate Delivery Systems," Bioconjugate Chem., 2009, 20(1):5-14.
Jha, D. et al., "CyLoP-1: A Novel Cysteine-Rich Cell-Penetrating Peptide for Cytosolic Delivery of Cargoes," Bioconj. Chem., 2011, 22(3):319-328.
Jiang, B. et al., "A Selective, Cell-Permeable Nonphosphorylated Bicyclic Peptidyl Inhibitor against Peptidyl-Prolyl Isomerase Pin1," J. Med. Chem., 58:6306-6312 (2015). Published Online: Jul. 21, 2015.
Joo, S. H. et al., "High-Throughput Sequence Determination of Cyclic Peptide Library Members by Partial Edman Degradation/Mass Spectrometry," J. Am. Chem. Soc., 2006, 128(39):13000-13009.
Josephson, L. et al., "High-Efficiency Intracellular Magnetic Labeling with Novel Superparamagnetic-Tat Peptide Conjugates," Bioconjugate Chem., 1999, 10(2):186-191.
Junkes, C. et al., "Cyclic antimicrobial R-, W-rich peptides: the role of peptide structure and E. coli outer and inner membranes in activity and the mode of action," European Biophysics Journal, 2011, 40(4):515-528.

(56) References Cited

OTHER PUBLICATIONS

Kaplan, I. M. et al., "Cationic TAT peptide transduction domain enters cells by macropinocytosis," Journal of Controlled Release, Jan. 2005,102(1):247-253.

Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.

Kerem, B. et al., "Identification of the cystic fibrosis gene: genetic analysis," Science, Sep. 1989, 245(4922):1073-1080.

Kohli, R. M. et al., "Biomimetic synthesis and optimization of cyclic peptide antibiotics," Nature, Aug. 2002, 418:658-661.

Kritzer, J. A. et al., "Rapid selection of cyclic peptides that reduce α-synuclein toxicity in yeast and animal models," Nature Chemical Biology, Sep. 2009, 5(9):655-663.

Kundu, R. et al., "Hybrid Organic—Inorganic Inhibitors of a PDZ Interaction that Regulates the Endocytic Fate of CFTR," Angew. Chem. Int. Ed., Jul. 2012, 51(29):7217-7220.

Kwon, Y-U et al., "Quantitative Comparison of the Relative Cell Permeability of Cyclic and Linear Peptides," Chemistry & Biology, Jun. 2007, 14(6):671-677.

LaMontagne, K. R. Jr. et al., "Protein tyrosine phosphatase PTP1B suppresses p210 bcr-abl-induced transformation of Rat-1 fibroblasts and promotes differentiation of K562 cells," Proc. Natl. Acad. Sci. U. S. A., Nov. 1998, 95(24):14094-14099.

Lindgren M. et al., "Classes and Prediction of Cell-Penetrating Peptides," Chapter 1 In: Cell-Penetrating Peptides: Methods and Protocols, Methods in Molecular Biology, vol. 683, pp. 3-19, Springer Science+Business Media, LLC 2011.

LaRochelle, J. R. et al., "Fluorescence Correlation Spectroscopy Reveals Highly Efficient Cytosolic Delivery of Certain Penta-Arg Proteins and Stapled Peptides," Journal of the American Chemical Society, 2015, 137:2536-2541.

Lattig-Tunnemann, G. et al., "Backbone rigidity and static presentation of guanidinium groups increases cellular uptake of arginine-rich cell-penetrating peptides," Nature Communications, 2011, 2:453. 6 pages DOI:10.1038/ncomms1459.

Leduc, A-M et al., "Helix-stabilized cyclic peptides as selective inhibitors of steroid receptor—coactivator interactions," Proc. Natl. Acad. Sci. U.S.A., Sep. 2003, 100(20):11273-11278.

Lee, H. J. et al., "PDZ domains and their binding partners: structure, specificity, and modification," Cell Communication and Signaling, 2010, 8: 8. 18 pages.

Lee, J. et al., "Using marine natural products to discover a protease that catalyzes peptide macrocyclization of diverse substrates," J. Am. Chem. Soc., Feb. 2009, 131(6):2122-2124.

Lessard, L. et al., "The two faces of PTP1B in cancer," Biochim. Biophys. Acta, Mar. 2010, 1804(3):613-619. doi: 10.1016/j.bbapap. 2009.09.018. Epub Sep. 24, 2009.

Li, S. et al, "Photolithographic synthesis of cyclic peptide arrays using a differential deprotection strategy," Chem. Commun., 2005, 5:581-583.

Li, S. et al., "Fluoride enhances the activity of fungicides that destabilize cell membranes," Bioorganic & Medicinal Chemistry Letters, 2012, 22(9):3317-3322.

Lian, W. et al., "Cell-permeable bicyclic peptide inhibitors against intracellular proteins," J. Am. Chem. Soc., Jul. 2014, 136(28):9830-9833. Published Online: Jun. 27, 2014.

Lian, W. et al., "Screening Bicyclic Peptide Libraries for Protein—Protein Interaction Inhibitors: Discovery of a Tumor Necrosis Factor-α Antagonist," J. Am. Chem. Soc., 2013, 135(32):11990-11995.

Lin, K-J, et al., "QSAR studies of antimicrobial α,β-polypeptides," Pharmaceutical Biotechnology, 2003, 10(5):299-303 (with English Abstract).

Liu, J. et al., "Nanostructured Materials Designed for Cell Binding and Transduction," Biomacromolecules, 2001, 2(2):362-368. Published Online: Apr. 19, 2001.

Liu, R. et al., "A Novel Peptide-Based Encoding System for "One-Bead One-Compound " Peptidomimetic and Small Molecule Combinatorial Libraries," J. Am. Chem. Soc., 2002, 124(26):7678-7680. Published Online: Jun. 6, 2002.

Liu, T. et al., "High-Throughput Screening of One-Bead-One-Compound Libraries: Identification of Cyclic Peptidyl Inhibitors against Calcineurin/NFAT Interaction," ACS Comb. Sci., 2011, 13(5):537-546. Published Online: Aug. 16, 2011.

Liu, T. et al., "Membrane Permeable Cyclic Peptidyl Inhibitors against Human Peptidylprolyl Isomerase Pin1," J. Med. Chem., 2010, 53(6):2494-2501.

Liu, Y. et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.

Lu, K. P. et al., "The prolyl isomerase PIN1: a pivotal new twist in phosphorylation signalling and disease," Nat. Rev. Mol. Cell Biol., Nov. 2007, 8:904-916.

Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.

Maiolo, J. R. et al., "Effects of cargo molecules on the cellular uptake of arginine-rich cell-penetrating peptides," Biochim. Biophys. Acta., Jul. 2005, 1712(2):161-172.

Maly, D. J. et al., "Combinatorial Strategies for Targeting Protein Families: Application to the Proteases," Chembiochem, Jan. 2002, 3(1):16-37.

Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915. Published Online: Jan. 12, 2002.

Mandal, D. et al., "Cell-Penetrating Homochiral Cyclic Peptides as Nuclear-Targeting Molecular Transporters," Angew. Chem. Int. Ed., 2011, 50:9633-9637.

Marsault, E. et al., "Macrocycles Are Great Cycles: Applications, Opportunities, and Challenges of Synthetic Macrocycles in Drug Discovery," J. Med. Chem., 2011, 54(7):1961-2004. Published Online: Mar. 7, 2011.

Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.

Millward, S. W. et al., "Design of Cyclic Peptides That Bind Protein Surfaces with Antibody-Like Affinity," ACS Chem Biol., 2007, 2(9):625-634. Published Online: Sep. 21, 2007.

Millward, S. W. et al., "A General Route for Post-Translational Cyclization of mRNA Display Libraries," J. Am. Chem. Soc., 2005, 127(41):14142-14143. Published Online: Sep. 27, 2005.

Miranda, E. et al., "A Cyclic Peptide Inhibitor of HIF-1 Heterodimerization That Inhibits Hypoxia Signaling in Cancer Cells," Journal of the American Chemical Society, 2013, 135(28):10418-10425.

Miskolzie, M. et al., "An NMR conformational analysis of cyclic bradykinin mimics. Evidence for a β-turn," Journal of Biomolecular Structure & Dynamics, 2000, 17(6):947-955.

Mitra, S. et al., "Highly sensitive peptide-based probes for protein tyrosine phosphatase activity utilizing a fluorogenic mimic of phosphotyrosine," Bioorg. Med. Chem. Lett., Dec. 2005, 15(23):5142-5145.

Morais Cabral, J. H. et al., "Crystal structure of a PDZ domain," Nature, Aug. 1996, 382:649-652.

Moore, J. D. et al., "Pin1 inhibitors: Pitfalls, progress and cellular pharmacology," Bioorg. Med. Chem. Lett., Aug. 2013, 23(15):4283-4291. doi: 10.1016/j.bmcl.2013.05.088. Epub Jun. 6, 2013.

Mosmann, T., "Rapid colorimetric assay for cellular growth and survival: Application to proliferation and cytotoxicity assays," J. Immunol. Methods, Dec. 1983, 65(1-2):55-63.

Mueller, J. et al., "Comparison of Cellular Uptake Using 22 CPPs in 4 Different Cell Lines," Bioconjugate Chem., 2008, 19(12):2363-2374.

Muratovska, A. et al., "Conjugate for efficient delivery of short interfering RNA (siRNA) into mammalian cells," FEBS Lett., Jan. 2004, 558(1-3):63-68.

(56) References Cited

OTHER PUBLICATIONS

Nakase, I. et al., "Efficient Intracellular Delivery of Nucleic Acid Pharmaceuticals Using Cell-Penetrating Peptides," Acc. Chem. Res., 2012, 45(7):1132-1139.

Nakase, I. et al., "Interaction of arginine-rich peptides with membrane-associated proteoglycans is crucial for induction of actin organization and macropinocytosis," Biochemistry, 2007, 46:492-501.

Ngu-Schwemlein, M. et al., "In vitro synergy between some cationic amphipathic cyclooctapeptides and antibiotics," Australian Journal of Chemistry, 2015, 68(2):218-223.

Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.

Nori, A. et al., "Tat-conjugated synthetic macromolecules facilitate cytoplasmic drug delivery to human ovarian carcinoma cells," Bioconjugate Chem., Jan.-Feb. 2003, 14(1):44-50.

Ocampo-Garcia, B. E. et al., "Design and biological evaluation of 99mTc-N2S2-Tat(49-57)-c(RGDyK): A hybrid radiopharmaceutical for tumors expressing $\alpha(v)\beta(3)$ integrins," Nuclear Medicine and Biology (2013), 40(4):481-487.

Oh, D. et al, "Enhanced Cellular Uptake of Short Polyarginine Peptides through Fatty Acylation and Cyclization," Molecular Pharmaceutics, 2014, 11(8):2845-2854.

Oh, D. et al., "Amphiphilic Bicyclic Peptides as Cellular Delivery Agents," ChemMedChem, 2014, 9(11):2449-2453.

Oh, D. et al., "Antibacterial activities of amphiphilic cyclic cell-penetrating peptides against multidrug-resistant pathogens," Molecular Pharmaceutics, 2014, 11(10):3528-3536.

Okamoto, H. et al., "Conformational transitions of cyclic D,L-peptides," Journal of Computational Chemistry, 2009, 30(6):962-973.

Palm-Apergi, C. et al., "The membrane repair response masks membrane disturbances caused by cell-penetrating peptide uptake," FASEB J., Jan. 2009, 23(1):214-223.

Pawson, T. et al., "Assembly of Cell Regulatory Systems Through Protein Interaction Domains," Science, Apr. 2003, 300(5618):445-452.

Pham, W. et al., "Enhancing Membrane Permeability by Fatty Acylation of Oligoarginine Peptides," Chembiochem, Aug. 2004, 5(8):1148-1151.

Pomilio, A. B. et al., "Naturally-Occurring Cyclopeptides: Structures and Bioactivity," Current Organic Chemistry, Nov. 2006, 10(16):2075-2121.

Pooga, M. et al., "Cellular translocation of proteins by transportation," FASEB J., 2001, 15(8):1451-1453.

Pritz, S. et al., "Synthesis of Biologically Active Peptide Nucleic Acid-Peptide Conjugates by Sortase-Mediated Ligation," Journal of Organic Chemistry, 2007, 72(10):3909-3912.

Qian, Z. et al., "Efficient delivery of cyclic peptides into mammalian cells with short sequence motifs," ACS Chem. Biol., 2013, 8:423-431. Published Online: Nov. 6, 2012.

Qian, Z. et al., "Discovery and Mechanism of Highly Efficient Cyclic Cell-Penetrating Peptides," Biochemistry, 2016, 55:2601-2612. Published Online: Apr. 18, 2016.

Qian, Z. et al., "Early endosomal escape of a cyclic cell-penetrating peptide allows effective cytosolic cargo delivery," Biochemistry, 2014, 53:4034-4046. Published Online: Jun. 4, 2014.

Qian, Z. et al., "Intracellular Delivery of Peptidyl Ligands by Reversible Cyclization: Discovery of a PDZ Domain Inhibitor that Rescues CFTR Activity," Angew. Chem. Int. Ed., 2015, 54:5874-5878. Published Online: Mar. 17, 2015.

Qian, Z. et al., "Monitoring the cytosolic entry of cell-penetrating peptides using a pH-sensitive fluorophore," Chem. Commun., 2015, 51:2162-2165. Published Online: Dec. 17, 2014.

Qin, C. et al., "Optimization of Antibacterial Cyclic Decapeptides," J. Comb. Chem., 2004, 6(3):398-406.

Ren, L. et al., "Substrate Specificity of Protein Tyrosine Phosphatases 1B, RPTPα, SHP-1, and SHP-2," Biochemistry, 2011, 50(12):2339-2356.

Rezai, T. et al., "Testing the Conformational Hypothesis of Passive Membrane Permeability Using Synthetic Cyclic Peptide Diastereomers," J. Am. Chem. Soc., 2006, 128(8):2510-2511.

Rezai, T. et al., "Conformational Flexibility, Internal Hydrogen Bonding, and Passive Membrane Permeability: Successful in Silico Prediction of the Relative Permeabilities of Cyclic Peptides," J. Am. Chem. Soc., 2006, 128(43):14073-14080.

Richard, J. P. et al., "Cellular uptake of unconjugated TAT peptide involves clathrin-dependent endocytosis and heparan sulfate receptors," J. Biol. Chem., 2005, 280:15300-15306.

Ricouart, A. et al., "Design of potent protein kinases inhibitors using the bisubstrate approach," Journal of Medicinal Chemistry, 1991, 34(1):73-78.

Riedl, S. J. et al., "Molecular mechanisms of caspase regulation during apoptosis," Nat. Rev. Mol. Cell Biol., Nov. 2004, 5:897-907.

Roberts, K. D. et al., "Efficient synthesis of thioether-based cyclic peptide libraries," Tetrahedron Letters, Nov. 1998, 39(45):8357-8360.

Roberts, K. E. et al., "Computational Design of a PDZ Domain Peptide Inhibitor that Rescues CFTR Activity," PLos Computational Biology, Apr. 2012, 8(4):e1002477. 12 pages doi:10.1371/journal.pcbi.1002477.

Rothbard, J. B. et al., "Conjugation of arginine oligomers to cyclosporin A facilitates topical delivery and inhibition of inflammation," Nature Medicine, 2000, 6(11):1253-1257.

Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.

Rueping, M. et al., "Cellular Uptake Studies with β-Peptides," ChemBioChem, Mar. 2002, 3(2-3):257-259.

Rusnati, M. et al., "Multiple Interactions of HIV-I Tat Protein with Size-defined Heparin Oligosaccharides," J. Biol. Chem., Oct. 1999, 274(40):28198-28205.

Saar, K. et al., "Cell-penetrating peptides: A comparative membrane toxicity study," Anal. Biochem., 2005, 345:55-65.

Sako, Y. et al., "Ribosomal synthesis of bicyclic peptides via two orthogonal inter-side-chain reactions," J. Am. Chem. Soc., Jun. 2008, 130(23):7232-7234. doi: 10.1021/ja800953c. Epub May 14, 2008.

Salvado, I. et al., "Membrane-disrupting iridium(III) oligocationic organometallopeptides," Chemical Communications, 2016, 52(73):11008-11011.

Schafmeister, C. E. et al., "An All-Hydrocarbon Cross-Linking System for Enhancing the Helicity and Metabolic Stability of Peptides," J. Am. Chem. Soc., 2000, 122(24):5891-5892.

Schmidt, N. et al., "Arginine-rich cell-penetrating peptides," FEBS Lett., 2010, 584:1806-1813.

Schwarze, S. R. et al., "In vivo protein transduction: delivery of a biologically active protein into the mouse," Science, Sep. 1999, 285(5433):1569-1572.

Scott, C. P. et al., "Production of cyclic peptides and proteins in vivo," Proc. Natl. Acad. Sci. U. S. A., Nov. 1999, 96(24):13638-13643.

Shirazi, A. N. et al, "Cysteine and arginine-rich peptides as molecular carriers," Bioorg. Med. Chem. Lett., 2016, 26:656-661.

Shirazi, A. N. et al., "Cyclic Peptide-Capped Gold Nanoparticles as Drug Delivery Systems," Molecular Pharmaceutics, 2013, 11:500-511.

Shirazi, A. N. et al., "Design and Biological Evaluation of Cell-Penetrating Peptide—Doxorubicin Conjugates as Prodrugs," Molecular Pharmaceutics, 2013, 10:488-499.

Slee, E. A. et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.

Songyang, Z. et al., "Recognition of Unique Carboxyl-Terminal Motifs by Distinct PDZ Domains," Science, Jan. 1997, 275(5296):73-77.

Stanford, S. M. et al., "High-throughput screen using a single-cell tyrosine phosphatase assay reveals biologically active inhibitors of tyrosine phosphatase CD45," Proc. Natl. Acad. Sci. U. S. A., Aug. 2012, 109(35):13972-13977.

(56) References Cited

OTHER PUBLICATIONS

Stewart, J. M. et al., "Bradykinin antagonists: Anti-cancer drugs for the new millennium?" Peptides for the New Millennium, Proceedings of the American Peptide Symposium, 16th, Minneapolis, MN, United States, Jun. 26, 1999-Jul. 1, 1999 (2000), Meeting Date 1999, 219-221. Fields, G. B. et al., (eds.), Kluwer Academic Publishers, Dordrecht, Neth.
Stewart, K. M. et al., "Cell-penetrating peptides as delivery vehicles for biology and medicine," Org. Biomol. Chem., Jul. 2008, 6(13):2242-2255. doi: 10.1039/b719950c. Epub Apr. 15, 2008.
Suhorutsenko, J. et al., "Cell-penetrating peptides, PepFects, show no evidence of toxicity and immunogenicity in vitro and in vivo," Bioconjugate Chem., Nov. 2011, 22(11):2255-2262. doi: 10.1021/bc200293d. Epub Oct. 10, 2011.
Sun, Y. et al., "A thioester ligation approach to amphipathic bicyclic peptide library," Org. Lett., May 2001, 3(11):1681-1684.
Tam, J. P. et al., "Disulfide bond formation in peptides by dimethyl sulfoxide. Scope and applications," J. Am. Chem. Soc., 1991, 113(17):6657-6662.
Tavassoli, A. et al., "Inhibition of HIV Budding by a Genetically Selected Cyclic Peptide Targeting the Gag-TSG101 Interaction," ACS Chemical Biology, 2008, 3(12):757-764.
Thakkar, A. et al., "Traceless Capping Agent for Peptide Sequencing by Partial Edman Degradation and Mass Spectrometry," Anal. Chem., 2006, 78(16):5935-5939.
Thornberry, N. A. et al., "A Combinatorial Approach Defines Specificities of Members of the Caspase Family and Granzyme B. Functional Relationships Established for Key Mediators of Apoptosis," J. Biol. Chem., Jul. 1997, 272(29):17907-17911.
Traboulsi, H. et al., "Macrocyclic Cell Penetrating Peptides: A Study of Structure-Penetration Properties," Bioconjugate Chemistry, 2015, 26:405-411.
Trinh, T. B. et al., "Discovery of a Direct Ras Inhibitor by Screening a Combinatorial Library of Cell-Permeable Bicyclic Peptides," ACS Comb Sci., 2016, 18:75-85. Published Online: Dec. 8, 2015.
Tse, B. N. et al., "Translation of DNA into a Library of 13 000 Synthetic Small-Molecule Macrocycles Suitable for in Vitro Selection," J. Am. Chem. Soc., 2008, 130(46):15611-15626.
Turner, R. A. et al., "Click chemistry as a macrocyclization tool in the solid-phase synthesis of small cyclic peptides," Org. Lett., Nov. 2007, 9(24): 5011-5014. Epub Oct. 23, 2007.
Tyagi, M. et al., "Internalization of HIV-1 tat requires cell surface heparan sulfate proteoglycans," J. Biol. Chem., Feb. 2001, 276(5):3254-3261. Epub Oct. 6, 2000.
Upadhyaya, P. et al., "Inhibition of Ras signaling by blocking Ras-effector interactions with cyclic peptide," Angew. Chem. Int. Ed., May 2015, 54:7602-7606. Published Online: May 7, 2015.
Van Goor, F. et al., "Correction of the F508del-CFTR protein processing defect in vitro by the investigational drug VX-809," Proc. Natl. Acad. Sci. U. S. A., Nov. 2011, 108(46):18843-18848.

Varkouhi, A. K. et al., "Endosomal escape pathways for delivery of biologicals," J. Controlled Release, May 2011, 151(3):220-228. Epub Nov. 13, 2010.
Wadia, J. S. et al., "Transmembrane delivery of protein and peptide drugs by TAT-mediated transduction in the treatment of cancer," Advanced Drug Delivery Reviews, Feb. 2005, 57(4):579-596. Epub Dec. 19, 2004.
Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.
Wang, C-W. et al., "Increased potency of a novel D-β-naphthylalanine-substituted antimicrobial peptide against fluconazole-resistant fungal pathogens," FEMS Yeast Research, 2009, 9(6):967-970.
Wender, P. A. et al., "The design, synthesis, and evaluation of molecules that enable or enhance cellular uptake: Peptoid molecular transporters," Proc. Natl. Acad. Sci. U. S. A., Nov. 2000, 97(24):13003-13008.
White, T. R. et al., "On-resin N-methylation of cyclic peptides for discovery of orally bioavailable scaffolds," Nat. Chem. Biol., Sep. 2011, 7(11): 810-817.
Wolde, M. et al., "Targeting CAL as a negative regulator of DeltaF508-CFTR cell-surface expression: an RNA interference and structure-based mutagenetic approach," J. Biol. Chem., Mar. 2007, 282(11):8099-8109. Epub Dec. 11, 2006.
Wu, G. et al., "Structural basis of IAP recognition by Smac/DIABLO," Nature, Dec. 2000, 408(6815):1008-1012.
Wu, X. et al., "Inhibition of Ras—effector interactions by cyclic peptides," Med. Chem. Commun., 2013, 4:378-382. Published Online: Nov. 27, 2012.
Xie, L. et al., "Cellular Effects of Small Molecule PTP1B Inhibitors on Insulin Signaling," Biochemistry, 2003, 42(44):12792-12804.
Yin, J. et al., "Genetically encoded short peptide tag for versatile protein labeling by Sfp phosphopantetheinyl transferase," Proc. Natl. Acad. Sci. U. S. A., Nov. 2005, 102(44):15815-15820.
Zabolotny, J. M. et al., "PTP1B regulates leptin signal transduction in vivo," Dev. Cell, Apr. 2002, 2(4):489-495.
Zhao, K. et al., "Enhanced activity of cyclic transporter sequences driven by phase behavior of peptide-liquid complexes," Soft Matter, 2012, 8(24): 6430-6433.
Ming, Z. et al., "Synthesis of RGD containing peptides and their vasodilation effect," Preparative Biochemistry & Biotechnology, 2000, 30(3):247-256.
Ziegler, A. et al., "Interaction of the protein transduction domain of HIV-1 TAT with heparan sulfate: binding mechanism and thermodynamic parameters," Biophys. J., Jan. 2004, 86(1):254-263.
Ziegler, A., "Thermodynamic studies and binding mechanisms of cell-penetrating peptides with lipids and glycosaminoglycans," Advanced Drug Delivery Reviews, Mar. 2008, 60(4-5):580-597. Epub Oct. 22, 2007.

\* cited by examiner

FIG. 5A
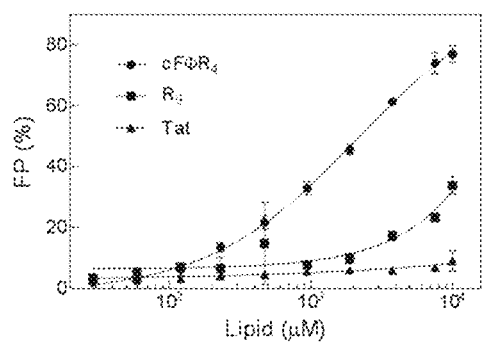
FIG. 5B
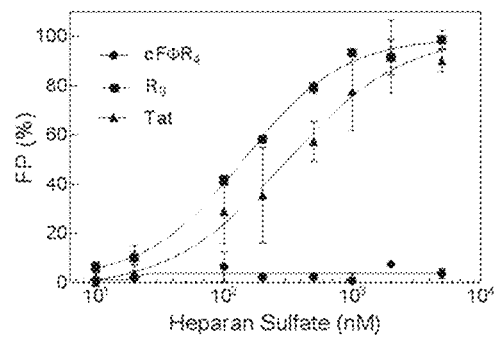
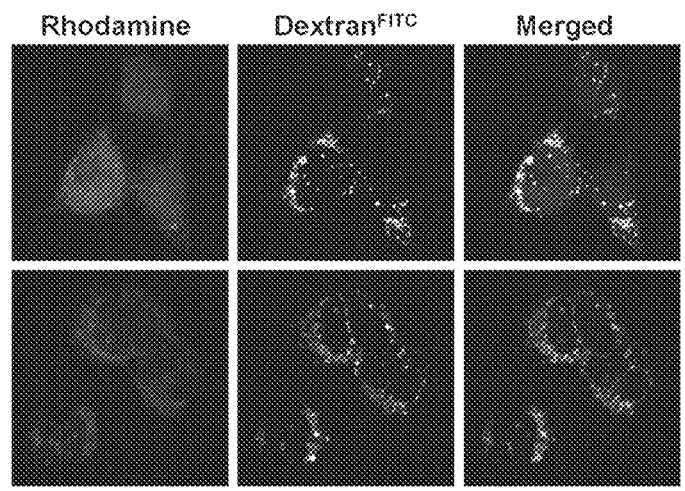
FIG. 6A
FIG. 6B

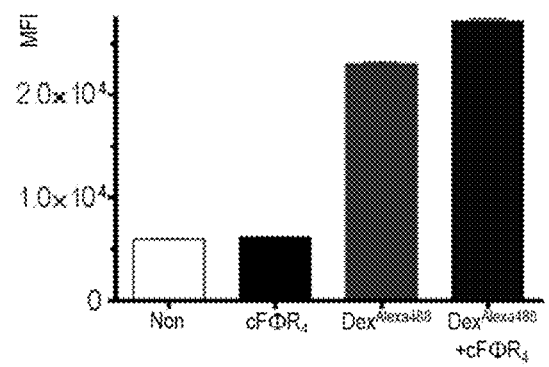
FIG. 7
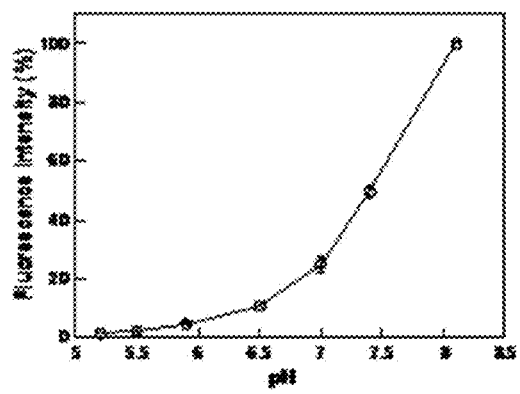
FIG. 8
FIG. 9A
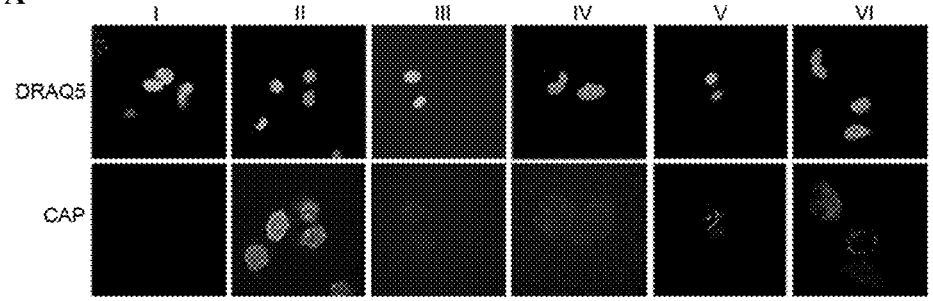
FIG. 9B
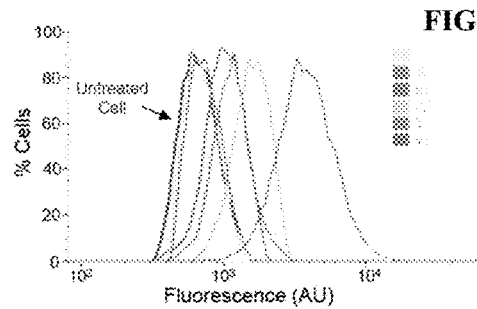
FIG. 9C
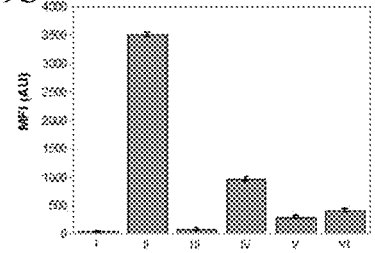

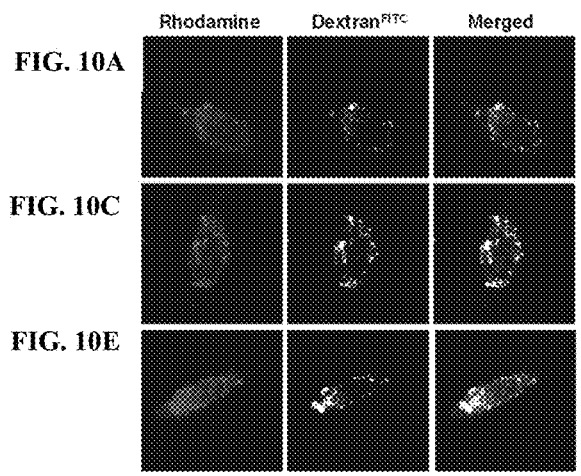
FIG. 10A
FIG. 10C
FIG. 10E
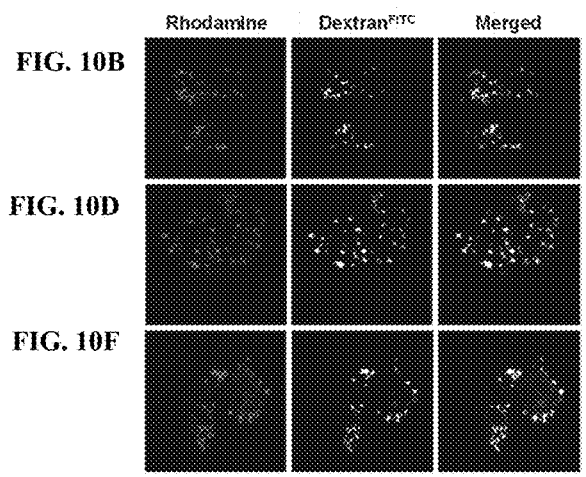
FIG. 10B
FIG. 10D
FIG. 10F

FIG. 18A
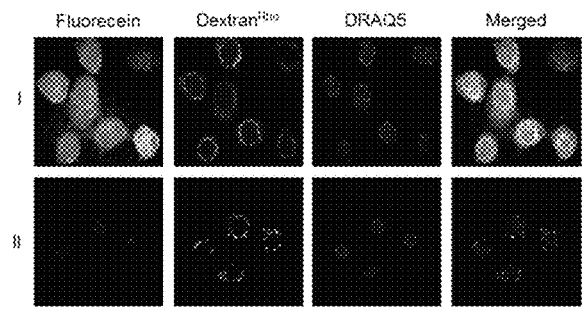
FIG. 18B
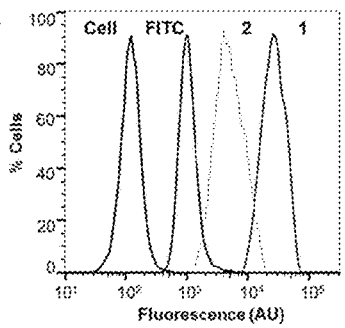
FIG. 19A
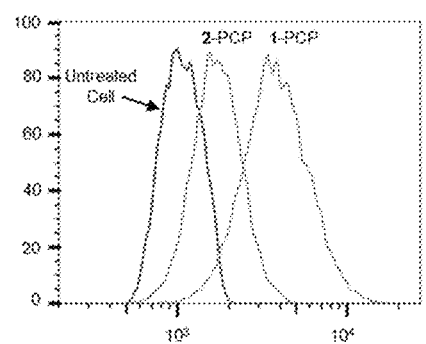
FIG. 19B
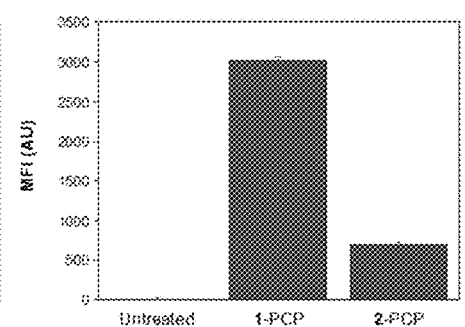
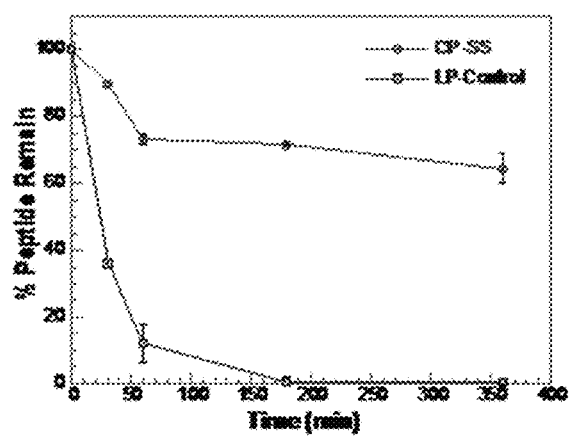
FIG. 20

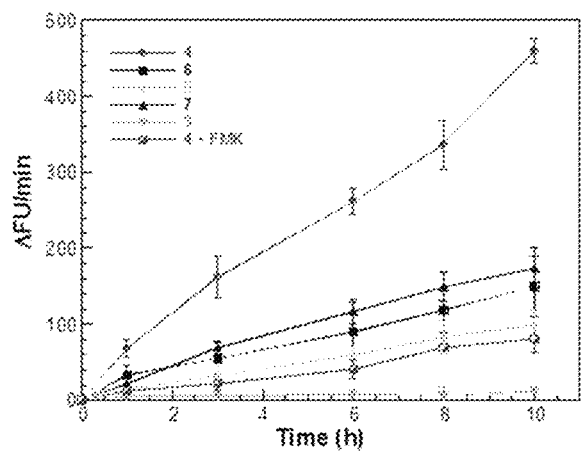
FIG. 21
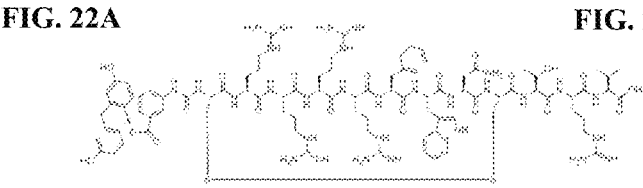
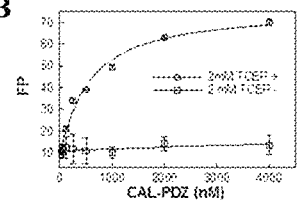
FIG. 22A  FIG. 22B
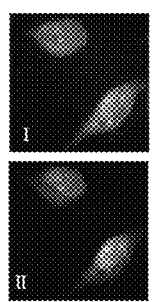
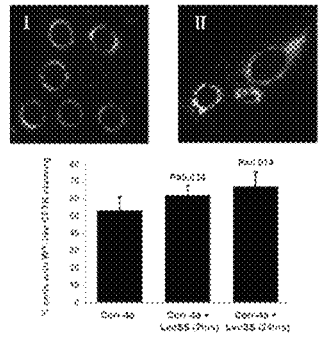
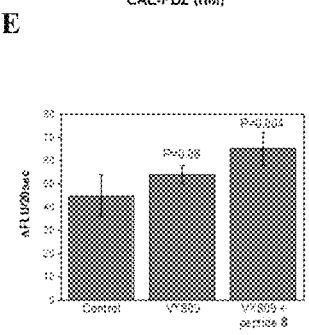
FIG. 22C  FIG. 22D  FIG. 22E

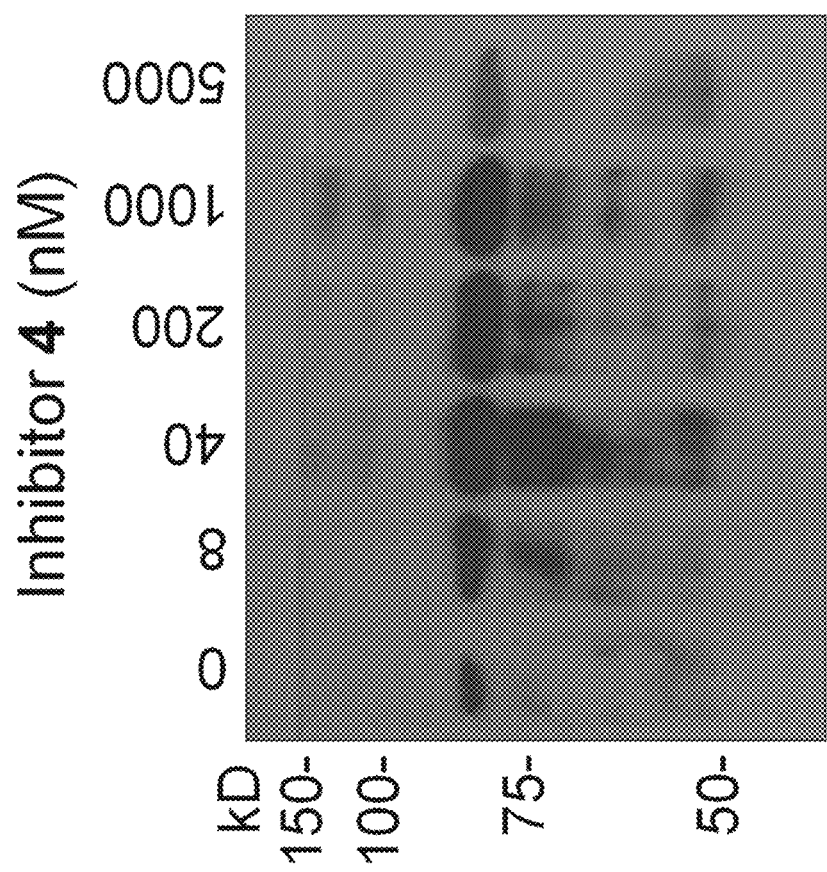

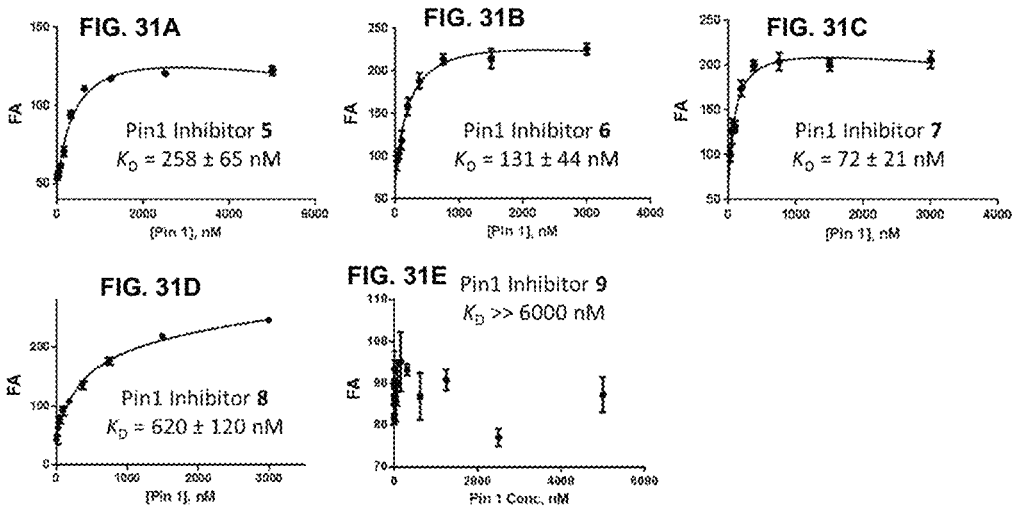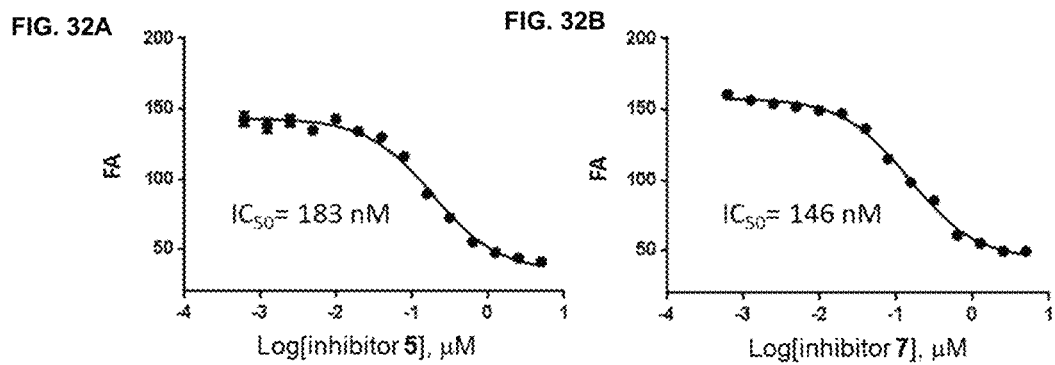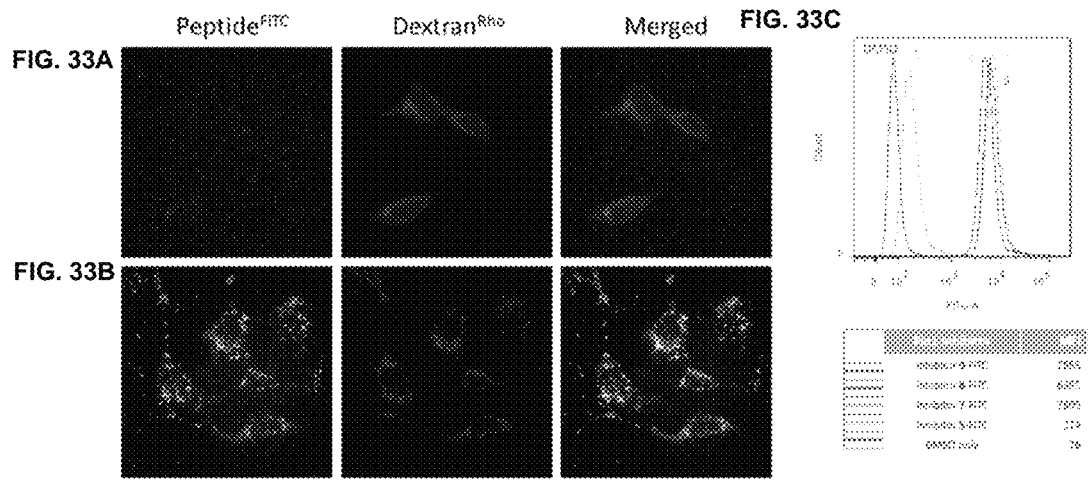

FIG. 35A
FIG. 35B
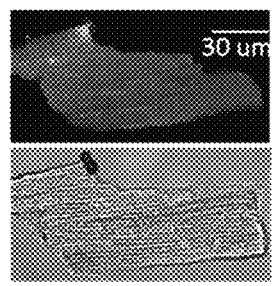 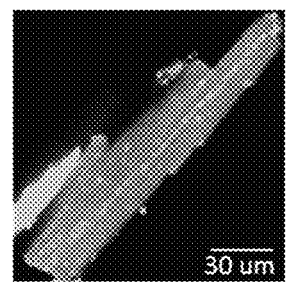 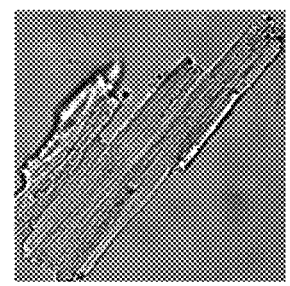
FIG. 35C
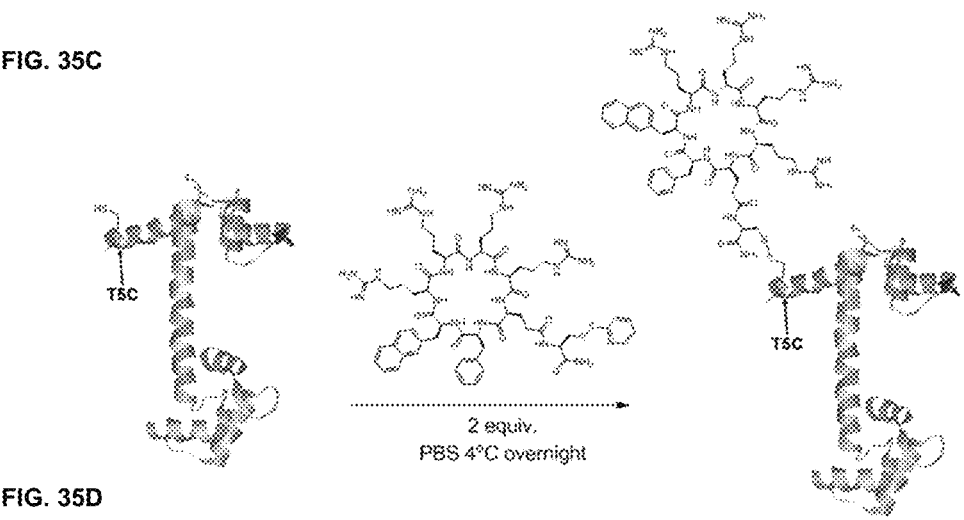
FIG. 35D
 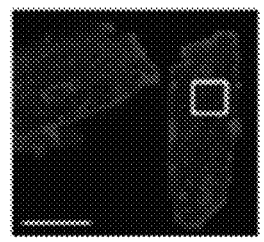 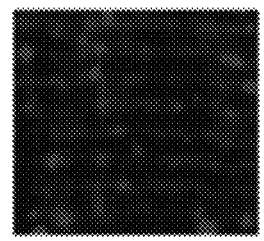

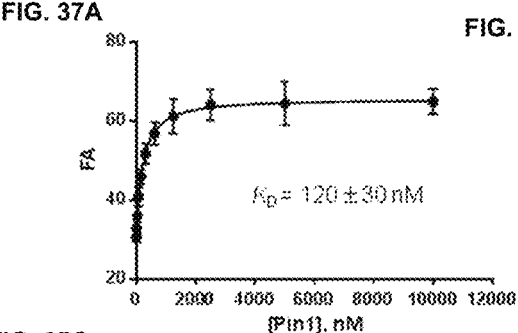
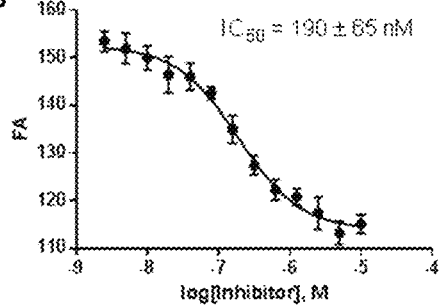
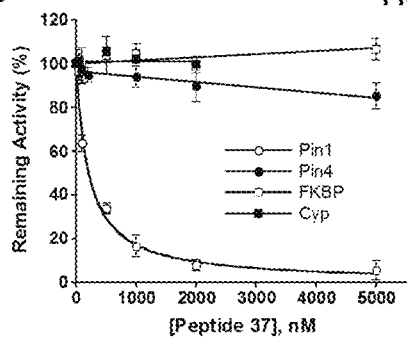
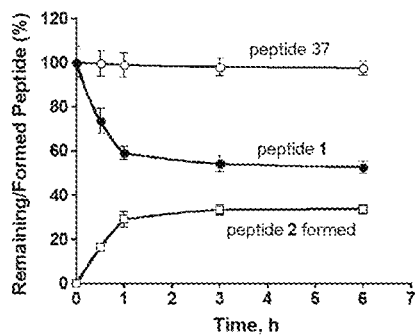
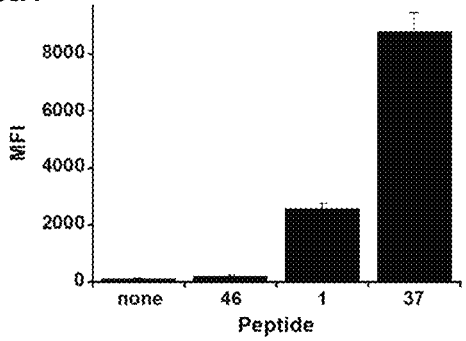
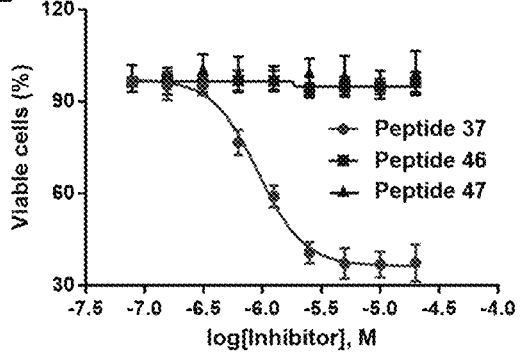
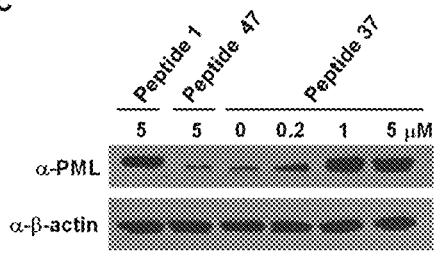
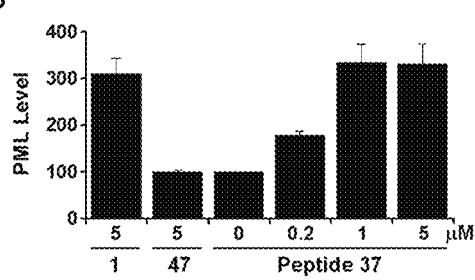

SEQUENCE LISTING

<160> NUMBER OF SEQ ID NOS: 246

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 1

Phe Xaa Arg Arg Arg Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 2

Phe Xaa Arg Arg Arg Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (6)..(6)
<223> OTHER INFORMATION: selenocysteine

<400> SEQUENCE: 3

Phe Xaa Arg Arg Arg Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-napthylalanine

<400> SEQUENCE: 4

Arg Arg Arg Xaa Phe Gln
1               5

<210> SEQ ID NO 5
<211> LENGTH: 6
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-napthylalanine

<400> SEQUENCE: 5

Arg Arg Arg Arg Xaa Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 6

Phe Xaa Arg Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-napthylalanine

<400> SEQUENCE: 7

Phe Xaa Arg Arg Arg Arg Gln
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-napthylalanine

<400> SEQUENCE: 8

Phe Xaa Arg Arg Arg Arg Gln
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 9

Phe Xaa Arg Arg Arg Arg Gln
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 10

Phe Xaa Arg Arg Arg Arg Gln
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-napthylalanine

<400> SEQUENCE: 11

Arg Arg Phe Arg Xaa Arg Gln
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: L-napthylalanine

<400> SEQUENCE: 12

Phe Arg Arg Arg Arg Xaa Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-napthylalanine

<400> SEQUENCE: 13

Arg Arg Phe Arg Xaa Arg Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
```

```
<223> OTHER INFORMATION: L-napthylalanine

<400> SEQUENCE: 14

Arg Arg Xaa Phe Arg Arg Gln
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Cys Arg Arg Arg Arg Phe Trp Gln
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-napthylalanine

<400> SEQUENCE: 16

Phe Phe Xaa Arg Arg Arg Arg Gln
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-napthylalanine

<400> SEQUENCE: 17

Phe Phe Xaa Arg Arg Arg Arg Gln
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: L-napthylalanine

<400> SEQUENCE: 18

Arg Phe Arg Phe Arg Xaa Arg Gln
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(1)
<223> OTHER INFORMATION: selenocysteine

<400> SEQUENCE: 19

Xaa Arg Arg Arg Arg Phe Trp Gln
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Cys Arg Arg Arg Arg Phe Trp Gln
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 21

Phe Xaa Arg Arg Arg Arg Gln Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 22

Phe Xaa Arg Arg Arg Arg Gln Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 23

Phe Xaa Arg Arg Arg Arg Arg Gln
1               5

<210> SEQ ID NO 24
<211> LENGTH: 8
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 24

Phe Xaa Arg Arg Arg Arg Arg Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-napthylalanine
<220> FEATURE:
<221> NAME/KEY: MISC_FEATURE
<222> LOCATION: (8)..(8)
<223> OTHER INFORMATION: L-norleucine

<400> SEQUENCE: 25

Arg Arg Arg Arg Xaa Phe Asp Xaa Cys
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-napthylalanine

<400> SEQUENCE: 26

Phe Xaa Arg Arg Arg
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Phe Trp Arg Arg Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-napthylalanine

<400> SEQUENCE: 28

Arg Arg Arg Xaa Phe
1               5
```

```
<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Arg Arg Arg Trp Phe
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Arg Arg Arg Arg Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Ala Ala Ala Ala Ala
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic Construct

<400> SEQUENCE: 32

Phe Phe Phe Phe
1

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: phosphocoumaryl amino propionic acid

<400> SEQUENCE: 33

Asp Glu Xaa Leu Ile
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34
```

Ala Ala Ala Ala Ala Ala Ala
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Arg Ala Arg Ala Arg
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Ala Asp Ala Asp
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: norleucine
<220> FEATURE:
<221> NAME/KEY: MISC_FEATURE
<222> LOCATION: (3)..(3)
<223> OTHER INFORMATION: selenocysteine

<400> SEQUENCE: 37

Asp Xaa Xaa Asp
1

<210> SEQ ID NO 38
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 2-aminobutyric acid

<400> SEQUENCE: 38

Xaa Thr Arg Val
1

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:

```
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 39

Pro Xaa Gly Xaa Tyr Arg
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-4-(phosphonodifluoromethyl)phenylalanine

<400> SEQUENCE: 40

Ser Xaa Ile Xaa Xaa Arg
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 41

Ile His Ile Xaa Ile Arg
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 42

Ala Ala Ile Xaa Xaa Arg
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: L-4-fluorophenylalanine
<220> FEATURE:
<221> NAME/KEY: MISC_FEATURE
<222> LOCATION: (3)..(3)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 43

Xaa Ser Xaa Xaa Val Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 44

Xaa Asn Pro Xaa Ala Arg
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 45

Thr Xaa Ala Xaa Gly Arg
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 46

Ala His Ile Xaa Ala Arg
1               5

<210> SEQ ID NO 47
```

```
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 47

Gly Asn Gly Xaa Pro Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 48

Phe Gln Xaa Xaa Ile Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 49

Ser Pro Gly Xaa His Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 50

Xaa Tyr Ile Xaa His Arg
1               5

<210> SEQ ID NO 51
<211> LENGTH: 6
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 51

Ser Val Pro Xaa His Arg
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 52

Ala Ile Pro Xaa Asn Arg
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 53

Xaa Ser Ile Xaa Gln Phe
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 54

Ala Ala Xaa Xaa Phe Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-phenylglycine

<400> SEQUENCE: 55

Asn Thr Xaa Xaa Xaa Arg
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine

<400> SEQUENCE: 56

Ile Pro Xaa Xaa Xaa Arg
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 57

Gln Xaa Xaa Xaa Xaa Arg
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 58

Asn Ala Xaa Xaa Gly Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 59

Asn Thr Tyr Xaa Ala Arg
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 60

Glu Ala Xaa Xaa Val Arg
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 61

Ile Val Xaa Xaa Ala Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 62

Tyr Thr Xaa Xaa Ala Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 63

Asn Xaa Xaa Xaa Ile Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 64

Xaa Asn Trp Xaa His Arg
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 65

Tyr Xaa Val Xaa Ile Arg
```

```
<210> SEQ ID NO 66
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: X4 = L-4-(phosphonodifluoromethyl)phenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 66

Asn Ser Ala Xaa Gly Arg
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 67

Thr Asn Val Xaa Ala Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 68

Asn Thr Val Xaa Thr Arg
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 69

Ser Ile Thr Xaa Tyr Arg
1               5

<210> SEQ ID NO 70
<211> LENGTH: 6
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 70

Asn Xaa Asn Xaa Leu Arg
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine

<400> SEQUENCE: 71

Tyr Asn Asn Xaa Xaa Arg
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 72

Asn Tyr Asn Xaa Gly Arg
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 73

Ala Trp Asn Xaa Ala Arg
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 74

Val Thr His Xaa Tyr Arg
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 75

Pro Xaa His Xaa Xaa Arg
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 76

Asn Xaa His Xaa Gly Arg
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 77

Pro Ala His Xaa Gly Arg
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 78

Ala Tyr His Xaa Ile Arg
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 79

Asn Xaa Glu Xaa Tyr Arg
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 80

Val Ser Ser Xaa Thr Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: sarcosine
<220> FEATURE:
<221> NAME/KEY: MISC_FEATURE
<222> LOCATION: (3)..(3)
<223> OTHER INFORMATION: D-phosphothreonine
<220> FEATURE:
<221> NAME/KEY: MISC_FEATURE
<222> LOCATION: (4)..(4)
<223> OTHER INFORMATION: L-pipecolic acid
<220> FEATURE:
<221> NAME/KEY: MISC_FEATURE
<222> LOCATION: (5)..(5)
<223> OTHER INFORMATION: L-beta-naphthylalanine

<400> SEQUENCE: 81

Ala Xaa Xaa Xaa Xaa Tyr Asn Lys
1               5

<210> SEQ ID NO 82
```

```
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid

<400> SEQUENCE: 82

Xaa Ala Xaa Xaa Xaa Xaa Arg Ala Xaa
1               5

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid

<400> SEQUENCE: 83

Xaa Ala Xaa Xaa Xaa Xaa Arg Ala Ala Xaa
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid

<400> SEQUENCE: 84

Xaa Ala Xaa Thr Xaa Xaa Arg Ala Ala Xaa
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid

<400> SEQUENCE: 85

Xaa Ala Xaa Thr Ala Xaa Arg Ala Ala Xaa
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (9)..(9)
<223> OTHER INFORMATION: rhodamine B

<400> SEQUENCE: 86

Phe Xaa Arg Arg Arg Arg Gln Lys Xaa
1               5

<210> SEQ ID NO 87
<211> LENGTH: 9
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (9)..(9)
<223> OTHER INFORMATION: dexamethasone

<400> SEQUENCE: 87

Phe Xaa Arg Arg Arg Arg Gln Lys Xaa
1               5

<210> SEQ ID NO 88
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: dexamethasone

<400> SEQUENCE: 88

Lys Xaa Gly Arg Lys Lys Arg Arg Gln Arg Arg Arg Pro Pro Gln Tyr
1               5                   10                  15

<210> SEQ ID NO 89
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine

<400> SEQUENCE: 89

Phe Xaa Arg Arg Arg Arg Gln Lys Phe Ile Thr Cys
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (14)..(14)
<223> OTHER INFORMATION: rhodamine B

<400> SEQUENCE: 90

Phe Xaa Arg Arg Arg Arg Gln Arg Arg Arg Arg Arg Lys Xaa
1               5                   10

<210> SEQ ID NO 91
<211> LENGTH: 14
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (14)..(14)
<223> OTHER INFORMATION: rhodamine B

<400> SEQUENCE: 91

Phe Xaa Arg Arg Arg Arg Gln Ala Ala Ala Ala Ala Lys Xaa
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (13)..(13)
<223> OTHER INFORMATION: rhodamine B

<400> SEQUENCE: 92

Phe Xaa Arg Arg Arg Arg Gln Phe Phe Phe Phe Lys Xaa
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (8)..(8)
<223> OTHER INFORMATION: 8-amino-3,6-dioxaoctanoic acid
<220> FEATURE:
<221> NAME/KEY: MISC_FEATURE
<222> LOCATION: (11)..(11)
<223> OTHER INFORMATION: phosphocoumaryl amino propionic acid

<400> SEQUENCE: 93

Phe Xaa Arg Arg Arg Arg Gln Xaa Asp Glu Xaa Leu Ile
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: 8-amino-3,6-dioxaoctanoic acid
<220> FEATURE:
<221> NAME/KEY: MISC_FEATURE
<222> LOCATION: (13)..(13)
<223> OTHER INFORMATION: phosphocoumaryl amino propionic acid

<400> SEQUENCE: 94
```

```
Arg Arg Arg Arg Arg Arg Arg Arg Xaa Asp Glu Xaa Leu Ile
1               5                   10                  15
```

<210> SEQ ID NO 95
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: 8-amino-3,6-dioxaoctanoic acid
<220> FEATURE:
<221> NAME/KEY: MISC_FEATURE
<222> LOCATION: (13)..(13)
<223> OTHER INFORMATION: phosphocoumaryl amino propionic acid

<400> SEQUENCE: 95

```
Arg Lys Lys Arg Arg Gln Arg Arg Xaa Asp Glu Xaa Leu Ile
1               5                   10                  15
```

<210> SEQ ID NO 96
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: 8-amino-3,6-dioxaoctanoic acid
<220> FEATURE:
<221> NAME/KEY: MISC_FEATURE
<222> LOCATION: (20)..(20)
<223> OTHER INFORMATION: phosphocoumaryl amino propionic acid

<400> SEQUENCE: 96

```
Arg Gln Ile Lys Ile Trp Phe Gln Asn Arg Arg Met Lys Trp Lys Lys
1               5                   10                  15

Xaa Asp Glu Xaa Leu Ile
            20
```

<210> SEQ ID NO 97
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (12)..(12)
<223> OTHER INFORMATION: L-2-naphthylalanine
<220> FEATURE:
<221> NAME/KEY: MISC_FEATURE
<222> LOCATION: (14)..(14)
<223> OTHER INFORMATION: L-2,3-diaminopropionic acid
<220> FEATURE:
<221> NAME/KEY: MISC_FEATURE
<222> LOCATION: (16)..(16)
<223> OTHER INFORMATION: rhodamine B

<400> SEQUENCE: 97

```
Xaa Ala Ala Ala Ala Ala Lys Arg Arg Arg Arg Xaa Phe Xaa Lys Xaa
1               5                   10                  15
```

<210> SEQ ID NO 98

```
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (14)..(14)
<223> OTHER INFORMATION: L-2-naphthylalanine
<220> FEATURE:
<221> NAME/KEY: MISC_FEATURE
<222> LOCATION: (16)..(16)
<223> OTHER INFORMATION: L-2,3-diaminopropionic acid
<220> FEATURE:
<221> NAME/KEY: MISC_FEATURE
<222> LOCATION: (18)..(18)
<223> OTHER INFORMATION: rhodamine B

<400> SEQUENCE: 98

Xaa Ala Ala Ala Ala Ala Ala Ala Lys Arg Arg Arg Arg Xaa Phe Xaa
1               5                   10                  15

Lys Xaa

<210> SEQ ID NO 99
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: L-2-naphthylalanine
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: L-2,3-diaminopropionic acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: rhodamine B

<400> SEQUENCE: 99

Xaa Arg Ala Arg Ala Arg Arg Arg Arg Xaa Phe Xaa Lys Xaa
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (1)..(1)
<223> OTHER INFORMATION: trimesic acid
<220> FEATURE:
<221> NAME/KEY: MISC_FEATURE
<222> LOCATION: (12)..(12)
<223> OTHER INFORMATION: L-2-naphthylalanine
<220> FEATURE:
<221> NAME/KEY: MISC_FEATURE
<222> LOCATION: (14)..(14)
<223> OTHER INFORMATION: L-2,3-diaminopropionic acid
<220> FEATURE:
<221> NAME/KEY: MISC_FEATURE
<222> LOCATION: (16)..(16)
<223> OTHER INFORMATION: rhodamine B

<400> SEQUENCE: 100

Xaa Asp Ala Asp Ala Asp Lys Arg Arg Arg Arg Xaa Phe Xaa Lys Xaa
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: L-2-naphthylalanine
<220> FEATURE:
<221> NAME/KEY: MISC_FEATURE
<222> LOCATION: (13)..(13)
<223> OTHER INFORMATION: rhodamine B

<400> SEQUENCE: 101

Ala Ala Ala Ala Ala Arg Arg Arg Arg Xaa Phe Lys Xaa
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: L-2-naphthylalanine
<220> FEATURE:
<221> NAME/KEY: MISC_FEATURE
<222> LOCATION: (15)..(15)
<223> OTHER INFORMATION: rhodamine B

<400> SEQUENCE: 102

Ala Ala Ala Ala Ala Ala Ala Arg Arg Arg Arg Xaa Phe Lys Xaa
1               5                   10                  15

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline

<400> SEQUENCE: 103

Phe Xaa Arg Arg Arg Arg Cys Lys
1               5
```

<210> SEQ ID NO 104
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (7)..(7)
<223> OTHER INFORMATION: selenocysteine

<400> SEQUENCE: 104

Phe Xaa Arg Arg Arg Arg Xaa Lys
1               5

<210> SEQ ID NO 105
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-norleucine
<220> FEATURE:
<221> NAME/KEY: MISC_FEATURE
<222> LOCATION: (3)..(3)
<223> OTHER INFORMATION: selenocysteine
<220> FEATURE:
<221> NAME/KEY: MISC_FEATURE
<222> LOCATION: (5)..(5)
<223> OTHER INFORMATION: 7-amino-4-methylcourmarin

<400> SEQUENCE: 105

Asp Xaa Xaa Asp
1

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (8)..(8)
<223> OTHER INFORMATION: L-norleucine

<400> SEQUENCE: 106

Arg Arg Arg Arg Xaa Phe Asp Xaa Cys Asp
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-homoproline
<220> FEATURE:

```
<221> NAME/KEY: MISC_FEATURE
<222> LOCATION: (8)..(8)
<223> OTHER INFORMATION: L-norleucine

<400> SEQUENCE: 107

Arg Arg Arg Arg Xaa Phe Asp Xaa Cys Asp
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (8)..(8)
<223> OTHER INFORMATION: L-norleucine
<220> FEATURE:
<221> NAME/KEY: MISC_FEATURE
<222> LOCATION: (9)..(9)
<223> OTHER INFORMATION: selenocysteine

<400> SEQUENCE: 108

Arg Arg Arg Arg Xaa Phe Asp Xaa Xaa Asp
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: L-norleucine
<220> FEATURE:
<221> NAME/KEY: MISC_FEATURE
<222> LOCATION: (12)..(12)
<223> OTHER INFORMATION: selenocysteine
<220> FEATURE:
<221> NAME/KEY: MISC_FEATURE
<222> LOCATION: (14)..(14)
<223> OTHER INFORMATION: 7-amino-4-methylcourmarin

<400> SEQUENCE: 109

Arg Arg Arg Arg Arg Arg Arg Arg Arg Asp Xaa Xaa Cys Xaa
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic Construct

<400> SEQUENCE: 110

Cys Arg Arg Arg Arg Phe Trp Gln Cys Thr Arg Val
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: selenocysteine
<220> FEATURE:
<221> NAME/KEY: MISC_FEATURE
<222> LOCATION: (9)..(9)
<223> OTHER INFORMATION: selenocysteine

<400> SEQUENCE: 111

Xaa Arg Arg Arg Arg Phe Trp Gln Xaa Thr Arg Val
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Synthetic Construct

<400> SEQUENCE: 112

Cys Arg Arg Arg Arg Phe Trp Gln Cys
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine

<400> SEQUENCE: 113

Phe Xaa Arg Arg Arg Arg Pro Thr Pro
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-2-naphthylalanine

<400> SEQUENCE: 114

Phe Xaa Arg Arg Arg Arg Pro Cys Pro
1               5

<210> SEQ ID NO 115
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (10)..(10)
<223> OTHER INFORMATION: L-beta-naphthylalanine

<400> SEQUENCE: 115
```

```
Thr Asn Val Xaa Ala Arg Arg Arg Arg Xaa Phe Gln
1               5                   10
```

<210> SEQ ID NO 116
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (10)..(10)
<223> OTHER INFORMATION: L-beta-naphthylalanine

<400> SEQUENCE: 116

```
Ser Val Pro Xaa His Arg Arg Arg Arg Xaa Phe Gln
1               5                   10
```

<210> SEQ ID NO 117
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine
<220> FEATURE:
<221> NAME/KEY: MISC_FEATURE
<222> LOCATION: (10)..(10)
<223> OTHER INFORMATION: L-beta-naphthylalanine

<400> SEQUENCE: 117

```
Ile Pro Xaa Xaa Xaa Arg Arg Arg Arg Xaa Phe Gln
1               5                   10
```

<210> SEQ ID NO 118
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: sarcosine
<220> FEATURE:
<221> NAME/KEY: MISC_FEATURE
<222> LOCATION: (3)..(3)
<223> OTHER INFORMATION: D-phosphothreonine
<220> FEATURE:
<221> NAME/KEY: MISC_FEATURE
<222> LOCATION: (4)..(4)
<223> OTHER INFORMATION: L-pipecolic acid
<220> FEATURE:
<221> NAME/KEY: MISC_FEATURE
<222> LOCATION: (5)..(5)
<223> OTHER INFORMATION: L-beta-naphthylalanine

<400> SEQUENCE: 118

```
Ala Xaa Xaa Xaa Xaa Tyr Gln Lys
1               5

<210> SEQ ID NO 119
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: L-2,3-diaminopropionic acid

<400> SEQUENCE: 119

Xaa Ala Xaa Xaa Xaa Xaa Arg Ala Xaa Phe Xaa Arg Arg Arg Arg Xaa
1               5                   10                  15

Lys

<210> SEQ ID NO 120
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
```

-continued

```
<222> LOCATION: (10)..(10)
<223> OTHER INFORMATION: L-2,3-diaminopropionic acid
<220> FEATURE:
<221> NAME/KEY: MISC_FEATURE
<222> LOCATION: (13)..(13)
<223> OTHER INFORMATION: L-beta-naphthylalanine
<220> FEATURE:
<221> NAME/KEY: MISC_FEATURE
<222> LOCATION: (18)..(18)
<223> OTHER INFORMATION: L-2,3-diaminopropionic acid

<400> SEQUENCE: 120

Xaa Ala Xaa Xaa Xaa Xaa Arg Ala Ala Xaa Phe Asn Xaa Arg Arg Arg
1               5                   10                  15

Arg Xaa Lys

<210> SEQ ID NO 121
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-pipecolic acid
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 121

Xaa Ala Xaa Thr Xaa Xaa Arg Ala Ala Xaa Phe Xaa Arg Arg Arg Arg
1               5                   10                  15

Xaa Lys

<210> SEQ ID NO 122
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (6)..(6)
```

```
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 122

Xaa Ala Xaa Thr Ala Xaa Arg Ala Ala Xaa Phe Xaa Arg Arg Arg Arg
1               5                   10                  15

Xaa Lys

<210> SEQ ID NO 123
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline

<400> SEQUENCE: 123

Phe Xaa Arg Arg Arg Arg Cys Lys
1               5

<210> SEQ ID NO 124
<211> LENGTH: 16
<212> TYPE: PRT
<213> ORGANISM: Artificial Sequence
<220> FEATURE:
<223> OTHER INFORMATION: Synthetic Construct

<400> SEQUENCE: 124

Arg Gln Ile Lys Ile Trp Phe Gln Asn Arg Arg Met Lys Trp Lys Lys
1               5                   10                  15

<210> SEQ ID NO 125
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: 2-aminobutyric acid
<220> FEATURE:
<221> NAME/KEY: MISC_FEATURE
<222> LOCATION: (5)..(5)
<223> OTHER INFORMATION: 7-amino-4-methylcourmarin

<400> SEQUENCE: 125

Asp Met Xaa Asp Xaa
1               5

<210> SEQ ID NO 126
<211> LENGTH: 10
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (8)..(8)
<223> OTHER INFORMATION: L-norleucine

<400> SEQUENCE: 126

Arg Arg Arg Arg Xaa Phe Asp Xaa Cys Asp
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (8)..(8)
<223> OTHER INFORMATION: L-norleucine

<400> SEQUENCE: 127

Arg Arg Arg Arg Xaa Phe Asp Xaa Cys Asp
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (8)..(8)
<223> OTHER INFORMATION: L-norleucine
<220> FEATURE:
<221> NAME/KEY: MISC_FEATURE
<222> LOCATION: (9)..(9)
<223> OTHER INFORMATION: selenocysteine

<400> SEQUENCE: 128

Arg Arg Arg Arg Xaa Phe Asp Xaa Xaa Asp
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Nle
<220> FEATURE:
<221> NAME/KEY: MISC_FEATURE
<222> LOCATION: (12)..(12)
<223> OTHER INFORMATION: 2-aminobutyric acid
<220> FEATURE:
<221> NAME/KEY: MISC_FEATURE
<222> LOCATION: (14)..(14)
<223> OTHER INFORMATION: 7-amino-4-methylcourmarin
```

<400> SEQUENCE: 129

Arg Arg Arg Arg Arg Arg Arg Arg Asp Xaa Xaa Asp Xaa
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic Construct

<400> SEQUENCE: 130

Cys Arg Arg Arg Arg Phe Trp Gln Cys Thr Arg Val
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 2-aminobutyric acid
<220> FEATURE:
<221> NAME/KEY: MISC_FEATURE
<222> LOCATION: (9)..(9)
<223> OTHER INFORMATION: 2-aminobutyric acid

<400> SEQUENCE: 131

Xaa Arg Arg Arg Arg Phe Trp Gln Xaa Thr Arg Val
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic Construct

<400> SEQUENCE: 132

Cys Arg Arg Arg Arg Phe Trp Gln Cys Thr Arg Val
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Synthetic Construct

<400> SEQUENCE: 133

Arg Arg Arg Arg Arg Arg Arg Arg Arg
1               5

<210> SEQ ID NO 134
<211> LENGTH: 11
<212> TYPE: PRT
<213> ORGANISM: Artificial Sequence
<220> FEATURE:
<223> OTHER INFORMATION: Synthetic Construct

<400> SEQUENCE: 134

Tyr Gly Arg Lys Lys Arg Arg Gln Arg Arg Arg
1               5                   10

<210> SEQ ID NO 135
<211> LENGTH: 16
<212> TYPE: PRT
<213> ORGANISM: Artificial Sequence
<220> FEATURE:
<223> OTHER INFORMATION: Synthetic Construct

<400> SEQUENCE: 135

Arg Gln Ile Lys Ile Trp Phe Gln Asn Arg Arg Met Lys Trp Lys Lys
1               5                   10                  15

<210> SEQ ID NO 136
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 136

Pro Xaa Gly Xaa Tyr Arg
1               5

<210> SEQ ID NO 137
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-4-(phosphonodifluoromethyl)phenylalanine

<400> SEQUENCE: 137

Ser Xaa Ile Xaa Xaa Arg
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 138

Ile His Ile Xaa Ile Arg
1               5

<210> SEQ ID NO 139
<211> LENGTH: 6

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 139

Ala Ala Ile Xaa Xaa Arg
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-4-fluorophenylalanine
<220> FEATURE:
<221> NAME/KEY: MISC_FEATURE
<222> LOCATION: (3)..(3)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 140

Xaa Ser Xaa Xaa Val Arg
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 141

Xaa Asn Pro Xaa Ala Arg
1               5

<210> SEQ ID NO 142
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
```

```
<400> SEQUENCE: 142

Tyr Xaa Ala Xaa Gly Arg
1               5

<210> SEQ ID NO 143
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 143

Ala His Ile Xaa Ala Arg
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 144

Gly Asn Gly Xaa Pro Arg
1               5

<210> SEQ ID NO 145
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 145

Phe Gln Xaa Xaa Ile Arg
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 146

Ser Pro Gly Xaa His Arg
1               5
```

```
<210> SEQ ID NO 147
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 147

Xaa Tyr Ile Xaa His Arg
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 148

Ser Val Pro Xaa His Arg
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 149

Ala Ile Pro Xaa Asn Arg
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 150

Xaa Ser Ile Xaa Gln Phe
1               5

<210> SEQ ID NO 151
<211> LENGTH: 6
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 151

Ala Ala Xaa Xaa Phe Arg
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-phenylglycine

<400> SEQUENCE: 152

Asn Thr Xaa Xaa Xaa Arg
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine

<400> SEQUENCE: 153

Ile Pro Xaa Xaa Xaa Arg
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
```

```
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 154

Gln Xaa Xaa Xaa Xaa Arg
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 155

Asn Ala Xaa Xaa Gly Arg
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 156

Asn Thr Tyr Xaa Ala Arg
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 157

Glu Ala Xaa Xaa Val Arg
1               5

<210> SEQ ID NO 158
<211> LENGTH: 6
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 158

Ile Val Xaa Xaa Ala Arg
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 159

Tyr Thr Xaa Xaa Ala Arg
1               5

<210> SEQ ID NO 160
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 160

Asn Xaa Xaa Xaa Ile Arg
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine
```

```
<400> SEQUENCE: 161

Xaa Asn Trp Xaa His Arg
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 162

Tyr Xaa Val Xaa Ile Arg
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 163

Asn Ser Ala Xaa Gly Arg
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 164

Thr Asn Val Xaa Ala Arg
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 165

Asn Thr Val Xaa Thr Arg
1               5
```

```
<210> SEQ ID NO 166
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 166

Ser Ile Thr Xaa Tyr Arg
1               5

<210> SEQ ID NO 167
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 167

Asn Xaa Asn Xaa Leu Arg
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine

<400> SEQUENCE: 168

Tyr Asn Asn Xaa Xaa Arg
1               5

<210> SEQ ID NO 169
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 169

Asn Tyr Asn Xaa Gly Arg
1               5

<210> SEQ ID NO 170
<211> LENGTH: 6
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 170

Ala Trp Asn Xaa Ala Arg
1               5

<210> SEQ ID NO 171
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 171

Val Thr His Xaa Tyr Arg
1               5

<210> SEQ ID NO 172
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-homoproline

<400> SEQUENCE: 172

Pro Xaa His Xaa Xaa Arg
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 173

Asn Xaa His Xaa Gly Arg
1               5

<210> SEQ ID NO 174
<211> LENGTH: 6
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 174

Pro Ala His Xaa Gly Arg
1               5

<210> SEQ ID NO 175
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 175

Ala Tyr His Xaa Ile Arg
1               5

<210> SEQ ID NO 176
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-homoproline
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 176

Asn Xaa Glu Xaa Tyr Arg
1               5

<210> SEQ ID NO 177
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine

<400> SEQUENCE: 177

Val Ser Ser Xaa Thr Arg
1               5

<210> SEQ ID NO 178
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
```

```
<223> OTHER INFORMATION: L-4-(phosphonodifluoromethyl)phenylalanine
<220> FEATURE:
<221> NAME/KEY: MISC_FEATURE
<222> LOCATION: (10)..(10)
<223> OTHER INFORMATION: L-beta-naphthylalanine

<400> SEQUENCE: 178

Thr Asn Val Xaa Ala Arg Arg Arg Arg Xaa Phe Gln
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (10)..(10)
<223> OTHER INFORMATION: L-beta-naphthylalanine

<400> SEQUENCE: 179

Ser Val Pro Xaa His Arg Arg Arg Arg Xaa Phe Gln
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (4)..(4)
<223> OTHER INFORMATION: L-4-(phosphonodifluoromethyl)phenylalanine
<220> FEATURE:
<221> NAME/KEY: MISC_FEATURE
<222> LOCATION: (5)..(5)
<223> OTHER INFORMATION: L-norleucine
<220> FEATURE:
<221> NAME/KEY: MISC_FEATURE
<222> LOCATION: (10)..(10)
<223> OTHER INFORMATION: L-beta-naphthylalanine

<400> SEQUENCE: 180

Ile Pro Xaa Xaa Xaa Arg Arg Arg Arg Xaa Phe Gln
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: sarcosine
<220> FEATURE:
<221> NAME/KEY: MISC_FEATURE
<222> LOCATION: (3)..(3)
<223> OTHER INFORMATION: D-phosphothreonine
<220> FEATURE:
<221> NAME/KEY: MISC_FEATURE
<222> LOCATION: (4)..(4)
```

<223> OTHER INFORMATION: L-homoproline
<220> FEATURE:
<221> NAME/KEY: MISC_FEATURE
<222> LOCATION: (5)..(5)
<223> OTHER INFORMATION: L-beta-naphthylalanine

<400> SEQUENCE: 181

Ala Xaa Xaa Xaa Xaa Tyr Gln Lys
1               5

<210> SEQ ID NO 182
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid
<220> FEATURE:
<221> NAME/KEY: MISC_FEATURE
<222> LOCATION: (11)..(11)
<223> OTHER INFORMATION: L-beta-naphthylalanine
<220> FEATURE:
<221> NAME/KEY: MISC_FEATURE
<222> LOCATION: (16)..(16)
<223> OTHER INFORMATION: L-2,3-diaminopropionic acid

<400> SEQUENCE: 182

Xaa Ala Xaa Xaa Xaa Xaa Arg Ala Xaa Phe Xaa Arg Arg Arg Arg Lys
1               5                   10                  15

<210> SEQ ID NO 183
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-homoproline

```
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 183

Xaa Ala Xaa Xaa Xaa Xaa Arg Ala Ala Xaa Phe Xaa Arg Arg Arg Arg
1               5                   10                  15

Xaa Lys

<210> SEQ ID NO 184
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 184

Xaa Ala Xaa Thr Xaa Xaa Arg Ala Ala Xaa Phe Xaa Arg Arg Arg Arg
1               5                   10                  15

Xaa Lys

<210> SEQ ID NO 185
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
```

<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 185

Xaa Ala Xaa Thr Ala Xaa Arg Ala Ala Xaa Phe Xaa Arg Arg Arg Arg
1               5                   10                  15

Xaa Lys

<210> SEQ ID NO 186
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-naphthylalanine

<400> SEQUENCE: 186

Phe Xaa Arg Arg Arg Arg Gln
1               5

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-naphthylalanine

<400> SEQUENCE: 187

Phe Phe Xaa Arg Arg Arg Arg Gln
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-naphthylalanine

<400> SEQUENCE: 188

Phe Xaa Arg Arg Arg Arg Gln
1               5

```
<210> SEQ ID NO 189
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-naphthylalanine

<400> SEQUENCE: 189

Phe Xaa Arg Arg Arg Arg Arg Gln
1               5

<210> SEQ ID NO 190
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-naphthylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 190

Cys Phe Xaa Arg Arg Arg Arg Gln
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D-naphthylalanine

<400> SEQUENCE: 191

Phe Xaa Arg Arg Arg Arg Gln
1               5

<210> SEQ ID NO 192
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-naphthylalanine

<400> SEQUENCE: 192

Phe Xaa Arg Arg Arg Arg Arg Gln
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic Construct
<220> FEATURE:
```

<221> NAME/KEY: MISC_FEATURE
<222> LOCATION: (5)..(5)
<223> OTHER INFORMATION: L-naphthylalanine

<400> SEQUENCE: 193

Arg Arg Phe Arg Xaa Arg Gln
1               5

<210> SEQ ID NO 194
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-naphthylalanine

<400> SEQUENCE: 194

Phe Phe Xaa Arg Arg Arg Arg Gln
1               5

<210> SEQ ID NO 195
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: L-naphthylalanine

<400> SEQUENCE: 195

Arg Phe Arg Phe Arg Xaa Arg Gln
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: L-naphthylalanine

<400> SEQUENCE: 196

Phe Xaa Arg Arg Arg Gln
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: L-naphthylalanine

<400> SEQUENCE: 197

Phe Arg Arg Arg Arg Xaa Gln
1               5

<210> SEQ ID NO 198

```
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L-naphthylalanine

<400> SEQUENCE: 198

Arg Arg Phe Arg Xaa Arg Gln
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: L-naphthylalanine

<400> SEQUENCE: 199

Arg Arg Xaa Phe Arg Arg Gln
1               5

<210> SEQ ID NO 200
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-phosphothreonine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 200

Xaa Ala Xaa Xaa Xaa Xaa Arg Ala Ala Xaa Phe Xaa Arg Arg Arg Arg
1               5                   10                  15

Xaa Lys
```

<210> SEQ ID NO 201
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 201

Xaa Ala Xaa Thr Xaa Xaa Arg Ala Ala Xaa Phe Xaa Arg Arg Arg Arg
1               5                   10                  15

Xaa Lys

<210> SEQ ID NO 202
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

```
<400> SEQUENCE: 202

Xaa Pro Xaa Asp Xaa Xaa Arg Ala Ala Xaa Phe Xaa Arg Arg Arg
1               5                   10                  15

Lys

<210> SEQ ID NO 203
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 203

Xaa Phe Xaa Thr Xaa Xaa Arg Ala Ala Xaa Phe Xaa Arg Arg Arg
1               5                   10                  15

Xaa Lys

<210> SEQ ID NO 204
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: L-N(alpha)-methylphenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
```

```
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 204

Xaa Xaa Gly Thr Xaa Xaa Arg Ala Ala Xaa Phe Xaa Arg Arg Arg Arg
1               5                   10                  15

Lys

<210> SEQ ID NO 205
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: L-phenylglycine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 205

Xaa Xaa His Glu Xaa Xaa Arg Ala Ala Xaa Phe Xaa Arg Arg Arg Arg
1               5                   10                  15

Xaa Lys

<210> SEQ ID NO 206
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: L-N(alpha)-methylphenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
```

```
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 206

Xaa Xaa Ile Glu Xaa Xaa Arg Ala Ala Xaa Phe Xaa Arg Arg Arg Arg
1               5                   10                  15

Xaa Lys

<210> SEQ ID NO 207
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-phenylglycine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 207

Xaa His Xaa Thr Xaa Xaa Arg Ala Ala Xaa Phe Xaa Arg Arg Arg Arg
1               5                   10                  15

Xaa Lys

<210> SEQ ID NO 208
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid
<220> FEATURE:
<221> NAME/KEY: MISC_FEATURE
<222> LOCATION: (11)..(11)
<223> OTHER INFORMATION: L-beta-naphthylalanine
<220> FEATURE:
<221> NAME/KEY: MISC_FEATURE
<222> LOCATION: (16)..(16)
<223> OTHER INFORMATION: L-2,3-diaminopropionic acid

<400> SEQUENCE: 208

Xaa Pro Xaa Asp Xaa Xaa Arg Ala Xaa Phe Xaa Arg Arg Arg Arg Xaa
1               5                   10                  15
Lys

<210> SEQ ID NO 209
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (8)..(8)
<223> OTHER INFORMATION: L-2,3-diaminopropionic acid
<220> FEATURE:
<221> NAME/KEY: MISC_FEATURE
<222> LOCATION: (10)..(10)
<223> OTHER INFORMATION: L-beta-naphthylalanine
<220> FEATURE:
<221> NAME/KEY: MISC_FEATURE
<222> LOCATION: (15)..(15)
<223> OTHER INFORMATION: L-2,3-diaminopropionic acid

<400> SEQUENCE: 209

Xaa Pro Xaa Asp Xaa Xaa Arg Xaa Phe Xaa Arg Arg Arg Arg Xaa Lys
1               5                   10                  15

<210> SEQ ID NO 210
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
```

```
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: L-beta-naphthylalanine

<400> SEQUENCE: 210

Xaa Phe Xaa Thr Xaa Xaa Arg Ala Xaa Phe Xaa Arg Arg Arg Arg Xaa
1               5                   10                  15

Lys

<210> SEQ ID NO 211
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (8)..(8)
<223> OTHER INFORMATION: L-2,3-diaminopropionic acid
<220> FEATURE:
<221> NAME/KEY: MISC_FEATURE
<222> LOCATION: (10)..(10)
<223> OTHER INFORMATION: L-beta-naphthylalanine
<220> FEATURE:
<221> NAME/KEY: MISC_FEATURE
<222> LOCATION: (15)..(15)
<223> OTHER INFORMATION: L-2,3-diaminopropionic acid

<400> SEQUENCE: 211

Xaa Phe Xaa Thr Xaa Xaa Arg Xaa Phe Xaa Arg Arg Arg Arg Xaa Lys
1               5                   10                  15

<210> SEQ ID NO 212
<211> LENGTH: 17
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (11)..(11)
<223> OTHER INFORMATION: L-beta-naphthylalanine
<220> FEATURE:
<221> NAME/KEY: MISC_FEATURE
<222> LOCATION: (16)..(16)
<223> OTHER INFORMATION: L-2,3-diaminopropionic acid

<400> SEQUENCE: 212

Xaa Pro Xaa Asp Xaa Xaa Ala Ala Xaa Phe Xaa Arg Arg Arg Arg Xaa
1               5                   10                  15
Lys

<210> SEQ ID NO 213
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 213
```

-continued

```
Xaa Pro Xaa Asp Xaa Xaa Arg Ala Ala Xaa Phe Xaa Arg Arg Arg Arg
1               5                   10                  15

Xaa Lys

<210> SEQ ID NO 214
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 214

Xaa Pro Xaa Asp Xaa Xaa Arg Ala Ala Xaa Phe Xaa Arg Arg Arg Arg
1               5                   10                  15

Xaa Lys

<210> SEQ ID NO 215
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (11)..(11)
<223> OTHER INFORMATION: L-2,3-diaminopropionic acid
<220> FEATURE:
<221> NAME/KEY: MISC_FEATURE
<222> LOCATION: (13)..(13)
```

```
<223> OTHER INFORMATION: L-beta-naphthylalanine
<220> FEATURE:
<221> NAME/KEY: MISC_FEATURE
<222> LOCATION: (18)..(18)
<223> OTHER INFORMATION: L-2,3-diaminopropionic acid

<400> SEQUENCE: 215

Xaa Pro Xaa Asp Xaa Xaa Arg Ala Ala Ala Xaa Phe Xaa Arg Arg Arg
1               5                   10                  15

Arg Xaa Lys

<210> SEQ ID NO 216
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 216

Xaa Pro Xaa Asp Xaa Xaa Arg Tyr Ala Xaa Phe Xaa Arg Arg Arg Arg
1               5                   10                  15

Xaa Lys

<210> SEQ ID NO 217
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
```

<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 217

Xaa Pro Xaa Asp Xaa Xaa Arg Val Ala Xaa Phe Xaa Arg Arg Arg Arg
1               5                   10                  15

Xaa Lys

<210> SEQ ID NO 218
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 218

Xaa Pro Xaa Asp Xaa Xaa Arg Arg Ala Xaa Phe Xaa Arg Arg Arg Arg
1               5                   10                  15

Xaa Lys

<210> SEQ ID NO 219
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:

<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 219

Xaa Pro Xaa Asp Xaa Xaa Arg Asp Ala Xaa Phe Xaa Arg Arg Arg Arg
1               5                   10                  15

Xaa Lys

<210> SEQ ID NO 220
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 220

Xaa Phe Xaa Thr Xaa Xaa Arg Ser Phe Xaa Phe Xaa Arg Arg Arg Arg
1               5                   10                  15

Xaa Lys

<210> SEQ ID NO 221
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE

```
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 221

Xaa Pro Xaa Asp Xaa Xaa Arg Arg Phe Xaa Phe Xaa Arg Arg Arg Arg
1               5                   10                  15

Xaa Lys

<210> SEQ ID NO 222
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 222

Xaa Pro Xaa Asp Xaa Xaa Arg Arg Val Xaa Phe Xaa Arg Arg Arg Arg
1               5                   10                  15

Xaa Lys

<210> SEQ ID NO 223
```

```
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 223

Xaa Pro Xaa Asp Xaa Xaa Arg Arg Arg Xaa Phe Xaa Arg Arg Arg
1               5                   10                  15

Xaa Lys

<210> SEQ ID NO 224
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 224
```

```
Xaa Pro Xaa Asp Xaa Xaa Arg Arg Asp Xaa Phe Xaa Arg Arg Arg Arg
1               5                   10                  15

Xaa Lys

<210> SEQ ID NO 225
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 225

Xaa Phe Xaa Thr Xaa Xaa Arg Gly Ala Xaa Phe Xaa Arg Arg Arg Arg
1               5                   10                  15

Xaa Lys

<210> SEQ ID NO 226
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
```

```
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 226

Xaa Phe Xaa Thr Xaa Xaa Arg Ala Phe Xaa Phe Xaa Arg Arg Arg
1               5                   10                  15

Xaa Lys

<210> SEQ ID NO 227
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 227

Xaa Phe Phe Thr Xaa Xaa Arg Ala Phe Xaa Phe Xaa Arg Arg Arg
1               5                   10                  15

Xaa Lys

<210> SEQ ID NO 228
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 3,4-difluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
```

```
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 228

Xaa Phe Xaa Thr Xaa Xaa Arg Ala Phe Xaa Phe Xaa Arg Arg Arg Arg
1               5                   10                  15

Xaa Lys

<210> SEQ ID NO 229
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-chlorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 229

Xaa Phe Xaa Thr Xaa Xaa Arg Ala Phe Xaa Phe Xaa Arg Arg Arg Arg
1               5                   10                  15

Xaa Lys

<210> SEQ ID NO 230
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
```

<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 230

Xaa Phe His Thr Xaa Xaa Arg Ala Phe Xaa Phe Xaa Arg Arg Arg Arg
1               5                   10                  15

Xaa Lys

<210> SEQ ID NO 231
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-bromophenylalanin
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 231

Xaa Phe Xaa Thr Xaa Xaa Arg Ala Phe Xaa Phe Xaa Arg Arg Arg Arg
1               5                   10                  15

Xaa Lys

<210> SEQ ID NO 232
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-L-4-fluorophenylalanine
<220> FEATURE:
<221> NAME/KEY: MISC_FEATURE
<222> LOCATION: (5)..(5)

```
-continued

<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 232

Xaa Ala Xaa Thr Xaa Xaa Thr Ala Ala Xaa Phe Xaa Arg Arg Arg Arg
1               5                   10                  15

Xaa Lys

<210> SEQ ID NO 233
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: 4-L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 233

Xaa Val Xaa Thr Xaa Xaa Arg Ala Ala Xaa Phe Xaa Arg Arg Arg Arg
1               5                   10                  15

Xaa Lys

<210> SEQ ID NO 234
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
```

```
<220> FEATURE:
<221> NAME/KEY: MISC_FEATURE
<222> LOCATION: (2)..(2)
<223> OTHER INFORMATION: D-2-L-4-fluorophenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 234

Xaa Xaa Xaa Thr Xaa Xaa Arg Ala Phe Xaa Phe Xaa Arg Arg Arg Arg
1               5                   10                  15

Xaa Lys

<210> SEQ ID NO 235
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: D-3-L-4-fluorophenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 235

Xaa Xaa Xaa Thr Xaa Xaa Arg Ala Phe Xaa Phe Xaa Arg Arg Arg Arg
```

```
1               5                   10                  15

Xaa Lys

<210> SEQ ID NO 236
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: D-4-L-4-fluorophenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 236

Xaa Xaa Xaa Thr Xaa Xaa Arg Ala Phe Xaa Phe Xaa Arg Arg Arg Arg
1               5                   10                  15

Xaa Lys

<210> SEQ ID NO 237
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: D-4-Cyanophenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
```

```
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 237

Xaa Xaa Xaa Thr Xaa Xaa Arg Ala Phe Xaa Phe Xaa Arg Arg Arg Arg
1               5                   10                  15

Xaa Lys

<210> SEQ ID NO 238
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: D-4-phenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 238

Xaa Xaa Xaa Ile Xaa Xaa Arg Ala Phe Xaa Phe Xaa Arg Arg Arg Arg
1               5                   10                  15

Xaa Lys

<210> SEQ ID NO 239
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
```

```
<222> LOCATION: (2)..(2)
<223> OTHER INFORMATION: D-4-phenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-beta-naphthylalanine
<220> FEATURE:
<221> NAME/KEY: MISC_FEATURE
<222> LOCATION: (6)..(6)
<223> OTHER INFORMATION: L-homoproline
<220> FEATURE:
<221> NAME/KEY: MISC_FEATURE
<222> LOCATION: (7)..(7)
<223> OTHER INFORMATION: L-beta-naphthylalanine
<220> FEATURE:
<221> NAME/KEY: MISC_FEATURE
<222> LOCATION: (11)..(11)
<223> OTHER INFORMATION: L-2,3-diaminopropionic acid
<220> FEATURE:
<221> NAME/KEY: MISC_FEATURE
<222> LOCATION: (13)..(13)
<223> OTHER INFORMATION: L-beta-naphthylalanine
<220> FEATURE:
<221> NAME/KEY: MISC_FEATURE
<222> LOCATION: (18)..(18)
<223> OTHER INFORMATION: L-2,3-diaminopropionic acid

<400> SEQUENCE: 239

Xaa Xaa Xaa Asp Xaa Xaa Xaa Arg Ala Phe Xaa Phe Xaa Arg Arg Arg
1               5                   10                  15

Arg Xaa Lys

<210> SEQ ID NO 240
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (2)..(2)
<223> OTHER INFORMATION: D-4-phenylalanine
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (4)..(4)
<223> OTHER INFORMATION: D-homogluatamine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
```

-continued

```
<222> LOCATION: (17)..(17)
<223> OTHER INFORMATION: L-2,3-diaminopropionic acid

<400> SEQUENCE: 240

Xaa Xaa Xaa Xaa Xaa Xaa Arg Ala Phe Xaa Phe Xaa Arg Arg Arg Arg
1               5                   10                  15

Xaa Lys

<210> SEQ ID NO 241
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (15)..(15)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 241

Xaa Phe Xaa Thr Xaa Xaa Arg Ala Phe Xaa Arg Arg Arg Arg Xaa Phe
1               5                   10                  15

Xaa Lys

<210> SEQ ID NO 242
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
```

```
<223> OTHER INFORMATION: L-2,3-diaminopropionic acid
<220> FEATURE:
<221> NAME/KEY: MISC_FEATURE
<222> LOCATION: (13)..(13)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 242

Xaa Phe Xaa Thr Xaa Xaa Arg Ala Phe Xaa Arg Arg Xaa Phe Arg Arg
1               5                   10                  15

Xaa Lys

<210> SEQ ID NO 243
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (12)..(12)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 243

Xaa Phe Xaa Thr Xaa Xaa Arg Ala Phe Xaa Arg Xaa Arg Phe Arg Arg
1               5                   10                  15

Xaa Lys

<210> SEQ ID NO 244
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: L-4-fluorophenylalanine
<220> FEATURE:
<221> NAME/KEY: MISC_FEATURE
<222> LOCATION: (5)..(5)
<223> OTHER INFORMATION: L-homoproline
```

```
<220> FEATURE:
<221> NAME/KEY: MISC_FEATURE
<222> LOCATION: (6)..(6)
<223> OTHER INFORMATION: L-beta-naphthylalanine
<220> FEATURE:
<221> NAME/KEY: MISC_FEATURE
<222> LOCATION: (10)..(10)
<223> OTHER INFORMATION: L-2,3-diaminopropionic acid
<220> FEATURE:
<221> NAME/KEY: MISC_FEATURE
<222> LOCATION: (15)..(15)
<223> OTHER INFORMATION: L-beta-naphthylalanine
<220> FEATURE:
<221> NAME/KEY: MISC_FEATURE
<222> LOCATION: (17)..(17)
<223> OTHER INFORMATION: L-2,3-diaminopropionic acid

<400> SEQUENCE: 244

Xaa Phe Xaa Thr Xaa Xaa Arg Ala Phe Xaa Arg Arg Arg Arg Xaa Phe
1               5                   10                  15

Xaa Lys

<210> SEQ ID NO 245
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: sarcosine
<220> FEATURE:
<221> NAME/KEY: MISC_FEATURE
<222> LOCATION: (3)..(3)
<223> OTHER INFORMATION: D-phosphothreonine
<220> FEATURE:
<221> NAME/KEY: MISC_FEATURE
<222> LOCATION: (4)..(4)
<223> OTHER INFORMATION: L-homoproline
<220> FEATURE:
<221> NAME/KEY: MISC_FEATURE
<222> LOCATION: (5)..(5)
<223> OTHER INFORMATION: L-beta-naphthylalanine

<400> SEQUENCE: 245

Ala Xaa Xaa Xaa Xaa Tyr Gln Lys
1               5

<210> SEQ ID NO 246
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: trimesic acid
<220> FEATURE:
<221> NAME/KEY: MISC_FEATURE
<222> LOCATION: (3)..(3)
<223> OTHER INFORMATION: sarcosine
<220> FEATURE:
<221> NAME/KEY: MISC_FEATURE
<222> LOCATION: (5)..(5)
<223> OTHER INFORMATION: L-beta-naphthylalanine
<220> FEATURE:
<221> NAME/KEY: MISC_FEATURE
<222> LOCATION: (9)..(9)
<223> OTHER INFORMATION: L-2,3-diaminopropionic acid
<220> FEATURE:
<221> NAME/KEY: MISC_FEATURE
<222> LOCATION: (11)..(11)
```

```
<223> OTHER INFORMATION: L-beta-naphthylalanine
<220> FEATURE:
<221> NAME/KEY: MISC_FEATURE
<222> LOCATION: (16)..(16)
<223> OTHER INFORMATION: L-2,3-diaminopropionic acid

<400> SEQUENCE: 246

Xaa Ala Xaa Ala Xaa Arg Ala Ala Xaa Phe Xaa Arg Arg Arg Arg Xaa
1               5                   10                  15

Lys
```

CELL PENETRATING PEPTIDES AND METHODS OF MAKING AND USING THEREOF

CROSS REFERENCE TO RELATED APPLICATIONS

This application is a continuation in part of U.S. patent application Ser. No. 15/312,878, filed on Nov. 21, 2016, now U.S. Pat. No. 10,626,147, which is a national phase application of International Patent Application No. PCT/US2015/032043, filed May 21, 2015, which claims the priorities of U.S. Provisional Application 62/158,351, filed May 7, 2015, and U.S. Provisional Application 62/001,535, filed May 21, 2014, the entire contents of each of which are herein incorporated by reference in its entirety.

STATEMENT REGARDING FEDERALLY FUNDED RESEARCH

This invention was made with government support under grant numbers GM062820, GM110208, and CA132855 awarded by the National Institutes of Health. The government has certain rights in this invention.

BACKGROUND

The plasma membrane presents a major challenge in drug discovery, especially for biologics such as peptides, proteins and nucleic acids. One potential strategy to subvert the membrane barrier and deliver the biologics into cells is to attach them to "cell-penetrating peptides (CPPs)". Despite three decades of investigation, the fundamental basis for CPP activity remains elusive. CPPs that enter cells via endocytosis must exit from endocytic vesicles in order to reach the cytosol. Unfortunately, the endosomal membrane has proven to be a significant barrier towards cytoplasmic delivery by these CPPs; often a negligible fraction of the peptides escapes into the cell interior (El-Sayed, A et al. *AAPS J.*, 2009, 11, 13-22; Varkouhi, A K et al. *J. Controlled Release*, 2011, 151, 220-228; Appelbaum, J S et al. *Chem. Biol.*, 2012, 19, 819-830). What are thus needed are new cell penetrating peptides and compositions comprising such peptides that can be used to deliver agents to various cell types. The compositions and methods disclosed herein address these and other needs.

SUMMARY

Disclosed herein are compounds having activity as cell penetrating peptides. In some examples, the compounds can comprise a cell penetrating peptide moiety and a cargo moiety. The cargo moiety can comprise one or more detectable moieties, one or more therapeutic moieties, one or more targeting moieties, or any combination thereof.

In some examples, the cell penetrating peptide moiety is cyclic. In some examples, the cell penetrating peptide moiety and cargo moiety together are cyclic; this is referred to herein as an "endocyclic" configuration. In some examples, the cell penetrating peptide moiety is cyclic and the cargo moiety is appended to the cyclic cell penetrating peptide moiety structure; this is referred to herein as an "exocyclic" configuration. In some examples, the cargo moiety is cyclic and the cell penetrating peptide moiety is cyclic, and together they form a fused bicyclic system; this is referred to herein as a "bicyclic" configuration.

In some examples, the compounds can be of Formula I:

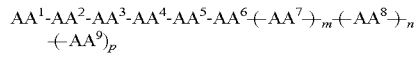

wherein $AA^1$, $AA^2$, $AA^3$, $AA^4$, $AA^5$, $AA^6$, $AA^7$, $AA^8$, and $AA^9$ (i.e., $AA^1$-$AA^9$) are each independently an amino acid; and m, n and p are independently selected from 0 and 1. In other examples, of Formula I, there can be more than 9 amino acids, such that when m and p are 1, n is 2 or more. These larger peptides are disclosed with each of formula herein, e.g., IA, II, IIa, IIb, and IIc. In some examples three or more amino acids are arginine and one or more are phenylalanine. In still other examples one or more amino acids is naphthylalanine or tryptophan.

In some examples, the cell penetrating peptide moiety is cyclic, and the compounds can be of Formula Ia:

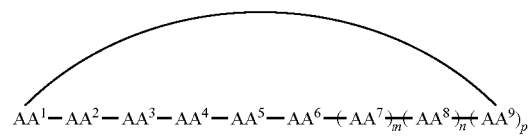

wherein $AA^1$-$AA^9$, m, n, and p are as defined in Formula I, and wherein the curved line indicates a covalent bond.

In some examples, the compound further comprises a cargo moiety, and the compounds can be of Formula II:

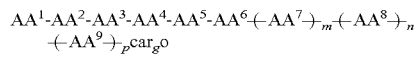

wherein the cargo moiety can comprise a detectable moiety, a therapeutic moiety, a targeting moiety, or a combination thereof and $AA^1$-$AA^9$, m, n, and p are as defined in Formula I.

In some examples, the cell penetrating peptide moiety and cargo moiety together are cyclic, and the compounds are of Formula IIa:

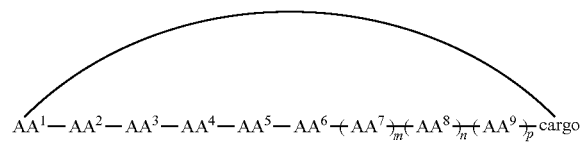

wherein the cargo moiety is as defined in Formula II and $AA^1$-$AA^9$, m, n and p are as defined in Formula I.

In some examples, the cell penetrating peptide moiety is cyclic and the cargo moiety is appended to the cyclic cell penetrating peptide moiety structure, and the compounds are of Formula IIb:

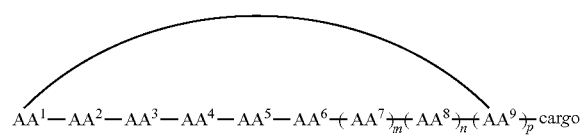

wherein the cargo moiety is as defined in Formula II and $AA^1$-$AA^9$, m, n and p are as defined in Formula I.

In some examples, the cargo moiety is cyclic and the cell penetrating peptide moiety is cyclic, and together they form a fused bicyclic system, and the compounds are of Formula IIc:

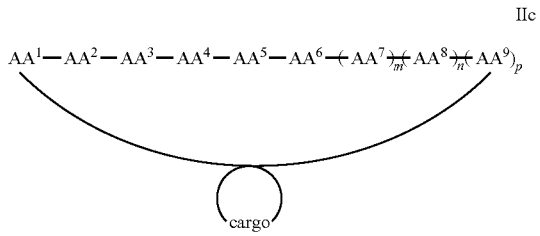

wherein the cargo moiety is as defined in Formula II and $AA^1$-$AA^9$, m, n and p are as defined in Formula I.

The amino acids can be coupled by a peptide bond. The amino acids can be coupled to the cargo moiety at the amino group, the carboxylate group, or the side chain.

In some examples, at least one amino acid comprises naphthylalanine or an analogue or derivative thereof. In some examples, at least three of the amino acids independently comprise arginine or an analogue or derivative thereof. In some examples, at least one amino acid comprises phenylalanine or an analogue or derivative thereof. In some examples of, at least one amino acid comprises glutamine or an analogue or derivative thereof.

In some examples, the cell penetrating peptide moiety can by any of SEQ ID NO:1 to SEQ ID NO:90. In some examples, the cell penetrating peptide moiety can be a variant of any of SEQ ID NO:1 to SEQ ID NO:90.

The cargo moiety can comprise any cargo of interest, for example a linker moiety, a detectable moiety, a therapeutic moiety, a targeting moiety, and the like, or any combination thereof.

The cargo moiety can be attached to the cell penetrating peptide moiety at the amino group, the carboxylate group, or the side chain of any of the amino acids of the cell penetrating peptide moiety (e.g., at the amino group, the carboxylate group, or the side chain or any of $AA^1$-$AA^9$).

In some examples, the therapeutic moiety comprises a targeting moiety. The targeting moiety can comprise, for example, a sequence of amino acids that can target one or more enzyme domains. In some examples, the targeting moiety can comprise an inhibitor against a protein that can play a role in a disease, such as cancer, cystic fibrosis, diabetes, obesity, or combinations thereof. In some examples, the therapeutic moiety can comprise a targeting moiety that can act as an inhibitor against Ras (e.g., K-Ras), PTP1B, Pin1, Grb2 SH2, CAL PDZ, and the like, or combinations thereof.

Also disclosed herein are compositions that comprise the compounds described herein. Also disclosed herein are pharmaceutically-acceptable salts and prodrugs of the disclosed compounds.

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating, preventing, or ameliorating cancer in a subject. The methods include administering to a subject an effective amount of one or more of the compounds or compositions described herein, or a pharmaceutically acceptable salt thereof. The methods of treatment or prevention of cancer described herein can further include treatment with one or more additional agents (e.g., an anti-cancer agent or ionizing radiation).

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation.

In some examples of the methods of treating of treating, preventing, or ameliorating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating, preventing, or ameliorating the metabolic disorder in a subject, the compound or composition administered to the subject can comprise a therapeutic moiety that can comprise a targeting moiety that can act as an inhibitor against PTP1B.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating, preventing, or ameliorating the immune disorder in a subject, the compound or composition administered to the subject can comprise a therapeutic moiety that can comprise a targeting moiety that can act as an inhibitor against Pin1.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

The details of one or more embodiments of the invention are set forth in the accompanying drawings and the description below. Other features, objects, and advantages of the invention will be apparent from the description and drawings, and from the claims.

DESCRIPTION OF FIGURES

The accompanying Figures, which are incorporated in and constitute a part of this specification, illustrate several aspects described below.

FIGS. 5A and 5B display the binding of FITC-labeled cFΦR$_4$, R$_9$ and Tat to (FIG. 5A) SUV and (FIG. 5B) heparin sulfate.

FIGS. 6A and 6B display representative live-cell confocal images of HEK293 cells treated for 2 h with rhodamine B-labeled peptides and fluid-phase uptake marker, dextran$^{FITC}$. (FIG. 6A) Cells treated with 5 μM cFΦR$_4$-A$_5$ and dextran$^{FITC}$ in the same Z-section. (FIG. 6B) Cells treated with 5 μM cFΦR$_4$-R$_5$ and dextran$^{FITC}$ in the same Z-section.

FIG. 7 displays the effect of cFΦR$_4$ on the endocytosis of dextran$^{Alexa488}$ by HeLa cells. HeLa cells were treated with clear DMEM containing no supplement, 1 μM cFΦR$_4$ only, 100 μM dextran$^{Alexa488}$ only, or both 1 μM cFΦR$_4$ and 100 μM dextran$^{Alexa488}$. MFI, mean fluorescence intensity.

FIG. 8 displays the effect of pH on CAP fluorescence. cFΦR$_4$-PCP was dephosphorylated by alkaline phosphatase and purified by HPLC and its fluorescence at indicated pH's was measured.

FIGS. 9A, 9B, and 9C display the internalization of pCAP-containing peptides into cultured cells: I, untagged PCP; II, cFΦR$_4$-PCP; III, cFΦR$_4$-PCP and Na$_3$VO$_4$; IV, R$_9$-PCP; V, Tat-PCP; and VI, Antp-PCP. (FIG. 9A) Representative live-cell confocal images of HEK293 cells treated with 5 μM peptides. Top panel, nuclear stain with DRAQS; bottom panel, CAP fluorescence in the same Z-section. (FIG. 9B) Flow cytometry of HeLa cells treated with 0 or 10 μM peptides. (FIG. 9C) CAP fluorescence from (FIG. 9B) after subtraction of background fluorescence (untreated cells). MFI, mean fluorescence intensity.

FIGS. 10A, 10B, 10C, 10D, 10E, and 10F displays representative live-cell confocal microscopic images of HEK293 cells treated for 2 h with rhodamine B-labeled peptides (5 μM each) and fluid-phase endocytosis marker, dextran$^{FITC}$ (0.5 mg/mL). The red fluorescence of rhodamine B and the green fluorescence of dextran$^{FITC}$ from the same Z-section and their merged image are shown in each panel. The enlarged images of a typical cell(s) are shown in each case in order to show the intracellular distribution of the internalized peptides. (FIG. 10A) Cells treated with bicyclo(FΦR$_4$-A$_5$)$^{Rho}$; (FIG. 10B) monocyclo(FΦR$_4$-A$_5$)$^{Rho}$; (FIG. 10C) bicyclo(FΦR$_4$-A$_7$)$^{Rho}$; (FIG. 10D) monocyclo(FΦR$_4$-A$_7$)$^{Rho}$; (FIG. 10E) bicyclo(FΦR$_4$—RARAR)$^{Rho}$; and (FIG. 10F) bicyclo(FΦR$_4$-DADAD)$^{Rho}$.

(FIG. 11A) Structures of CPP-S-S-GFP conjugates; and (FIG. 11B) Live-cell confocal images of mammalian cells after 2-h treatment with 1 μM GFP (I), Tat-S-S-GFP (II), or cFΦR$_4$-S-S-GFP (III) and nuclear stain DRAQS. All images were recorded in the same Z-section.

(FIG. 12A) Western blot analysis of the global pY protein levels of NIH 3T3 cells after treatment with 0-500 nM PTP1B or cFΦR$_4$-PTP1B (IB: anti-pY antibody 4G10); and (FIG. 12B) Same samples as in (FIG. 12A) were analyzed by SDS-PAGE and coomassie blue staining. M, molecular-weight markers.

(FIG. 13A) Comparison of the serum stability of cFΦR$_4$, Tat, R$_9$, and Antp; and (FIG. 13B) Cytotoxicity of cFΦR$_4$. The indicated cell lines were treated with DMSO (control), 5 μM, or 50 μM cFΦR$_4$ for 24 h and the percentage of live cells was determined by MTT assay.

(FIG. 17A) Synthesis of disulfide-bond cyclized peptide. (FIG. 17B) Synthesis of thioether-bond cyclized peptide. Reagents and conditions: (a) Standard Fmoc/HATU chemistry; (b) piperidine/DMF; (c) 3,3'-dithiodipropionic acid/DIC; (d) β-mercaptoethanol/DMF; (e) modified reagent K; (f) trituration; (g) DMSO/DPBS (pH 7.4). (h) 4-bromobutyric acid/DIC; (i) 1% TFA/DCM; (j) 1% DIPEA/DMF; PG, protecting group. Trt, trityl; Mmt, methoxytrityl. (FIG. 17C) Structures of FITC labeled peptides 1 and 2. (FIG. 17D) Structures of pCAP (phosphocoumaryl aminopropionic acid) containing peptides 1-PCP and 2-PCP. (FIG. 17E) Structures of Amc (7-amino-4-methylcourmarin) containing caspase fluorogenic substrates 3-7. (FIG. 17F) Structures of FITC labeled CAL-PDZ domain ligands 9-11.

FIGS. 18A and 18B display (FIG. 18A) Live-cell confocal microscopic images of HeLa cells treated with 5 μM FITC-labeled peptide 1 (I) or 2 (II), endocytosis marker Dextran$^{Rho}$ (0.5 mg mL$^{-1}$), and nuclear stain DRAQS. Images in different fluorescence channels were all recorded in the same Z-section. (FIG. 18B) Flow cytometry of HeLa cells treated with 5 μM FITC-labeled peptides 1, 2, or FITC alone.

FIGS. 19A and 19B display: (FIG. 19A) FACS analysis of HeLa cells treated with 0 or 5 μM peptides 1-PCP, 2-PCP for 2 h; and (FIG. 19B) CAP fluorescence from (FIG. 19A) after subtraction of background fluorescence (untreated cell). MFI, mean fluorescence intensity.

FIG. 20 displays a comparison of the proteolytic stability of peptides 1 and 2.

FIG. 21 displays the time-dependent release of fluorogenic coumarin product by Jurkat cells treated with peptides 3-7 (5 μM) in the absence and presence of 100 μM caspase inhibitor Z-VAD(OMe)-FMK (FMK).

FIGS. 22A, 22B, 22C, 22D, and 22E display: (FIG. 22A) Structure of CAL-PDZ inhibitor 8. (FIG. 22B) Binding of peptide 8 to CAL-PDZ domain in the presence or absence of reducing reagent. (FIG. 22C) Live-cell microscopic images of HeLa cells treated with peptide 8 (5 μM) and DRAQS in the same Z-section. I, green fluorescence of internalized peptide 8; II, overlay of green peptide fluorescence and blue nuclear stain. (FIG. 22D) Immunofluorescent staining showing the distribution of CFTR in the presence or absence of Corr-4a (10 μM) and unlabeled peptide 8 (50 μM). (FIG. 22E) SPQ assays showing CFTR-specific stimulation-induced fluorescence increase in slope in the absence or presence of VX809 (20 μM) and peptide 8 (50 μM). P values were calculated from two-tailed t-test.

(FIG. 25A) Lineweaver-Burk plots for PTP1B-catalyzed hydrolysis of pNPP (0-24 mM) in the presence of varying concentrations of inhibitor 2 (0, 22.5, 45, and 90 nM). (FIG. 25B) Secondary plot of the Michaelis constant ratio (K/K$_0$) as a function of.

(FIG. 26A) live-cell confocal microscopic images (same Z-section) of A549 lung cancer cells after treatment for 2 h with 5 µM FITC-labeled inhibitor 2 (top panel) or 4 (bottom panel) and endocytosis marker dextran$^{Rho}$ (1.0 mg/mL); (FIG. 26B) Lineweaver-Burk plot showing competitive inhibition of PTP1B by 0, 28, 56, and 112 nM inhibitor 4; and (FIG. 26C) Sensitivity of various PTPs to inhibition by inhibitor 4 (all activities were relative to that in the absence of inhibitor).

FIGS. 29A, 29B, 29C, and 29D display: (FIG. 29A) Global pY protein levels in A549 cells after treatment with 0-5 µM inhibitor 4 for 2 h; (FIG. 29B) SDS-PAGE analysis (Coomassie blue staining) of the same samples from (FIG. 29A) shows uniform sample loading in all lanes; (FIG. 29C) Effect of inhibitor 4 on insulin receptor phosphorylation at Tyr$^{1162}$ and Tyr$^{1163}$ sites. HepG2 cells were treated with indicated concentrations of inhibitor 4 for 2 h and then stimulated with insulin (100 nM) for 5 min, followed by SDS-PAGE and immunoblotting with anti-IRpY$^{1162}$/pY$^{1163}$ antibody; and (FIG. 29D) Quantitation of IR pY levels from (FIG. 29C) (data shown are the mean±SD from five independent experiments).

FIGS. 31A, 31B, 31C, 31D, and 31E display the FA analysis of the binding of Pin1 inhibitor 5-9 to Pin1, respectively.

FIGS. 32A and 32B display the competition for binding to Pin1 by inhibitors 5 and 7. Each reaction contained 0.1 µM FITC-labeled inhibitor 5, 1 µM Pin1, and 0-5 µM unlabeled inhibitor 5 (FIG. 3A) or inhibitor 7 (FIG. 32B) and the FA value was measured and plotted against the competitor concentration.

FIGS. 33A, 33B, and 33C display the cellular uptake of Pin1 inhibitors. Live-cell confocal microscopic images of HEK293 cells treated with 5 µM FITC-labeled Pin1 inhibitor 5 A (FIG. 33A) or 7 (FIG. 33B) and 1 mg/mL endocytosis marker Dextran$^{Rho}$ for 2 h. All images were recorded at the same Z-section. (FIG. 33C) FACS analysis of HeLa cells after 2-h treatment with DMSO or 5 µM FITC-labeled Pin1 inhibitor 5, 7, 8, or 9. MFI, mean fluorescence intensity. Procedure: Hela cells were cultured in six-well plates (2×10$^5$ cells per well) for 24 h. On the day of experiment, the cells were incubated with 5 µM FITC labeled bicyclic peptide or control monocylic peptide in phenol red-free DMEM supplemented with 1% FBS. After 2 h, the peptide solution was removed, and the cells were washed with DPBS, treated with 0.25% trypsin for 5 min, washed again with DPBS. Finally, the cells were resuspended in the flow cytometry buffer and analyzed by flow cytometry (BD FACS Aria), with excitation at 535 nm.

FIGS. 35A, 35B, 35C, and 35D display live cell confocal images of mouse ventricular cardiac myocytes after treatment for 3 h with 5 µM c(FΦRRRRQ)-K(FITC) (FIG. 35A) and c(fΦRrRrQ)-K(FITC) (FIG. 35B). FIG. 35C displays labeling of calmodulin (T5C) with cyclic cell penetrating peptide through a disulfide bond. FIG. 35D displays live cell confocal images of mouse ventricular cardiac myocytes after treatment for 3 h with 6 µM cFΦR4-conjugated Cy3-labeled calmodulin.

FIGS. 37A, 37B, 37C, and 37D displays the characterization of peptide 37. (FIG. 37A) Binding to FITC-labeled peptide 37 to Pin1 as analyzed by fluorescent anisotropy (FA). (FIG. 37B) Competition between peptide 37 and FITC-labeled peptide 1 (100 nM) for binding to Pin1 (400 nM) as monitored by FA. (FIG. 37C) Effect of peptide 37 on the cis-trans isomerase activity of Pin1, Pin4, FKBP12, and cyclophilin A using Suc-Ala-Glu-Pro-Phe-pNA as substrate. (FIG. 37D) Comparison of the serum stability of peptides 1 and 37.

FIGS. 38A, 38B, 38C, and 38D display cellular activity of peptide 37. (FIG. 38A) Cellular uptake of peptides 1, 37, and 46 (5 µM) by HeLa cells as analyzed by flow cytometry. MFI, mean fluorescence intensity; none, untreated cells (no peptide). (FIG. 38B) Anti-proliferative effect of peptides 37, 46, and 47 on HeLa cells as measured by MTT assay. (FIG. 38C) Western blots showing the effect of peptides 1, 37 and 47 on the protein level of PML in HeLa cells. β-Actin was used as loading control. (FIG. 38D) Quantification of western blot results from (FIG. 38C). Data reported were after background subtraction and represent the mean±SD from 3 independent experiments.

DETAILED DESCRIPTION

Figure 1A:
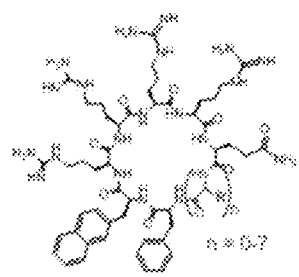
FIGS. 1A, 1B, and 1C display structures showing cargo attachment during endocyclic (A), exocyclic (B), and bicyclic (C) delivery of cargos (shown in light grey) by cFΦR$_4$.

The compounds, compositions, and methods described herein may be understood more readily by reference to the following detailed description of specific aspects of the disclosed subject matter and the Examples and Figures included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "anticancer" refers to the ability to treat or control cellular proliferation and/or tumor growth at any concentration.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are compounds having activity as cell penetrating peptides. In some examples, the compounds can comprise a cell penetrating peptide moiety and a cargo moiety. The cargo moiety can comprise one or more detectable moieties, one or more therapeutic moieties, one or more targeting moieties, or any combination thereof.

In some examples, the cell penetrating peptide moiety is cyclic. In some examples, the cell penetrating peptide moiety and cargo moiety together are cyclic. In some examples, the cell penetrating peptide moiety is cyclic and the cargo moiety is appended to the cyclic cell penetrating peptide moiety structure. In some examples, the cargo moiety is cyclic and the cell penetrating peptide moiety is cyclic, and together they form a fused bicyclic system.

The cell penetrating peptide moiety can comprise five or more, more specifically six or more, for example, six to twelve, or six to nine amino acids. When there are six to nine amino acids the compounds can be of Formula I:

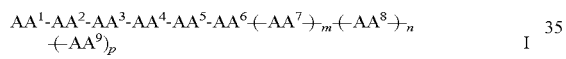

$$\text{I}$$

wherein $AA^1$, $AA^2$, $AA^3$, $AA^4$, $AA^5$, $AA^6$, $AA^7$, $AA^8$, and $AA^9$ (i.e., $AA^1$-$AA^9$) are each independently an amino acid; and m, n and p are independently selected from 0 and 1. Wherein there are more than 9 amino acids, Formula I can have m and p each be 1 and n can be 2 or more, e.g., 2 to 10 or 2 to 5. In some examples three or more amino acids are arginine and one or more are phenylalanine. In still other examples one or more amino acids is naphthylalanine or tryptophan.

In some examples, the compounds can be of Formula I:

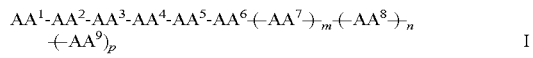

$$\text{I}$$

wherein $AA^1$, $AA^2$, $AA^3$, $AA^4$, $AA^5$, $AA^6$, $AA^7$, $AA^8$, and $AA^9$ (i.e., $AA^1$-$AA^9$) are each independently an amino acid; and m, n and p are independently selected from 0 and 1.

In some examples, the cell penetrating peptide moiety is cyclic, and the compounds can be of Formula Ia:

Ia

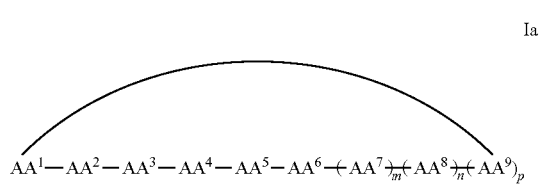

wherein $AA^1$-$AA^9$, m, n, and p are as defined in Formula I, and wherein the curved line indicates a covalent bond. The curved line can be a covalent bond in the backbone of the peptide (i.e., the carboxylic acid of one AA forming an amide bond with the α-amine of another AA), a bond between the side chains of two AAs, a bond from one side chain of an AA to either the backbone carboxylic acid or α-amine of another AA, or a disulfide bond between two AAs.

In some examples, the compound further comprises a cargo moiety, and the compounds can be of Formula II:

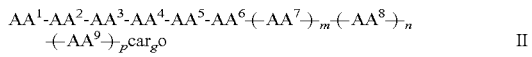

$$\text{II}$$

wherein the cargo moiety can comprise a detectable moiety, a therapeutic moiety, a targeting moiety, or a combination thereof and $AA^1$-$AA^9$, m, n, and p are as defined in Formula I.

In some examples, the cell penetrating peptide moiety and cargo moiety together are cyclic, and the compounds are of Formula IIa:

IIa

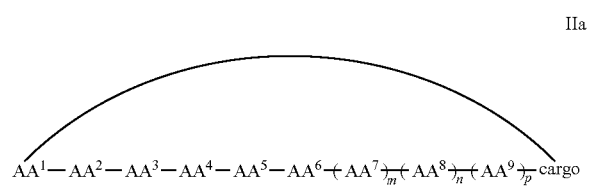

wherein the cargo moiety is as defined in Formula II and $AA^1$-$AA^9$, m, n and p are as defined in Formula I.

In some examples, the cell penetrating peptide moiety is cyclic and the cargo moiety is appended to the cyclic cell penetrating peptide moiety structure, and the compounds are of Formula IIb:

IIb

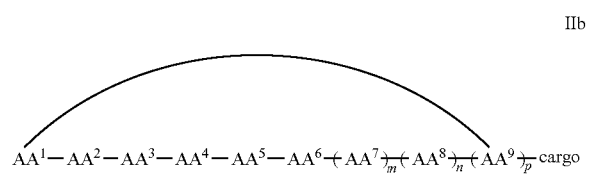

wherein the cargo moiety is as defined in Formula II and $AA^1$-$AA^9$, m, n and p are as defined in Formula I.

In some examples, the cargo moiety is cyclic and the cell penetrating peptide moiety is cyclic, and together they form a fused bicyclic system, and the compounds are of Formula IIc:

IIc

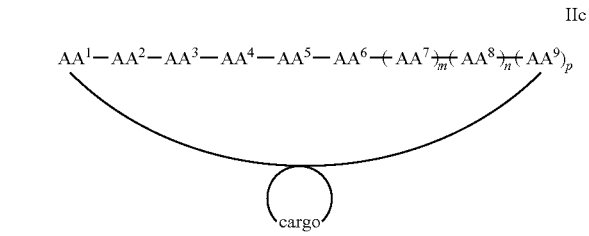

wherein the cargo moiety is as defined in Formula II and $AA^1$-$AA^9$, m, n and p are as defined in Formula I.

Cell Penetrating Peptide

The cell penetrating peptide moeity comprises at least 5, more specifically, at least 6 amino acids, even more specifically from from 6 to 12, from 6 to 9, from 6 to 7, from 7 to 8, from 8 to 9, and more specifically 6, 7, 8, or 9 amino acids. For the endocyclic motif, at least 5 amino acids can be used. It is also disclosed herein that for the endocyclic structure, some amino acids in the penetrating peptide moiety can also be part of the cargo moiety. For example, a peptide penetrating moiety FNalRR can be formed when from FNal and an cargo moiety with two Args. In this case, the two Arg residues perform dual functions. Thus, in some cases the sequence of the cargo moiety is taken into account when referring to the peptide penetrating moiety.

For the exocyclic motif, at least 6 amino acids can be used with, for example, glutamine being used to attach the cargo.

Each amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrolysine. Non-natural amino acids can also be the D-isomer of the natural amino acids. Examples of suitable amino acids include, but are not limited to, alanine, alloisoleucine, arginine, asparagine, aspartic acid, cysteine, glutamine, glutamic acid, glycine, histidine, isoleucine, leucine, lysine, methionine, naphthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* |
|---|---|
| alanine | Ala (A) |
| allosoleucine | AIle |
| arginine | Arg (R) |
| asparagine | Asn (N) |
| aspartic acid | Asp (D) |
| cysteine | Cys (C) |
| cyclohexylalanine | Cha |
| 2,3-diaminopropionic acid | Dap |
| 4-fluorophenylalanine | Fpa ($\Sigma$) |
| glutamic acid | Glu (E) |
| glutamine | Gln (Q) |
| glycine | Gly (G) |
| histidine | His (H) |
| homoproline | Pip ($\Theta$) |
| isoleucine | Ile (I) |
| leucine | Leu (L) |
| lysine | Lys (K) |
| methionine | Met (M) |
| napthylalanine | Nal ($\Phi$) |
| norleucine | Nle ($\Omega$) |
| phenylalanine | Phe (F) |
| phenylglycine | Phg ($\Psi$) |
| 4-(phosphonodifluoromethyl)phenylalanine | $F_2Pmp$ ($\Lambda$) |
| pipecolic acid | Pp ($\vartheta$) |
| proline | Pro (P) |
| sarcosine | Sar ($\Xi$) |
| selenocysteine | Sec (U) |
| serine | Ser (S) |
| threonine | Thr (T) |
| tyrosine | Tyr (Y) |
| tryptophan | Trp (W) |
| valine | Val (V) |

*single letter abbreviations: when shown incapital letters herein it indicates the L-amino acid form, when shown in lower case herein it indicates the D-amino acid form The amino acids can be coupled by a peptide bond. The amino acids can be coupled to the cargo moiety at the amino group, the carboxylate group, or the side chain.

In some examples of Formula I, at least one amino acid comprises naphthylalanine or tryptophan, or analogues or derivatives thereof. In some examples of Formula I, at least three of the amino acids independently comprise arginine or an analogue or derivative thereof. In some examples of Formula I, at least one amino acid comprises phenylalanine, phenylglycine, or histidine, or analogues or derivatives thereof. In some examples of Formula I, at least one amino acid comprises glutamine or an analogue or derivative thereof.

In some examples, the cell penetrating peptide (CPP) moiety can be any of the sequences listed in Table 2. In some examples, the cell penetrating peptide can be the reverse of any of the sequences listed in Table 2. In some examples, the cell penetrating peptide sequence can be a cyclic form of any of the sequences listed in Table 2.

TABLE 2

CPP sequences - linear or cyclic

| SEQ ID NO | CPP sequence | #AA's | #R residues |
|---|---|---|---|
| 1 | F$\Phi$RRRQ | 6 | 3 |
| 2 | F$\Phi$RRRC | 6 | 3 |
| 3 | F$\Phi$RRRU | 6 | 3 |
| 4 | RRR$\Phi$FQ | 6 | 3 |
| 5 | RRRR$\Phi$F | 6 | 4 |
| 6 | F$\Phi$RRRR | 6 | 4 |
| 7 | F$\phi$RrRq | 7 | 3 |
| 8 | F$\phi$RrRQ | 7 | 3 |
| 9 | F$\Phi$RRRRQ | 7 | 4 |
| 10 | f$\Phi$RrRrQ | 7 | 4 |
| 11 | RRFR$\Phi$RQ | 7 | 4 |
| 12 | FRRRR$\Phi$Q | 7 | 4 |
| 13 | rRFR$\Phi$RQ | 7 | 4 |
| 14 | RR$\Phi$FRRQ | 7 | 4 |
| 15 | CRRRRFWQ | 7 | 4 |
| 16 | Ff$\Phi$RrRrQ | 8 | 4 |
| 17 | FF$\Phi$RRRRQ | 8 | 4 |
| 18 | RFRFR$\Phi$RQ | 8 | 4 |
| 19 | URRRRFWQ | 8 | 4 |
| 20 | CRRRRFWQ | 8 | 4 |
| 21 | F$\Phi$RRRRQK | 8 | 4 |
| 22 | F$\Phi$RRRRQC | 8 | 4 |
| 23 | f$\Phi$RrRrRQ | 8 | 5 |
| 24 | F$\Phi$RRRRRQ | 8 | 5 |
| 25 | RRRR$\Phi$FD$\Omega$C | 9 | 4 |
| 26 | F$\Phi$RRR | 5 | 3 |
| 27 | FWRRR | 5 | 3 |
| 28 | RRR$\Phi$F | 5 | 3 |
| 29 | RRRWF | 5 | 3 |

$\Phi$ = L-naphthylalanine;
$\phi$ = D-naphthylalanine;
$\Omega$ = L-norleucine

Certain embodiments of the invention include amino acid sequences wherein at least four consecutive amino acids have alternating chirality. As used herein, chirality refers to the "D" and "L" isomers of amino acids. In particular embodiments of the invention, at least four consecutive amino acids have alternating chirality and the remaining amino acids are L-amino acids. In other embodiments, the peptides of the invention comprise a four amino acid sequence having D-L-D-L chirality. In still other embodiments, the peptides of the invention comprise a four amino acid sequence having L-D-L-D chirality.

In embodiments, peptides of the invention comprise two consecutive L-amino acids. In further embodiments, peptides of the invention comprise two consecutive L-amino acids separating two D-amino acids. In yet further embodiments, peptides of the invention comprise two consecutive L-amino acids separating two D-amino acids and at least four consecutive amino acids having alternating chirality, such as, but not limited to peptide sequences with D-L-L-D-L-D or L-D-L-L-D-L-D chirality. In even further embodiments, peptides of the invention comprise two consecutive L-amino acids separating two D-amino acids and at least five consecutive amino acid having alternating chirality, such as, but not limited to peptide sequences with D-L-L-D-L-D-L or L-D-L-L-D-L-D-L chirality.

In embodiments, peptides of the invention comprise two consecutive D-amino acids. In further embodiments, peptides of the invention comprise two consecutive D-amino acids separating two L-amino acids. In still further embodiments of the invention, peptides of the invention comprise two consecutive D-amino acids separating two L-amino acids and at least four consecutive amino acids having alternating chirality, such as, but not limited to peptide sequences with L-D-D-L-D-L. In even further embodiments of the invention, peptides of the invention comprise two consecutive D-amino acids separating two L-amino acids and at least five consecutive amino acids having alternating chirality, such as, but not limited to peptide sequences with L-D-D-L-D-L-D.

In some embodiments, the amino acid sequence with alternating chirality comprises about at least about 4 amino acids, at least about 5 amino acids, at least about 6 amino acids, at least about 7 amino acids, at least about 8 amino acids or at least about 9 amino acids. In embodiments, the amino acid sequence with alternating chirality comprises of from about 4 amino acids to about 9 amino acids, or about 5 amino acids to about 6 amino acids, or about 7 amino acids to about 9 amino acids, or about 8 amino acids to about 9 amino acids, or about 4 amino acids to about 8 amino acids, or about 4 amino acids to about 7 amino acids, or about 4 amino acids to about 6 amino acids, or about 4 amino acids to about 5 amino acids.

In particular embodiments, the cyclic cell-penetrating peptides of the invention demonstrate improved cellular uptake efficiency as compared to c(FΦRRRRQ) (290-1F).

As used herein cellular uptake efficiency refers to the ability of a cyclic peptide sequence to traverse a cell membrane. In embodiments, cellular uptake of the cyclic, cell penetrating peptide is not dependent on a receptor or a cell type.

In particular embodiments, uptake efficiency is determined by comparing (i) the amount of a cyclic cell-penetrating peptide of the invention internalized by a cell type (e.g., HeLa cells) to (ii) the amount of c(FΦRRRRQ) (290-1F) internalized by the same cell type. To measure cellular uptake efficiency, the cell type may be incubated in the presence of a cell-penetrating peptide of the invention for a specified period of time (e.g., 30 minutes, 1 hour, 2 hours, etc.) after which the amount of the cell-penetrating peptide internalized by the cell is quantified. Separately, the same concentration of c(FΦRRRRQ) (290-1F) is incubated in the presence of the cell type over the same period of time, and the amount of the second peptide internalized by the cell is quantified. Quantification can be achieved by fluorescently labeling the cell-penetrating peptide (e.g., with a FTIC dye) and measuring the fluorescence intensity using techniques well-known in the art.

In certain embodiments, peptides of the invention comprising at least four consecutive amino acid having alternating chirality have an uptake efficiency that is superior to that of a second cyclic peptide wherein the second cyclic peptide has an otherwise identical amino acid sequence consisting of L-amino acids. In some embodiments, uptake efficiency can be improved by at least about 1.5 fold, at least about 2 fold, at least about 2.5 fold, at least about 3 fold, at least about 3.5 fold, at least about 4 fold, at least about 4.5 fold, at least about 5 fold, at least about 5.5 fold, at least about 6 fold, at least about 6.5 fold, at least about 7 fold, at least about 7.5 fold, at least about 8 fold, at least about 8.5 fold, at least about 9 fold, at 9.5 fold, or at least about 10 fold. In other embodiments, the uptake efficiency can be improved within the range of from about 1.5 fold to about 10 fold, or about 2 fold to about 10 fold, or about 2 fold to about 9.5 fold, or about 2 fold to about 9 fold, or about 2 fold to about 8.5 fold, or about 2 fold to about 8 fold, or about 2 fold to about 7.5 fold, or about 2 fold to about 7 fold, or about 2 fold to about 6.5 fold, or about 2 fold to about 6 fold, or about 2.5 fold to about 7 fold, or about 3 fold to about 7 fold, or about 3.5 fold to about 7 fold, or about 4 to about 7, or about 4.5 fold to about 7 fold, or about 5 fold to about 7 fold, or about 5.5 fold to about 7 fold, or about 6 fold to about 7 fold.

In certain embodiments, peptides of the invention comprising at least four consecutive amino acid having alternating chirality have a superior uptake efficiency as compared to c(FΦRRRRQ) (290-1F). In some embodiments, uptake efficiency can be improved by at least about 1.5 fold, at least about 2 fold, at least about 2.5 fold, at least about 3 fold, at least about 3.5 fold, at least about 4 fold, at least about 4.5 fold, at least about 5 fold, at least about 5.5 fold, at least about 6 fold, at least about 6.5 fold, at least about 7 fold, at least about 7.5 fold, at least about 8 fold, at least about 8.5 fold, at least about 9 fold, at 9.5 fold, or at least about 10 fold. In other embodiments, the uptake efficiency can be improved within the range of from about 1.5 fold to about 10 fold, or about 2 fold to about 10 fold, or about 2 fold to about 9.5 fold, or about 2 fold to about 9 fold, or about 2 fold to about 8.5 fold, or about 2 fold to about 8 fold, or about 2 fold to about 7.5 fold, or about 2 fold to about 7 fold, or about 2 fold to about 6.5 fold, or about 2 fold to about 6 fold, or about 2.5 fold to about 7 fold, or about 3 fold to about 7 fold, or about 3.5 fold to about 7 fold, or about 4 to about 7, or about 4.5 fold to about 7 fold, or about 5 fold to about 7 fold, or about 5.5 fold to about 7 fold, or about 6 fold to about 7 fold.

In certain embodiments, the peptides of the invention comprise at least one hydrophobic residue. In further embodiments, the peptides of the invention comprise two hydrophobic residues. In still further embodiments, the peptides of the invention comprise at least two hydrophobic residues. In certain embodiments, at least one hydrophobic residue is an aromatic hydrophobic residue. In particular embodiments, at least one hydrophobic residue is selected from the group consisting of naphthylalanine, phenylalanine, tryptophan, and tyrosine. In further embodiments, at least one hydrophobic residue is selected from the group consisting of naphthylalanine and phenylalanine. In certain embodiments, peptides of the invention comprise at least one naphthylalanine. In yet other embodiments, peptides of the invention comprise at least one phenylalanine. In still other embodiments, peptides of the invention comprise at least one phenylalanine and at least one naphthylalanine. In certain embodiments of the invention, the peptide comprises at least one hydrophobic residue in the $AA^1$, $AA^2$, or $AA^3$ position. In certain embodiments of the invention, the peptide comprises at least one aromatic hydrophobic residue in the $AA^1$, $AA^2$, or $AA^3$ position. In further embodiments of the invention, the peptide comprises at least one hydrophobic residue selected from the group consisting of naphthylalanine and phenylalanine in the $AA^1$, $AA^2$, or $AA^3$ position.

In some examples, the cell penetrating peptide moiety can by any of SEQ ID NO:1 to SEQ ID NO:29. In some examples, the cell penetrating peptide moiety can be a variant of any of SEQ ID NO:1 to SEQ ID NO:29. Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 3 and are referred to as conservative substitutions.

TABLE 3

Amino Acid Substitutions
Exemplary Conservative Substitutions

| | |
|---|---|
| Ala replaced by ser | Leu replaced by ile or val |
| Arg replaced by lys or gln | Lys replaced by arg or gln |
| Asn replaced by gln or his | Met replaced by leu or ile |
| Asp replaced by glu | Phe replaced by met, leu, tyr, or fpa |
| Cys replaced by ser | Ser replaced by thr |
| Gln replaced by asn or lys | Thr replaced by ser |
| Glu replaced by asp | Trp replaced by tyr |
| Gly replaced by pro | Tyr replaced by trp or phe |
| His replaced by asn or gln | Val replaced by ile or leu |
| Ile replaced by leu or val | Nal replaced by Trp or Phe |

Substantial changes in function are made by selecting substitutions that are less conservative than those in Table 3, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, argininyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

It is understood that one way to define the variants of the disclosed cell penetrating peptide moieties is through defining the variants in terms of homology/identity to specific known sequences. For example, SEQ ID NO:1 to SEQ ID NO:29 each sets forth a particular sequence. Specifically disclosed are variants of these peptide that have at least, 85%, 90%, 95%, or 97% homology to SEQ ID NO:1 to SEQ ID NO:29. Those of skill in the art readily understand how to determine the homology of two proteins. For example, the homology can be calculated after aligning the two sequences so that the homology is at its highest level.

In addition to variants of SEQ ID NO:1 to SEQ ID NO:29 are derivatives of these peptides which also function in the disclosed methods and compositions. Derivatives are formed by replacing one or more residues with a modified residue, where the side chain of the residue has been modified. Additional examples are shown in Tables 6 and 18 and include variants thereof.

Cargo Moiety

The cargo moiety can comprise any cargo of interest, for example a linker moiety, a detectable moiety, a therapeutic moiety, a targeting moiety, and the like, or any combination thereof. In some examples, the cargo moiety can comprise one or more additional amino acids (e.g., K, UK, TRV); a linker (e.g., bifunctional linker LC-SMCC); coenzyme A; phosphocoumaryl amino propionic acid (pCAP); 8-amino-3,6-dioxaoctanoic acid (miniPEG); L-2,3-diaminopropionic acid (Dap or J); L-β-naphthylalanine; L-pipecolic acid (Pip); sarcosine; trimesic acid; 7-amino-4-methylcourmarin (Amc); fluorescein isothiocyanate (FITC); L-2-naphthylalanine; norleucine; 2-aminobutyric acid; Rhodamine B (Rho); Dexamethasone (DEX); or combinations thereof.

In some examples the cargo moiety can comprise any of those listed in Table 4, or derivatives or combinations thereof.

TABLE 4

Example cargo moieties

| SEQ ID NO | Abbreviation | Sequence* |
|---|---|---|
| 30 | R$_5$ | RRRRR |
| 31 | A$_5$ | AAAAA |
| 32 | F$_4$ | FFFF |
| 33 | PCP | DE(pCAP)LI |
| 34 | A$_7$ | AAAAAAA |
| 35 | | RARAR |
| 36 | | DADAD |
| 37 | | DΩUD |
| 38 | | UTRV |

*pCAP, phosphocoumaryl amino propionic acid; Ω, norleucine; U, 2-aminobutyric acid.

Detectable Moiety

The detectable moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethyl-porphyrin; Pt (II)-octaethylporphyrin; Pd (II) tetraphenyl-porphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; fluorescein isothiocyanate (FITC); eosin; iridium (III) ((N-methyl-benzimidazol-2-yl)-7-(diethyl-amino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphthofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the detectable moiety can comprise Rhodamine B (Rho), fluorescein isothiocyanate (FITC), 7-amino-4-methylcourmarin (Amc), green fluorescent protein (GFP), or derivatives or combinations thereof.

The detectable moiety can be attached to the cell penetrating peptide moiety at the amino group, the carboxylate group, or the side chain of any of the amino acids of the cell penetrating peptide moiety (e.g., at the amino group, the carboxylate group, or the side chain or any of $AA^1$-$AA^x$).

Therapeutic Moiety

The disclosed compounds can also comprise a therapeutic moiety. In some examples, the cargo moiety comprises a therapeutic moiety. The detectable moiety can be linked to a therapeutic moiety or the detectable moiety can also serve as the therapeutic moiety. Therapeutic moiety refers to a group that when administered to a subject will reduce one or more symptoms of a disease or disorder.

The therapeutic moiety can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens.

The therapeutic moiety can, for example, comprise an anticancer agent antiviral agent, antimicrobial agent, anti-inflammatory agent, immunosuppressive agent, anesthetics, or any combination thereof.

The therapeutic moiety can comprise an anticancer agent. Example anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, *Erwinia* L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The therapeutic moiety can also comprise a biopharmaceutical such as, for example, an antibody.

In some examples, the therapeutic moiety can comprise an antiviral agent, such as ganciclovir, azidothymidine (AZT), lamivudine (3TC), etc.

In some examples, the therapeutic moiety can comprise an antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

In some examples, the therapeutic moiety can comprise an anti-inflammatory agent.

In some examples, the therapeutic moiety can comprise dexamethasone (Dex).

In other examples, the therapeutic moiety comprises a therapeutic protein. For example, some people have defects in certain enzymes (e.g., lysosomal storage disease). It is disclosed herein to deliver such enzymes/proteins to human cells by linking to the enzyme/protein to one of the disclosed cell penetrating peptides. The disclosed cell penetrating peptides have been tested with proteins (e.g., GFP, PTP1B, actin, calmodulin, troponin C) and shown to work.

In some examples, the therapeutic moiety comprises a targeting moiety. The targeting moiety can comprise, for example, a sequence of amino acids that can target one or more enzyme domains. In some examples, the targeting moiety can comprise an inhibitor against an enzyme that can play a role in a disease, such as cancer, cystic fibrosis, diabetes, obesity, or combinations thereof. For example, the targeting moiety can comprise any of the sequences listed in Table 5.

TABLE 5

Example targeting moieties

| SEQ ID NO | Abbreviation* | Sequence |
|---|---|---|
| 39 | PΘGΛYR | Pro-Pip-Gly-F$_2$Pmp-Tyr- |
| 40 | SΘIΛΛR | Ser-Pip-Ile-F$_2$Pmp-F$_2$Pmp- |
| 41 | IHIΛIR | Ile-His-Ile-F$_2$Pmp-Ile- |
| 42 | AaIΛΘR | Ala-(D-Ala)-Ile-F$_2$Pmp-Pip- |
| 43 | ΣSΘAvR | Fpa-Ser-Pip-F$_2$Pmp-(D-Val)- |
| 44 | ΘnPΛAR | Pip-(D-Asn)-Pro-F$_2$Pmp-Ala- |
| 45 | TΨAΛGR | Tyr-Phg-Ala-F$_2$Pmp-Gly- |
| 46 | AHIΛaR | Ala-His-Ile-F$_2$Pmp-(D-Ala)- |
| 47 | GnGΛpR | Gly-(D-Asn)-Gly-F$_2$Pmp-(D-Pro)- |
| 48 | fQΘΛIR | (D-Phe)-Gln-Pip-F$_2$Pmp-Ile- |
| 49 | SPGΛHR | Ser-Pro-Gly-F$_2$Pmp-His- |
| 50 | ΘYIΛHR | Pip-Tyr-Ile-F$_2$Pmp-His- |
| 51 | SvPΛHR | Ser-(D-Val)-Pro-F$_2$Pmp-His- |
| 52 | AIPΛnR | Ala-Ile-Pro-F$_2$Pmp-(D-Asn)- |
| 53 | ΣSIΛQF | Fpa-Ser-Ile-F$_2$Pmp-Gln- |
| 54 | AaΨΛfR | Ala-(D-Ala)-Phg-F$_2$Pmp-(D-Phe)- |
| 55 | ntΨΛΨR | (D-Asn)-(D-Thr)-Phg-F$_2$Pmp-Phg- |
| 56 | IPΨΛΩR | Ile-Pro-Phg-F$_2$Pmp-Nle- |
| 57 | QΘΣΛΘR | Gln-Pip-Fpa-F$_2$Pmp-Pip- |
| 58 | nAΣΛGR | (D-Asn)-Ala-Fpa-F$_2$Pmp-Gly- |
| 59 | ntYΛAR | (D-Asn)-(D-Thr)-Tyr-F$_2$Pmp-Ala- |
| 60 | eAΨΛvR | (D-Glu)-Ala-Phg-F$_2$Pmp-(D-Val)- |
| 61 | IvΨΛAR | Ile-(D-Val)-Phg-F$_2$Pmp-Ala- |
| 62 | YtΨΛAR | Tyr-(D-Thr)-Phg-F$_2$Pmp-Ala- |
| 63 | nΘΨΛIR | (D-Asn)-Pip-Phg-F$_2$Pmp-Ile- |
| 64 | ΘnWΛHR | Pip-(D-Asn)-Trp-F$_2$Pmp-His- |
| 65 | YΘvΛIR | Tyr-Pip-(D-Val)-F$_2$Pmp-Ile- |
| 66 | nSAΛGR | (D-Asn)-Ser-(D-Ala)-F$_2$Pmp-Gly- |
| 67 | tnvΛaR | (D-Thr)-(D-Asn)-(D-Val)-F$_2$Pmp-(D-Ala)- |
| 68 | ntvΛtR | (D-Asn)-(D-Thr)-(D-Val)-F$_2$Pmp-(D-Thr)- |
| 69 | SItΛYR | Ser-Ile-(D-Thr)-F$_2$Pmp-Tyr- |
| 70 | nΣnΛlR | (D-Asn)-Fpa-(D-Asn)-F$_2$Pmp-(D-Leu)- |
| 71 | YnnΛΩR | Tyr-(D-Asn)-(D-Asn)-F$_2$Pmp-Nle- |
| 72 | nYnΛGR | (D-Asn)-Tyr-(D-Asn)-F$_2$Pmp-Gly- |
| 73 | AWnΛAR | Ala-Trp-(D-Asn)-F$_2$Pmp-Ala- |
| 74 | vtHΛYR | (D-Val)-(D-Thr)-His-F$_2$Pmp-Tyr- |
| 75 | PΨHΛΘR | Pro-Phg-His-F$_2$Pmp-Pip- |
| 76 | nΨHΛGR | (D-Asn)-Phg-His-F$_2$Pmp-Gly- |
| 77 | PAHΛGR | Pro-Ala-His-F$_2$Pmp-Gly- |
| 78 | AYHΛIR | Ala-Tyr-His-F$_2$Pmp-Ile- |
| 79 | nΘeΛYR | (D-Asn)-Pip-(D-Glu)-F$_2$Pmp-Tyr- |
| 80 | vSSΛtR | (D-Val)-Ser-Ser-F$_2$Pmp-(D-Thr)- |
| 81 | aΞt' ϑ Φ'YNK | ((D-Ala)-Sar-(D-pThr)-Pp-Nal-Tyr-Gln)-Lys |
| 82 | Tm(aΞt'ϑ Φ'RA)Dap | Tm((D-Ala)-Sar-(D-pThr)-Pp-Nal-Arg-Ala)-Dap |

TABLE 5-continued

Example targeting moieties

| SEQ ID NO | Abbreviation* | Sequence |
|---|---|---|
| 83 | Tm(aΞt'ϑ Φ'RAa)Dap | Tm((D-Ala)-Sar-(D-pThr)-Pp-Nal-Arg-Ala-(D-Ala))-Dap |
| 84 | Tm(aΞtϑ Φ'RAa)Dap | Tm((D-Ala)-Sar-(D-Thr)-Pp-Nal-Arg-Ala-(D-Ala))-Dap |
| 85 | Tm(aΞtaΦ'RAa)Dap | Tm((D-Ala)-Sar-(D-Thr)-(D-Ala)-Nal-Arg-Ala-(D-Ala))-Dap |

*Fpa, Σ: L-4-fluorophenylalanine; Pip, Θ: L-homoproline; Nle, Ω: L-norleucine; Phg, Ψ L-phenylglycine; F₂Pmp, Λ: L-4-(phosphonodifluoromethyl)phenylalanine; Dap, L-2,3-diaminopropionic acid; Nal, Φ': L-β-naphthylalanine; Pp,ϑ : L-pipecolic acid; Sar, Ξ: sarcosine; Tm, trimesic acid.

The targeting moitiey and cell penetrating peptide moiety can overlap, that is residues that form the cell penetrating peptide moiety can also be part of the sequence that forms the targeting moiety, and vice a versa.

The therapeutic moiety can be attached to the cell penetrating peptide moiety at the amino group, the carboxylate group, or the side chain of any of the amino acids of the cell penetrating peptide moiety (e.g., at the amino group, the carboxylate group, or the side chain or any of $AA^1$-$AA^x$). In some examples, the therapeutic moiety can be attached to the detectable moiety.

In some examples, the therapeutic moiety can comprise a targeting moiety that can act as an inhibitor against Ras (e.g., K-Ras), PTP1B, Pin1, Grb2 SH2, CAL PDZ, and the like, or combinations thereof.

Ras is a protein that in humans is encoded by the RAS gene. The normal Ras protein performs an essential function in normal tissue signaling, and the mutation of a Ras gene is implicated in the development of many cancers. Ras can act as a molecular on/off switch, once it is turned on Ras recruits and activates proteins necessary for the propagation of growth factor and other receptors' signal. Mutated forms of Ras have been implicated in various cancers, including lung cancer, colon cancer, pancreatic cancer, and various leukemias.

Protein-tyrosine phosphatase 1B (PTP1B) is a prototypical member of the PTP superfamily and plays numerous roles during eukaryotic cell signaling. PTP1B is a negative regulator of the insulin signaling pathway, and is considered a promising potential therapeutic target, in particular for the treatment of type II diabetes. PIP1B has also been implicated in the development of breast cancer.

Pin1 is an enzyme that binds to a subset of proteins and plays a role as a post phosphorylation control in regulating protein function. Pin1 activity can regulate the outcome of proline-directed kinase signaling and consequently can regulate cell proliferation and cell survival. Deregulation of Pin1 can play a role in various diseases. The up-regulation of Pin1 may be implicated in certain cancers, and the down-regulation of Pin1 may be implicated in Alzheimer's disease. Inhibitors of Pin1 can have therapeutic implications for cancer and immune disorders.

Grb2 is an adaptor protein involved in signal transduction and cell communication. The Grb2 protein contains one SH2 domain, which can bind tyrosine phosphorylated sequences. Grb2 is widely expressed and is essential for multiple cellular functions. Inhibition of Grb2 function can impair developmental processes and can block transformation and proliferation of various cell types.

It was recently reported that the activity of cystic fibrosis membrane conductance regulator (CFTR), a chloride ion channel protein mutated in cystic fibrosis (CF) patients, is negatively regulated by CFTR-associated ligand (CAL) through its PDZ domain (CAL-PDZ) (Wolde, M et al. *J. Biol. Chem.* 2007, 282, 8099). Inhibition of the CFTR/CAL-PDZ interaction was shown to improve the activity of ΔPhe508-CFTR, the most common form of CFTR mutation (Cheng, S H et al. *Cell* 1990, 63, 827; Kerem, B S et al. *Science* 1989, 245, 1073), by reducing its proteasome-mediated degradation (Cushing, P R et al. *Angew. Chem. Int. Ed.* 2010, 49, 9907). Thus, disclosed herein is a method for treating a subject having cystic fibrosis by administering an effective amount of a compound or composition disclosed herein. The compound or composition administered to the subject can comprise a therapeutic moiety that can comprise a targeting moiety that can act as an inhibitor against CAL PDZ. Also, the dcompositions or compositions disclosed herein can be administered with a molecule that corrects the CFTR function.

Specific Examples

In some examples, the compounds can be of Formula I:

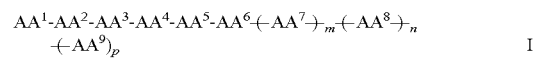

I wherein $AA^1$, $AA^2$, $AA^3$, $AA^4$, $AA^5$, $AA^6$, $AA^7$, $AA^8$, and $AA^9$ (i.e., $AA^1$-$AA^9$) are each independently an amino acid; and m, n and p are independently selected from 0 and 1.

In some examples of Formula I, m, n, and p are 0 and the compounds are of Formula I-1:

     I-1 wherein $AA^1$-$AA^6$ are as defined in Formula I.

In some examples of Formula I, m is 1, and n and p are 0, and the compounds are of Formula I-2:

     I-2 wherein $AA^1$-$AA^7$ are as defined in Formula I.

In some examples of Formula I, m and n are 1, p is 0, and the compounds are of Formula I-3:

     I-3 wherein $AA^1$-$AA^8$ are as defined in Formula I.

In some examples of Formula I, m, n, and p are 1, and the compounds are of Formula I-4:

     I-4 wherein $AA^1$-$AA^9$ are as defined in Formula I.

In some examples, the cell penetrating peptide moiety is cyclic, and the compounds can be of Formula Ia:

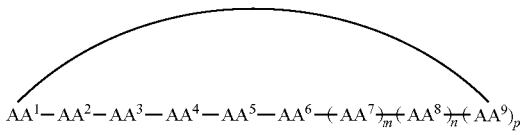

Ia wherein $AA^1$-$AA^9$, m, n, and p are as defined in Formula I, and wherein the curved line indicates a covalent bond.

In some examples of Formula Ia, m, n, and p are 0 and the compounds are of Formula Ia-1:

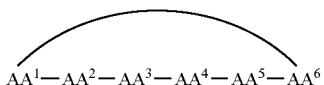

Ia-1 wherein $AA^1$-$AA^6$ are as defined in Formula I.

In some examples of Formula Ia, m is 1, and n and p are 0, and the compounds are of Formula Ia-2:

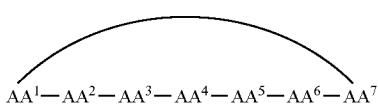

Ia-2 wherein $AA^1$-$AA^7$ are as defined in Formula I.

In some examples of Formula Ia, m and n are 1, p is 0, and the compounds are of Formula Ia-3:

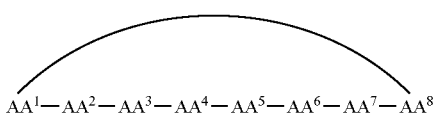

Ia-3 wherein $AA^1$-$AA^8$ are as defined in Formula I.

In some examples of Formula Ia, m, n, and p are 1, and the compounds are of Formula Ia-4:

Ia-4 wherein $AA^1$-$AA^9$ are as defined in Formula I.

In some examples, the compound further comprises a cargo moiety, and the compounds can be of Formula II:

$$AA^1\text{-}AA^2\text{-}AA^3\text{-}AA^4\text{-}AA^5\text{-}AA^6\text{-}(AA^7)_m\text{-}(AA^8)_n\text{-}(AA^9)_p\text{-}cargo \quad \text{II}$$

wherein the cargo moiety can comprise a detectable moiety, a therapeutic moiety, a targeting moiety, or a combination thereof and $AA^1$-$AA^9$, m, n, and p are as defined in Formula I.

In some examples of Formula II, m, n, and p are 0 and the compounds are of Formula II-1:

$$AA^1\text{-}AA^2\text{-}AA^3\text{-}AA^4\text{-}AA^5\text{-}AA^6\text{-}cargo \quad \text{II-1}$$

wherein $AA^1$-$AA^6$ are as defined in Formula I and cargo is as defined in Formula II.

In some examples of Formula II, m is 1, and n and p are 0, and the compounds are of Formula II-2:

$$AA^1\text{-}AA^2\text{-}AA^3\text{-}AA^4\text{-}AA^5\text{-}AA^6\text{-}AA^7\text{-}cargo \quad \text{II-2}$$

wherein $AA^1$-$AA^7$ are as defined in Formula I and cargo is as defined in Formula II.

In some examples of Formula II, m and n are 1, p is 0, and the compounds are of Formula II-3:

$$AA^1\text{-}AA^2\text{-}AA^3\text{-}AA^4\text{-}AA^5\text{-}AA^6\text{-}AA^7\text{-}AA^8\text{-}cargo \quad \text{II-3}$$

wherein $AA^1$-$AA^8$ are as defined in Formula I and cargo is as defined in Formula II.

In some examples of Formula II, m, n, and p are 1, and the compounds are of Formula II-4:

$$AA^1\text{-}AA^2\text{-}AA^3\text{-}AA^4\text{-}AA^5\text{-}AA^6\text{-}AA^7\text{-}AA^8\text{-}AA^9\text{-}cargo \quad \text{II-4}$$

wherein $AA^1$-$AA^9$ are as defined in Formula I and cargo is as defined in Formula II.

In some examples, the cell penetrating peptide moiety and cargo moiety together are cyclic, and the compounds are of Formula IIa:

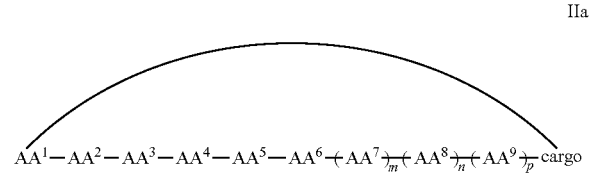

IIa wherein the cargo moiety is as defined in Formula II and $AA^1$-$AA^9$, m, n and p are as defined in Formula I.

In some examples of Formula IIa, m, n, and p are 0 and the compounds are of Formula IIa-1:

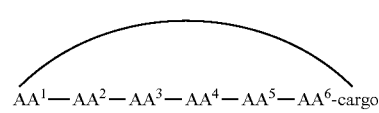

IIa-1 wherein $AA^1$-$AA^6$ are as defined in Formula I and cargo is as defined in Formula II. Also disclosed herein is Formula IIa-1 wherein one of AA1-AA6 is absent (i.e., 5 amino acids in the endocyclic structure.

In some examples of Formula IIa, m is 1, and n and p are 0, and the compounds are of Formula IIa-2:

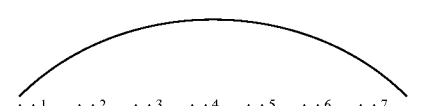

IIa-2 wherein $AA^1$-$AA^7$ are as defined in Formula I and cargo is as defined in Formula II.

In some examples of Formula IIa, m and n are 1, p is 0, and the compounds are of Formula IIa-3:

IIa-3

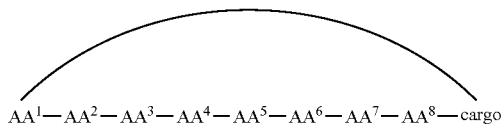

wherein $AA^1$-$AA^8$ are as defined in Formula I and cargo is as defined in Formula II.

In some examples of Formula IIa, m, n, and p are 1, and the compounds are of Formula IIa-4:

IIa-4

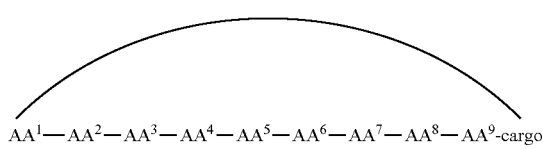

wherein $AA^1$-$AA^9$ are as defined in Formula I and cargo is as defined in Formula II.

In some examples, the cell penetrating peptide moiety is cyclic and the cargo moiety is appended to the cyclic cell penetrating peptide moiety structure, and the compounds are of Formula IIb:

IIb

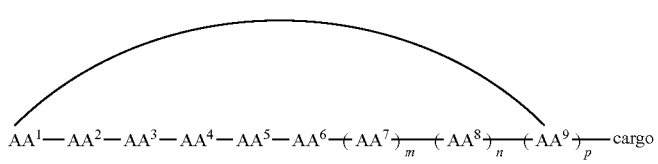

wherein the cargo moiety is as defined in Formula II and $AA^1$-$AA^9$, m, n and p are as defined in Formula I.

In some examples of Formula IIb, m, n, and p are 0 and the compounds are of Formula IIb-1:

IIb-1

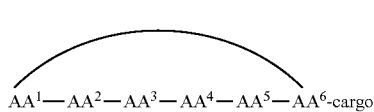

wherein $AA^1$-$AA^6$ are as defined in Formula I and cargo is as defined in Formula II.

In some examples of Formula IIb, m is 1, and n and p are 0, and the compounds are of Formula IIb-2:

IIb-2

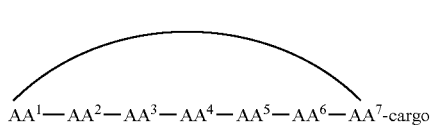

wherein $AA^1$-$AA^7$ are as defined in Formula I and cargo is as defined in Formula II.

In some examples of Formula IIb, m and n are 1, p is 0, and the compounds are of Formula IIb-3:

IIb-3

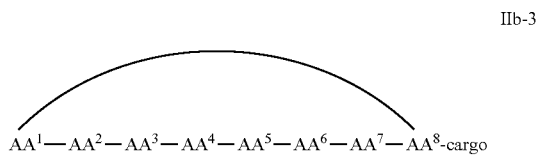

wherein $AA^1$-$AA^8$ are as defined in Formula I and cargo is as defined in Formula II.

In some examples of Formula IIb, m, n, and p are 1, and the compounds are of Formula IIb-4:

IIb-4

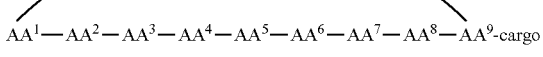

wherein $AA^1$-$AA^9$ are as defined in Formula I and cargo is as defined in Formula II.

In some examples, the cargo moiety is cyclic and the cell penetrating peptide moiety is cyclic, and together they form a fused bicyclic system, and the compounds are of Formula IIc:

IIc

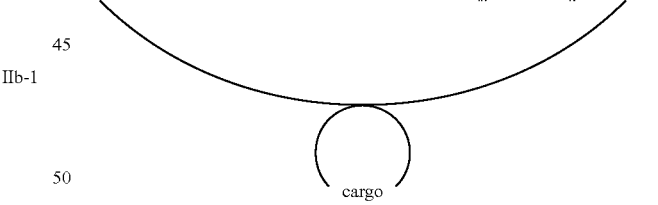

wherein the cargo moiety is as defined in Formula II and $AA^1$-$AA^9$, m, n and p are as defined in Formula I.

In some examples of Formula IIc, m, n, and p are 0 and the compounds are of Formula IIc-1:

IIc-1

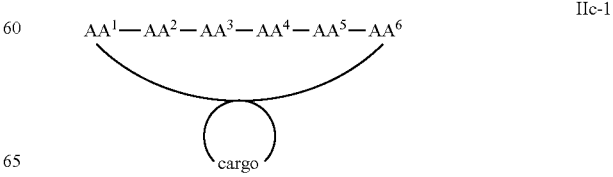

wherein AA$^1$-AA$^6$ are as defined in Formula I and cargo is as defined in Formula II.

In some examples of Formula IIc, m is 1, and n and p are 0, and the compounds are of Formula IIc-2:

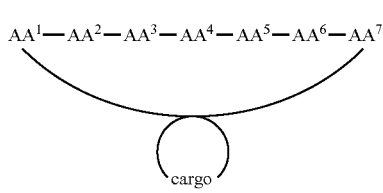

IIc-2 wherein AA$^1$-AA$^7$ are as defined in Formula I and cargo is as defined in Formula II.

In some examples of Formula IIc, m and n are 1, p is 0, and the compounds are of Formula IIc-3:

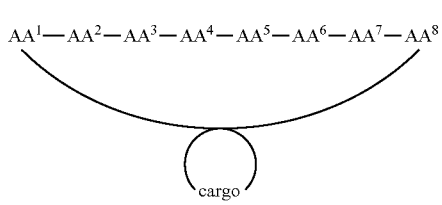

IIc-3 wherein AA$^1$-AA$^8$ are as defined in Formula I and cargo is as defined in Formula II.

In some examples of Formula IIc, m, n, and p are 1, and the compounds are of Formula IIc-4:

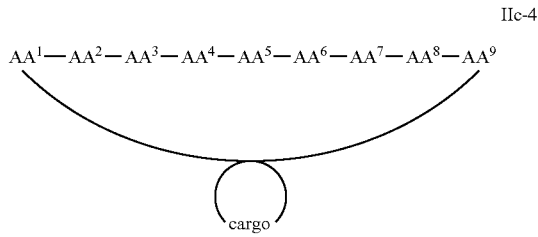

IIc-4 wherein AA$^1$-AA$^9$ are as defined in Formula I and cargo is as defined in Formula II.

In some examples, the compounds can comprise any of the compounds in Table 6. Further examples are shown in Table 18 below.

TABLE 6

Example compounds

| SEQ ID NO | Abbreviation | Sequence |
|---|---|---|
| 86 | cF$\Phi$R$_4$$^{Rho}$ | cyclo(F$\Phi$RRRRQ)-K(Rho) |
| 87 | cF$\Phi$R$_4$$^{Dex}$ | cyclo(F$\Phi$RRRRQ)-K(Dex) |
| 88 | Tat$^{Dex}$ | K(Dex)-GRKKRRQRRRPPQY |
| 89 | cF$\Phi$R$_4$$^{FITC}$ | cyclo(F$\Phi$RRRRQ)-K(FITC) |
| 90 | cF$\Phi$R$_4$-R$_5$ | cyclo(F$\Phi$RRRRQ)-RRRRR-K(Rho) |
| 91 | cF$\Phi$R$_4$-A$_5$ | cyclo(F$\Phi$RRRRQ)-AAAAA-K(Rho) |
| 92 | cF$\Phi$R$_4$-F$_4$ | cyclo(F$\Phi$RRRRQ)-FFFF-K(Rho) |
| 93 | cF$\Phi$R$_4$-PCP | cyclo(F$\Phi$RRRRQ)-miniPEG-DE(pCAP)LI |
| 94 | R$_9$-PCP | RRRRRRRRR-miniPEG-DE(pCAP)LI |
| 95 | Tat-PCP | RKKRRQRRR-miniPEG-DE(pCAP)LI |
| 96 | Antp-PCP | RQIKIWFQNRRMKWKK-miniPEG-DE(pCAP)LI |
| 97 | bicyclo(F$\Phi$R$_4$-A$_5$)$^{Rho}$ | [Tm(AAAAA)K(RRRR$\Phi$F)J]-K(Rho) |
| 98 | bicyclo(F$\Phi$R$_4$-A$_7$)$^{Rho}$ | [Tm(AAAAAAA)K(RRRR$\Phi$F)J]-K(Rho) |
| 99 | bicyclo(F$\Phi$R$_4$-RARAR)$^{Rho}$ | [Tm(RARAR)K(RRRR$\Phi$F)J]-K(Rho) |
| 100 | bicyclo(F$\Phi$R$_4$-DADAD)$^{Rho}$ | [Tm(DADAD)K(RRRR$\Phi$F)J]-K(Rho) |
| 101 | monocyclo(F$\Phi$R$_4$-A$_5$)$^{Rho}$ | cyclo(AAAAARRRR$\Phi$F)-K(Rho) |
| 102 | monocyclo(F$\Phi$R$_4$-A$_7$)$^{Rho}$ | cyclo(AAAAAAARRRR$\Phi$F)-K(Rho) |
| 103 | | S———S—<br>└—CH$_2$CH$_2$CO-F$\Phi$RRRRCK(FITC) |
| 104 | | CH$_3$CH$_2$CH$_2$CO-F$\Phi$RRRRUK(FITC) |
| 105 | | D$\Omega$UD-Amc |
| 106 | | S———S—<br>└—CH$_2$CH$_2$CO-RRRR$\Phi$FD$\Omega$CD-A$^{mc}$ |
| 107 | | ┌———S—<br>└—CH$_2$CH$_2$CO-RRRR$\Phi$FD$\Omega$CD-A$^{mc}$ |
| 108 | | CH$_3$CH$_2$CH$_2$CO-RRRR$\Phi$FD$\Omega$UD-A$^{mc}$ |
| 109 | | RRRRRRRRD$\Omega$UC-Amc |

TABLE 6-continued

Example compounds

| SEQ ID NO | Abbreviation | Sequence |
|---|---|---|
| 110 | | FITC-CRRRRFW$_Q$CTRV (with S—S bridge between the two C residues) |
| 111 | | FITC-URRRRFW$_Q$UTRV |
| 112 | | FITC-CRRRRFW$_Q$C (with S—S bridge between the two C residues) |
| 113 | cFΦR$_4$-PTP1B | |
| 114 | cFΦR$_4$-PCP | |
| 115 | cyclo((D-Thr)-(D-Asn)-(D-Val)-F$_2$Pmp-(D-Ala)-Arg-Arg-Arg-Arg-Nal-Phe-Gln) | cyclo(tnvΛaRRRRΦ'FQ) |
| 116 | cyclo(Ser-(D-Val)-Pro-F$_2$Pmp-His-Arg-Arg-Arg-Arg-Nal-Phe-Gln) | cyclo(SvPΛHRRRR Φ'FQ) |
| 117 | cyclo(Ile-Pro-Phg-F$_2$Pmp-Nle-Arg-Arg-Arg-Arg-Nal-Phe-Gln) | cyclo(IPΨΛΩRRRRΦ'FQ) |
| 118 | cyclo((D-Ala)-Sar-(D-pThr)-Pp-Nal-Tyr-Gln)-Lys | cyclo(aΞt$^ϑ$Φ'YQ)-K |
| 119 | bicyclo[Tm((D-Ala)-Sar-(D-pThr)-Pp-Nal-Arg-Ala)-Dap-(Phe-Nal-Arg-Arg-Arg-Arg-Dap)]-Lys | bicyclo[Tm(aΞ$^ϑ$Φ'RA)J(FΦ'RRRRJ)]-K |
| 120 | bicyclo[Tm((D-Ala)-Sar-(D-pThr)-Pp-Nal-Arg-Ala-(D-Ala))-Dap-(Phe-Nal-Arg-Arg-Arg-Arg-Dap)]-Lys | bicyclo[Tm(aΞt$^ϑ$Φ'RAa)J(FNΦ'RRRRJ)]-K |
| 121 | bicyclo[Tm((D-Ala)-Sar-(D-Thr)-Pp-Nal-Arg-Ala-(D-Ala))-Dap-(Phe-Nal-Arg-Arg-Arg-Arg-Dap)]-Lys | bicyclo[Tm(aΞ$^ϑ$Φ'RAa)J(FΦ'RRRRJ)]-K |
| 122 | bicyclo[Tm((D-Ala)-Sar-(D-Thr)-(D-Ala)-Nal-Arg-Ala-(D-Ala))-Dap-(Phe-Nal-Arg-Arg-Arg-Arg-Dap)]-Lys | bicyclo[Tm(aΞtaΦ'RAa)J(FΦ'RRRRJ)]-K |
| 123 | Peptide 1 | S——S bridged: CH$_2$CH$_2$CO-FΦRRRRCK(FITC)-NH$_2$ |
| 124 | Peptide 2 | CH$_3$CH$_2$CH$_2$CO-FΦRRRRUK(FITC)-NH$_2$ |
| 125 | Peptide 3 | Ac-DMUD-Amc |
| 126 | Peptide 4 | S——S bridged: CH$_2$CH$_2$CO-RRRRΦFDΩCD-A$^{mc}$ |
| 127 | Peptide 5 | S——S bridged: CH$_2$CH$_2$CO-RRRRΦFDΩCD-A$^{mc}$ |
| 128 | Peptide 6 | CH$_3$CH$_2$CH$_2$CO-RRRRΦFDΩUD-A$^{mc}$ |
| 129 | Peptide 7 | A$^c$-RRRRRRRRDΩUD-A$^{mc}$ |
| 130 | Peptide 8 | FITC-CRRRRFWQCTRV-OH (with S—S bridge between the two C residues) |
| 131 | Peptide 9 | FITC-URRRRFWQUTRV-OH |
| 132 | Peptide 11 | FITC-CRRRRFWQCTRV-NH$_2$ (with S—S bridge between the two C residues) |
| 178 | Monocyclic Inhibitor 1 | cyclo(D-Thr-D-Asn-D-Val-F$_2$Pmp-D-Ala-Arg-Arg-Arg-Arg-Nal-Phe-Gln) |
| 179 | Monocyclic Inhibitor 2 | cyclo(Ser-D-Val-Pro-F$_2$Pmp-His-Arg-Arg-Arg-Arg-Nal-Phe-Gln) |
| 180 | Monocyclic Inhibitor 3 | cyclo(Ile-Pro-Phg-F$_2$Pmp-Nle-Arg-Arg-Arg-Arg-Nal-Phe-Gln) |

TABLE 6-continued

Example compounds

| SEQ ID NO | Abbreviation | Sequence |
|---|---|---|
| 181 | Pin1 inhibitor 5 | cyclo(D-Ala-Sar-D-pThr-Pip-Nal-Tyr-Gln)-Lys-NH$_2$ |
| 182 | Pin1 inhibitor 6 | bicyclo[Tm(D-Ala-Sar-D-pThr-Pip-Nal-Arg-Ala)-Dap-(Phe-Nal-Arg-Arg-Arg-Arg-Dap)]-Lys-NH$_2$ |
| 183 | Pin1 inhibitor 7 | bicyclo[Tm(D-Ala-Sar-D-pThr-Pip-Nal-Arg-Ala-D-Ala)-Dap-(Phe-Nal-Arg-Arg-Arg-Arg-Dap)]-Lys-NH$_2$ |
| 184 | Pin1 inhibitor 8 | bicyclo[Tm(D-Ala-Sar-D-Thr-Pip-Nal-Arg-Ala-D-Ala)-Dap-(Phe-Nal-Arg-Arg-Arg-Arg-Dap)]-Lys-NH$_2$ |
| 185 | Pin1 inhibitor 9 | bicyclo[Tm(D-Ala-Sar-D-Thr-D-Ala-Nal-Arg-Ala-D-Ala)-Dap-(Phe-Nal-Arg-Arg-Arg-Arg-Dap)]-Lys-NH$_2$ |

*Fpa, Σ: L-4-fluorophenylalanine; Pip, Θ: L-homoproline; Nle, Ω: L-norleucine; Phg, Ψ L-phenylglycine; F$_2$Pmp, Λ: L-4-(phosphonodifluoromethyl)phenylalanine; Dap, J: L-2,3-diaminopropionic acid; Nal, Φ': L-β-naphthylalanine; Pp, ϑ: L-pipecolic acid; Sar, Ξ: sarcosine; Tm, trimesic acid; Φ, L-2-naphthylalanine; Rho, rhodamine B; Dex, dexamethasone; FITC, fluorescein isothiocyanate; miniPEG, 8-amine-3,6-dioxaoctanoic acid; pCAP, phosphocoumaryl amino propionic acid; Amc, 7-amino-4-methylcourmarin; FITC, fluorescein isothiocyanate; U, 2-aminobutyric acid.

TABLE 7

Previously reported cell penetrating peptides

| SEQ ID NO | Abbreviation | Sequence |
|---|---|---|
| 133 | R$_9$ | RRRRRRRRR |
| 134 | Tat | YGRKKRRQRRR |
| 135 | Antp | RQIKIWFQNRRMKWKK |

Also disclosed herein are compositions comprising the compounds described herein.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl) phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N,N-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Use

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, *Erwinia* L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples of the methods of treating of treating, preventing, or ameliorating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating, preventing, or ameliorating the metabolic disorder in a subject, the compound or composition administered to the subject can comprise a therapeutic moiety that can comprise a targeting moiety that can act as an inhibitor against PTP1B. In one particular example of this method the subject is obese and the method comprises treating the subject for obesity by administering a composition as disclosed herein.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating, preventing, or ameliorating the immune disorder in a subject, the compound or composition administered to the subject can comprise a therapeutic moiety that can comprise a targeting moiety that can act as an inhibitor against Pin1.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E.W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The disclosed compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth to illustrate the methods and results according to the disclosed subject matter. These examples are not intended to be inclusive of all aspects of the subject matter disclosed herein, but rather to illustrate representative methods and results. These examples are not intended to exclude equivalents and variations which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1

Cyclic heptapeptide cyclo(F$\Phi$RRRRQ) (cF$\Phi$R$_4$, where $\Phi$ is L-2-naphthylalanine) was found to be efficiently internalized by mammalian cells. In this study, its mechanism of internalization was investigated by perturbing various endocytic events through the introduction of pharmacologic agents and genetic mutations. The results show that cF$\Phi$R$_4$ can bind directly to membrane phospholipids, can be internalized into human cancer cells through endocytosis, and can escape from early endosomes into the cytoplasm. Its cargo capacity was examined with a wide variety of molecules including small-molecule dyes, linear and cyclic peptides of various charged states, and proteins. Depending on the nature of the cargos, they may be delivered by endocyclic (insertion of cargo into the cFΦR$_4$ ring), exocyclic (attachment of cargo to the Gln side chain), or bicyclic approaches (fusion of cFΦR$_4$ and cyclic cargo rings). The overall delivery efficiency (i.e., delivery of cargo into the cytoplasm and nucleus) of cFΦR$_4$ was 4-12-fold higher than those of nonaarginine (R$_9$), HIV Tat derived peptide (Tat), or penetratin (Antp). The higher delivery efficiency, coupled with superior serum stability, minimal toxicity, and synthetic accessibility, renders cFΦR$_4$ a useful transporter for intracellular cargo delivery and a suitable system for investigating the mechanism of endosomal escape.

Introduction

The plasma membrane presents a major challenge in drug discovery, especially for biologics such as peptides, proteins and nucleic acids. One potential strategy to subvert the membrane barrier and deliver the biologics into cells is to attach them to "cell-penetrating peptides (CPPs)". Since the initial observation that HIV trans-activator of transcription, Tat, internalizes into mammalian cells and activates viral replication in the late 1980s (Frankel, A D and Pabo, C O. *Cell*, 1988, 55, 1189-1193; Green, M and Loewenstein, P M. *Cell*, 1988, 55, 1179-1188) a large number of CPPs consisting of 6-20 residues have been reported (Langel, Ü. *Cell-penetrating peptides: methods and protocols*, Humana Press, New York, 2011, p xv; Schmidt, N et al. *FEBS Lett.*, 2010, 584, 1806-1813; Futaki, S. *Adv. Drug Delivery Rev.*, 2005, 57, 547-558; Stewart, K M et al. *Org. Biomol. Chem.*, 2008, 6, 2242-2255; Deshayes, S et al. *Cell. Mol. Life Sci.*, 2005, 62, 1839-1849; Goun, E A et al. *ChemBioChem*, 2005, 7, 1497-1515). CPPs have been used to deliver small-molecule drugs (Rothbard, J B et al. *Nat. Med.*, 2000, 6, 1253-1257; Nori, A et al. *Bioconjugate Chem.*, 2003, 14, 44-50), DNA (Hoyer, J and Neundorf, I. *Acc. Chem. Res.*, 2012, 45, 1048-1056; Eguchi, A et al. *J. Biol. Chem.*, 2001, 276, 26204-26210), RNA (Nakase, I et al. *Acc. Chem. Res.*, 2012, 45, 1132-1139; Andaloussi, S E et al. *Nucleic Acids Res.*, 2011, 39, 3972-3987; Jeong, J H et al. *Bioconjugate Chem.*, 2009, 20, 5-14; Muratovska, A and Eccles, M R. *FEBSLett.*, 2004, 558, 63-68), proteins (Wadia, J S and Dowdy, S F. *Adv. Drug Delivery Rev.*, 2005, 57, 579-596; Pooga, M et al. *FASEB J.*, 2001, 15, 1451-1453; Schwarze, S R et al. *Science*, 1999, 285, 1569-1572), and nanoparticles (Josephson, L et al. *Bioconjugate Chem.*, 1999, 10, 186-191; Gupta, B et al. *Adv. Drug Delivery Rev.*, 2005, 57, 637-651; Liu, J et al. *Biomacromolecules*, 2001, 2, 362-8), into mammalian cells and tissues through either covalent attachment or electrostatic association. Many CPPs display minimal toxicity and immunogenicity at physiologically relevant concentrations (Saar, K et al. *Anal. Biochem.*, 2005, 345, 55-65; Suhorutsenko, J et al. *Bioconjugate Chem.*, 2011, 22, 2255-2262) and the incorporation of specific unnatural amino acids (Rueping, M et al. *ChemBioChem*, 2002, 3, 257-259) and other chemical moieties (Cooley, C B et al. *J. Am. Chem. Soc.*, 2009, 131, 16401-16403; Pham, W et al. *Chembiochem*, 2004, 5, 1148-1151) have been found to increase stability and cytosolic delivery.

Despite three decades of investigation, the fundamental basis for CPP activity remains elusive. Two distinct and non-mutually exclusive mechanisms have been proposed for the CPPs whose primary sequences are characterized by having multiple arginine residues. In the first mechanism (direct membrane translocation), the arginine guanidinium groups interact with phospholipids of the plasma membrane to generate neutral ion pairs that passively diffuse across the membrane (Herce, H D and Garcia, A E. *Proc. Natl. Acad. Sci. U.S.A.*, 2007, 104, 20805-20810; Hirose, H et al. *Mol. Ther.*, 2012, 20, 984-993) or promote the formation of transient pores that permit the CPPs to traverse the lipid bilayer (Herce, H D et al. *Biophys. J.*, 2009, 97, 1917-1925; Palm-Apergi, C et al. *FASEB J.*, 2009, 23, 214-223). In the second mechanism, CPPs associate with cell surface glycoproteins and membrane phospholipids, internalize into cells through endocytosis (Richard, J P et al. *J. Biol. Chem.*, 2005, 280, 15300-15306; Ferrari, A et al. *Mol. Ther.*, 2003, 8, 284-294; Fittipaldi, A et al. *J. Biol. Chem.*, 2003, 278, 34141-34149; Kaplan, I M et al. *J. Controlled Release*, 2005, 102, 247-253; Nakase, I et al. *Biochemistry*, 2007, 46, 492-501) and subsequently exit from endosomes into the cytoplasm. Taken together, the majority of data show that at low CPP concentrations, cellular uptake occurs mostly through endocytosis, whereas direct membrane translocation becomes prevalent at concentrations above 10 μM (Duchardt, F et al. *Traffic*, 2007, 8, 848-866). However, the mechanism(s) of entry and the efficiency of uptake may vary with the CPP identity, cargo, cell type, and other factors (Mueller, J et al. *Bioconjugate Chem.*, 2008, 19, 2363-2374; Maiolo, J R et al. *Biochim. Biophys. Acta.*, 2005, 1712, 161-172).

CPPs that enter cells via endocytosis must exit from endocytic vesicles in order to reach the cytosol. Unfortunately, the endosomal membrane has proven to be a significant barrier towards cytoplasmic delivery by these CPPs; often a negligible fraction of the peptides escapes into the cell interior (El-Sayed, A et al. *AAPS J.*, 2009, 11, 13-22; Varkouhi, A K et al. *J. Controlled Release*, 2011, 151, 220-228; Appelbaum, J S et al. *Chem. Biol.*, 2012, 19, 819-830). For example, even in the presence of the fusogenic hemagglutinin peptide HA2, which has been demonstrated to enhance endosomal cargo release, >99% of a Tat-Cre fusion protein remains entrapped in macropinosomes 24 h after initial uptake (Kaplan, I M et al. *J. Controlled Release*, 2005, 102, 247-253). Recently, two new types of CPPs with improved endosomal escape efficiencies have been discovered. Appelbaum et al. showed that folded miniature proteins containing a discrete penta-arginine motif were able to effectively overcome endosomal entrapment and reach the cytosol of mammalian cells (Appelbaum, J S et al. *Chem. Biol.*, 2012, 19, 819-830). This motif consists of five arginines across three turns of an α-helix, and proteins containing this motif were released from early (Rab5$^+$) endosomes into the cell interior. It has also been found that cyclization of certain arginine-rich CPPs enhances their cellular uptake (Qian, Z et al. *ACS Chem. Biol.*, 2013, 8, 423-431; Lattig-Tunnemann, G et al. *Nat. Commun.*, 2011, 2, 453; Mandal, D et al. *Angew. Chem. Int. Ed.*, 2011, 50, 9633-9637; Zhao, K et al. *Soft Matter*, 2012, 8, 6430-6433). Small amphipathic cyclic peptides such as cyclo (FΦRRRRQ) (cFΦR$_4$, where Φ is L-2-naphthylalanine) are internalized by mammalian cells in an energy-dependent manner, and enter the cytoplasm and nucleus with efficiencies 2-5-fold higher than that of nonaarginine (R$_9$) (Qian, Z et al. *ACS Chem. Biol.*, 2013, 8, 423-431). Moreover, membrane impermeable cargos such as phosphopeptides can be inserted into the cFΦR$_4$ ring resulting in their delivery into the cytoplasm of target cells. However, insertion of a cargo into the cyclic peptide ring, which is referred to herein as the "endocyclic" delivery method (FIG. 1A), is limited to relatively short peptides (≤7 amino acids), as large rings display poor internalization efficiency (Qian, Z et al. *ACS Chem. Biol.*, 2013, 8, 423-431).

Figure 1B:
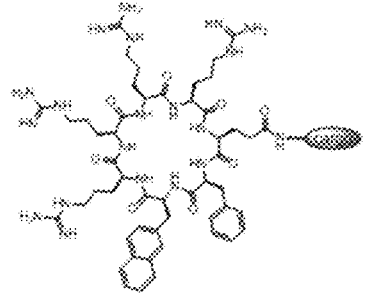
Figure 1C:
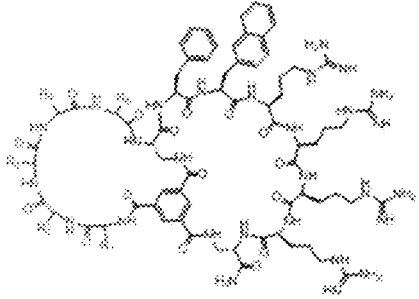

To gain insight into the cFΦR$_4$ mechanism of action and potentially design cyclic CPPs of still higher efficiency, herein the internalization mechanism of cFΦR$_4$ was investigated through the use of artificial membranes and pharmacologic agents as well as genetic mutations that perturb various endocytic events. The data show that cFΦR$_4$ can bind directly to the plasma membrane phospholipids and can enter cells through endocytosis. Like the miniature proteins displaying the penta-arginine motif (Appelbaum, J S et al. *Chem. Biol.*, 2012, 19, 819-830), cFΦR$_4$ can escape from the early endosomes into the cytosol. The ability of cFΦR$_4$ to deliver a wide range of cargo molecules, including linear peptides of varying charges, cyclic peptides, and large proteins, into the cytoplasm of mammalian cells by exocyclic (attachment of cargo to the Gln side chain; FIG. 1B) or bicyclic delivery methods (fusion of the cFΦR$_4$ and cyclic cargo rings; FIG. 1C) was also examined. It was found that cFΦR$_4$ is tolerant to the size and nature of cargos and efficiently transported all of the cargos tested into the cytoplasm and nucleus of mammalian cells. In addition, cFΦR$_4$ exhibits superior stability against proteolysis over linear CPPs but minimal cytotoxicity. cFΦR$_4$ therefore provides a practically useful transporter for cytosolic cargo delivery as well as a system for investigating the mechanism of early endosomal cargo release.

Materials.

Reagents for peptide synthesis were purchased from Advanced ChemTech (Louisville, Ky.), NovaBiochem (La Jolla, Calif.), or Anaspec (San Jose, Calif.). 2,2'-Dipyridyl disulfide, Lissamine rhodamine B sulfonyl chloride, fluorescein isothiocyanate (FITC), dexamethasone (Dex), coenzyme A trilithium salt, FITC-labeled dextran (dextran$^{FITC}$) and human serum were purchased from Sigma-Aldrich (St. Louis, Mo.). Cell culture media, fetal bovine serum (FBS), penicillin-streptomycin, 0.25% trypsin-EDTA, Hoescht 33342, Alexa488-labeled dextran (dextran$^{Alexa488}$), Dulbecco's phosphate-buffered saline (DPBS) (2.67 mM potassium chloride, 1.47 mM potassium phosphate monobasic, 137 mM sodium chloride, 8.06 mM sodium phosphate dibasic), and Lipofectamine 2000 were purchased from Invitrogen (Carlsbad, Calif.). PD-10 desalting columns were purchased from GE-Healthcare (Piscataway, N.J.). Nuclear staining dye DRAQ5™ was purchased from Thermo Scientific (Rockford, Ill.), while cell proliferation kit (MTT) was purchased from Roche (Indianapolis, Ind.). Anti-phosphotyrosine (pY) antibody (clone 4G10) was purchased from Millipore (Temecula, Calif.).

Rink resin LS (100-200 mesh, 0.2 mmol/g) was purchased from Advanced ChemTech. LC-SMCC (succinimidyl-4-[N-maleimidomethyl]cyclohexane-1-carboxy-[6-amidocaproate]) was purchased from Thermo Scientific (Rockford, Ill.), while 1-palmitoyl-2-oleoyl-sn-glycero-3-phosphocholine (POPC), 1-palmitoyl-2-oleoyl-sn-glycero-3-phospho(1'-rac-glycerol) (sodium salt) (POPG), 1-palmitoyl-2-oleoyl-sn-glycero-3-phophoethanolamine (POPE), sphingomyelin (Brain, Porcine), and cholesterol were purchased from Avanti Polar Lipids (Alabaster, Ala.). Heparan sulfate (HO-03103, Lot # HO-10697) was obtained from Celcus Laboratories (Cincinnati, Ohio).

Peptide Synthesis and Labeling.

Peptides were synthesized on Rink Resin LS (0.2 mmol/g) using standard Fmoc chemistry. The typical coupling reaction contained 5 equiv of Fmoc-amino acid, 5 equiv of 2-(7-aza-1H-benzotriazole-1-yl)-1,1,3,3-tetramethyluronium hexafluorophosphate (HATU) and 10 equiv of diisopropylethylamine (DIPEA) and was allowed to proceed with mixing for 75 min. After the addition of the last (N-terminal) residue, the allyl group on the C-terminal Glu residue was removed by treatment with Pd(PPh$_3$)$_4$ and phenylsilane (0.1 and 10 equiv, respectively) in anhydrous DCM (3×15 min). The N-terminal Fmoc group was removed by treatment with 20% piperidine in DMF and the peptide was cyclized by treatment with benzotriazole-1-yl-oxy-tris-pyrrolidino-phosphonium hexafluorophosphate (PyBOP)/HOBt/DIPEA (5, 5, and 10 equiv) in DMF for 3 h. The peptides were deprotected and released from the resin by treatment with 82.5:5:5:5:2.5 (v/v) TFA/thioanisole/water/phenol/ethanedithiol for 2 h. The peptides were triturated with cold ethyl ether (3×) and purified by reversed-phase HPLC on a C18 column. The authenticity of each peptide was confirmed by MALDI-TOF mass spectrometry.

Peptide labeling with FITC was performed by dissolving the purified peptide (~1 mg) in 300 μL of 1:1:1 (vol/vol) DMSO/DMF/150 mM sodium bicarbonate (pH 8.5) and mixing with 10 μL of FITC in DMSO (100 mg/mL). After 20 min at room temperature, the reaction mixture was subjected to reversed-phase HPLC on a C18 column to isolate the FITC-labeled peptide. To generate rhodamine- and Dex-labeled peptides (FIG. 2), an N$^ε$-4-methoxytrityl-L-lysine was added to the C-terminus. After the solid phase peptide synthesis, the lysine side chain was selectively deprotected using 1% (v/v) trifluoroacetic acid in CH$_2$Cl$_2$. The resin was incubated with Lissamine rhodamine B sulfonyl chloride/DIPEA (5 equiv each) in DMF overnight. The peptides were fully deprotected, triturated with diethyl ether, and purified by HPLC. The Dex-labeled peptide was produced by incubating the resin with dexamethasone-21-thiopropionic acid/HBTU/DIPEA (5, 5, and 10 equiv) in DMF for 3 h (Appelbaum, J S et al. *Chem. Biol.*, 2012, 19, 819-830). The peptide was then deprotected, triturated, and purified by HPLC. Bicyclic peptides, phosphocoumaryl aminopropionic acid (pCAP), and pCAP-containing peptides (PCPs) were synthesized as previously described (Lian, W et al. *J. Am. Chem. Soc.*, 2013, 135, 11990-11995; Mitra, S and Barrios, A M. *Bioorg. Med. Chem. Lett.*, 2005, 15, 5124-5145; Stanford, S M et al. *Proc. Natl. Acad. Sci. U.S.A.*, 2012, 109, 13972-13977). The authenticity of each peptide was confirmed by MALDI-TOF mass spectrometry.

Preparation of cFΦR$_4$-Protein Conjugates.

The gene coding for the catalytic domain of PTP1B (amino acids 1-321) was amplified by the polymerase chain reaction using PTP1B cDNA as template and oligonucleotides 5'-ggaattccatatggagatggaaaaggagttcgagcag-3' and 5'-gggatccgtcgacattgtgtggctccaggattcgtftgg-3' as primers. The resulting DNA fragment was digested with endonucleases Nde I and Sal I and inserted into prokaryotic vector pET-22b(+)-ybbR (Yin, J et al. *Proc. Natl. Acad. Sci. U.S.A.*, 2005, 102, 15815-15820). This cloning procedure resulted in the addition of a ybbR tag (VLDSLEFIASKL) to the N-terminus of PTP1B. Expression and purification of the ybbR tagged PTP1B were carried out as previously described (Ren, L et al. *Biochemistry*, 2011, 50, 2339-2356).

Figure 3:
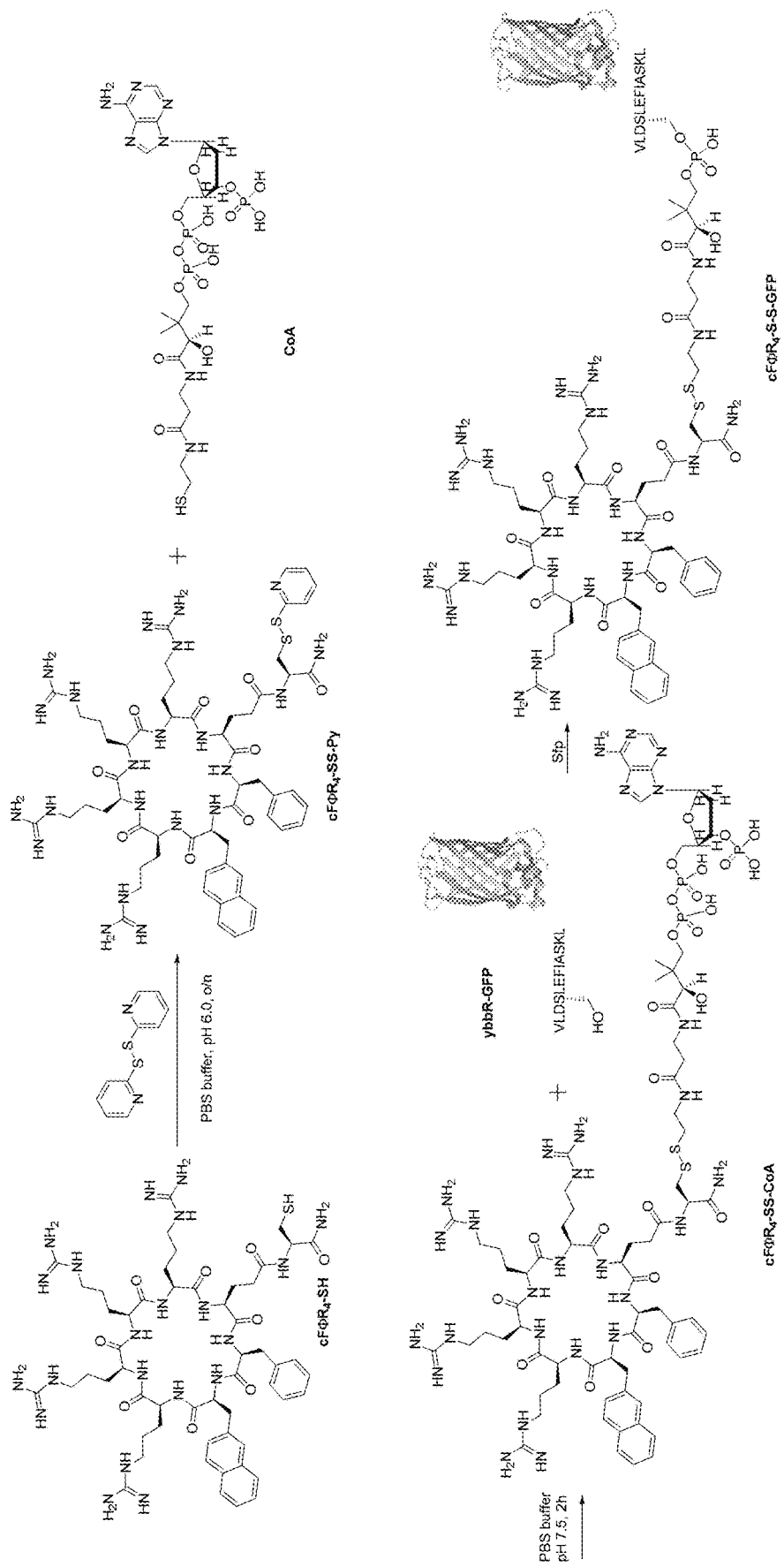
FIG. 3 displays a scheme showing the synthesis of cFΦR$_4$-S-S-GFP.
Figure 4:
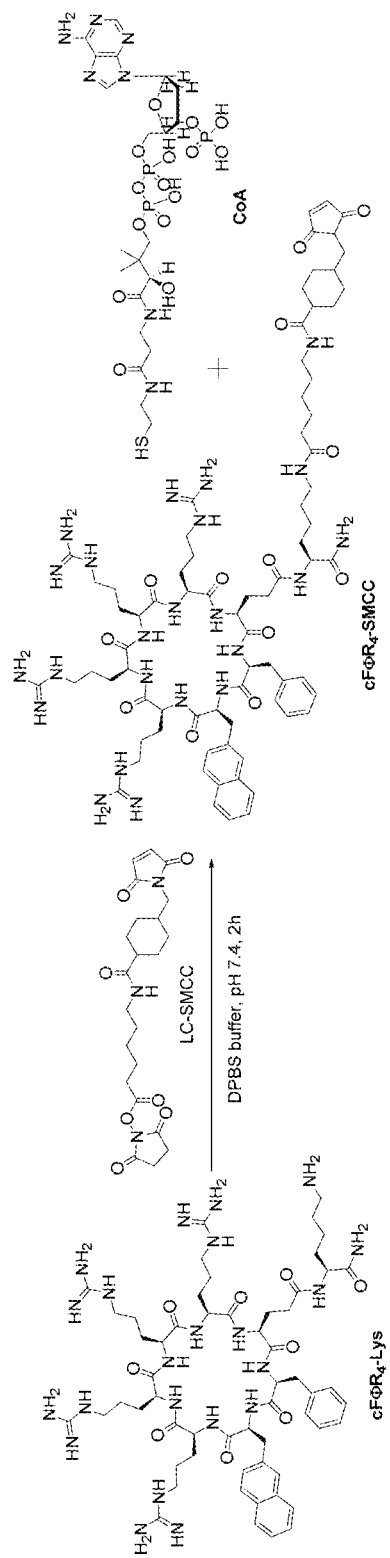
FIG. 4 displays a scheme showing the synthesis of cFΦR$_4$-PTP1B.
Figure 4:
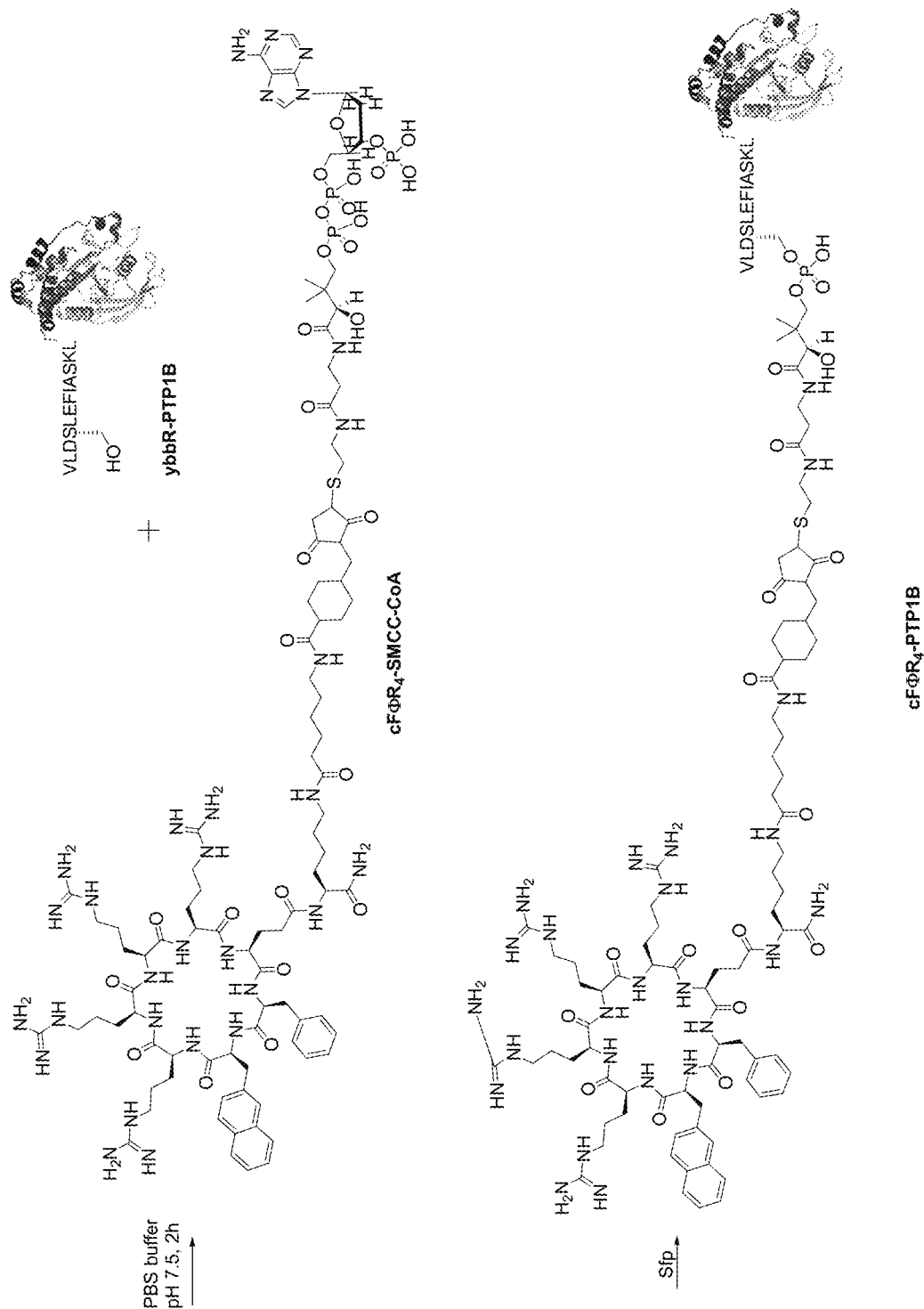

Peptide cFΦR$_4$ containing a C-terminal cysteine (cFΦR$_4$-SH, ~10 μmol; FIG. 3) was dissolved in 1 mL of degassed DPBS and mixed with 2,2'-dipyridyl disulfide (5 equiv) dissolved in acetone (0.5 mL). After 2 h at room temperature, the reaction product cFΦR$_4$-SS-Py was purified by reversed-phase HPLC. The product was incubated with coenzyme A (2 equiv) in DPBS for 2 h. The resulting cFΦR$_4$-SS-CoA adduct was purified again by reversed-phase HPLC. Green fluorescent protein (GFP) containing an N-terminal ybbR tag (VLDSLEFIASKL) and a C-terminal six-histidine tag was expressed in *Escherichia coli* and purified as previously described (Yin, J et al. *Proc. Natl. Acad. Sci. U.S.A.*, 2005, 102, 15815-15820). Next, ybbR-GFP (30 μM), cFΦR$_4$-SS-CoA (30 μM), and phosphopantetheinyl transferase Sfp (0.5 μM) were mixed in 50 mM HEPES (pH 7.4), 10 mM MgCl2 (total volume 1.5 mL) and incubated at 37° C. for 15 min. The labeled protein, cFΦR$_4$-S-S-GFP (FIG. 3), was separated from unreacted cFΦR$_4$-SS-CoA by passing the reaction mixture through a PD-10 desalting column. GFP conjugated to Tat (Tat-S-S-GFP) and cFΦR$_4$-conjugated PTP1B (cFΦR$_4$-PTP1B) were prepared in a similar fashion (FIG. 4).

Peptide containing a C-terminal lysine (cFΦR$_4$-Lys, ~10 µmol; FIG. 4) was synthesized on the solid phase, deprotected and released from the support, dissolved in degassed DPBS (pH 7.4, 1 mL), and mixed with bifunctional linker LC-SMCC (5 equiv) dissolved in DMSO (0.2 mL). After incubation at room temperature for 2 h, the reaction product cFΦR$_4$-SMCC (FIG. 4) was purified by reversed-phase HPLC equipped with a C18 column. The product was then mixed with coenzyme A (2 equiv) in DPBS and incubated for 2 h. The resulting cFΦR$_4$-SMCC-CoA adduct was purified again by reversed-phase HPLC. Next, ybbR-tagged PTP1B (30 µM), cFΦR$_4$-SMCC-CoA (30 µM), and phosphopantetheinyl transferase Sfp (0.5 µM) were mixed in 50 mM HEPES (pH 7.4), 10 mM MgCl$_2$ (total volume of 1.5 mL) and incubated at 37° C. for 15 min. The labeled protein (cFΦR$_4$-PTP1B; FIG. 4) was separated from unreacted cFΦR$_4$-SMCC-CoA by passing the reaction mixture through a PD-10 desalting column eluted with DPBS.

Cell Culture and Transfection.

HEK293, HeLa, MCF-7, NIH 3T3 and A549 cells were maintained in medium consisting of DMEM, 10% FBS and 1% penicillin/streptomycin. Jurkat, H1650, and H1299 cells were grown in RPMI-1640 supplemented with 10% FBS and 1% penicillin/streptomycin. Cells were cultured in a humidified incubator at 37° C. with 5% CO$_2$. For HeLa cells transfection, cells were seeded onto 96-well plate at a density of 10,000 cells/well. Following attachment, cells were transfected with plasmids encoding Rab5-green fluorescent protein fusion (Rab5-GFP), Rab7-GFP (Addgene plasmid #28047), glucocorticoid receptor (C638G)-GFP fusion (GR-GFP) (Holub, J M et al. *Biochemistry*, 2013, 50, 9036-6046), DsRed-Rab5 WT (Addgene plasmid #13050) or DsRed-Rab5$^{Q79L}$ (Addgene plasmid #29688) following Lipofectamine 2000 manufacturer protocols.

Preparation of Small Unilamellar Vesicles (SUVs).

SUVs were prepared by modifying a previously reported procedure (Magzoub, M et al. *Biochim. Biophys. Acta*, 2002, 1563, 53-63). A proper lipid mixture was dissolved in chloroform in a test tube. The lipid mixture was dried gently by blowing argon over the solution, and kept in a desiccator overnight. The dried lipids were rehydrated in DPBS to final total lipid concentration of 10 mM. The suspension was rigorously mixed by vortexing and sonication on ice until it became clear. A typical preparation yields a homogeneous solution containing vesicles with average diameter of ~80 nm and polydispersity (PdI) index of <0.15 as determined by dynamic light scattering measurements using Zeta Sizer Nano Series (Malvern, Brookhaven, Conn.). The SUV solution was stored at 4° C. and used for FP experiments on the same day.

Fluorescence Polarization.

A typical experiment was performed by incubating 100 nM FITC-labeled peptide with varying concentrations of heparan sulfate (0-5,000 nM) in DPBS for 2 h at room temperature. The FP values were measured on a Molecular Devices Spectramax M5 spectrofluorimeter, with excitation and emission wavelengths at 485 and 525 nm, respectively. EC$_{50}$ were determined by plotting the FP values as a function of heparan sulfate concentrations and fitted to a four-parameter logistic curve with GraphPad PRISM ver.6 software.

To obtain the EC50 value of CPP with lipid membranes, the FP experiment was similarly conducted using 100 nM FITC-labeled peptide with increasing concentrations of SUV solutions (0-10 mM) in DPBS. The FP values were similarly measured, plotted, and analyzed.

Image Analysis.

Raw images were uniformly modified using imageJ. Pearson's correlation coefficient (R) was obtained from endosomal regions using Just Another Colocalization Plugin (JACoP) (Bolte, S and Cordelieres, F P. *J. Microsc.*, 2006, 224, 213-232). For GR-GFP translocation assay, individual GFP and Hoescht images were loaded into a customized CellProfiler pipeline and colored to grey (Carpenter, A E et al. *Genome Biol.*, 2006, 7, R100). Nuclei were distinguished from the Hoescht image via Otsu automatic three-class thresholding, with pixels of the middle intensity class assigned to background. Clumped objects were identified using Laplacian of Gaussian modeling and separated by shape. The nuclear region was defined as the diameter of the Hoescht objects shrunken by 1 µm, while the cytosolic ring region was defined as the region between the nuclear diameter and the nuclear diameter expanded 2 µm. The translocation ratio was defined as the mean GFP signal inside the nuclear region divided by the mean GFP signal within the cytosolic region measured per cell, and 30-70 cells from 15-30 images were captured for each condition tested.

Confocal Microscopy.

To examine the co-localization between rhodamine-labeled cyclic peptide)(cFΦR$_4^{Rho}$) and Rab5$^+$ or Rab7$^+$ endosomes, HeLa cells transfected with Rab5-GFP or Rab7-GFP were plated (200 µL, 10$^4$ cells/well, 96-well glass bottom MatriPlates) the day prior to the experiment. On the day of experiment, HeLa cells were treated with 1 µM cFΦR$_4^{Rho}$ in DMEM media supplemented with 300 nM Hoescht 33342 for 30 min. After that, the cells were washed with HKR buffer (10 mM HEPES, pH 7.4, 140 mM NaCl, 2 mM KCl, 1 mM CaCl$_2$, 1 mM MgCl$_2$) and imaged using a PerkinElmer LiveView spinning disk confocal microscope.

For GR translocation assay, HeLa cells transfected with GR-GFP were plated as described above (Holub, J M et al. Biochemistry, 2013, 50, 9036-6046). The cells were treated for 30 min with DMEM media containing 1 µM Dex or Dex-peptide conjugate and 300 nM Hoescht 33342 and imaged using a Zeiss Axiovert 200M epifluorescence microscope outfitted with Ziess Axiocam mRM camera and an EXFO-Excite series 120 Hg arc lamp. To examine the effect of endocytosis inhibitors, transfected HeLa cells were pretreated for 30 min with clear DMEM containing the inhibitors before incubation with Dex or Dex-peptide conjugates. To test whether Rab5 activity is required for endosomal escape, HeLa cells were transfected with GR-GFP and DsRed-Rab5 WT or DsRed-Rab5$^{Q79L}$ before treatment with Dex or Dex-peptide conjugate and imaged as described above (Appelbaum, J S et al. *Chem. Biol.*, 2012, 19, 819-830).

To examine the internalization of rhodamine-labeled peptides, 5×10$^4$ HEK293 cells were plated in a 35 mm glass-bottomed microwell dish (MatTek). On the day of experiment, the cells were incubated with the peptide solution (5 µM) and 0.5 mg/mL dextran$^{FITC}$ at 37° C. for 2 h. The cells were gently washed with DPBS twice and imaged on a Visitech Infinity 3 Hawk 2D-array live cell imaging confocal microscope. To detect the internalization of pCAP-containing peptides, HEK293 cells were similarly plated and incubated with the peptide solution (5 µM) at 37° C. for 60 min. After removal of the medium, the cells were gently washed with DPBS containing sodium pervanadate (1 mM) twice and incubated for 10 min in DPBS containing 5 µM nuclear staining dye DRAQS. The resulting cells were washed with DPBS twice and imaged on a spinning disk confocal microscope (UltraView Vox CSUX1 system). To monitor GFP internalization, $5 \times 10^4$ HEK293 cells were seeded in a 35 mm glass-bottomed microwell dish and cultured overnight. Cells were treated with cFΦR$_4$-S-S-GFP (1 µM) at 37° C. for 2 h. After removal of the medium, the cells were incubated in DPBS containing 5 µM DRAQS for 10 min. The cells were washed with DPBS twice and imaged on a Visitech Infinity 3 Hawk 2D-array live cell imaging confocal microscope.

Flow Cytometry.

To quantify the delivery efficiencies of pCAP-containing peptides, HeLa cells were cultured in six-well plates ($5 \times 10^5$ cells per well) for 24 h. On the day of experiment, the cells were incubated with 10 µM pCAP-containing peptide in clear DMEM with 1% FBS at 37° C. for 2 h. The cells were washed with DPBS containing 1 mM sodium pervanadate, detached from plate with 0.25% trypsin, suspended in DPBS containing 1% bovine serum albumin, and analyzed on a BD FACS Aria flow cytometer with excitation at 355 nm. Data were analyzed with Flowjo software (Tree Star).

To estimate the effect of cFΦR$_4$ on endocytosis, HeLa cells were seeded in six-well plates ($5 \times 10^5$ cells per well) and allowed to adhere overnight. Following adherence, cells were treated with clear DMEM containing no supplement, 1 µM cFΦR$_4$ peptide, 100 µM dextran$^{Alexa488}$ (Life Technologies, D-22910), or both 1 µM cyclic peptide and 100 µM dextran$^{Alexa488}$ for 30 min under standard cell culture conditions. The cells were washed with DPBS twice, removed from the plate with 0.25% trypsin, diluted into clear DMEM containing 10% FBS, pelleted at 300 g for 5 min, washed once with DPBS and resuspended in 200 µL of DPBS. Whole-cell dextran uptake was analyzed on a BD Accuri C6 flow cytometer using the manufacturer FL1 laser and filter set.

Immunoblotting.

NIH 3T3 cells were cultured in full growth media to reach 80% confluence. The cells were starved in serum free media for 3 h and treated with different concentrations of cFΦR$_4$-PTP1B or untagged PTP1B for 2 h, followed by 30 min incubation in media supplemented with 1 mM sodium pervanadate. The solutions were removed and the cells were washed with cold DPBS twice. The cells were detached and lysed in 50 mM Tris-HCl, pH 7.4, 150 mM NaCl, 1% NP-40, 10 mM sodium pyrophosphate, 5 mM iodoacetic acid, 10 mM NaF, 1 mM EDTA, 2 mM sodium pervanadate, 0.1 mg/mL phenylmethanesulfonyl fluoride, 1 mM benzamidine, and 0.1 mg/mL trypsin inhibitor. After 30 min incubation on ice, the cell lysate was centrifuged at 15,000 rpm for 25 min in a microcentrifuge. The total cellular proteins were separated by SDS-PAGE and transferred electrophoretically to PVDF membrane, which was immunoblotted using anti-pY antibody 4G10.

Serum Stability Test.

The stability tests were carried by modifying a previously reported procedure (Nguyen, L T et al. PLoS One, 2010, 5, e12684). Diluted human serum (25%) was centrifuged at 15,000 rpm for 10 min, and the supernatant was collected. A peptide stock solution was diluted into the supernatant to a final concentration of 5 µM for cFΦR$_4$ and Antp and 50 µM for peptides R9 and Tat and incubated at 37° C. At various time points (0-6 h), 200-µL aliquots were withdrawn and mixed with 50 µl of 15% trichloroacetic acid and incubated at 4° C. overnight. The final mixture was centrifuged at 15,000 rpm for 10 min in a microcentrifuge, and the supernatant was analyzed by reversed-phase HPLC equipped with a C18 column (Waters). The amount of remaining peptide (%) was determined by integrating the area underneath the peptide peak (monitored at 214 nm) and compared with that of the control reaction (no serum).

Cytotoxicity Assay.

MTT assays were performed to evaluate cyclic peptide's cytotoxicity against several mammalian cell lines (Mosmann, T. J. Immunol. Methods, 1983, 65, 55-63). One hundred µL of MCF-7, HEK293, H1299, H1650, A549 ($1 \times 10^5$ cells/mL) cells were placed in each well of a 96-well culture plate and allowed to grow overnight. Varying concentrations of the peptide (5 or 50 µM) were added to the each well and the cells were incubated at 37° C. with 5% $CO_2$ for 24 to 72 h. Ten µL of MTT stock solution was added into each well. Addition of 10 µL of the solution to the growth medium (no cell) was used as a negative control. The plate was incubated at 37° C. for 4 h. Then 100 µL of SDS-HCl solubilizing buffer was added into each well, and the resulting solution was mixed thoroughly. The plate was incubated at 37° C. for another 4 h. The absorbance of the formazan product was measured at 570 nm using a Molecular Devices Spectramax M5 plate reader. Each experiment was performed in triplicates and the cells without any peptide added were treated as control.

cFΦR$_4$ Binds to Membrane Phospholipids.

It was previously observed that incubation of 1 µM FITC-labeled cyclic peptide cFΦR$_4^{FITC}$ with vesicles containing negatively charged phospholipids (90% phosphatidylcholine (PC) and 10% phosphatidylglycerol (PG)) resulted in quenching of the peptide fluorescence, consistent with direct binding of cFΦR$_4$ to phospholipids (Qian, Z et al. ACS Chem. Biol., 2013, 8, 423-431). To test the potential role of membrane binding during endocytic uptake of CPPs, SUVs that mimic the outer membrane of mammalian cells (45% PC, 20% phosphatidylethanolamine, 20% sphingomyelin, and 15% cholesterol) were prepared and tested for binding to FITC-labeled cFΦR$_4$, R9, and Tat (each at 100 nM) by a fluorescence polarization (FP) assay. cFΦR$_4$ bound to the neutral SUVs with an EC50 value (lipid concentration at which half of cFΦR$_4^{FITC}$ is bound) of 2.1±0.1 mM (FIG. 5A). R9 showed much weaker binding to the artificial membrane (EC50>10 mM), whereas Tat did not bind at all. Next, the CPPs were tested for binding to heparan sulfate, which was previously proposed to be the primary binding target of cationic CPPs (Nakase, I et al. Biochemistry, 2007, 46, 492-501; Rusnati, M et al. J. Biol. Chem., 1999, 274, 28198-28205; Tyagi, M et al. J. Biol. Chem., 2001, 276, 3254-3261; Ziegler, A and Seelig, J. Biophys. J., 2004, 86, 254-263; Goncalves, E et al. Biochemistry, 2005, 44, 2692-2702; Ziegler, A. Adv. Drug Delivery Rev., 2008, 60, 580-597). R9 and Tat both bound to heparan sulfate with high affinity, having EC50 values of 144 and 304 nM, respectively (FIG. 5B). Under the same condition, cFΦR$_4$ showed no detectable binding to heparan sulfate. These results are in agreement with the previous observations that non-amphipathic cationic CPPs (e.g., Tat and R9) bind tightly with cell surface proteoglycans (e.g. heparan sulfate) but only weakly with membrane lipids (Ziegler, A. Adv. Drug Delivery Rev., 2008, 60, 580-597). The insufficient number of positive charges of cFΦR$_4$ is likely responsible for its lack of strong electrostatic interaction with heparan sulfate. On the other hand, the amphipathic nature and the more rigid cyclic structure of cFΦR$_4$ should facilitate its binding to neutral lipid membranes. These data, together with the inhibition pattern by various endocytic inhibitors described above, suggest that cFΦR$_4$ can bind directly to the plasma membrane phospholipids and can be internalized by all of the endocytic mechanisms in a piggyback manner.

Intracellular Delivery of Peptidyl Cargos.

Since endocyclic delivery by cFΦR$_4$ is limited to a heptapeptide or smaller cargos (Qian, Z et al. *ACS Chem. Biol.*, 2013, 8, 423-431), in this study the ability of cFΦR$_4$ to deliver cargos of varying sizes and physicochemical properties attached to the Gln side chain (FIG. 1B, exocyclic delivery) was tested. First, positively charged (RRRRR), neutral (AAAAA), hydrophobic (FFFF), and negatively charged peptides [DE(pCAP)LI] were covalently attached to cFΦR$_4$. The first three peptides were labeled with rhodamine B at a C-terminal lysine side chain (FIG. 2), and their internalization into HEK293 cells was examined by live-cell confocal microscopy. Cells incubated for 2 h with 5 μM peptide cFΦR$_4$-A$_5$ (FIG. 6A) or cFΦR$_4$-R5 (FIG. 6B) showed evidence of both punctuate and diffuse fluorescence, with the latter distributed almost uniformly throughout the cell. In contrast, the fluid phase endocytic marker dextran$^{FITC}$ displayed predominantly punctuate fluorescence, indicative of endosomal localization. The diffuse rhodamine fluorescence suggests that a fraction of the peptides reached the cytosol and nucleus of the cells. Co-incubation of cells with cFΦR$_4$ (1 μM) and dextran$^{Alexa488}$ increased the internalization of the endocytic marker by 15% (FIG. 7), suggesting that cFΦR$_4$ can activate endocytosis in cultured cells. cFΦR$_4$-F$_4$ was not tested due to its poor aqueous solubility.

Figure 2:
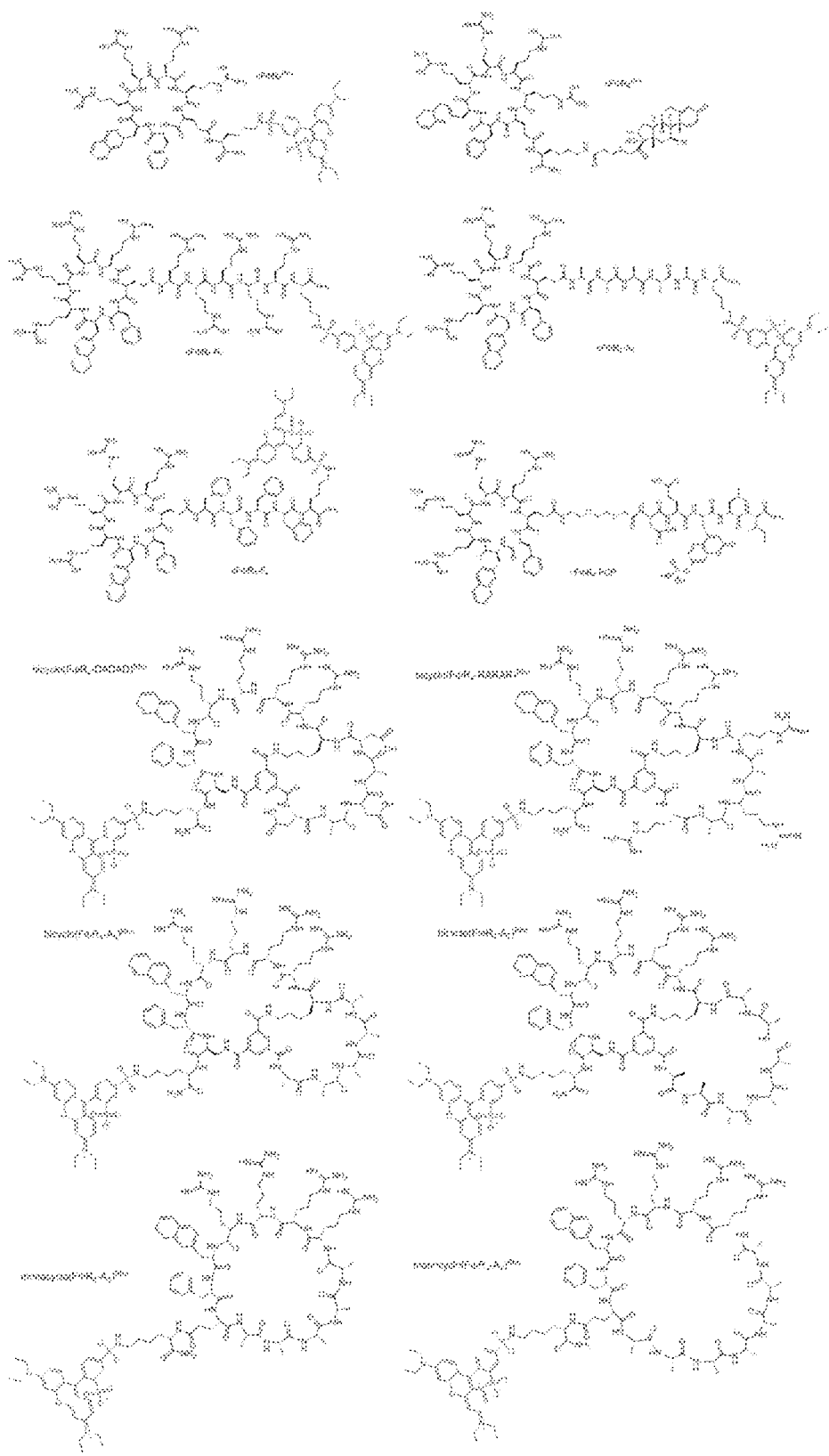
FIG. 2 displays the structures of some of the peptides used in this study.

Peptide cFΦR4-DE(pCAP)LI (cFΦR4-PCP; FIG. 2) was designed to test the ability of cFΦR$_4$ to deliver negatively charged cargos as well as to compare the cytoplasmic delivery efficiency of cFΦR$_4$ with those of other widely used CPPs such as R9, Tat, and penetratin (Antp). Thus, untagged PCP [Ac-DE(pCap)LI-NH$_2$] and PCP conjugated to R9 (R$_9$-PCP), Tat (Tat-PCP), or Antp (Antp-PCP) were also prepared. Note that cFΦR$_4$-PCP carries a net charge of zero at physiological pH. pCAP is non-fluorescent, but upon entering the cell interior, should be rapidly dephosphorylated by endogenous protein tyrosine phosphatases (PTPs) to produce a fluorescent product, coumaryl aminopropionic acid (CAP, excitation 355 nm; emission 450 nm) (Mitra, S and Barrios, A M. *Bioorg. Med. Chem. Lett.*, 2005, 15, 5124-5145; Stanford, S M et al. *Proc. Natl. Acad. Sci. U.S.A.*, 2012, 109, 13972-13977). When assayed against a PTP panel in vitro, all four CPP-PCP conjugates were efficiently dephosphorylated (Table 8). This assay detects only the CPP-cargo inside the cytoplasm and nucleus, where the catalytic domains of all known mammalian PTPs are localized (Alonso, A et al. *Cell*, 2004, 117, 699-711). Further, CAP is fluorescent only in its deprotonated state (pKa=7.8); even if some dephosphorylation occurs inside the endosome (pH 6.5-4.5) or lysosome (pH 4.5), it would contribute little to the total fluorescence (FIG. 8). Treatment of HEK293 cells with 5 μM cFΦR$_4$-PCP for 60 min resulted in diffuse blue fluorescence throughout the cell, suggesting that cFΦR$_4$-PCP reached the cell interior, whereas the untagged PCP failed to enter cells under the same condition (FIG. 9A). When HEK293 cells were pretreated with the PTP inhibitor sodium pervanadate for 1 h prior to incubation with cFΦR$_4$-PCP (5 μM), the CAP fluorescence in the cells diminished to background levels. HEK293 cells treated with R$_9$-PCP, Antp-PCP, or Tat-PCP under identical conditions showed weak fluorescence, consistent with the poor ability of these peptides to access the cell interior (FIG. 9A). To quantify the relative intracellular PCP delivery efficiency, HeLa cells were treated with each peptide and analyzed by fluorescence activated cell sorting (FIG. 9B). cFΦR$_4$-PCP was most efficiently internalized by the HeLa cells, with a mean fluorescence intensity (MFI) of 3510 arbitrary units (AU), whereas R$_9$-PCP, Antp-PCP, Tat-PCP, and untagged PCP produced MFI values of 960, 400, 290, and 30 AU, respectively (FIG. 9C). Again, when cells were treated with cFΦR$_4$-PCP in the presence of sodium pervanadate, the amount of CAP fluorescence was reduced to near background levels (70 AU). Thus, cFΦR$_4$ is capable of delivering peptidyl cargos of varying physicochemical properties into the cytoplasm with efficiencies 3.7-12-fold higher than R$_9$, Antp, and Tat.

TABLE 8

Kinetic Activities ($k_{cat}/K_M$, $M^{-1}$ $s^{-1}$) of Recombinant PTPs against pCAP-Containing Peptides$^a$

| PTP | cFΦR$_4$-PCP | Tat-PCP | R$_9$-PCP | Antp-PCP |
| --- | --- | --- | --- | --- |
| PTP1B | 37100 | 13800 | 14700 | 17400 |
| TCPTP | 2780 | 560 | 457 | 970 |
| SHP2 | 7400 | 2290 | 248 | 2210 |
| CD45 | 35100 | 21800 | 2940 | 22300 |
| VHR | 2460 | 1460 | 6240 | 2030 |

$^a k_{cat}/K_M$ was measured as previously described (Ren, L et al. *Biochemistry*, 2011, 50, 2339-2356).

Intracellular Delivery of Cyclic Peptides.

In recent years, there has been much interest in cyclic peptides as therapeutic agents and biomedical research tools (Driggers, E M et al. *Nat. Rev. Drug Discov.*, 2008, 7, 608-624; Marsault, E and Peterson, M L. *J. Med. Chem.*, 2011, 54, 1961-2004). For example, cyclic peptides are effective for inhibition of protein-protein interactions (Lian, W et al. *J. Am. Chem. Soc.*, 2013, 135, 11990-11995; Liu, T et al. *ACS Comb. Sci.*, 2011, 13, 537-546; Dewan, V et al. *ACS Chem. Biol.*, 2012, 7, 761-769; Wu, X et al. *Med. Chem. Commun.*, 2013, 4, 378-382), which are challenging targets for conventional small molecules. A major obstacle in developing cyclic peptide therapeutics is that they are generally impermeable to the cell membrane (Kwon, Y U and Kodadek, T. *Chem. Biol.*, 2007, 14, 671-677; Rezai, T et al. *J. Am. Chem. Soc.*, 2006, 128, 2510-2511; Chatterjee, J et al. *Acc. Chem. Res.*, 2008, 41, 1331-1342). The attempt to deliver cyclic peptides by cFΦR$_4$ by the endocyclic method had only limited success; increase in the cargo size from 1 to 7 residues led to progressively poorer cellular uptake, likely because the larger, more flexible rings bind more poorly to the cell membrane (Qian, Z et al. *ACS Chem. Biol.*, 2013, 8, 423-431). To overcome this limitation, a bicyclic peptide system was explored, in which one ring contains a CPP motif (e.g., FΦR$_4$) while the other ring consists of peptide sequences specific for the desired targets (FIG. 1C). The bicyclic system should in principle be able to accommodate cargos of any size, because the cargo does not change the structure of the CPP ring and should have less impact on its delivery efficiency. The additional rigidity of a bicyclic structure should also improve its metabolic stability as well as the target-binding affinity and specificity. The bicyclic peptides were readily synthesized by forming three amide bonds between a trimesoyl scaffold and three amino groups on the corresponding linear peptide (i.e., the N-terminal amine, the side chain of a C-terminal diaminopropionic acid (Dap), and the side chain of a lysine (or ornithine, Dap) imbedded in between the CPP and target-binding motifs) (Lian, W et al. *J. Am. Chem. Soc.*, 2013, 135, 11990-11995). To test the validity of this approach, FΦR$_4$ was chosen in the C-terminal ring as the CPP moiety and peptides of different lengths and charges (AAAAA, AAAAAAA, RARAR, or DADAD) were chosen as cargo (Table 8, compounds 13-16). For comparison, two monocyclic peptides containing FΦR$_4$ as transporter and peptides A$_5$ and A$_7$ as cargos (Table 8, compounds 17 and 18) were also prepared. All of the peptides were labeled at a C-terminal lysine side chain with rhodamine B (FIG. 2) and their internalization into HEK293 cells was examined by live-cell confocal microscopy. Treatment of cells with 5 µM peptide for 2 h resulted in efficient internalization of all six peptides (FIG. 10), although FACS analysis indicated that the uptake of bicyclo(FΦR$_4$-A$_5$)$^{Rho}$ was ~3-fold more efficient than the corresponding monocyclic peptide (compound 17). The intracellular distribution of the internalized peptides was quite different between the bicyclic and monocyclic peptides. While the four bicyclic peptides showed evidence for their presence in both the cytoplasm/nucleus (as indicated by the diffuse rhodamine fluorescence) and the endosomes (as indicated by the fluorescence puncta), the monocyclic peptides exhibited predominantly punctuate fluorescence that overlapped with that of the endocytic marker dextran$^{FITC}$. In all cases, the endocytic marker displayed only punctuate fluorescence, indicating that the endosomes were intact in the cells treated with the peptides. These results indicate that the increased structural rigidity of the bicyclic peptides facilitates both the initial uptake by endocytosis and endosomal release, presumably because of their improved binding to the plasma and endosomal membranes. The bicyclic system may provide a general strategy for intracellular delivery of cyclic and bicyclic peptides.

Intracellular Delivery of Protein Cargos.

Figure 11A:
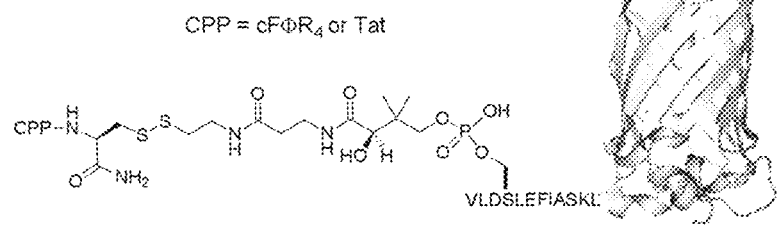
FIGS. 11A and 11B display.
Figure 11B:
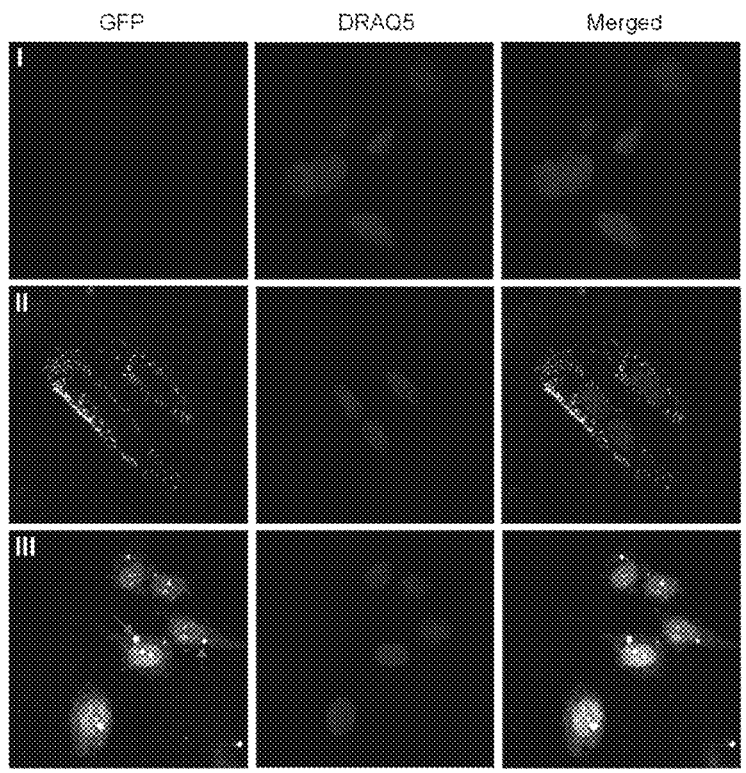

To test whether cFΦR$_4$ is capable of transporting full-length proteins into mammalian cells, GFP was attached to the N-terminus of cFΦR$_4$ through a disulfide bond (FIG. 11A and FIG. 3). GFP was chosen because of its intrinsic fluorescence. The disulfide exchange reaction is highly specific, efficient, and reversible; upon entering the cytoplasm, the CPP-S-S-protein conjugate can be rapidly reduced to release the native protein. Although cFΦR$_4$ can be directly attached to a native or engineered surface cysteine residue(s) on a cargo protein, a GFP variant containing a 12-amino acid ybbR tag at its N-terminus was used and phosphopantetheinyl transferase Sfp was used to enzymatically attach cFΦR$_4$ to the ybbR tag (Yin, J et al. Proc. Natl. Acad. Sci. U.S.A., 2005, 102, 15815-15820). This permitted the attachment of a single cFΦR$_4$ unit to GFP in a site-specific manner. For comparison, a Tat-S-S-GFP conjugate was generated in the same manner. Incubation of HEK293 cells in the presence of 1 µM cFΦR$_4$—S-S-GFP resulted in accumulation of green fluorescence inside the cells (FIG. 11B). The fluorescence signal was diffuse and present throughout the entire cell volume, but with higher concentrations in the nucleus. Some of the cells contained small spots of intense green fluorescence (indicated by arrows in FIG. 11B), which may represent endosomally sequestered cFΦR$_4$-S-S-GFP or aggregated GFP inside the cell. The untagged GFP was unable to enter cells, whereas Tat-S-S-GFP entered cells less efficiently than cFΦR$_4$-S-S-GFP (FIG. 11B); FACS analysis of HaLa cells treated with 1 µM protein revealed a 5.5-fold higher total intracellular fluorescence for the latter. The fluorescence puncta in the cell periphery as well as lack of any detectable fluorescence in the nuclear region of Tat-S-S-GFP treated cells indicate that Tat-S-S-GFP is mostly entrapped in the endosomes, in agreement with previous reports (Kaplan, I M et al. J. Controlled Release, 2005, 102, 247-253). Thus, with a protein as cargo, cFΦR$_4$ also has higher efficiency than Tat with regard to both initial uptake and endosomal escape.

Figure 12A:
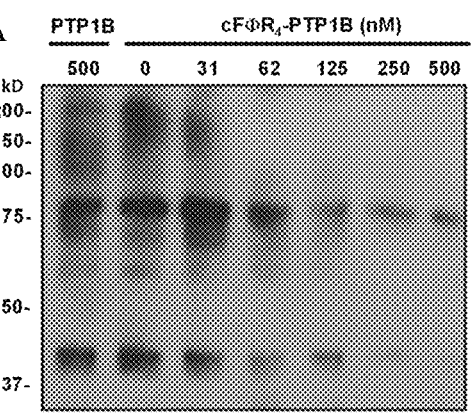
FIGS. 12A and 12B display.
Figure 12B:
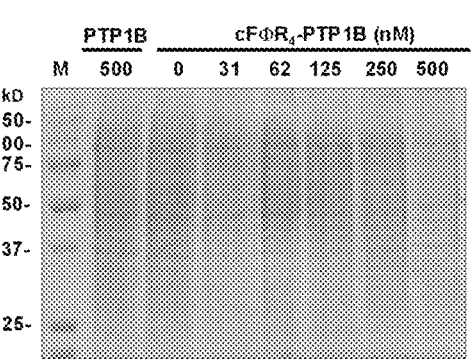

To demonstrate the generality of cFΦR$_4$ for protein delivery, a functional enzyme, the catalytic domain of PTP1B (amino acids 1-321), was chosen to be delivered into the cell interior. To show that a non-cleavable linkage is also compatible with the delivery method, cFΦR$_4$ was conjugated to ybbR-tagged PTP1B via a thioether bond (cFΦR$_4$-PTP1B) (FIG. 4). In vitro assay using p-nitrophenyl phosphate as substrate showed that addition of the cFΦR$_4$ tag does not affect the catalytic activity of PTP1B (Table 9). NIH 3T3 cells were incubated for 2 h in the presence of untagged PTP1B or cFΦR$_4$-PTP1B and their global pY protein levels were analyzed by anti-pY western blotting (FIG. 12A). Treatment of the cells with cFΦR$_4$-PTP1B, but not untagged PTP1B, resulted in concentration-dependent decrease in pY levels of most, but not all, proteins. The total cellular protein levels, as detected by Coomassie blue staining, were unchanged (FIG. 12B), indicating that the observed decrease in pY levels was due to dephosphorylation of the pY proteins by cFΦR$_4$-PTP1B and/or secondary effects caused by the introduction of cFΦR$_4$-PTP1B (e.g., inactivation of cellular protein tyrosine kinases). Interestingly, different proteins exhibited varying dephosphorylation kinetics. Several proteins in the 150-200 kD range were completely dephosphorylated upon the addition of 62 nM cFΦR$_4$-PTP1B, whereas proteins of ~80 kD remained phosphorylated at 500 nM cFΦR$_4$-PTP1B. The changes in the pY pattern are consistent with the broad substrate specificity of PTP1B (Ren, L et al. Biochemistry, 2011, 50, 2339-2356) and very similar to that caused by overexpression of PTP1B inside the cytosol of mammalian cells (LaMontagne Jr., K R et al. Proc. Natl. Acad. Sci. U.S.A., 1998, 95, 14094-14099). These results indicate that cFΦR$_4$ can deliver PTP1B into the interior of NIH 3T3 cells in the catalytically active form and to sufficient levels to perturb the cell signaling process. cFΦR$_4$ thus provides a tool for introducing other functional proteins, especially proteins that cannot be genetically expressed (e.g., toxic and chemically modified proteins), into mammalian cells in order to study their cellular functions.

TABLE 9

| Kinetic Activities ($k_{cat}/K_M$, M$^{-1}$ s$^{-1}$) of PTP1B and cFΦR$_4$-PTP1B against pNPP[a] | |
|---|---|
| enzyme | $k_{cat}/K_M$ (M$^{-1}$ s$^{-1}$) |
| PTP1B | 1340 |
| cFΦR$_4$-PTP1B | 1600 |

[a]pNPP = p-nitrophenyl phosphate; $k_{cat}/K_M$ was measured as previously described (Ren, L et al. Biochemistry, 2011, 50, 2339-2356).

Stability and Cytotoxicity of cFΦR$_4$.

Figure 13A:
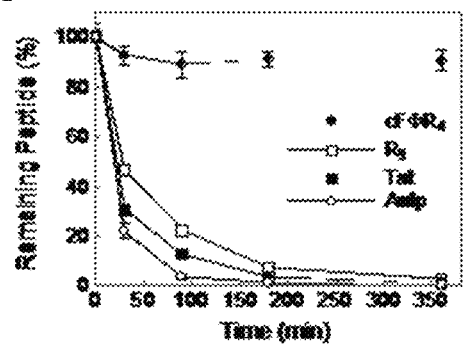
FIGS. 13A and 13B display.
Figure 13B:
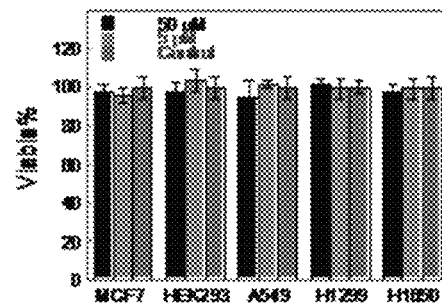
Figure 14A:
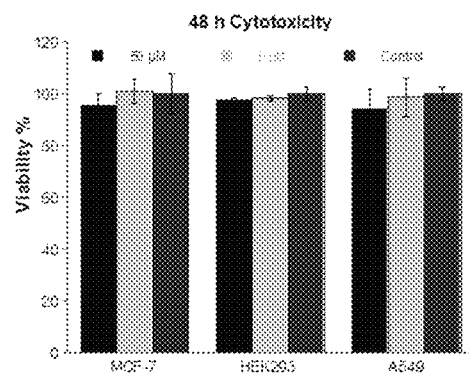
FIGS. 14A and 14B display MTT assay of various mammalian cells after treatment with cFΦR$_4$ (5 or 50 μM) for (FIG. 14A) 48 h or (FIG. 14B) 72 h.
Figure 14B:
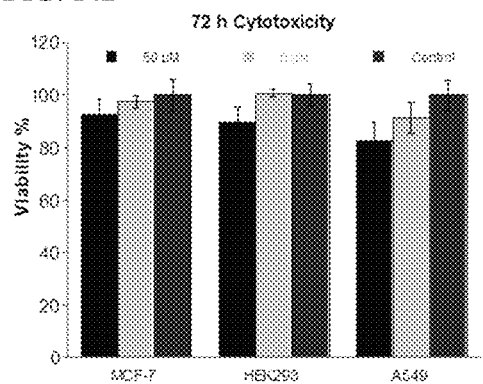

The relative stability of cFΦR$_4$, R$_9$, Tat, and Antp (Table 8, compounds 19-22) against proteolytic degradation was determined by incubating the CPPs in 25% human serum at 37° C. and following the disappearance of the full-length peptides by reversed-phase HPLC. The cationic tryptophan-containing peptide, Antp, was least stable among the four CPPs; it was degraded at a half-life of <20 min and was completely digested after 2 h (FIG. 13A). R9 and Tat were slightly more stable than Antp, having half-lives of ~30 min. In contrast, cFΦR$_4$ was remarkably stable against serum proteases. There was less than 10% degradation after 6 h of incubation; after 24 h of incubation in the serum, >70% of cFΦR$_4$ remained intact. Numerous other studies have also demonstrated that cyclization of peptides increases their proteolytic stabilities (Nguyen, L T et al. PLoS One, 2010, 5, e12684). The potential cytotoxicity of cFΦR$_4$ was assessed by MTT assays with five different human cell lines (HEK293, MCF-7, A549, H1650, and H1299). After 24 or 48 h of incubation with up to 50 µM cFΦR$_4$, there was no significant growth inhibition for any of the cell lines (FIG. 13B and FIG. 14). After 72 h, a slight growth inhibition (up to 20%) was observed at 50 µM (FIG. 14). Thus, cFΦR$_4$ is relatively nontoxic to mammalian cells.

Figure 15:
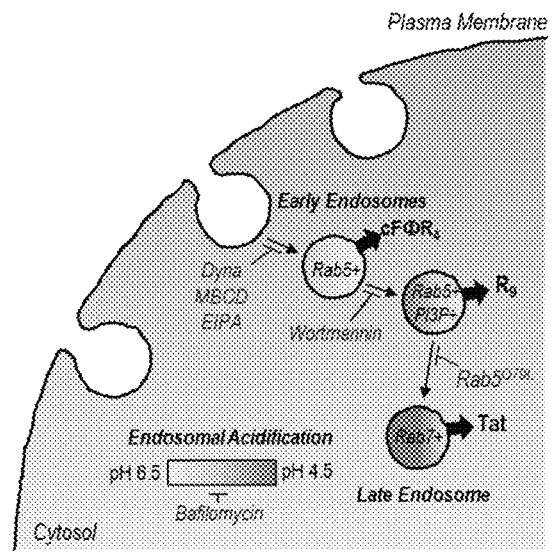
FIG. 15 displays a diagram showing the points along the endocytic pathway where cFΦR$_4$, R$_9$, and Tat escape into the cytoplasm and where specific inhibitors are proposed to function.

In this study, it was demonstrated that cFΦR$_4$ can be effective for exocyclic delivery of small-molecule, peptide, and protein cargos into the cytoplasm and nucleus of mammalian cells. By using a pCAP-containing peptide as cargo/reporter, it was shown that cFΦR$_4$ can be 3.7-12-fold more efficient than R9, Tat, and Antp for cytoplasmic cargo delivery, making cFΦR$_4$ one of the most active CPPs known to date. Although modification of polybasic CPPs such as addition of hydrophobic acyl groups has previously been reported to enhance cellular uptake by a similar magnitude (Pham, W et al. *Chembiochem*, 2004, 5, 1148-1151), these previous studies have not established whether the enhanced uptake translates into a similar increase in the cytoplasmic CPP concentration. The pCAP-based reporter system described herein can provide a simple, robust method to quantitatively assess the cytoplasmic delivery efficiency of other CPPs. Several lines of evidence indicate that cFΦR$_4$ can enter cells through multiple endocytic mechanisms, including its failure to enter cells at 4° C. or in the presence of sodium azide, partial overlap between the fluorescence puncta of cFΦR$_4^{Rho}$ and the fluid phase endocytic marker dextran$^{FITC}$, colocalization of cFΦR$_4^{Rho}$ and endosomal proteins Rab5 and Rab7, and decreased cFΦR$_4^{Dex}$ uptake upon administration of endocytic inhibitors. The minimal effect of the PI3K inhibitor wortmannin and the Rab5 Q79L mutation on the cytoplasmic delivery of cFΦR$_4$, in addition to the strong colocalization observed between cFΦR$_4$ and Rab5$^+$ endosomes, suggest that cFΦR$_4$ can escape from early endosomes (FIG. 15). In comparison, Tat has been demonstrated to enter cells through endocytosis and release from late endosomes, while R9 escapes endosomes prior to Rab7 recruitment (Appelbaum, J S et al. *Chem. Biol.*, 2012, 19, 819-830). Early endosomal release can offer advantages, especially for peptide and protein cargos, since it can minimize cargo degradation by late endosomal and lysosomal proteases and denaturation caused by acidification during endosomal maturation. Indeed, both GFP and PTP1B delivered into the cytoplasm by cFΦR$_4$ were in their folded, active forms, as evidenced by the green fluorescence and the ability to dephosphorylate intracellular pY proteins, respectively. Additionally, due to its more rigid structure, cFΦR$_4$ can be more stable against proteolytic degradation than linear peptides, and due to its smaller size, cFΦR$_4$ can be less expensive to synthesize and potentially less likely to interfere with the cargo function. These properties can make cFΦR$_4$ a useful transporter for cytosolic delivery of small-molecule to protein cargos. Direct protein delivery can provide a useful research tool, e.g., for studying the cellular function of a protein, as it can offer improved temporal control over DNA transfection and subsequent gene expression and can allow delivery of chemically modified proteins and proteins whose overexpression can cause toxicity. The ability of cFΦR$_4$ to escape from early endosomes and its simple structure can also provide an excellent system for elucidating the mechanism of endosomal escape and the factors that influence the escape efficiency.

Example 2

Cyclization of peptide ligands can be effective for improving their stability against proteolytic degradation and in some cases their cell permeability. However, this strategy is not compatible with proteins that recognize peptide ligands in the extended conformations (e.g., β-strand and α-helix). In this work, a general strategy for intracellular delivery of linear peptide ligands was developed, by fusing them with an amphipathic sequence motif (e.g., RRRRΦF, where Φ is L-naphthylalanine) and cyclizing the resulting conjugate through a disulfide bond. The cyclized peptides can have enhanced proteolytic stability and membrane permeability; upon entering the cytoplasm/nucleus of a cell, the disulfide bond can be cleaved by the reducing intracellular environment to release the linear, biologically active peptide. This strategy was applied to generate cell permeable peptides as caspase substrates and inhibitors against the CAL PDZ domain for potential treatment of cystic fibrosis.

Figure 16:
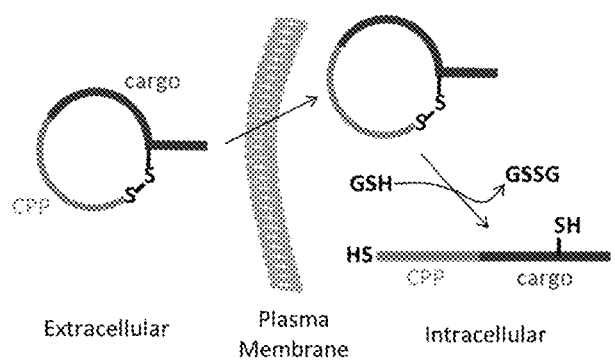
FIG. 16 displays scheme showing the reversible cyclization strategy for delivering linear peptidyl cargos into mammalian cells. GSH, glutathione.
Figure 17A:
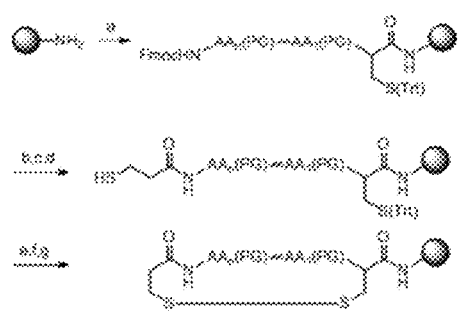
FIGS. 17A, 17B, 17C, 17D, 17E, and 17F display.
Figure 17B:
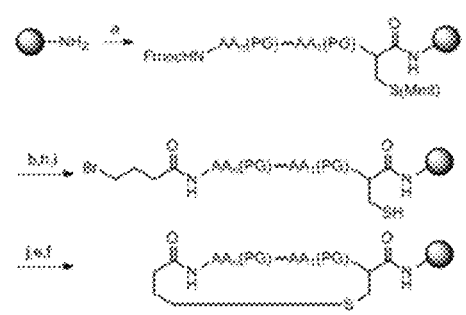
Figure 17C:
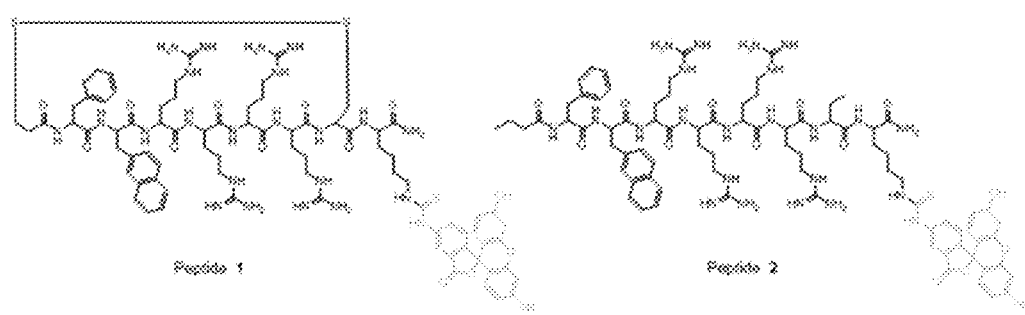
Figure 17D:
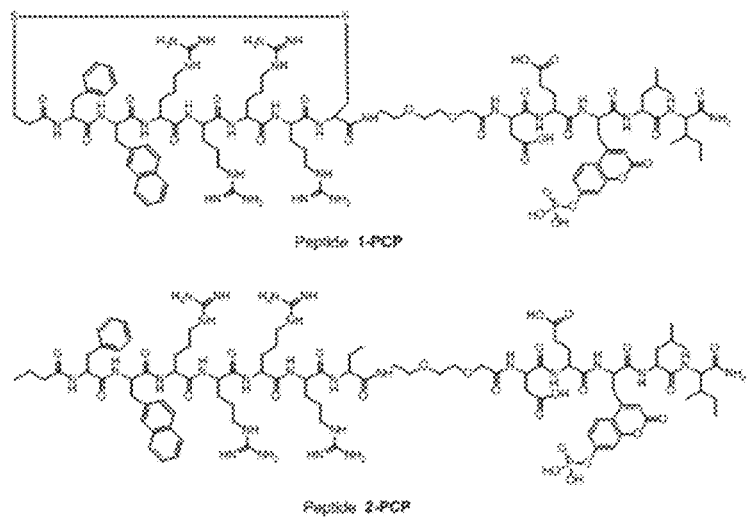
Figure 17E:
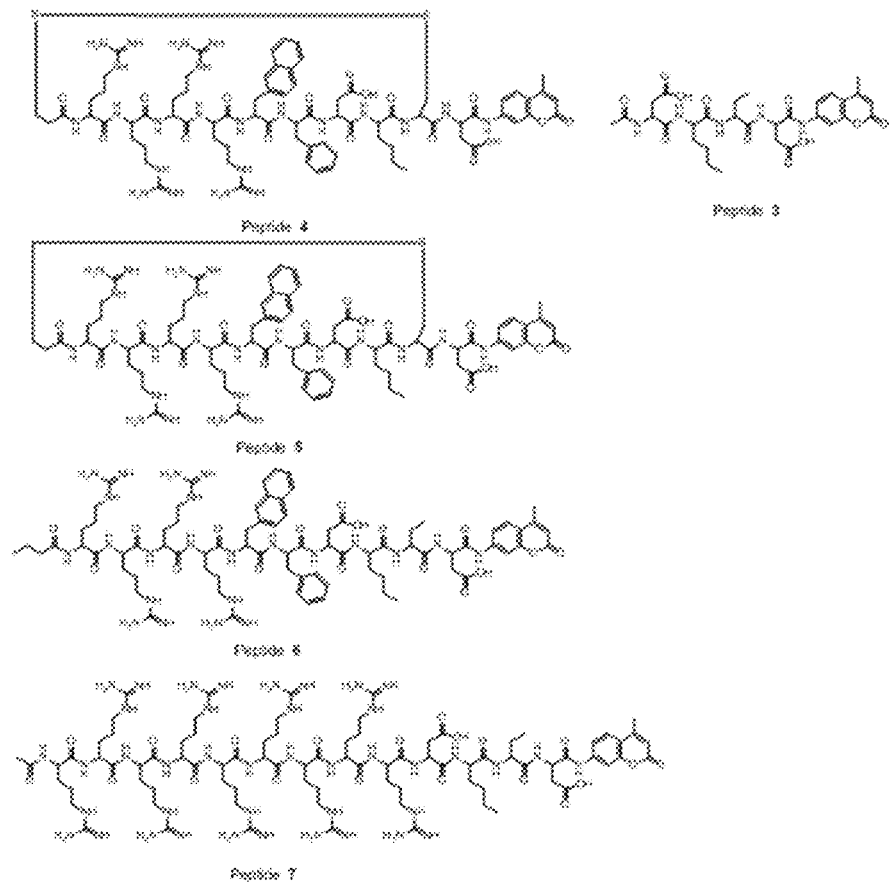
Figure 17F:
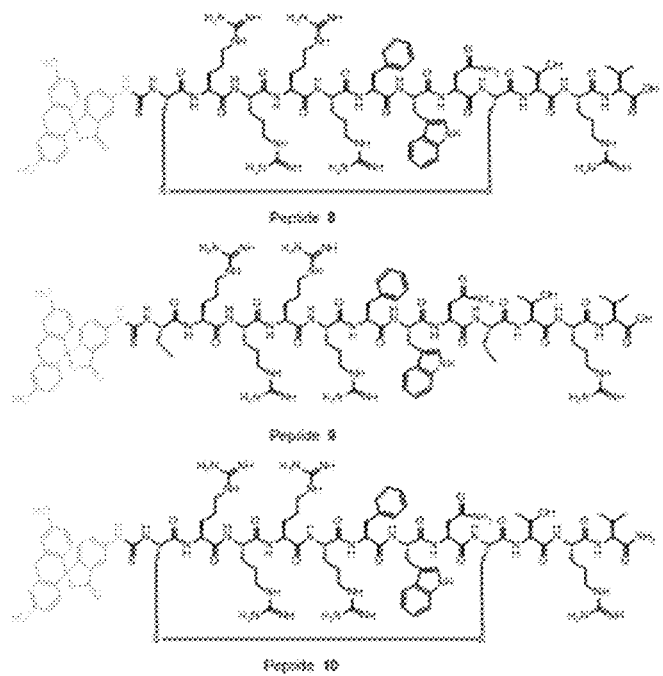

The applicability of linear peptides as drugs is often limited by their susceptibility to proteolytic cleavage and poor membrane permeability. Cyclization of peptides can be effective for improving their proteolytic stability (Nguyen, L T et al. *PLoS One*, 2010, 5, e12684). Moreover, it was recently reported that cyclization of certain amphipathic peptides (e.g., FΦRRRR, where Φ is L-2-naphthylalanine) can render them cell permeable through an active transport mechanism (Qian, Z et al. *ACS Chem. Biol.* 2013, 8, 423). Biologically active cyclic peptides can be delivered into the cytoplasm and nucleus of mammalian cells by incorporating into them these short sequence motifs (Qian, Z et al. *ACS Chem. Biol.* 2013, 8, 423). However, in many circumstances, binding to a molecular target (e.g., PDZ (Doyle, D A et al. *Cell* 1996, 85, 1067; Morais Cabral, J H et al., *Nature* 1996, 382, 649) and BIR domains (Wu, G et al. *Nature* 2000, 408, 1008)) can require that the peptidyl ligand exist in its extended conformation (e.g., α-helix and β-strand) and cyclization may interfere with target binding. Herein, a potentially general strategy for delivering linear peptide ligands into mammalian cells through reversible, disulfide bond-mediated cyclization is examined. When present in the oxidizing extracellular environment, the peptides can exist as macrocycles, which can have enhanced stability against proteolysis and cell permeability. Upon entering the cell (i.e., cytoplasm and/or nucleus), the disulfide bond can be reduced by the intracellular thiols to produce the linear, biologically active peptides (FIG. 16) (Cascales, L et al. *J. Biol Chem.* 2011, 286, 36932; Jha, D et al. *Bioconj Chem.* 2011, 22, 319).

Materials.

Reagents for peptide synthesis were purchased from Advanced ChemTech (Louisville, Ky.), NovaBiochem (La Jolla, Calif.), or Anaspec (San Jose, Calif.). Rink resin LS (100-200 mesh, 0.2 mmol/g) was purchased from Advanced ChemTech. Dextrane$^{Rho}$, trypsin and α-chymotrypsin were purchased from Sigma-Aldrich (St. Louis, Mo.). Cell culture media, fetal bovine serum, penicillin-streptomycin, 0.25% trypsin-EDTA, and DPBS were purchased from Invitrogen (Carlsbad, Calif.). Nuclear staining dye DRAQ5 was purchased from Thermo Scientific (Rockford, Ill.). Caspase-3, Human, recombinant protein was purchased from EMD Chemicals (San Diego, Calif.).

Peptide Synthesis.

Most peptides were synthesized on Rink Resin LS (0.2 mmol/g) using standard Fmoc chemistry. The typical coupling reaction contained 5 equiv of Fmoc-amino acid, 5 equiv of 2-(7-aza-1H-benzotriazole-1-yl)-1,1,3,3-tetramethyluronium hexafluorophosphate (HATU) and 10 equiv of diisopropylethylamine (DIPEA) and was allowed to proceed with mixing for 75 min. The peptides were deprotected and released from the resin by treatment with 92.5:2.5:2.5:2.5

(v/v) trifluoroacetic acid (TFA)/water/phenol/triisopropylsilane (TIPS) for 2 h. The peptides were triturated with cold ethyl ether (3×) and purified by reversed-phase HPLC equipped with a C18 column. Peptide labeling with fluorescein isothiocyanate (FITC) was performed by dissolving the purified peptides (~1 mg each) in 300 μL of 1:1:1 DMSO/DMF/150 mM sodium bicarbonate (pH 8.5) and mixing with 10 μL of FITC in DMSO (100 mg/mL). After 20 min at room temperature, the reaction mixture was subjected to reversed-phase HPLC on a $C_{18}$ column to isolate the FITC-labeled peptide.

To generate disulfide bond mediated cyclic peptides, the 3,3'-dithiodipropionic acid (10 equiv) were coupled on the N-terminal using 10 equiv N,N'-Diisopropylcarbodiimide (DIC) and 0.1 equiv 4-(dimethylamino)pyridine (DMAP) in anhydrous DCM for 2 h after the removal of the N-terminal Fmoc protection group by treatment with 20% (v/v) piperidine in DMF. The resin then was incubated in 20% β-mercaptoethanol in DMF for 2 h twice to expose the free thiol. Triturated crude linear peptides were incubated in 5% DMSO in pH 7.4 PBS buffer overnight (Tam, J P et al. *J. Am. Chem. Soc.* 1991, 113, 6657), followed by trituration and HPLC purification as described above (Tam, J P et al. *J. Am. Chem. Soc.* 1991, 113, 6657).

To produce thioether mediated cyclic peptides, 4-bromobutyric acid (10 equiv) was coupled on the N-terminal using 10 equiv DIC and 0.1 equiv DMAP in anhydrous DCM for 2 h after the removal of the N-terminal Fmoc protection group by treatment with 20% (v/v) piperidine in DMF. The 4-methoxytrityl (Mmt) protection group on the L-cysteine side chain was selectively removed using 1% trifluoroacetic acid (TFA) in DCM. Thioether formation was conducted by incubating the resin in 1% DIPEA in DMF under nitrogen protection overnight. The cyclized peptide was then triturated and purified as described above (Roberts, K D et al. *Tetrahedron Lett.* 1998, 39, 8357).

Fmoc-Asp(Wang-resin)-AMC (AMC=7-amino-4-methylcoumarin) (NovaBiochem) was used as a solid support to synthesize fluorogenic caspase substrates. Standard Fmoc chemistry was employed to synthesize the peptide on solid phase. These peptides were released from the resin by the treatment with 95:2.5:2.5 (v/v) TFA/phenol/water for 2 h (Maly, D J et al. *J. Org. Chem.* 2002, 67, 910).

Cell Culture.

HeLa cells were maintained in medium consisting of DMEM, 10% fetal bovine serum (FBS) and 1% penicillin/streptomycin. Jurkat cells were maintained in medium consisting of RPMI-1640, 10% FBS and 1% penicillin/streptomycin. The bronchial epithelial CFBE cell line, homozygous for the ΔF508-CFTR mutation, was maintained in DMEM containing L-glutamine supplemented with 10% FBS and 1% penicillin/streptomycin. The tissue culture plates were coated using human fibronectin (1 mg/ml), collagen I bovine (3 mg/ml), and bovine serum albumin (1 mg/ml) Cells were cultured in a humidified incubator at 37° C. with 5% $CO_2$.

Confocal Microscopy.

To detect peptide internalization, 1 mL of HeLa cell suspension (5×10⁴ cells) was seeded in a 35 mm glass-bottomed microwell dish (MatTek) and cultured overnight. Cells were gently washed with DPBS twice and treated with FITC labeled peptides (5 μM) and dextran$^{Rho}$ (0.5 mg mL$^{-1}$) in phenol-red free DMEM containing 1% serum at 37° C. for 1 h in the presence of 5% $CO_2$. After removal of the medium, the cells were gently washed with DPBS twice and incubated with 5 μM DRAQS in DPBS for 10 min. The cells were again washed with DPBS twice and imaged on a Visitech Infinity 3 Hawk 2D-array live cell imaging confocal microscope. Images were captured under the same parameters and adjusted under the same setting using MetaMorph (Molecular Devices).

Flow Cytometry.

HeLa cells were cultured in six-well plates (5×10⁵ cells per well) for 24 h. On the day of experiment, the cells were incubated with 5 μM FITC labeled peptide in clear DMEM with 1% FBS at 37° C. for 2 h. The cells were washed with DPBS, detached from plate with 0.25% trypsin, diluted into clear DMEM containing 10% FBS, pelleted at 250 g for 5 min, washed once with DPBS and resuspended in DPBS containing 1% bovine serum albumin, and analyzed on a BD FACS Aria flow cytometer. Data were analyzed with Flowjo software (Tree Star).

To quantify the delivery efficiencies of PCP-conjugated peptides, HeLa cells were cultured in six-well plates (5×10⁵ cells per well) for 24 h. On the day of experiment, the cells were incubated with 5 μM pCAP-containing peptide in clear DMEM with 1% FBS at 37° C. for 2 h. The cells were washed with DPBS containing 1 mM sodium pervanadate, detached from plate with 0.25% trypsin, suspended in DPBS containing 1% bovine serum albumin, and analyzed on a BD FACS Aria flow cytometer with excitation at 355 nm.

Peptide Proteolysis Stability Assay.

The stability tests were carried out by slightly modifying a previously reported procedure (Frackenpohl, J et al. *Chembiochem* 2001, 2, 445). 24 μL of 1.5 mM peptide solution was incubated at 37° C. with 30 μL 50 μM of α-chymotrypsin and 30 μL 50 μM of trypsin in 200 μL of working buffer (50 mM Tris-HCl, pH 8.0, NaCl (100 mM), $CaCl_2$ (10 mM)). At various time points (0-12 h), 40 μL aliquots were withdrawn and mixed with 40 μL of 15% trichloroacetic acid and incubated at 4° C. overnight. The final mixture was centrifuged at 15,000 rpm for 10 min in a microcentrifuge, and the supernatant was analyzed by reversed-phase HPLC equipped with a C18 column (Waters). The amount of remaining peptide (%) was determined by integrating the area underneath the peptide peak (monitored at 214 nm) and compared with that of control reaction (no proteases).

In Cellulo Fluorimetric Assay.

100 μL of Jurkat cell suspension (5×10⁵ cells/mL) was seeded in 96-well plate one hour prior to the experiment. Ten μL of staurosporine stock solution (10 μM) was added into half of the wells to induce apoptosis, while 10 μL of media was added to the other wells. After 1 h incubation, caspase-3 fluorogenic substrates were added to the cells to a final concentration of 5 μM. The fluorescence of the released coumarin was measured on the Spectramax M5 plate reader with excitation and emission wavelengths at 360 and 440 nm at various times points (0-6 h). The fluorescence unit (FU) increases between induced and uninduced cells were plotted against the time to present caspase-3 activities measured using various fluorogenic substrates in living cell in real-time. Three independent sets of experiments, each performed in triplicate, were conducted.

In Vitro Fluorimetric Assay.

0.5 μL (100 U/μL) caspase-3 enzyme was first incubated with 90 μL of reaction buffer (50 mM HEPES, pH 7.4, 100 mM NaCl, 10 mM DTT) for 30 min in 96-well plate. Fluorogenic substrates (10 μL, 100 μM) were mixed into the above solutions to start the reactions, and the plate was measured on a Spectramax M5 plate reader (Ex=360 nm, Em=440 nm) (Molecular Devices). Fluorescence units (FU) increase at one-minute intervals was correlated to the release of Amc due to protease activity. The ΔFU/min was calculated from the linear portion of the reaction curve. Reported values are averages of three trials with the standard deviation indicated.

Fluorescence Anisotropy.

The full fluorescence anisotropy (FA) titration experiment was performed by incubating 100 nM fluorophore-labeled peptidyl ligands with varying concentrations (0-6 µM) of CAL-PDZ (Cushing, P R et al. *Biochemistry* 2008, 47, 10084) in FA buffer (20 mM HEPES, pH 7.4, 150 mM NaCl, 5 mM glutathione, 0.1% (w/v) bovine serum albumin) for 2 h at room temperature. The FA values were measured on a Molecular Devices Spectramax M5 spectrofluorimeter, with excitation and emission wavelengths at 485 nm and 525 nm, respectively. Equilibrium dissociation constants ($K_D$) were determined by plotting the fluorescence anisotropy values as a function of CAL-PDZ concentration. The titration curves were fitted to the following equation, which assumes a 1:1 binding stoichiometry $$Y = \frac{\left(A_{min} + \left(A_{max} \times \frac{Q_b}{Q_f} - A_{min}\right)\left(\frac{(L+x+K_D) - \sqrt{((L+x+K_D)^2 - 4Lx)}}{2L}\right)\right)}{\left(1 + \left(\frac{Q_b}{Q_f} - 1\right)\left(\frac{(L+x+K_D) - \sqrt{((L+x+K_D)^2 - 4Lx)}}{2L}\right)\right)}$$

where Y is the measured anisotropy at a given CAL-PDZ concentration x; L is the bicyclic peptide concentration; $Q_b/Q_f$ is the correction fact for dye-protein interaction; $A_{max}$ is the maximum anisotropy when all the peptides are bound to CAP-PDZ, while $A_{min}$ is the minimum anisotropy when all the peptides are free.

Immunofluorescent Staining.

Briefly, the bronchial epithelial CFBE cells, homozygous for the DF508-CFTR mutation, were treated with 10 mM Corr-4a in the presence and absence of 50 µM unlabeled peptide 8. After the treatments, cells were fixed in cold methanol for 20 min. The slides were then incubated in 1% BSA/PBS for 10 min, followed by incubation at 37° C. for 1 h with mouse anti-human monoclonal CFTR antibody (R&D Systems). Thereafter, the slides were incubated at 37° C. for 45 min with Alexa Fluor® 488-conjugated anti-mouse IgG2a secondary antibody. Cells were visualized on a Leica TCS SP2 AOBS confocal laser scanning microscope. All measurements were conducted in a double-blinded manner by two independent investigators.

SPQ Intracellular Chloride Concentration Assay.

A SPQ (6-Methoxy-N-(3-sulfopropyl)quinolinium) assay was utilized to estimate the transport activity of ΔF508-CFTR activity in CFBE cells, as the fluorescence of SPQ is negatively correlated with increasing concentration of intracellular chloride (Illsley, N P and Verkman, A S. *Biochemistry* 1987, 26, 1215). CFBE cells were grown on 96-well plate, which was pre-coated with 1 mg/ml human fibronectin, 3 mg/ml collagen I bovine, and 1 mg/ml bovine serum albumin, using DMEM media supplemented with L-glutamine and 10% FBS. Cells were first treated in the presence or absence of 20 µM CFTR corrector VX809 (Van Goor, F et al. *Proc. Natl. Acad. Sci.* U.S.A. 2011, 108, 18843) for 24 h and 50 µM CAL-PDZ domain inhibitors for 1 h. Cells were then loaded with SPQ using hypotonic shock at 37° C. for 15 min with 10 mM SPQ containing 1:1 (v/v) Opti-MEM/ water solution. The cells were then washed and incubated twice for 10 min with fluorescence quenching NaI buffer (130 mM NaI, 5 mM KNO$_3$, 2.5 mM Ca(NO$_3$)$_2$, 2.5 mM Mg(NO$_3$)$_2$, 10 mM D-glucose, 10 mM N-(2-hydroxyethyl) piperazine-N'-(2-ethanesulfonic) acid (HEPES, pH 7.4)). Subsequently, the cells were switched to a dequenching isotonic NaNO$_3$ buffer (identical to NaI buffer except that 130 mM NaI was replaced with 130 mM NaNO$_3$) with a CFTR activation cocktail (10 µM forskolin and 50 µM genistein). Fluorescence non-specific to CFTR-mediated iodide efflux was measured by incubating the cells with the activation cocktail and the CFTR specific inhibitor GlyH101 (10 µM). The effects of CAL-PDZ inhibitors were evaluated by the fluorescence increasing rate above the basal level. The fluorescence of dequenched SPQ was measured using the plate reader VICTOR X3 (Perkin Elmer) with excitation wavelength at 350 nm and DAPI emission filter. The data was presented as mean±standard deviation from at least three individual experiments.

A homodectic amphipathic cyclic peptide, cyclo (FΦRRRRQ) (cFΦR$_4$), has been reported as a highly active cell-penetrating peptide (CPP) which can enter the cytoplasm of mammalian cells through endocytosis and endosomal escape (Qian, Z et al. *ACS Chem. Biol.* 2013, 8, 423). To test the validity of the reversible cyclization strategy, a N-3-mercaptopropionyl-FΦRRRRCK-NH$_2$ peptide was synthesized and then cyclized by forming an intramolecular disulfide bond (FIG. 17; Table 10, peptide 1). A linear peptide of the same sequence (Table 10, peptide 2) was also synthesized by replacing the N-terminal 3-mercaptopropionyl group with a butyryl group and the C-terminal cysteine with 2-aminobutyric acid (Abu or U). Both peptides were labeled at a C-terminal lysine residue with fluorescein isothiocyanate (FITC) and their cellular uptake was assessed by live-cell confocal microscopy and flow cytometry. HeLa cells treated with the cyclic peptide (5 µM) showed strong, diffuse green fluorescence throughout the entire cell volume, whereas the endocytosis marker, rhodamine-labeled dextran (dextran$^{Rho}$), exhibited only punctuate fluorescence in the cytoplasmic region (FIG. 18A). The nearly uniform distribution of FITC fluorescence in both cytoplasmic and nuclear regions suggests that the cyclic peptide was efficiently internalized by HeLa cells and like the parent cyclic peptide, cFΦR$_4$, was able to efficiently escape from the endosome. In contrast, cells treated with the linear control peptide showed much weaker intracellular fluorescence under the same imaging condition. Quantitation of the total intracellular fluorescence by fluorescence-activated cell sorting (FACS) gave mean fluorescence intensity (MFI) of 27, 100, 5530, and 1200 arbitrary units (AU), for cells treated with the disulfide cyclized peptide, linear peptide, and FITC alone, respectively (FIG. 18B). A highly negatively charged pentapeptide, Asp-Glu-pCAP-Leu-Ile (PCP, where pCAP is phosphocoumaryl aminopropionic acid), was also used as cargo and attached to peptides 1 and 2 through a polyethyleneglycol linker (FIG. 17). pCAP is non-fluorescent but, when delivered into the mammalian cytoplasm, undergoes rapid dephosphorylation to generate a fluorescent product, coumaryl aminopropionic acid (CAP) (Stanford, S M et al. *Proc. Natl. Acad. Sci.* U.S.A. 2012, 109, 13972). The pCAP assay therefore provides a quantitative assessment of the cytoplasmic/nuclear concentrations of different CPPs (Qian, Z et al. *ACS Chem. Biol.* 2013, 8, 423). FACS analysis of HeLa cells treated with 5 µM peptide 1-PCP and peptide 2-PCP gave MFI values of 3020 and 700, respectively (FIG. 19). Thus, the above results indicate that cyclization of FΦRRRR through a disulfide bond can have a similar effect to the N-to-C cyclization and can increase its cellular uptake efficiency by ~5-fold (Qian, Z et al. *ACS Chem. Biol.* 2013, 8, 423). In addition, cyclization by disulfide bond formation can enhance the proteolytic resistance of the peptide. Incubation of peptide 1 with a protease cocktail for 12 h resulted in <50% degradation, whereas the linear peptide 2 was degraded with a half-life of ~20 min under the same condition (FIG. 20).

TABLE 10

Sequences of peptides.

| SEQ ID NO | Peptide ID | Peptide Sequence[a] |
|---|---|---|
| 123 | 1 | S————————S⎤<br>⎣—CH$_2$CH$_2$CO-FΦRRRRCK(FITC)-NH$_2$ |
| 124 | 2 | CH$_3$CH$_2$CH$_2$CO-FΦRRRRUK(FITC)-NH$_2$ |
| 125 | 3 | Ac-DMUD-Amc |
| 126 | 4 | S————————S——⎤<br>⎣—CH$_2$CH$_2$CO-RRRRΦFDΩCD-A$^{mc}$ |
| 127 | 5 | ⎡————————S——⎤<br>⎣—CH$_2$CH$_2$CO-RRRRΦFDΩCD-A$^{mc}$ |
| 128 | 6 | CH$_3$CH$_2$CH$_2$CO-RRRRΦFDΩUD-A$^{mc}$ |
| 129 | 7 | A$^c$-RRRRRRRRRDΩUD-A$^{mc}$ |
| 130 | 8 | ⎡—S————S—⎤<br>FITC-CRRRRFWQCTRV-OH |
| 131 | 9 | FITC-URRRRFWQUTRV-OH |
| 132 | 11 | ⎡—S————S—⎤<br>FITC-CRRRRFWQCTRV-NH$_2$ |

[a]Amc, 7-amino-4-methylcoumarin; FITC, fluorescein isothiocyanate; Φ, L-2-naphthylalanine; Ω, norleucine; U, 2-aminobutyric acid.

To illustrate the utility of the reversible cyclization strategy, it was used to deliver specific caspase substrates into cells and monitor intracellular caspase activities in real time (Riedl, S J and Shi, Y. Nat. Rev. Mol. Cell Biol. 2004, 5, 897). Although peptidyl coumarin derivatives have been widely used to detect caspase activities in vitro (Maly, D J et al. Chembiochem 2002, 3, 16), they are generally not suitable for in vivo applications due to impermeability to the mammalian cell membrane. To generate a cell permeable caspase substrate, a caspase 3/7 substrate, Ac-Asp-Nle-Abu-Asp-Amc (Thornberry, N A et al. J. Biol. Chem. 1997, 272, 17907) (Table 10, peptide 3, where Amc is 7-amino-4-methylcoumarin and Nle is norleucine), was fused with the CPP motif RRRRΦF. The fusion peptide was subsequently cyclized by the addition of a 3-mercaptopropionyl group to its N-terminus, replacement of the C-terminal Abu with a cysteine, and formation of an intramolecular disulfide bond, to give cyclic peptide 4 (Table 10). For comparison, an isosteric but irreversibly cyclized peptide (Table 10, peptide 5) was synthesized by forming a thioether bond between an N-terminal bromobutyryl moiety and the C-terminal cysteine (FIG. 17). A linear control peptide of the same sequence was also prepared as described above (Table 10 peptide 6). Finally, the caspase 3/7 substrate was conjugated to non-aarginine (R9) to generate a positive control peptide (Table 10, peptide 7). In vitro kinetic analysis revealed that fusion of the caspase 3/7 substrate to RRRRΦF and R9 decreased its activity by 53% and 72%, respectively, relative to peptide 3, whereas cyclization by thioether formation rendered the peptide inactive toward recombinant caspase 3 (Table 11). The activity of peptide 4 toward caspase 3 could not be reliably determined because the caspase assay required a reducing environment, which would cleave the disulfide bond. Given the structural similarity between peptides 4 and 5, it can be assumed that peptide 4 in the cyclic form is also inactive toward caspases, but has similar activity to peptide 6 after reductive cleavage of the disulfide bond.

TABLE 11

In vitro activity of various fluorogenic substrates against recombinant caspase-3 enzyme.

| Peptide ID | ΔFU/min |
|---|---|
| 3 | 159 ± 19 |
| 5 | No detectable activity |
| 6 | 74.7 ± 5.5 |
| 7 | 45.3 ± 6.5 |

Jurkat cells were pretreated with the kinase inhibitor staurosporin to induce caspase activities and thus apoptosis (Belmokhtar, C A et al. Biochem. J. 1996, 315, 21). These cells were then incubated with peptides 3-7 and the amount of Amc released was monitored at various time points (0-10 h). The impermeable caspase substrate (peptide 3) produced little fluorescence increase over the 10-h period (FIG. 21). Peptide 4 produced the fastest fluorescence increase, reaching 459 fluorescence units (FU), followed by peptides 7 and 6. Peptide 5, which is inactive toward caspase 3, also produced AMC in a time-dependent manner, albeit at a much slower rate (99 FU). This slow rate of AMC release can be attributed to hydrolysis by other intracellular proteases and peptidases. Consistent with this interpretation, pretreatment of Jurkat cells with a pancaspase inhibitor Z-VAD(OMe)-FMK (Slee, E A et al. Biochem J. 1996, 315, 21) followed by incubation with peptide 4 released AMC at a rate that was similar to that of peptide 5 alone. One explanation of the above observations is that both peptides 4 and 5 can enter the cell interior efficiently, but only peptide 4 can be converted into the linear caspase substrate inside the cells.

Many protein-protein interactions (PPIs) are mediated by protein domains binding short peptides in their extended conformations (e.g., α-helix and β-strand) (Pawson, T and Nash, P. Science 2003, 300, 445). For example, the PDZ domain is a common structural domain of 80-90 amino acids found in the signaling proteins of bacteria to man (Doyle, D A et al. Cell 1996, 85, 1067; Morais Cabral, J H et al., Nature 1996, 382, 649; Lee, H J and Zheng, J J. Cell Commun. Signal. 2010, 8, 8). PDZ domains recognize specific sequences at the C-termini of their binding partners and the bound peptide ligands are in their extended β-strand conformation (Doyle, D A et al. Cell 1996, 85, 1067; Songyang, Z et al. Science 1997, 275, 73). It was recently reported that the activity of cystic fibrosis membrane conductance regulator (CFTR), a chloride ion channel protein mutated in cystic fibrosis (CF) patients, is negatively regulated by CFTR-associated ligand (CAL) through its PDZ domain (CAL-PDZ) (Wolde, M et al. J. Biol. Chem. 2007, 282, 8099). Inhibition of the CFTR/CAL-PDZ interaction was shown to improve the activity of ΔPhe508-CFTR, the most common form of CFTR mutation (Cheng, S H et al. Cell 1990, 63, 827; Kerem, B S et al. Science 1989, 245, 1073), by reducing its proteasome-mediated degradation (Cushing, P R et al. Angew. Chem. Int. Ed. 2010, 49, 9907). Previous library screening and rational design have identified several peptidyl inhibitors of the CAL-PDZ domain of moderate potencies ($K_D$ values in the high nM to low µM range) (Cushing, P R et al. *Angew. Chem. Int. Ed.* 2010, 49, 9907; Roberts, K E et al. *PLos Comput. Biol.* 2008, 8, e1002477; Kundu, R et al. *Angew. Chem. Int. Ed.* 2012, 51, 7217-7220). However, none of the peptide inhibitors were cell permeable, limiting their therapeutic potential.

Starting with a hexapeptide ligand for the CAL-PDZ domain, WQVTRV (Roberts, K E et al. *PLos Comput. Biol.* 2008, 8, e1002477), a disulfide-mediated cyclic peptide was designed by adding the sequence CRRRRF to its N-terminus and replacing the Val at the −3 position with a cysteine (Table 10, peptide 8). Thus, in peptide 8, the tryptophan residue at the −5 position was designed to serve the dual function of PDZ binding and membrane translocation. To facilitate affinity measurements and quantitation of its cellular uptake, a FITC group was added to the N-terminus of peptide 8. FA analysis showed that in the absence of a reducing agent, peptide 8 showed no detectable binding to CAL-PDZ domain (FIG. 22A). In the presence of 2 mM tris(carboxylethyl)phosphine, which can reduce the disulfide bond, peptide 8 bound to the CAL-PDZ domain with a $K_D$ value of 489 nM. Peptide 8 was readily cell permeable; incubation of HeLa cells with 5 µM peptide 8 for 2 h resulted in intense and diffuse fluorescence throughout the entire cell (FIG. 22B).

Figure 25A:
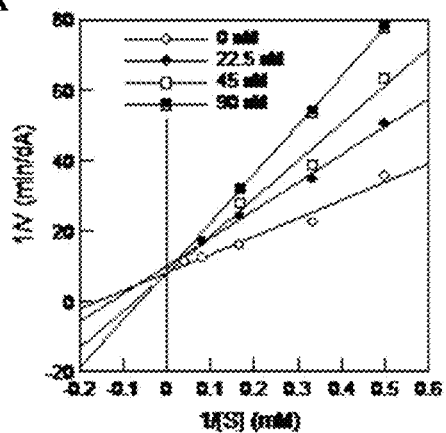
FIGS. 25A and 25B display the competitive inhibition of PTP1B by monocyclic peptide inhibitor 2.

As expected, peptide 8 is readily cell permeable (FIG. 25C). Bronchial epithelial CFBE cells, which are homozygous for the ΔF508-CFTR mutation, were treated with 10 µM Corr-4a in the presence and absence of 50 µM unlabeled peptide 8. Peptide 8, by inhibiting the function of CAL-PDZ domain, is expected to increase the amount of ΔF508-CFTR protein transferred to the plasma membrane, whereas Corr-4a is a small molecule that helps folding of ΔF508-CFTR protein delivered to the plasma membrane. Immunostaining of untreated cells (FIG. 25D, panel I) showed that most of the expressed ΔF508-CFTR was in the endoplasmic reticulum surrounding the cell nucleus. In contrast, treatment of cells with Corr-4a and peptide 8 resulted in much greater amounts of the protein at the cell surface (FIG. 25D panel II). Quantitation of the cell population revealed that a small but significant percentage of cells have wild-type like distribution of ΔF508-CFTR at the cell surface (FIG. 25D). Finally, an SPQ assay was utilized to quantitate the ion channel activity of ΔF508-CFTR CFBE cells untreated or treated with CTFR folding corrector VX809 and peptide 8. Again, VX809 and peptide 8 acted synergistically to improve the function of the channel activity of ΔF508-CFTR (FIG. 25E).

Example 3

Cyclic peptides have great potential as therapeutic agents and research tools but are generally impermeable to the cell membrane. Fusion of the cyclic peptides with a cyclic cell-penetrating peptide can produce bicyclic peptides that can be cell permeable and can retain the ability to recognize specific intracellular targets. Application of this strategy to protein tyrosine phosphatase 1B and peptidyl prolyl cis-trans isomerase Pin1 resulted in potent, selective, proteolytically stable, and biologically active inhibitors against the enzymes.

Cyclic peptides (and depsipeptides) exhibit a wide range of biological activities (Pomilio, A B et al. *Curr. Org. Chem.* 2006, 10, 2075-2121). Several innovative methodologies have recently been developed to synthesize cyclic peptides, either individually (Meutermans, W D F et al. *J. Am. Chem. Soc.* 1999, 121, 9790-9796; Schafmeister, C E et al. *J. Am. Chem. Soc.* 2000, 122, 5891-5892; Sun, Y et al. *Org. Lett.* 2001, 3, 1681-1684; Kohli, R M et al. *Nature* 2002, 418, 658-661; Qin, C et al. *J. Comb. Chem.* 2004, 6, 398-406; Turner, R A et al. *Org. Lett.* 2007, 9, 5011-5014; Hili, R et al. *J. Am. Chem. Soc.* 2010, 132, 2889-2891; Lee, J et al. *J. Am. Chem. Soc.* 2009, 131, 2122-2124; Frost, J R et al. *ChemBioChem* 2013, 14, 147-160) or combinatorially (Eichler, J et al. *Mol. Divers.* 1996, 1, 233-240; Giebel, L B et al. *Biochemistry* 1995, 34, 15430-15435; Scott, C P et al. *Proc. Natl. Acad. Sci. USA* 1999, 96, 13638-13643; Millward, S W et al. *J Am. Chem. Soc.* 2005, 127, 14142-14143; Sako, Y et al. *J. Am. Chem. Soc.* 2008, 130, 7232-7234.; Li, S et al. *Chem. Commun.* 2005, 581-583.; Joo, S H et al. *J. Am. Chem. Soc.* 2006, 128, 13000-13009; Heinis, C et al. *Nat. Chem. Biol.* 2009, 5, 502-507; Tse, B N et al. *J. Am. Chem. Soc.* 2008, 130, 15611-15626), and screen them for biological activity. A particularly exciting application of cyclic peptides is the inhibition of protein-protein interactions (PPIs) (Leduc, A M et al. *Proc. Natl. Acad. Sic. USA* 2003, 100, 11273-11278; Millward, S W et al. *ACS Chem Biol* 2007, 2, 625-634; Tavassoli, A et al. *ACS Chem. Biol.* 2008, 3, 757-764.; Wu, X et al. *Med. Chem. Commun.* 2013, 4, 378-382; Birts, C N et al. *Chem. Sci.* 2013, 4, 3046-3057; Kawakami, T et al. *ACS Chem. Biol.* 2013, 8, 1205-1214; Lian, W et al. *J. Am. Chem. Soc.* 2013, 135, 11990-11995), which remain challenging targets for conventional small molecules. However, a major limitation of cyclic peptides is that they are generally impermeable to the cell membrane, precluding any application against intracellular targets, which include most of the therapeutically relevant PPIs. Although formation of intramolecular hydrogen bonds (Rezai, T et al. *J. Am. Chem. Soc.* 2006, 128, 14073-14080) or $N^{\alpha}$-methylation of the peptide backbone (Chatterjee, J et al. *Acc. Chem. Res.* 2008, 41, 1331-1342; White, T R et al. *Nat. Chem. Biol.* 2011, 7, 810-817) can improve the membrane permeability of certain cyclic peptides, alternative strategies to increase the cell permeability of cyclic peptides are clearly needed.

Protein-tyrosine phosphatase 1B (PTP1B) is a prototypical member of the PTP superfamily and plays numerous roles during eukaryotic cell signaling. Because of its role in negatively regulating insulin and leptin receptor signaling, PTP1B is a valid target for treatment of type II diabetes and obesity (Elchelby, M et al. *Science* 1999, 283, 1544-1548; Zabolotny, J M et al. *Dev. Cell* 2002, 2, 489-495). A large number of PTP1B inhibitors have been reported (He, R et al. in New Therapeutic Strategies for Type 2 Diabetes: Small Molecule Approaches. Ed. R. M. Jones, RSC Publishing 2012, pp 142), however, none of them have succeeded in the clinic. Designing PTP inhibitors is challenging because most of the phosphotyrosine (pY) isosteres, such as difluorophosphonomethyl phenylalanine ($F_2$Pmp) (Burke Jr., T R et al. *Biochem. Biophys. Res. Commun.* 1994, 204, 129-134), are impermeable to the cell membrane. Additionally, because all PTPs share a similar active site, achieving selectivity for a single PTP has been difficult. Herein, a potentially general approach to designing cell-permeable cyclic peptidyl inhibitors against intracellular proteins such as PTP1B is reported.

Materials.

Fmoc-protected amino acids were purchased from Advanced ChemTech (Louisville, Ky.), Peptides International (Louisville, Ky.), or Aapptec (Louisville, Ky.). Fmoc-F2Pmp-OH was purchased from EMD Millipore (Darmstadt, Germany). Aminomethyl-ChemMatrix resin (0.66 mmol/g) was from SJPC (Quebec, Canada). Rink resin LS (100-200 mesh, 0.2 mmol/g) and N-(9-fluorenylmethoxycarbonyloxy) succinimide (Fmoc-OSu) were purchased from Advanced ChemTech. O-Benzotriazole-N,N,N',N'-tetramethyluronium hexafluorophosphate (HBTU), 2-(7-aza-1H-benzotriazole-1-yl)-1,1,3,3-tetramethyluronium hexafluorophosphate (HATU), 1-hydroxybenzotriazole hydrate (HOBt) were purchased from Aapptec. Phenyl isothiocyanate in 1-mL sealed ampoules, fluorescein isothiocyanate (FITC), rhodamine B-labeled dextran (dextran$^{Rho}$) were purchased from Sigma-Aldrich. Cell culture media, fetal bovine serum (FBS), penicillin-streptomycin, 0.25% trypsin-EDTA, Dulbecco's phosphate-buffered saline (DPBS) (2.67 mM potassium chloride, 1.47 mM potassium phosphate monobasic, 137 mM sodium chloride, 8.06 mM sodium phosphate dibasic.), and anti-phospho-IR/IGF1R antibody were purchased from Invitrogen (Carlsbad, Calif.). Nuclear staining dye DRAQ5 and anti-β-actin antibody were purchased from Thermo Scientific (Rockford, Ill.). Antibody 4G10 was purchased from Millipore (Temecula, Calif.). All solvents and other chemical reagents were obtained from Sigma-Aldrich (St. Louis, Mo.) and were used without further purification unless noted otherwise.

Cell Culture.

A549, HEK293, and HepG2 cells were maintained in Dulbecco's modified Eagle medium (DMEM) supplemented with 10% FBS in a humidified incubator at 37° C. with 5% $CO_2$.

Protein Expression, Purification and Labeling.

The gene coding for the catalytic domain of PTP1B (amino acids 1-321) was amplified by the polymerase chain reaction using PTP1B cDNA as template and oligonucleotides 5'-ggaattccatatggagatggaaaaggagttcgagcag-3' and 5'-gggatccgtcgacattgtgtggctccaggattcgtttgg-3' as primers. The resulting DNA fragment was digested with endonucleases Nde I and Sal I and inserted into prokaryotic vector pET-22b(+)-ybbR (Yin, J et al. Proc. Natl. Acad. Sci. U.S.A. 2005, 102, 15815-15820). This cloning procedure resulted in the addition of a ybbR tag (VLDSLEFIASKL) to the N-terminus of PTP1B. Expression and purification of the ybbR-tagged PTP1B were carried out as previously described (Ren, L et al. Biochemistry 2011, 50, 2339-2356). Texas Red labeling of PTP1B was carried out by treating the ybbR-tagged PTP1B protein (80 μM) in 50 mM HEPES, pH 7.4, 10 mM $MgCl_2$ with Sfp phosphopantetheinyl transferase (1 μM) and Texas Red-CoA (100 μM) for 30 min at room temperature (Yin, J et al. Proc. Natl. Acad. Sci. U.S.A. 2005, 102, 15815-15820). The reaction mixture was passed through a G-25 fast-desalting column equilibrated in 30 mM HEPES, pH 7.4, 150 mM NaCl to remove any free dye molecules. The full-length human S16A/Y23A mutant Pin1 was expressed and purified from E. coli as previously described (Liu, T et al. J. Med. Chem. 2010, 53, 2494-2501).

Library Synthesis.

The cyclic peptide library was synthesized on 1.35 g of aminomethyl-ChemMatrix resin (0.57 mmol/g). The library synthesis was performed at room temperature unless otherwise noted. The linker sequence (BBM) was synthesized using standard Fmoc chemistry. The typical coupling reaction contained 5 equiv of Fmoc-amino acid, 5 equiv of HBTU and 10 equiv of diisopropylethylamine (DIPEA) and was allowed to proceed with mixing for 2 h. The Fmoc group was removed by treatment twice with 20% (v/v) piperidine in DMF (5+15 min), and the beads were exhaustively washed with DMF (6×). To spatially segregate the beads into outer and inner layers, the resin (after removal of N-terminal Fmoc group) was washed with DMF and water, and soaked in water overnight. The resin was quickly drained and suspended in a solution of Fmoc-Glu(δ-NHS)-OAll (0.10 equiv), Boc-Met-OSu (0.4 equiv) and N-methylmorpholine (2 equiv) in 20 mL of 1:1 (v/v) DCM/diethyl ether (Joo, S H et al. J. Am. Chem. Soc. 2006, 128, 13000-13009). The mixture was incubated on a carousel shaker for 30 min. The beads were washed with 1:1 DCM/diethyl ether (3×) and DMF (8×). Next, the Fmoc group was removed by piperidine treatment. Then, Fmoc-Arg(Pbf)-OH (4×), Fmoc-Nal-OH, and Fmoc-Phe-OH were sequentially coupled by standard Fmoc chemistry to half of the resin. The other half was coupled with the same amino acids in the reverse sequence. The resin was combined and the random sequence was synthesized by the split-and-pool method using 5 equiv of Fmoc-amino acids, 5 equiv HATU and 10 equiv DIPEA as the coupling agent. The coupling reaction was repeated once to ensure complete coupling at each step. For random positions, a 24-amino acid set was selected based on their structural diversity, metabolic stability, and commercial availability, including 10 proteinogenic α-L-amino acids (Ala, Asp, Gln, Gly, His, Ile, Ser, Trp, Pro, and Tyr), 5 nonproteinogenic α-L-amino acids (L-4-fluorophenylalanine (Fpa), L-homoproline (Pip), L-norleucine (Nle), L-phenylglycine (Phg) and L-4-(phosphonodifluoromethyl) phenylalanine ($F_2Pmp$)), and nine α-D-amino acids (D-2-naphthylalanine (D-Nal), D-Ala, D-Asn, D-Glu, D-Leu, D-Phe, D-Pro, D-Thr, and D-Val). To differentiate isobaric amino acids during PED-MS analysis, 4% (mol/mol) of $CD_3CO_2D$ was added to the coupling reactions of D-Ala, D-Leu, and D-Pro, while 4% $CH_3CD_2CO_2D$ was added to the Nle reactions. Fmoc-F2Pmp-OH (0.06 equiv) and Fmoc-Tyr-OH (0.54 equiv) was placed in the middle of the random positions using HATU/DIPEA. After the entire sequence was synthesized, the allyl group on the C-terminal Glu residue was removed by treatment with a DCM solution containing tetrakis(triphenylphosphine)palladium [Pd$(PPh_3)_4$, 0.25 equiv] and phenylsilane (5 equiv) for 15 min (3×). The beads were sequentially washed with 0.5% (v/v) DIPEA in DMF, 0.5% (w/v) sodium dimethyldithiocarbamate hydrate in DMF, DMF (3×), DCM (3×), and DMF (3×). The Fmoc group on the N-terminal random residue was removed by piperidine as described above. The beads were washed with DMF (6×), DCM (3×), and 1 M HOBt in DMF (3×). For peptide cyclization, a solution of PyBOP/HOBt/DIPEA (5, 5, 10 equiv, respectively) in DMF was mixed with the resin and the mixture was incubated on a carousel shaker for 3 h. The resin was washed with DMF (3×) and DCM (3×) and dried under vacuum for >1 h. Side-chain deprotection was carried out with a modified reagent K 78.5:7.5:5:5:2.5:1:1 (v/v) TFA/phenol/water/thioanisole/ethanedithiol/anisole/triisopropylsilane) for 3 h. The resin was washed with TFA and DCM and dried under vacuum before storage at ~20° C.

Library Screening and Peptide Sequencing.

Library resin (100 mg, 300,000 beads) was swollen in DCM, washed extensively with DMF, doubly distilled $H_2O$, and incubated in 1 mL of blocking buffer (PBS, pH 7.4, 150 mM NaCl, 0.05% Tween 20 and 0.1% gelatin) containing 20 nM Texas red-labeled PTP1B at 4° C. for 3 h. The beads were examined under an Olympus SZX12 microscope equipped with a fluorescence illuminator (Olympus America, Center Valley, Pa.) and the most intensely fluorescent beads were manually collected as positive hits. Beads containing encoding linear peptides were individually sequenced by partial Edman degradation-mass spectrometry (PED-MS) (Liu, T et al. J. Med. Chem. 2010, 53, 2494-2501).

Individual Peptide Synthesis and Labeling.

Monocyclic and bicyclic peptides were synthesized on Rink Resin LS (0.2 mmol/g) using standard Fmoc chemistry. For monocyclic peptides, after the last (N-terminal) residue was coupled, the allyl group on the C-terminal Glu residue was removed by treatment with Pd(PPh$_3$)$_4$ and phenylsilane (0.1 and 10 equiv, respectively) in anhydrous DCM (3×15 min). The N-terminal Fmoc group was removed by treatment with 20% (v/v) piperidine in DMF and the peptide was cyclized by treatment with PyBOP/HOBt/DIPEA (5, 5, and 10 equiv) in DMF for 3 h. For bicyclic peptides, the N-terminal Fmoc group was removed with piperidine and a trimesic acid was coupled on the N-terminal amine using HBTU as a coupling agent. The allyloxycarbonyl groups on the side chains of two Dap residues were removed by treatment with Pd(PPh$_3$)$_4$ and phenylsilane (0.1 and 10 equiv, respectively) in anhydrous DCM for 2 h. The resulting peptide was cyclized with PyBOP as described above. The peptides were deprotected and released from the resin by treatment with 82.5:5:5:5:2.5 (v/v) TFA/thioanisole/water/phenol/ethanedithiol for 2 h. The peptides were triturated with cold ethyl ether (3×) and purified by reversed-phase HPLC on a C18 column. The authenticity of each peptide was confirmed by MALDI-TOF mass spectrometry. Peptide labeling with FITC was performed by dissolving the purified peptide (~1 mg) in 300 µL of 1:1:1 (vol/vol) DMSO/DMF/150 mM sodium bicarbonate (pH 8.5) and mixing with 10 µL of FITC in DMSO (100 mg/mL). After 20 min at room temperature, the reaction mixture was subjected to reversed-phase HPLC on a C18 column to isolate the FITC-labeled peptide.

PTP Inhibition Assay.

PTP assays were performed in a quartz microcuvette (total volume 150 µL). The reaction mixture contains 100 mM Tris-HCl, pH 7.4, 50 mM NaCl, 2 mM EDTA, 1 mM TCEP, 0-1 µM of PTP inhibitor, and 500 µM para-nitrophenyl phosphate (pNPP). The enzymatic reaction was initiated by the addition of PTP (final concentration 15-75 nM) and monitored continuously at 405 nm on a UV-VIS spectrophotometer. Initial rates were calculated from the reaction progress curves (typically <60 s). The half-maximal inhibition constant (IC$_{50}$) was defined as the concentration of an inhibitor that reduced the enzyme activity to 50% and was obtained by plotting the rates (V) against the inhibitor concentration [I] and fitting the data against the equation $$V = \frac{V_0}{\left(1 + \frac{[I]}{IC_{50}}\right)}$$

where V$_0$ is the enzymatic reaction rate in the absence of inhibitor. The inhibition constant (K$_i$) was determined by measuring the initial rates at fixed enzyme concentration (15 nM) but varying concentrations of pNPP (0-24 mM) and inhibitor (0-112 nM). The reaction rate (V) was plotted against the pNPP concentration ([S]) and fitted against the equation $$\frac{1}{V} = K \times \frac{1}{[S]} + \frac{1}{V_{max}}$$

to obtain the Michaelis constant K. The K$_i$ value was obtained by plotting the K values against the inhibitor concentration [I] and fitted to equation $$\frac{K}{K_0} = 1 + \frac{[I]}{K_i}$$

where K$_0$ is the Michaelis constant in the absence of inhibitor ([I]=0).

Confocal Microscopy.

Approximately 5×10$^4$ A549 cells were seeded in 35-mm glass-bottomed microwell dish (MatTek) containing 1 mL of media and cultured for one day. A549 cells were gently washed with DPBS once and treated with the FITC-labeled PTP1B inhibitors (5 µM), dextran$^{Rho}$ (1 mg mL$^{-1}$) in growth media for 2 h at 37° C. in the presence of 5% CO$_2$. The peptide-containing media was removed and the cells were washed with DPBS three times and incubated for 10 min in 1 mL of DPBS containing 5 µM DRAQS. The cells were again washed with DPBS twice. Then the cells were imaged on a Visitech Infinity 3 Hawk 2D-array live cell imaging confocal microscope (with a 60× oil immersion lens) at 37° C. in the presence of 5% CO$_2$. Live-cell confocal microscopic imaging of HEK293 cells after treatment with FITC-labeled Pin1 inhibitors were similarly conducted.

Immunoblotting.

A549 cells were cultured in full growth media to reach 80% confluence. The cells were starved in serum free media for 3 h and treated with varying concentrations of PTP1B inhibitors for 2 h, followed by 30 min incubation in media supplemented with 1 mM sodium pervanadate. The solutions were removed and the cells were washed with cold DPBS twice. The cells were detached and lysed in 50 mM Tris-HCl, pH 7.4, 150 mM NaCl, 1% NP-40, 10 mM sodium pyrophosphate, 5 mM iodoacetic acid, 10 mM NaF, 1 mM EDTA, 2 mM sodium pervanadate, 0.1 mg/mL phenylmethanesulfonyl fluoride, 1 mM benzamidine, and 0.1 mg/mL trypsin inhibitor. After 30 min incubation on ice, the cell lysate was centrifuged at 15,000 rpm for 25 min in a microcentrifuge. The total cellular proteins were separated by SDS-PAGE and transferred electrophoretically to a PVDF membrane, which was immunoblotted using anti-phosphotyrosine antibody 4G10. The same samples were analyzed on a separate SDS-PAGE gel and stained by Coomassie brilliant blue to ascertain equal sample loading in all lanes.

To test the inhibitor's effect on insulin signaling pathway, HepG2 cells were cultured to reach 80% confluence. The cells were starved for 4 h in serum free DMEM media before being treated with PTP1B inhibitor (2 h), followed by stimulation with 100 nM insulin for 5 min. The samples were analyzed by SDS-PAGE as described above and immunoblotted using anti-phospho-IR/IGF1R antibody. The PVDF membrane was also probed by anti-β-actin antibody as the loading control.

Serum Stability Test.

The stability tests were carried by modifying a previously reported procedure (Nguyen, L T et al. PLoS One 2010, 5, e12684). Diluted human serum (25%) was centrifuged at 15,000 rpm for 10 min, and the supernatant was collected. A peptide stock solution was diluted into the supernatant to a final concentration of 5 µM and incubated at 37° C. At various time points (0-24 h), 200-µL aliquots were withdrawn and mixed with 50 µL of 15% trichloroacetic acid and incubated at 4° C. overnight. The final mixture was centrifuged at 15,000 rpm for 10 min in a microcentrifuge, and the supernatant was analyzed by reversed-phase HPLC equipped with a C18 column. The amount of remaining peptide (%) was determined by integrating the area underneath the peptide peak (monitored at 214 nm) and comparing with that of the control reaction (no serum).

Fluorescence Anisotropy.

FA experiments were carried out by incubating 100 nM FITC-labeled peptide with varying concentrations of protein in 20 mM HEPES (pH 7.4), 150 mM NaCl, 2 mM magnesium acetate, and 0.1% bovine serum albumin (BSA) for 2 h at room temperature. The FA values were measured on a Molecular Devices Spectramax M5 plate reader, with excitation and emission wavelengths at 485 and 525 nm, respectively. Equilibrium dissociation constants ($K_D$) were determined by plotting the FA values as a function of protein concentration and fitting the curve to the following equation:

$$Y = \frac{\left(A_{min} + \left(A_{max} \times \frac{Q_b}{Q_f} - A_{min}\right)\left(\frac{(L+x+K_D) - \sqrt{((L+x+K_D)^2 - 4Lx)}}{2L}\right)\right)}{\left(1 + \left(\frac{Q_b}{Q_f} - 1\right)\left(\frac{(L+x+K_D) - \sqrt{((L+x+K_D)^2 - 4Lx)}}{2L}\right)\right)}$$

where Y is the FA value at a given protein concentration x, L is the peptide concentration, $Q_b/Q_f$ is the correction factor for fluorophore-protein interaction, $A_{max}$ is the maximum FA value when all of the peptides are bound to protein, while $A_{min}$ is the minimum FA value when all of the peptides are free. FA competition assay was performed by incubating 100 nM FITC-labeled Pin1 inhibitor 5 with 1 µM Pin1, followed by the addition of 0-5 µM unlabeled inhibitor. The FA values were measured similarly on a pate reader. $IC_{50}$ values were obtained by plotting the FA values against the competitor concentration and curve fitting using the four-parameter dose-response inhibition equation (Prism 6, GraphPad).

Figure 23:
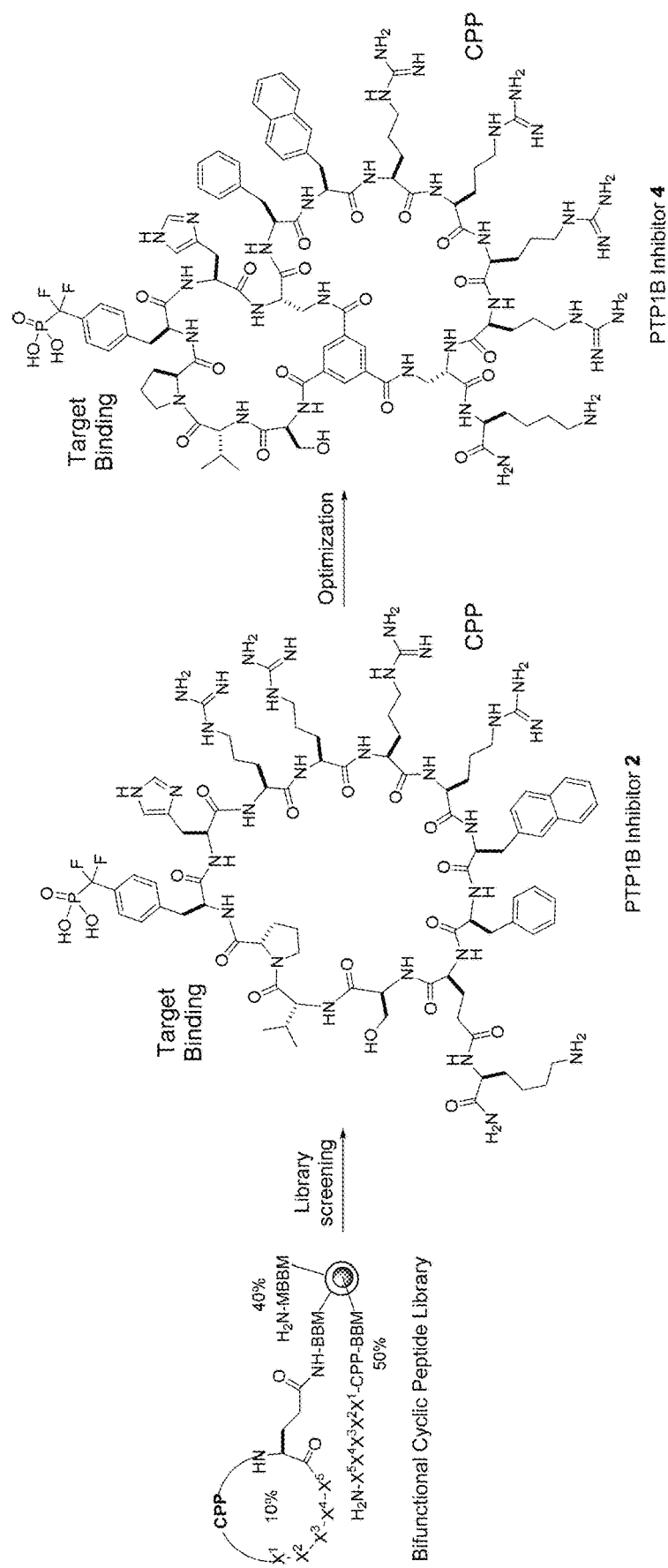
FIG. 23 displays a schematic of the evolution of a cell-permeable PTP1B inhibitor.
Figure 24:
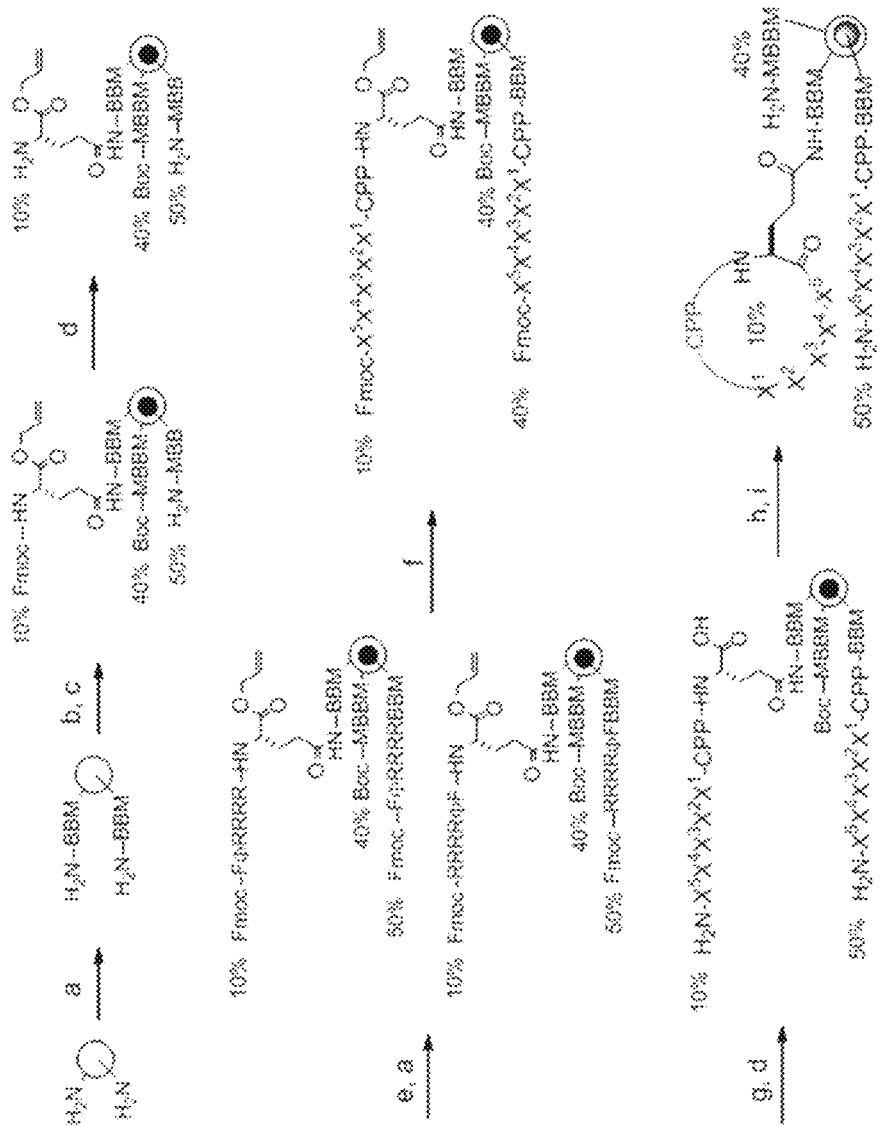
FIG. 24 displays a schematic of the design and synthesis of cyclic peptide library. Reagents and conditions: (a) standard Fmoc/HBTU chemistry; (b) soak in water; (c) 0.1 equiv Fmoc-Glu(δ-NHS)-OAll, 0.4 equiv Boc-Met-OH in Et$_2$O/CH$_2$Cl$_2$; (d) piperidine; (e) split into two parts; (f) split-andpool synthesis by Fmoc/HATU chemistry; (g) Pd(PPh$_3$)$_4$; (h) PyBOP, HOBt; and (i) Reagent K. X$^2$, 10% F$_2$Pmp and 90% Tyr; X$^1$ and X$^3$—X$^5$, random positions; Φ, L-2-naphthylalanine; CPP, cell-penetrating motif FΦR$_4$ or R$_4$ΦF.

A class of cell-penetrating peptides (CPPs), cyclo(Phe-Nal-Arg-Arg-Arg-Arg-Gln) (cFΦR4, where 0 or Nal is L-naphthylalanine), were recently discovered (Qian, Z et al. ACS Chem. Biol. 2013, 8, 423-431). Unlike previous CPPs, which are typically linear peptides and predominantly entrapped in the endosome, cFΦR4 can efficiently escape from the endosome into the cytoplasm. Short peptide cargos (1-7 aa) could be delivered into mammalian cells by directly incorporating them into the cFΦR$_4$ ring. The possibility of developing bifunctional cyclic peptides containing both cell-penetrating and target-binding sequences as cell-permeable inhibitors against intracellular proteins was examined. To generate specific inhibitors against PTP1B, a one-bead-two-compound library was synthesized on spatially segregated ChemMatrix resin (Liu, R et al. J. Am. Chem. Soc. 2002, 124, 7678-7680), in which each bead displayed a bifunctional cyclic peptide on its surface and contained the corresponding linear peptide in its interior as an encoding tag (FIG. 23 and FIG. 24). The bifunctional cyclic peptides all featured the amphipathic CPP motif FΦR$_4$ (or its inverse sequence RRRRΦF) on one side and a random pentapeptide sequence ($X^1X^2X^3X^4X^5$) on the other side, where $X^2$ represents a 9:1 (mol/mol) mixture of Tyr and F2Pmp while $X^1$ and $X^3$-$X^5$ are any of the 24 amino acids that included 10 proteinogenic L-amino acids (Ala, Asp, Gln, Gly, His, Ile, Pro, Ser, Tyr, Trp), 5 unnatural α-L-amino acids (F2Pmp, L-4-fluorophenylalanine (Fpa), L-norleucine (Nle), L-phenylglycine (Phg), L-pipecolic acid (Pip)), and 9 α-D-amino acids (D-Ala, D-Asn, D-Glu, D-Leu, L-β-naphthylalanine (D-Nal), D-Phe, D-Pro, D-Thr, and D-Val). The use of 9:1 Tyr/F2Pmp ratio at the $X^2$ position, together with a 5-fold reduction of the surface peptide loading, reduced the amount of F2Pmp-containing peptides at the bead surface by 50-fold, increasing the stringency and minimizing nonspecific binding during library screening (Chen, X et al. J. Comb. Chem. 2009, 11, 604-611). Screening of the library (theoretical diversity 6.6×10$^5$) against Texas red-labeled PTP1B resulted in 65 positive beads, which were individually sequenced by partial Edman degradation-mass spectrometry (PED-MS) (Thakkar, A et al. Anal. Chem. 2006, 78, 5935-5939) to give 42 complete sequences (Table 12). Interestingly, most of the selected PTP1B inhibitors contained the inverse CPP motif (RRRRΦF).

TABLE 12

Peptide Sequences Selected from Cyclic Peptide Library against PTP1B$^a$.

| SEQ ID NO. | Bead No. | Sequence |
|---|---|---|
| 136 | 1 | Pro-Pip-Gly-F$_2$Pmp-Tyr-Arg |
| 137 | 2 | Ser-Pip-Ile-F$_2$Pmp-F2Pmp-Arg |
| 138 | 3 | Ile-His-Ile-F$_2$Pmp-Ile-Arg |
| 139 | 4 | Ala-D-Ala-Ile-F$_2$Pmp-Pip-Arg |
| 140 | 5 | Fpa-Ser-Pip-F$_2$Pmp-D-Val-Arg |
| 141 | 6 | Pip-D-Asn-Pro-F$_2$Pmp-Ala-Arg |
| 142 | 7 | Tyr-Phg-Ala-F$_2$Pmp-Gly-Arg |
| 143 | 8 | Ala-His-Ile- F$_2$Pmp-D-Ala-Arg |
| 144 | 9 | Gly-D-Asn-Gly-F$_2$Pmp-D-Pro-Arg |
| 145 | 10 | D-Phe-Gln-Pip-F$_2$Pmp-Ile-Arg |
| 146 | 11 | Ser-Pro-Gly-F$_2$Pmp-His-Arg |
| 147 | 12 | Pip-Tyr-Ile-F$_2$Pmp-His-Arg |
| 148 | 13* | Ser-D-Val-Pro-F$_2$Pmp-His-Arg |
| 149 | 14 | Ala-Ile-Pro-F$_2$Pmp-D-Asn-Arg |
| 150 | 15 | Fpa-Ser-Ile-F$_2$Pmp-Gln-Phe |
| 151 | 16 | Ala-D-Ala-Phg-F$_2$Pmp-D-Phe-Arg |
| 152 | 17 | D-Asn-D-Thr-Phg-F$_2$Pmp-Phg-Arg |
| 153 | 18* | Ile-Pro-Phg-F$_2$Pmp-Nle-Arg |
| 154 | 19 | Gln-Pip-Fpa-F$_2$Pmp-Pip-Arg |
| 155 | 20 | D-Asn-Ala-Fpa-F$_2$Pmp-Gly-Arg |
| 156 | 21 | D-Asn-D-Thr-Tyr-F$_2$Pmp-Ala-Arg |
| 157 | 22 | D-Glu-Ala-Phg-F$_2$Pmp-D-Val-Arg |
| 158 | 23 | Ile-D-Val-Phg-F$_2$Pmp-Ala-Arg |
| 159 | 24 | Tyr-D-Thr-Phg-F$_2$Pmp-Ala-Arg |
| 160 | 25 | D-Asn-Pip-Phg-F$_2$Pmp-Ile-Arg |
| 161 | 26 | Pip-D-Asn-Trp-F$_2$Pmp-His-Arg |
| 162 | 27 | Tyr-Pip-D-Val-F$_2$Pmp-Ile-Arg |
| 163 | 28 | D-Asn-Ser-D-Ala-F$_2$Pmp-Gly-Arg |
| 164 | 29* | D-Thr-D-Asn-D-Val-F$_2$Pmp-D-Ala-Arg |
| 165 | 30 | D-Asn-D-Thr-D-Val-F$_2$Pmp-D-Thr-Arg |

TABLE 12-continued

Peptide Sequences Selected from Cyclic Peptide Library against PTP1B[a].

| SEQ ID NO. | Bead No. | Sequence |
|---|---|---|
| 166 | 31 | Ser-Ile-D-Thr-F2Pmp-Tyr-Arg |
| 167 | 32 | D-Asn-Fpa-D-Asn-F2Pmp-D-Leu-Arg |
| 168 | 33 | Tyr-D-Asn-D-Asn-F2Pmp-Nle-Arg |
| 169 | 34 | D-Asn-Tyr-D-Asn-F2Pmp-Gly-Arg |
| 170 | 35 | Ala-Trp-D-Asn-F2Pmp-Ala-Arg |
| 171 | 36 | D-Val-D-Thr-His-F2Pmp-Tyr-Arg |
| 172 | 37 | Pro-Phg-His-F2Pmp-Pip-Arg |
| 173 | 38 | D-Asn-Phg-His-F2Pmp-Gly-Arg |
| 174 | 39 | Pro-Ala-His-F2Pmp-Gly-Arg |
| 175 | 40 | Ala-Tyr-His-F2Pmp-Ile-Arg |
| 176 | 41 | D-Asn-Pip-D-Glu-F2Pmp-Tyr-Arg |
| 177 | 42 | D-Val-Ser-Ser-F2Pmp-D-Thr-Arg |

[a]Fpa, L-4-fluorophenylalanine; Pip, L-homoproline; Nle, L-norleucine; Phg, L-phenylglycine; F2Pmp, L-4-(phosphonodifluoromethyl)phenylalanine.
*Sequences subjected to further analysis.

Figure 25B:
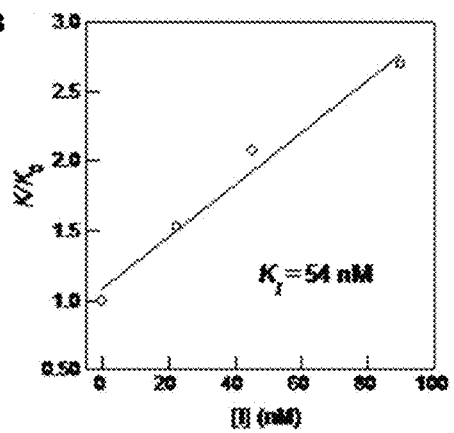
Figure 26A:
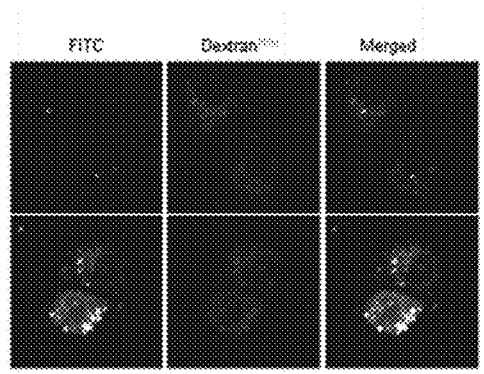
FIGS. 26A, 26B, and 26C display.

Three hit sequences (D-Thr-D-Asn-D-Val-F2Pmp-D-Ala-Arg-Arg-Arg-Arg-Nal-Phe-Gln (inhibitor 1), Ser-D-Val-Pro-F2Pmp-His-Arg-Arg-Arg-Arg-Nal-Phe-Gln (inhibitor 2), and Ile-Pro-Phg-F2Pmp-Nle-Arg-Arg-Arg-Arg-Nal-Phe-Gln (inhibitor 3)) were resynthesized and purified by HPLC. All three peptides are competitive PTP1B inhibitors (Table 13), with peptide 2 being most potent ($K_I$=54 nM) (FIG. 25). Confocal microscopic analysis of human cells treated with fluorescein isothiocyanate (FITC)-labeled inhibitor 2 indicated poor cellular uptake of the peptide (FIG. 26a). It has previously been shown that as the size of the cargo inserted into the cFΦR4 ring increases, the cellular uptake efficiency of the cyclic peptides decreases (Qian, Z et al. ACS Chem. Biol. 2013, 8, 423-431). Larger rings can be more conformationally flexible and may bind less tightly to the cell surface receptors (e.g., membrane phospholipids) during endocytosis. The negatively charged F2Pmp may also interact intramolecularly with the FΦR4 motif and interfere with its CPP function.

TABLE 13

Potency of Selected Monocyclic Peptide Inhibitors against PTP1B

| SEQ ID NO | Monocyclic Inhibitor | Sequence | $IC_{50}$ (nM) |
|---|---|---|---|
| 178 | 1 | cyclo(D-Thr-D-Asn-D-Val-F2Pmp-D-Ala-Arg-Arg-Arg-Arg-Nal-Phe-Gln) | ~100 |
| 179 | 2 | cyclo(Ser-D-Val-Pro-F2Pmp-His-Arg-Arg-Arg-Arg-Nal-Phe-Gln) | ~30 |
| 180 | 3 | cyclo(Ile-Pro-Phg-F2Pmp-Nle-Arg-Arg-Arg-Arg-Nal-Phe-Gln) | ~200 |

To improve the cell permeability of inhibitor 2, a bicyclic system in which the CPP motif is placed in one ring whereas the target-binding sequence constitutes the other ring (FIG. 23) was explored. The bicyclic system keeps the CPP ring to a minimal size which, according to the previously observed trend (Qian, Z et al. ACS Chem. Biol. 2013, 8, 423-431), can result in more efficient cellular uptake. The bicyclic system should be able to accommodate cargos of any size, because incorporation of the latter does not change the size of CPP ring and, therefore, should not affect the delivery efficiency of the cyclic CPP. The use of a rigid scaffold (e.g., trimesic acid) may also help keep the CPP and cargo motifs away from each other and minimize any mutual interference. The smaller rings of a bicyclic peptide, compared to its monocyclic counterpart, can result in greater structural rigidity and improved metabolic stability.

Figure 27:
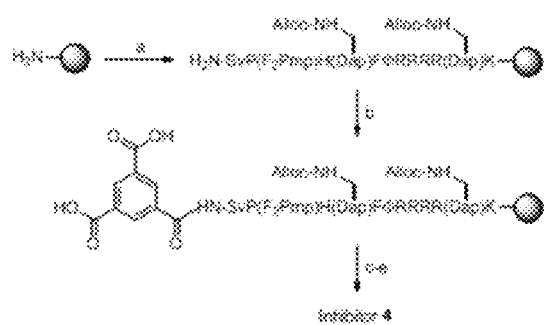
FIG. 27 displays the solid-phase synthesis of inhibitor 4. Reagents and conditions: a) standard Fmoc chemistry; b) trimesic acid, HBTU; c) Pd(PPh$_3$)$_4$, N-methylaniline; d) PyBOP; e) TFA.

To convert the monocyclic PTP1B inhibitor 2 into a bicyclic peptide, the Gln residue (used for attachment to the solid support and peptide cyclization) was replaced with (S)-2,3-diaminopropionic acid (Dap) and a second Dap residue was inserted at the junction of CPP and PTP1B-binding sequences (C-terminal to His) (FIG. 23). Synthesis of the bicycle was accomplished by the formation of three amide bonds between a trimesic acid and the N-terminal amine and the side chains of the two Dap residues (FIG. 27) (Lian, W et al. J. Am. Chem. Soc. 2013, 135, 11990-11995). Briefly, the linear peptide was synthesized on Rink amide resin using the standard Fmoc chemistry and $N^\beta$-alloxycarbonyl (Alloc)-protected Dap. After removal of the N-terminal Fmoc group, the exposed amine was acylated with trimesic acid. Removal of the Alloc groups with $Pd(PPh_3)_4$ followed by treatment with PyBOP afforded the desired bicyclic structure. To facilitate labeling with fluorescent probes, a lysine was added to the C-terminus. The bicyclic peptide (peptide 4) was deprotected by TFA and purified to homogeneity by HPLC.

Figure 26B:
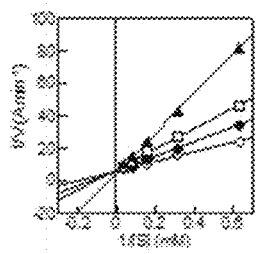
Figure 26C:
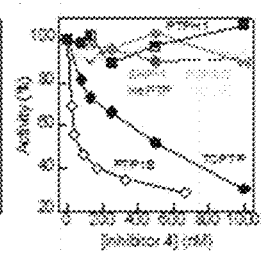
Figure 28:
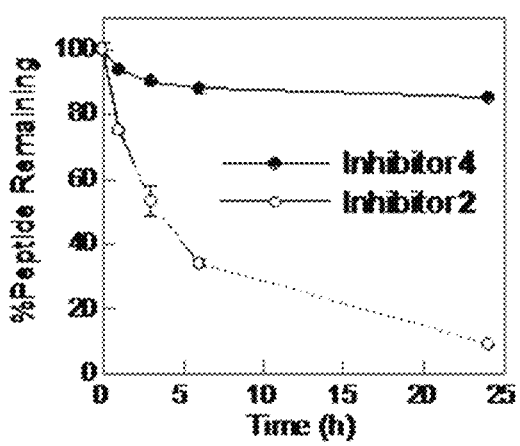
FIG. 28 displays a comparison of the serum stability of monocyclic PTP1B inhibitor 2 and bicyclic inhibitor 4.

Bicyclic peptide 4 can act as a competitive inhibitor of PTP1B, with a $K_I$ value of 37 nM (FIG. 26b). It can be highly selective for PTP1B. When assayed against p-nitrophenyl phosphate as a substrate (500 μM), inhibitor 4 had $IC_{50}$ values of 30 and 500 nM for PTP1B and TCPTP, respectively (FIG. 26c and Table 14). It exhibited minimal inhibition of any of the other PTPs tested (<10% inhibition of HePTP, SHP-1, PTPRC, PTPH1, or PTPRO at 1 μM inhibitor concentration). Inhibitor 4 has improved cell permeability over peptide 2, as detected by live-cell confocal microscopy of A549 cells treated with FITC-labeled inhibitor 4 (FIG. 26 a). The treated cells showed both diffuse fluorescence throughout the cytoplasm and nucleus as well as fluorescence puncta, indicating that a fraction of the inhibitors reached the cytoplasm and nucleus while the rest was likely entrapped in the endosomes. Incubation of inhibitor 4 in human serum for 24 h at 37° C. resulted in ~10% degradation, whereas 91% of inhibitor 2 was degraded under the same condition (FIG. 28). Overall, inhibitor 4 compares favorably with the small-molecule PTP1B inhibitors reported to date (Qian, Z et al. ACS Chem. Biol. 2013, 8, 423-431) with respect to potency, selectivity over the highly similar TCPTP (17-fold), cell permeability, and stability.

TABLE 14

Selectivity of Bicyclic Inhibitor 4 against Various PTPs[a]

| PTP | PTP1B | TCPTP | HePTP | PTPRC | SHP1 | PTPRO | PTPH1 |
|---|---|---|---|---|---|---|---|
| $IC_{50}$ (nM) | 30 ± 4 | 500 ± 250 | NA | NA | NA | NA | NA |

[a]NA, no significant inhibition at 1 µM inhibitor.

Figure 29B:
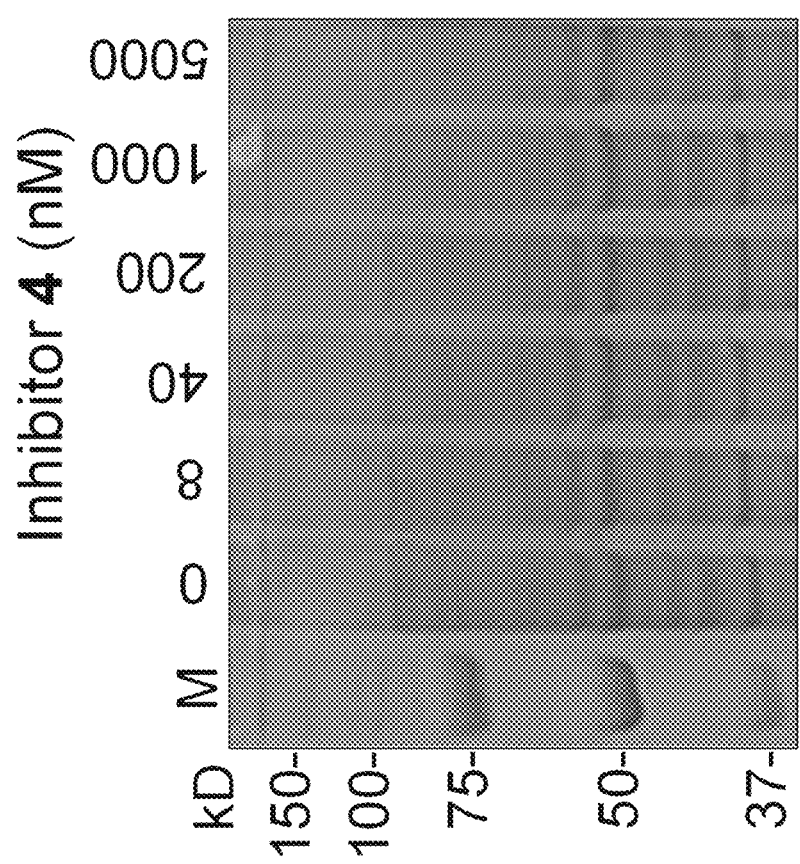
Figure 29C:
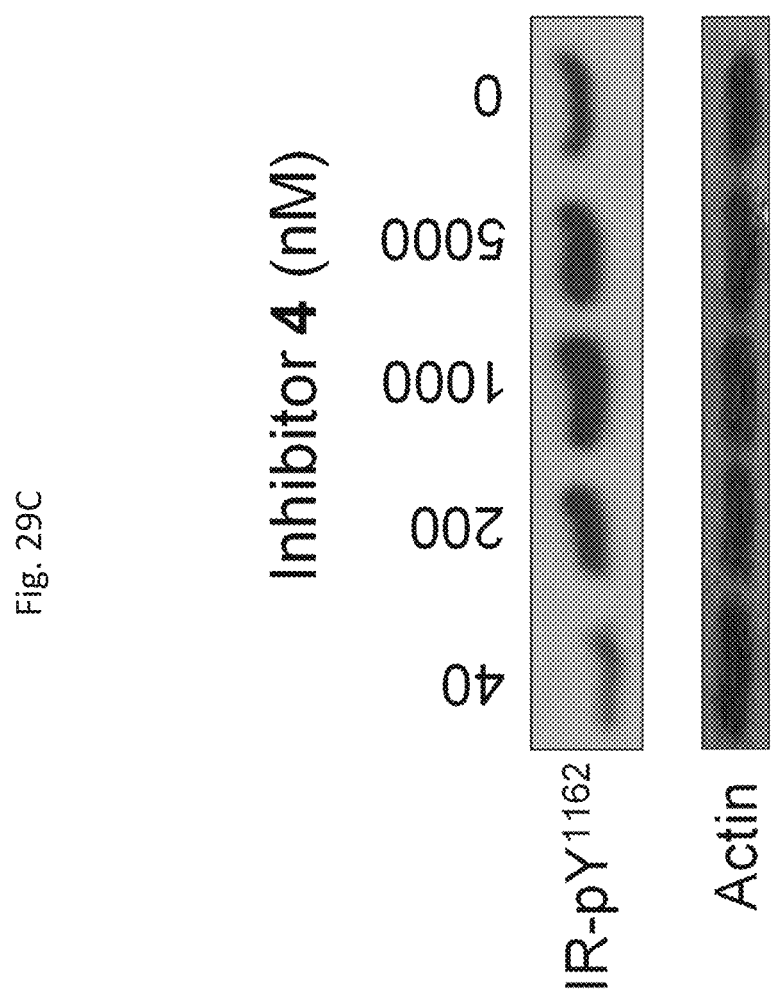
Figure 29D:
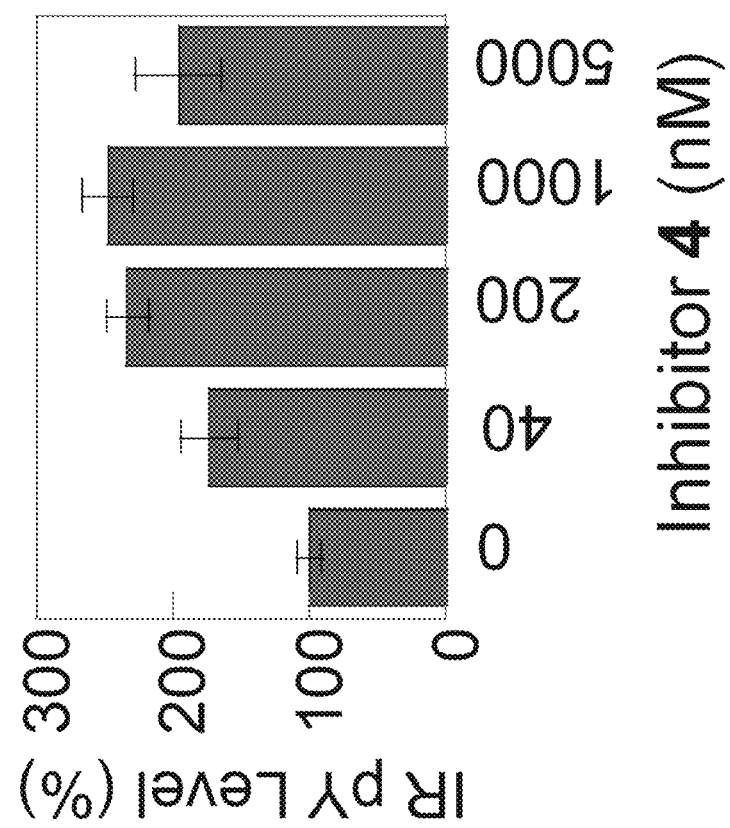

Inhibitor 4 was next tested for its ability to perturb PTP1B function during cell signaling. Treatment of A549 cells with inhibitor 4 (0-5 µM) resulted in dose-dependent increases in the phosphotyrosine (pY) levels of a large number of proteins, consistent with the broad substrate specificity of PTP1B (Ren, L et al. *Biochemistry* 2011, 50, 2339) (FIG. 29a). Analysis of the same samples by Coomassie blue staining showed similar amounts of proteins in all samples (FIG. 29b), indicating that the increased pY levels reflected increased phosphorylation (or decreased PTP reaction) instead of changes in the total protein levels. Remarkably, the increase in tyrosine phosphorylation was already apparent at 8 nM inhibitor 4. Interestingly, further increase in inhibitor concentration beyond 1 µM reversed the effect on tyrosine phosphorylation, an observation that was also made previously by Zhang and co-workers with a different PTP1B inhibitor (Xie, L et al. *Biochemistry* 2003, 42, 12792-12804). To obtain further evidence that the intracellular PTP1B was inhibited by peptide 4, the pY level of insulin receptor (IR), a well-established PTP1B substrate in vivo (Elchelby, M et al. *Science* 1999, 283, 1544-1548; Zabolotny, J M et al. *Dev. Cell* 2002, 2, 489-495), was monitored by immunoblotting with specific antibodies against the $pY^{1162}pY^{1163}$ site. Again, treatment with inhibitor 4 caused dose-dependent increase in insulin receptor phosphorylation up to 1 µM inhibitor and the effect leveled off at higher concentrations (FIG. 29c,d). Taken together, these data indicate that bicyclic inhibitor 4 can efficiently enter mammalian cells and can inhibit PTP1B in vivo. The decreased phosphorylation at higher inhibitor concentrations may be caused by nonspecific inhibition of other PTPs (which may in turn down regulate protein tyrosine kinases). It may also reflect the pleiotropic roles played by PTP1B, which can both negatively and positively regulate the activities of different protein kinases (Lessard, L et al. *Biochim. Biophys. Acta* 2010, 1804, 613).

Figure 30:
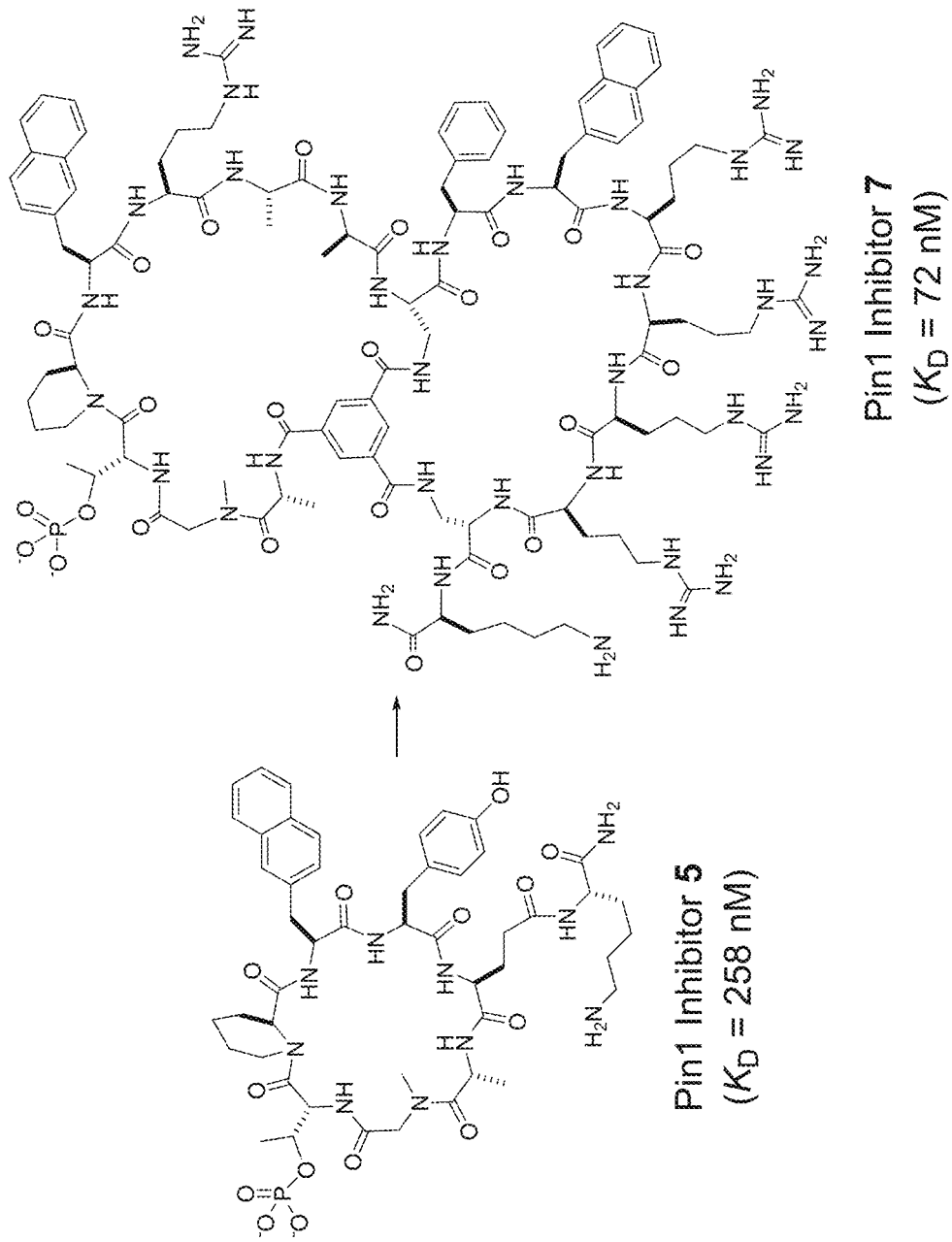
FIG. 30 displays the conversion of impermeable Pin1 inhibitor into a cell-permeable bicyclic inhibitor.
Figure 34:
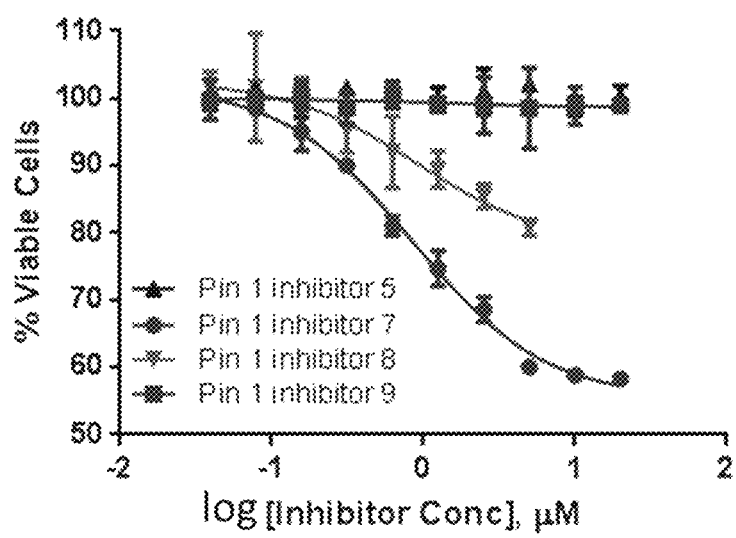
FIG. 34 displays the effect of Pin1 Inhibitors 5, 7, 8, and 9 on cancer cell proliferation. HeLa cells (100 µL/each well, 5×10$^4$ cells/mL) were seeded in a 96-well culture plate and allowed to grow overnight in DMEM supplemented with 10% FBS. Varying concentrations of Pin1 inhibitor (0-5 µM) were added to the wells and the cells were incubated at 37° C. with 5% CO$_2$ for 72 h. After that, 10 µL of a MTT stock solution (5 mg/mL) was added into each well. The plate was incubated at 37° C. for 4 h and 100 µL of SDS-HCl solubilizing solution was added into each well, followed by thorough mixing. The plate was incubated at 37° C. overnight and the absorbance of the formazan product was measured at 570 nm on a Molecular Devices Spectramax M5 plate reader. Each experiment was performed in triplicates and the cells untreated with peptide were used as control.

To test the generality of the bicyclic approach, it was applied to design cell permeable inhibitors against peptidyl prolyl cis-trans isomerase Pin1, a potential target for treatment of a variety of human diseases including cancer (Lu, K P and Zhou, X Z. *Nat. Rev. Mol. Cell Biol.* 2007, 8, 904-916), for which potent, selective, and biologically active inhibitors are still lacking (More, J D and Potter, A. *Bioorg. Med. Chem. Lett.* 2013, 23, 4283-91). Thus, a previously reported monocyclic peptide (5), which is a potent inhibitor against Pin1 in vitro ($K_D$ 258 nM) but membrane impermeable (Liu, T et al. *J. Med. Chem.* 2010, 53, 2494-2501), was fused with cFΦR$_4$ (FIG. 30). In addition, the L-Tyr at the pThr+3 position was replaced with an Arg to improve the aqueous solubility. The resulting bicyclic peptide 6 bound Pin1 with a $K_D$ value of 131 nM (Table 15 and FIG. 31). Insertion of a D-Ala at the pThr+5 position to increase the separation between the Pin1-binding and cell-penetrating motifs improved the inhibitor potency by ~2-fold ($K_D$=72 nM for inhibitor 7). Inhibitor 7 competed with FITC-labeled inhibitor 5 for binding to Pin1 (FIG. 32), indicating that they both can bind to the Pin1 active site. Substitution of D-Thr for D-pThr of inhibitor 7 reduced its potency by ~10-fold ($K_D$=620 nM for inhibitor 8, Table 16), whereas further replacement of the pipecolyl residue with D-Ala abolished Pin1 inhibitory activity (peptide 9). The bicyclic inhibitors 7-9 were cell permeable (FIG. 33). Treatment of HeLa cells with inhibitor 7 resulted in time- and dose-dependent inhibition of cell growth (45% inhibition after 3-day treatment at 20 µM inhibitor 7), whereas the monocyclic inhibitor 5 and inactive peptide 9 had no effect (FIG. 34). Peptide 8 also inhibited cell growth, but to a lesser extent than inhibitor 7.

TABLE 15

Dissociation Constants of Monocyclic and Bicyclic Peptides against Pin1 as Determined by FA Analysis

| SEQ ID NO | Pin1 Inhibitor | Sequence[a] | $K_D$ (nM) |
|---|---|---|---|
| 181 | 5 | cyclo(D-Ala-Sar-D-pThr-Pip-Nal-Tyr-Gln)-Lys-NH$_2$ | 258 ± 65 |
| 182 | 6 | bicyclo[Tm(D-Ala-Sar-D-pThr-Pip-Nal-Arg-Ala)-Dap-(Phe-Nal-Arg-Arg-Arg-Arg-Dap)]-Lys-NH$_2$ | 131 ± 44 |
| 183 | 7 | bicyclo[Tm(D-Ala-Sar-D-pThr-Pip-Nal-Arg-Ala-D-Ala)-Dap-(Phe-Nal-Arg-Arg-Arg-Arg-Dap)]-Lys-NH$_2$ | 72 ± 21 |
| 184 | 8 | bicyclo[Tm(D-Ala-Sar-D-Thr-Pip-Nal-Arg-Ala-D-Ala)-Dap-(Phe-Nal-Arg-Arg-Arg-Arg-Dap)]-Lys-NH$_2$ | 620 ± 120 |
| 185 | 9 | bicyclo[Tm(D-Ala-Sar-D-Thr-D-Ala-Nal-Arg-Ala-D-Ala)-Dap-(Phe-Nal-Arg-Arg-Arg-Arg-Dap)]-Lys-NH$_2$ | >>6000 |

[a]Dap, L-2,3-diaminopropionic acid; Nal, L-P-naphthylalanine; Pip, L-pipecolic acid; Sar, sarcosine; Tm, trimesic acid. For FA analysis, all peptides were labeled at the C-terminal lysine side-chain with FITC.

In conclusion, a potentially general approach to designing cell-permeable bicyclic peptides against intracellular targets was developed. These preliminary studies show that replacement of the PTP1B-binding motif with other peptide sequences of different physicochemical properties also resulted in their efficient delivery into cultured mammalian cells. The availability of a general intracellular delivery method should greatly expand the utility of cyclic peptides in drug discovery and biomedical research.

Example 4

Also discussed herein are the CPP sequences in Table 16. All uptake/delivery efficiencies are in Table 17 are relative to that of cFΦR$_4$ (290-1F, 100%). SUV1 are small unilamellar vesicles that mimic the neutral outer membrane of mammalian cells [45% phosphatidylcholine (PC), 20% phosphatidylethanolamine (PE), 20% sphingomyelin (SM), and 15% cholesterol (CHO)]. SUV2 are small unilamellar vesicles that mimic the negatively charged endosomal membrane of mammalian cells [50% PC, 20% PE, 10% phosphatidylinositol (PI), and 20% bis(monoacylglycerol)phosphate].

Measurements were carried out fluorescence polarization using FITC-labeled cyclic peptides against increasing concentrations of vesicles. Experiments were performed at pH 7.4 and 5.5 (pH inside late endosomes).

The overall delivery efficiency appears to correlate with the CPPs' binding affinity to the endosomal membrane at pH 7.4. i.e., tighter binding leads to higher delivery efficiency.

calmodulin. Mouse ventricular cardiac myocytes were incubated with 6 μM of the CPP-calmodulin conjugate for 3 h, and examined by live-cell confocal microscopy. The intracellular fluorescence signal was present throughout the entire cell volume and displayed a sarcomeric pattern (FIG. 35d), indicating the internalized calmodulin was properly integrated into the cellular machinery. These data indicate that the disclosed cyclic CPPs such as c(FΦRRRRQ) are uniquely capable of delivering small molecules as well as

TABLE 16

Cyclic CPPs and their cellular uptake and membrane binding properties.

|  | SEQ ID NO | CPP Sequence | Uptake Efficiency (%) | Membrane Binding $K_D$ (mM) | | | |
|---|---|---|---|---|---|---|---|
|  |  |  |  | SUV1 pH 7.4 | SUV1 pH 5.5 | SUV2 pH 7.4 | SUV2 pH 5.5 |
| 290-1F | 186 | c(FΦRRRRQ) | 100 | 4 | 1.1 | 0.66 | 0.63 |
| 290-12F | 187 | c(FfΦRrRrQ) | 681 | 0.8 |  | 0.026 | 0.004 |
| 290-9F | 188 | c(fΦRrRrQ) | 602 | 1.2 | 0.81 | 0.033 | 0.012 |
| 290-11F | 189 | c(fΦRrRrRQ) | 542 | 2.7 |  | 0.092 | 0.019 |
| 290-18F | 190 | c(FφrRrRq) | 205 | 0.75 |  | 0.04 | 0.022 |
| 290-13F | 191 | c(FφrRrRQ) | 200 | 0.68 |  | 0.28 | 0.04 |
| 290-6F | 192 | c(FΦRRRRRQ) | 184 | 2.2 |  | 0.12 | 0.019 |
| 290-3F | 193 | c(RRFRΦRQ) | 163 | 0.22 |  | 0.4 | 0.26 |
| 290-7F | 194 | c(FFΦRRRRQ) | 134 | 1.65 |  | 0.11 | 0.007 |
| 290-8F | 195 | c(RFRFRΦRQ) | 98 | 0.4 |  | 0.39 | 0.082 |
| 290-5F | 196 | c(FΦRRRQ) | 97 | 10.1 |  | 2.4 | 0.066 |
| 290-4F | 197 | c(FRRRRΦQ) | 59 | 7.24 |  | 0.54 | 0.11 |
| 290-10F | 198 | c(rRFRΦRQ) | 52 | 1.2 |  | 0.87 | 0.17 |
| 290-2F | 199 | c(RRΦFRRQ) | 47 | 1.95 |  | 0.69 | 0.025 |
| Tat |  |  | 32 | too weak | too weak | 3.3 | 4.5 |
| $R_9$ |  |  | 35 | too weak | too weak | 0.47 | 0.03 |

Φ = L-naphthylalanine;
φ = D-naphthylalanine;
f = D-phenylalanine;
r = D-arginine;
q = D-glutamine Example 5

Cardiomyocytes are in general difficult to transfect with DNA and delivering proteins into them by using previous CPPs have not been successful. There is therefore an unmet need for delivering therapeutic proteins into heart tissues.

The disclosed cyclic CPPs are very effective in delivering proteins into cardiomyocytes. Fluorescein isothiocyanate (FITC)-labeled cyclic CPPs [c(FΦRRRRQ)-K(FITC)-NH$_2$ and c(fΦRrRrQ)-K(FITC)-NH$_2$] were synthesized and their internalization into mouse ventricular cardiac myocytes was tested by treating the cells with 5 μM FITC-labeled peptide for 3 h. After washing away the extracellular peptides, the internalization of CPPs was examined by fluorescent live-cell confocal microscopy. Both peptides exhibited significant and predominantly diffused fluorescence throughout the cells, indicating efficient internalization of the CPPs into cardiac muscle cells (FIGS. 35a and 35b). Whether the cyclic CPPs are capable of transporting full-length proteins into cardiac muscle cells was tested. Calmodulin (with an engineered Thr5Cys), a multifunctional calcium-binding messenger protein, was conjugated to c(FΦRRRRQ)-C-NH$_2$ at the Cys residue near N-terminus through a disulfide bond. The disulfide exchange reaction is highly specific, efficient, and reversible. Further, upon entering the cytosol of cells, the disulfide linkage is expected to be reduced to release the native protein (FIG. 35c). The CPP-protein conjugate was chemically labeled on amino-groups with cyanine3, which permits visualization of the internalized proteins (likely in their native form) into cardiomyocytes with high efficiency, opening the door to future therapeutic applications.

Example 6

Pin1 is a phosphorylation-dependent peptidyl-prolyl cis/trans isomerase (PPIase). It contains an N-terminal WW domain and a C-terminal catalytic domain, both of which recognize specific phosphoserine (pSer)/phosphothreonine (pThr)-Pro motifs in their protein substrates. Through cis-trans isomerization of specific pSer/pThr-Pro bonds, Pin1 regulates the levels, activities, as well as intracellular localization of a wide variety of phosphoproteins. For example, Pin1 controls the in vivo stability of cyclin D1 and cyclin E and switches c-Jun, c-Fos, and NF-κB between their inactive unstable forms and active stable forms. Isomerization by Pin1 also regulates the catalytic activity of numerous cell-cycle signaling proteins such as phosphatase CDC25C and kinase Wee1. Finally, Pin1-catalyzed conformational changes in β-catenin and NF-κB lead to subcellular translocation.

Figure 36:
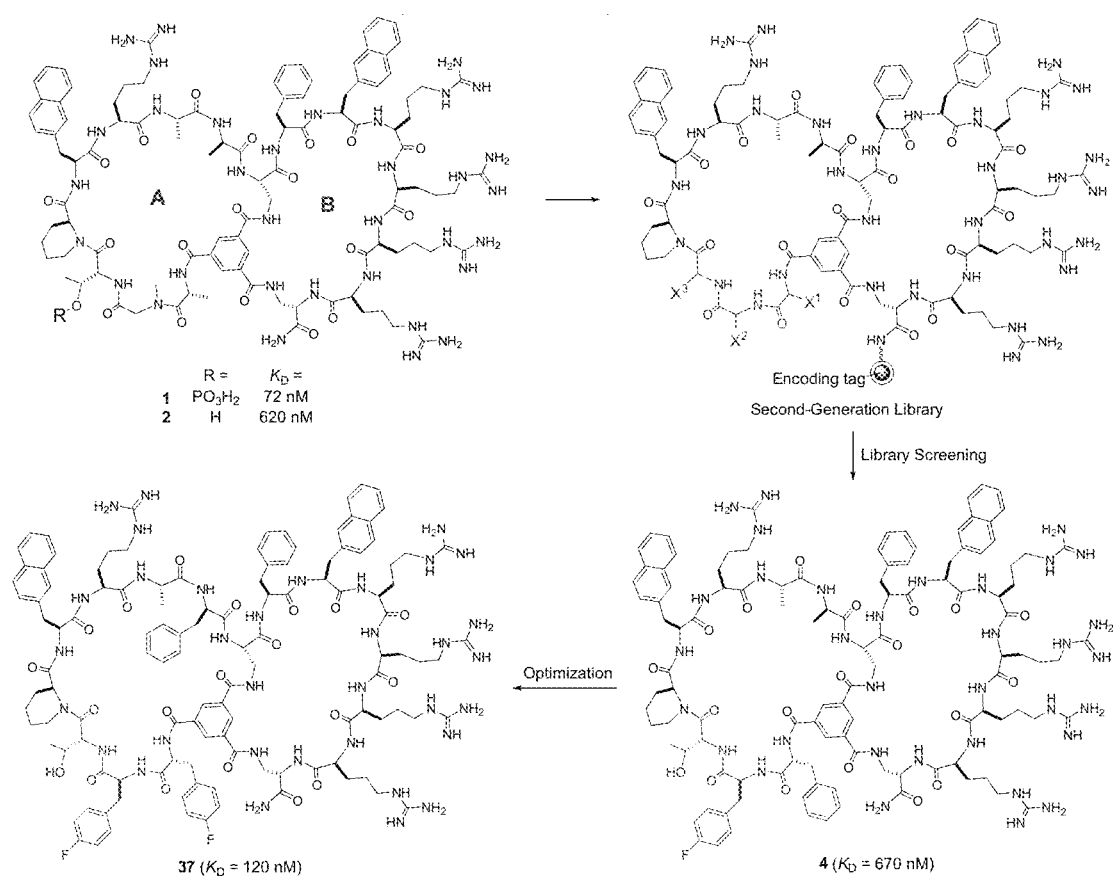
FIG. 36 displays the evolution of bicyclic peptide inhibitors against Pin1. The structural moieties derived from library screening are shown in grey, while the changes made during optimization are shown in light grey.

Given its critical roles in cell-cycle regulation and increased expression levels and activity in human cancers, Pin1 has been proposed as a potential target for the development of anticancer drugs. Pin1 is also implicated in neural degenerative diseases such as Alzheimer's disease. Therefore, there have been significant interests in developing specific inhibitors against Pin1. Small-molecule inhibitors such as Juglone, PiB, dipentamenthylene thiauram monosulfide and halogenated phenyl-isothiazolone (TME-001) generally lack sufficient potency and/or specificity. A number of potent peptidyl Pin1 inhibitors have been reported and are more selective than the small-molecule inhibitors. However, peptidyl inhibitors are generally impermeable to the cell membrane and therefore have limited utility as therapeutics or in vivo probes. A cell-permeable bicyclic peptidyl inhibitor against Pin1, in which one ring (A ring) featured a Pin1-binding phosphopeptide motif [D-pThr-Pip-Nal, where Pip and Nal are (R)-piperidine-2-carboxylic acid and L-naphthylalanine, respectively] while the second ring (B ring) contained a cell-penetrating peptide, Phe-Nal-Arg-Arg-Arg-Arg is shown in FIG. 36, peptide 1. Although the bicyclic peptidyl inhibitor is potent ($K_D$=72 nM) and active in cellular assays, its D-pThr moiety might be metabolically labile due to hydrolysis by nonspecific phosphatases. The negative charges of the phosphate group might also impede the cellular entry of the inhibitor. Here a non-phosphorylated bicyclic peptidyl inhibitor against Pin1 was prepared by screening a peptide library and hit optimization. The resulting bicyclic peptidyl inhibitor is potent and selective against Pin1 in vitro, cell-permeable, and metabolically stable in biological assays.

Although removal of the phosphoryl group of peptide 1 significantly reduced its potency against Pin1, the nonphosphorylated peptide (FIG. 36, peptide 2) was still a relatively potent Pin1 inhibitor ($K_D$=0.62 µM). The potency of peptide 2 might be further improved by optimizing the sequences flanking the D-Thr-Pip-Nal motif. So a second-generation bicyclic peptide library, bicyclo[Tm-($X^1X^2X^3$-Pip-Nal-Arg-Ala-D-Ala)-Dap-(Phe-Nal-Arg-Arg-Arg-Arg-Dap)]-β-Ala-β-Ala-Pra-β-Ala-Hmb-β-Ala-β-Ala-Met-resin (FIG. 35, where Tm was trimesic acid, Dap was 2,3-diaminopropionic acid, β-Ala was β-alanine, Pra was L-propargylglycine, and Hmb was 4-hydroxymethyl benzoic acid), by randomizing the three N-terminal residues of peptide 2. $X^1$ and $X^2$ represented any of the 27 amino acid building blocks that included 12 proteinogenic L-amino acids [Arg, Asp, Gln, Gly, His, Ile, Lys, Pro, Ser, Thr, Trp, and Tyr], 5 nonproteinogenic α-L-amino acids [L-4-fluorophenylalanine (Fpa), L-norleucine (Nle), L-ornithine (Orn), L-phenylglycine (Phg), and L-Nal], 6 α-D-amino acids [D-Ala, D-Asn, D-Glu, D-Leu, D-Phe, and D-Val], and 4 $N^α$-methylated L-amino acids [L-$N^α$-methylalanine (Mal), L-$N^α$-methylleucine (Mle), L-$N^α$-methylphenylalanine (Mpa), and sarcosine (Sar)], while $X^3$ was Asp, Glu, D-Asp, D-Glu, or D-Thr. Incorporation of these nonproteinogenic amino acids was expected to increase both the structural diversity and the proteolytic stability of the library peptides. The library had a theoretical diversity of 5×27×27 or 3645 different bicyclic peptides, most (if not all) of which were expected to be cell-permeable. The library was synthesized on 500 mg of TentaGel microbeads (130 µm, ~7.8×10⁵ beads/g, ~350 pmol peptides/bead). Peptide cyclization was achieved by forming three amide bonds between Tm and the N-terminal amine and the sidechain amines of the two Dap residues.

TABLE 17

Hit Sequences from Peptide Library Screening[a]

| hit | $X^1$ | $X^2$ | $X^3$ |
|---|---|---|---|
| 1 | Pro | Sar | D-Asp |
| 2 | Pro | Sar | D-Asp |
| 3 | D-Phe | Fpa | D-Thr |
| 4 | His | Phg | D-Thr |
| 5 | Mpa | Ile | D-Glu |
| 6 | Phg | His | D-Glu |
| 7 | Mpa | Gly | D-Thr |

[a]Hits 1-3 were selected from 1st-round screening, whereas hits 4-7 were selected after 2nd-round screening.

The β-Ala provides a flexible linker, while Pra serves as a handle for on-bead labeling of the bicyclic peptides with fluorescent probes through click chemistry. The ester linkage of Hmb enables selective release of the bicyclic peptides from the resin for solution-phase binding analysis. Finally, the C-terminal Met allows peptide release from the resin by CNBr cleavage prior to MS analysis.

The library (100 mg of resin) was screened against a S16A/Y23A mutant Pin1, which has a defective WW domain. The mutant Pin1 was produced as a maltose-binding protein (MBP) fusion at the N-terminus. During the first round of screening, Texas red-labeled MBP-Pin1 was incubated with the peptide library and fluorescent beads were removed from the library under a microscope. Three positive beads had substantially greater fluorescence intensities than the rest of hits and were directly subjected to peptide sequencing by partial Edman degradation mass spectroscopy (PED-MS) (Table 17). The other 13 fluorescent beads were subjected to a second round of screening, during which the bicyclic peptide on each bead was labeled with tetramethylrhodamine (TMR) azide at the Pra residue and released from the bead by treatment with a NaOH solution.

TABLE 18

Sequences and Pin1 Binding Affinities of Peptides Used

| SEQ ID NO | Peptide | Peptide sequence | $K_D$ (µM) |
|---|---|---|---|
| 200 | 1 | bicyclo[Tm-(D-Ala-Sar-D-pThr-Pip-Nal-Arg-Ala-D-Ala)-Dap-(Phe-Nal-Arg-Arg-Arg-Arg-Dap)]-Lys | 0.072 ± 0.021 |
| 201 | 2 | bicyclo[Tm-(D-Ala-Sar-D-Thr-Pip-Nal-Arg-Ala-D-Ala)-Dap-(Phe-Nal-Arg-Arg-Arg-Arg-Dap)]-Lys | 0.62 ± 0.12 |
| 202 | 3 | bicyclo[Tm-(Pro-Sar-D-Asp-Pip-Nal-Arg-Ala-D-Ala)-Dap-(Phe-Nal-Arg-Arg-Arg-Arg-Dap)]-Lys | 0.87 ± 0.17 |
| 203 | 4 | bicyclo[Tm-(D-Phe-Fpa-D-Thr-Pip-Nal-Arg-Ala-D-Ala)-Dap-(Phe-Nal-Arg-Arg-Arg-Arg-Dap)]-Lys | 0.67 ± 0.12 |

TABLE 18-continued

Sequences and Pin1 Binding
Affinities of Peptides Used

| SEQ ID NO | Peptide | Peptide sequence | $K_D$ (μM) |
|---|---|---|---|
| 204 | 5 | bicyclo[Tm-(Mpa-Gly-D-Thr-Pip-Nal-Arg-Ala-D-Ala)-Dap-(Phe-Nal-Arg-Arg-Arg-Arg-Dap)]-Lys | 1.08 ± 0.12 |
| 205 | 6 | bicyclo[Tm-(Phg-His-D-Glu-Pip-Nal-Arg-Ala-D-Ala)-Dap-(Phe-Nal-Arg-Arg-Arg-Arg-Dap)]-Lys | 1.47 ± 0.19 |
| 206 | 7 | bicyclo[Tm-(Mpa-Ile-D-Glu-Pip-Nal-Arg-Ala-D-Ala)-Dap-(Phe-Nal-Arg-Arg-Arg-Arg-Dap)]-Lys | 1.25 ± 0.20 |
| 207 | 8 | bicyclo[Tm-(His-Phg-D-Thr-Pip-Nal-Arg-Ala-D-Ala)-Dap-(Phe-Nal-Arg-Arg-Arg-Arg-Dap)]-Lys | 1.40 ± 0.24 |
| 208 | 9 | bicyclo[Tm-(Pro-Sar-D-Asp-Pip-Nal-Arg-Ala)-Dap-(Phe-Nal-Arg-Arg-Arg-Dap)]-Lys | 2.59 ± 0.37 |
| 209 | 10 | bicyclo[Tm-(Pro-Sar-D-Asp-Pip-Nal-Arg)-Dap-(Phe-Nal-Arg-Arg-Arg-Dap)]-Lys | 3.42 ± 0.61 |
| 210 | 11 | bicyclo[Tm-(D-Phe-Fpa-D-Thr-Pip-Nal-Arg-Ala)-Dap-(Phe-Nal-Arg-Arg-Arg-Dap)]-Lys | 0.90 ± 0.25 |
| 211 | 12 | bicyclo[Tm-(D-Phe-Fpa-D-Thr-Pip-Nal-Arg)-Dap-(Phe-Nal-Arg-Arg-Arg-Dap)]-Lys | 2.36 ± 0.48 |
| 212 | 13 | bicyclo[Tm-(Pro-Sar-D-Asp-Pip-Nal-Arg-Ala-β-Ala)-Dap-(Phe-Nal-Arg-Arg-Arg-Dap)]-Lys | 2.08 ± 0.31 |
| 213 | 14 | bicyclo[Tm-(Pro-Sar-D-Asp-Pip-Nal-Arg-β-Ala-D-Ala)-Dap-(Phe-Nal-Arg-Arg-Arg-Dap)]-Lys | 1.75 ± 0.18 |
| 214 | 15 | bicyclo[Tm-(Pro-Sar-D-Asp-Pip-Nal-Arg-β-Ala-β-Ala)-Dap-(Phe-Nal-Arg-Arg-Arg-Dap)]-Lys | 4.83 ± 0.96 |
| 215 | 16 | bicyclo[Tm-(Pro-Sar-D-Asp-Pip-Nal-Arg-Ala-D-Ala-D-Ala)-Dap-(Phe-Nal-Arg-Arg-Arg-Arg-Dap)]-Lys | 2.49 ± 0.57 |
| 216 | 17 | bicyclo[Tm-(Pro-Sar-D-Asp-Pip-Nal-Arg-Tyr-D-Ala)-Dap-(Phe-Nal-Arg-Arg-Arg-Arg-Dap)]-Lys | 2.17 ± 0.55 |
| 217 | 18 | bicyclo[Tm-(Pro-Sar-D-Asp-Pip-Nal-Arg-Val-D-Ala)-Dap-(Phe-Nal-Arg-Arg-Arg-Arg-Dap)]-Lys | 1.75 ± 0.24 |
| 218 | 19 | bicyclo[Tm-(Pro-Sar-D-Asp-Pip-Nal-Arg-Arg-D-Ala)-Dap-(Phe-Nal-Arg-Arg-Arg-Arg-Dap)]-Lys | 0.72 ± 0.09 |
| 219 | 20 | bicyclo[Tm-(Pro-Sar-D-Asp-Pip-Nal-Arg-Asp-D-Ala)-Dap-(Phe-Nal-Arg-Arg-Arg-Arg-Dap)]-Lys | 3.19 ± 0.50 |
| 220 | 21 | bicyclo[Tm-(D-Phe-Fpa-D-Thr-Pip-Nal-Arg-Ser-D-Phe)-Dap-(Phe-Nal-Arg-Arg-Arg-Arg-Dap)]-Lys | 0.57 ± 0.11 |
| 221 | 22 | bicyclo[Tm-(Pro-Sar-D-Asp-Pip-Nal-Arg-Arg-D-Phe)-Dap-(Phe-Nal-Arg-Arg-Arg-Arg-Dap)]-Lys | 0.48 ± 0.07 |
| 222 | 23 | bicyclo[Tm-(Pro-Sar-D-Asp-Pip-Nal-Arg-Arg-D-Val)-Dap-(Phe-Nal-Arg-Arg-Arg-Arg-Dap)]-Lys | 1.92 ± 0.19 |
| 223 | 24 | bicyclo[Tm-(Pro-Sar-D-Asp-Pip-Nal-Arg-Arg-D-Arg)-Dap-(Phe-Nal-Arg-Arg-Arg-Arg-Dap)]-Lys | 1.31 ± 0.10 |
| 224 | 25 | bicyclo[Tm-(Pro-Sar-D-Asp-Pip-Nal-Arg-Arg-D-Asp)-Dap-(Phe-Nal-Arg-Arg-Arg-Arg-Dap)]-Lys | 4.60 ± 1.42 |
| 225 | 26 | bicyclo[Tm-(D-Phe-4-Fpa-D-Thr-Pip-Nal-Arg-Gly-D-Ala)-Dap-(Phe-Nal-Arg-Arg-Arg-Arg-Dap)]-Lys | 0.74 ± 0.11 |
| 226 | 27 | bicyclo[Tm-(D-Phe-4-Fpa-D-Thr-Pip-Nal-Arg-Ala-D-Phe)-Dap-(Phe-Nal-Arg-Arg-Arg-Arg-Dap)]-Lys | 0.27 ± 0.08 |
| 227 | 28 | bicyclo[Tm-(D-Phe-Phe-D-Thr-Pip-Nal-Arg-Ala-D-Phe)-Dap-(Phe-Nal-Arg-Arg-Arg-Arg-Dap)]-Lys | 1.26 ± 0.28 |
| 228 | 29 | bicyclo[Tm-(D-Phe-3,4-diFPhe-D-Thr-Pip-Nal-Arg-Ala-D-Phe)-Dap-(Phe-Nal-Arg-Arg-Arg-Arg-Dap)]-Lys | 0.41 ± 0.10 |

TABLE 18-continued

Sequences and Pin1 Binding Affinities of Peptides Used

| SEQ ID NO | Peptide | Peptide sequence | $K_D$ (µM) |
|---|---|---|---|
| 229 | 30 | bicyclo[Tm-(D-Phe-4-ClPhe-D-Thr-Pip-Nal-Arg-Ala-D-Phe)-Dap-(Phe-Nal-Arg-Arg-Arg-Arg-Dap)]-Lys | 0.78 ± 0.05 |
| 230 | 31 | bicyclo[Tm-(D-Phe-His-D-Thr-Pip-Nal-Arg-Ala-D-Phe)-Dap-(Phe-Nal-Arg-Arg-Arg-Arg-Dap)]-Lys | 1.68 ± 0.17 |
| 231 | 32 | bicyclo[Tm-(D-Phe-4-BrPhe-D-Thr-Pip-Nal-Arg-Ala-D-Phe)-Dap-(Phe-Nal-Arg-Arg-Arg-Arg-Dap)]-Lys | 1.78 ± 0.42 |
| 232 | 33 | bicyclo[Tm-(D-Ala-4-Fpa-D-Thr-Pip-Nal-Arg-Ala-D-Ala)-Dap-(Phe-Nal-Arg-Arg-Arg-Dap)]-Lys | 1.49 ± 0.11 |
| 233 | 34 | bicyclo[Tm-(D-Val-4-Fpa-D-Thr-Pip-Nal-Arg-Ala-D-Ala)-Dap-(Phe-Nal-Arg-Arg-Arg-Arg-Dap)]-Lys | 1.07 ± 0.16 |
| 234 | 35 | bicyclo[Tm-(D-2-Fpa-Fpa-D-Thr-Pip-Nal-Arg-Ala-D-Phe)-Dap-(Phe-Nal-Arg-Arg-Arg-Arg-Dap)]-Lys | 0.59 ± 0.05 |
| 235 | 36 | bicyclo[Tm-(D-3-Fpa-Fpa-D-Thr-Pip-Nal-Arg-Ala-D-Phe)-Dap-(Phe-Nal-Arg-Arg-Arg-Arg-Dap)]-Lys | 0.39 ± 0.05 |
| 236 | 37 | bicyclo[Tm-(D-4-Fpa-Fpa-D-Thr-Pip-Nal-Arg-Ala-D-Phe)-Dap-(Phe-Nal-Arg-Arg-Arg-Arg-Dap)]-Lys | 0.12 ± 0.03 |
| 237 | 38 | bicyclo[Tm-(D-4-CyanoPhe-Fpa-D-Thr-Pip-Nal-Arg-Ala-D-Phe)-Dap-(Phe-Nal-Arg-Arg-Arg-Arg-Dap)]-Lys | 0.35 ± 0.04 |
| 238 | 39 | bicyclo[Tm-(D-4-Phe-Fpa-D-Ile-Pip-Nal-Arg-Ala-D-Phe)-Dap-(Phe-Nal-Arg-Arg-Arg-Arg-Dap)]-Lys | 0.46 ± 0.17 |
| 239 | 40 | bicyclo[Tm-(D-4-Phe-Fpa-D-Nle-Pip-Nal-Arg-Ala-D-Phe)-Dap-(Phe-Nal-Arg-Arg-Arg-Arg-Dap)]-Lys | 0.71 ± 0.12 |
| 240 | 41 | bicyclo[Tm-(D-4-Phe-Fpa-D-homoGlu-Pip-Nal-Arg-Ala-D-Phe)-Dap-(Phe-Nal-Arg-Arg-Arg-Arg-Dap)]-Lys | 0.87 ± 0.08 |
| 241 | 42 | bicyclo[Tm-(D-Phe-Fpa-D-Thr-Pip-Nal-Arg-Ala-D-Phe)-Dap-(Arg-Arg-Arg-Arg-Nal-Phe-Dap)]-Lys | 0.98 ± 0.18 |
| 242 | 43 | bicyclo[Tm-(D-Phe-Fpa-D-Thr-Pip-Nal-Arg-Ala-D-Phe)-Dap-(Arg-Arg-Nal-Phe-Arg-Arg-Dap)]-Lys | 1.38 ± 0.16 |
| 243 | 44 | bicyclo[Tm-(D-Phe-Fpa-D-Thr-Pip-Nal-Arg-Ala-D-Phe)-Dap-(Arg-Nal-Arg-Phe-Arg-Arg-Dap)]-Lys | 0.45 ± 0.05 |
| 244 | 45 | bicyclo[Tm-(D-Phe-Fpa-D-Thr-Pip-Nal-Arg-Ala-D-Phe)-Dap-(D-Arg-Arg-D-Arg-Arg-Nal-D-Phe-Dap)]-Lys | 3.10 ± 0.38 |
| 245 | 46 | cyclo(D-Ala-Sar-D-pThr-Pip-Nal-Tyr-Gln)-Lys | 0.24 ± 0.04 |
| 246 | 47 | bicyclo[Tm-(D-Ala-Sar-D-Thr-D-Ala-Nal-Arg-Ala-D-Ala)-Dap-(Phe-Nal-Arg-Arg-Arg-Arg-Dap)]-Lys | No binding |

The released peptides were incubated with 5 µM MBP-Pin1 and the increase of fluorescence anisotropy (FA) was measured. For bicyclic peptides that showed ≥50% FA increase (relative to the no-protein control), the corresponding beads (5 beads, which still contained the linear encoding peptides) were sequenced by PED-MS to give 4 additional complete sequences (Table 1). All 7 hit sequences contained a D-amino acid at the $X^3$ position, consistent with the previous observation that Pin1 prefers D-pThr over pThr at this position. There is a strong preference for hydrophobic especially aromatic hydrophobic residues at the $X^1$ position, but no obvious selectivity at the $X^2$ position.

Hit Optimization.

The 6 hit sequences (hits 1 and 2 have the same sequence) were resynthesized with a Lys added to their C-termini, labeled with fluorescein isothiocyanate (FITC), and tested for binding to Pin1 by FA (Table 18, peptides 3-8). All six peptides bound to Pin1 with moderate affinities ($K_D$~1 µM), but did not improve upon peptide 2 ($K_D$=0.62 µM). Peptides 3 and 4 were used for structure-activity relationship analysis and optimization. Either expanding or contracting the size of the Pin1-binding ring (A ring) decreased the binding affinity (Table 18, peptides 9-16). Replacement of the Ala residue of peptide 3 with amino acids containing side chains of different physicochemical properties including Arg, Asp, Ser, Tyr, and Val also failed to significantly improve the binding affinity (Table 18, peptide 17-21). On the other hand, modification of the D-Ala residue revealed that substitution of a D-Phe at this position increases the Pin1 inhibitory activity by ~2-fold ($K_D$=0.48 µM for peptide 22).

Peptide 4 was subjected to similar SAR studies. As observed for peptide 3, modification of the Ala residue of peptide 4 (into Gly) had little effect (peptide 26), but replacement of the D-Ala residue with D-Phe improved the binding affinity to Pin1 by ~2-fold (Table 18, $K_D$=0.27 μM for peptide 27). Modifications of the Fpa residue at the $X^2$ position (e.g., replacement with other halogenated phenylalanine analogs) all decreased the inhibitor potency (peptides 28-32). Likewise, removal of the aromatic side chain at the $X^1$ position was detrimental to Pin1 binding (peptides 33 and 34). However, substitution of halogenated D-Phe analogs improved the Pin1 binding activity (peptides 35-38). In particular, replacement of D-Phe with D-4-fluorophenylalanine (D-Fpa)] resulted in the most potent Pin1 inhibitor of this series ($K_D$=0.12 μM for peptide 37) (FIGS. 36 and 37*a*). Further attempts to modify the D-Thr residue or the CPP motif failed to improve the Pin1 activity (Table 18, peptides 39-45).

Biological Evaluation.

To determine whether peptide 37 binds to the catalytic site of Pin1, its ability to compete with peptide 1 for binding to Pin1 by FA analysis was examined. Peptide 1 had previously been shown to bind to the Pin1 active site. As expected, peptide 37 inhibited the binding of peptide 1 to Pin1 with an $IC_{50}$ value of 190 nM (FIG. 37*b*). Next, the catalytic activity of Pin1 toward a peptide substrate, Suc-Ala-Glu-Pro-Phe-pNA, in the presence of increasing concentrations of peptide 37 was monitored. Peptide 37 inhibited the Pin1 activity in a concentration-dependent manner, with an $IC_{50}$ value of 170 nM (FIG. 37*c*). These results demonstrate that peptide 37 binds at (or near) the active site of Pin1.

The selectivity of peptide 37 was assessed by two different tests. First, peptide 37 was tested for binding to a panel of arbitrarily selected proteins including bovine serum albumin (BSA), protein tyrosine phosphatases 1B, SHP1, and SHP2, the Grb2 SH2 domain, Ras, and tumor necrosis factor-a. Peptide 37 bound weakly to BSA ($K_D$~20 μM), but not any of the other six proteins. Peptide 37 was next tested for potential inhibition of Pin4, FKBP12, and cyclophilin A, the three other common human peptidyl-prolyl cis-trans isomerases. Although Pin4 is structurally similar to Pin1 and has partially overlapping functions with Pin1, peptide 37 only slightly inhibited Pin4 (~15% at 5 μM inhibitor), with an estimated $IC_{50}$ value of ~34 μM (FIG. 37*c*). Peptide 37 had no effect on the catalytic activity of FKBP12 or cyclophilin A up to 5 μM concentration. These data suggest that peptide 37 is a highly specific inhibitor of Pin1.

The metabolic stability of peptide 37 was evaluated by incubating it in human serum for varying periods of time and analyzing the reaction mixtures by reversed-phase HPLC. The pThr-containing Pin1 inhibitor 1 was used as a control. After 6 h of incubation, 97% of peptide 37 remained intact, while ~50% of bicyclic peptide 1 was degraded after 3 h (FIG. 37*d*). Loss of peptide 1 was accompanied by the concomitant appearance of a new peak in HPLC. Mass spectrometric analysis of the new species identified it as the dephosphorylation product of peptide 1 (peptide 2). This result is in agreement with our previous observation that the structurally constrained bicyclic peptides are highly resistant to proteolytic degradation. The D-pThr moiety remains susceptible to hydrolysis by the nonspecific phosphatases in human serum.

The cellular uptake efficiency of peptide 37, peptide 1, and a previously reported membrane-impermeable monocyclic Pin1 inhibitor (Table 18, peptide 46) was assessed by incubating HeLa cells with the FITC-labeled peptides (5 μM) for 2 h and quantifying the total intracellular fluorescence by flow cytometry analysis. As expected, untreated cells and cells treated with peptide 46 showed little cellular fluorescence, having mean fluorescence intensity (MFI) values of 101 and 193, respectively (FIG. 38*a*). By contrast, cells treated with peptides 1 and 37 gave MFI values of 2562 and 8792, respectively. Thus, peptide 37 is internalized by HeLa cells ~4-fold more efficiently than peptide 1. Presumably, the negative charged phosphate group of peptide 1 interacted electrostatically with the positively charged CPP motif and reduced the cellular uptake efficiency of the latter.

Inhibition of Pin1 activity has previously been shown to decrease cell proliferation. The effect of peptide 37 on the growth of HeLa cells was examined by using the MTT cell viability assay. The membrane impermeable peptide 46 and a cell-permeable but inactive (defective in Pin1 binding) bicyclic peptide (Table 18, peptide 47) were used as controls. Peptide 37 inhibited HeLa cell growth in a concentration-dependent manner, with an $IC_{50}$ value of 1.0 μM (FIG. 38*b*). As expected, neither peptide 46 nor 47 had any effect on cell growth. A time-course study also showed significant growth inhibition (>60%) after a 3-day treatment with 5 μM peptide 37, but not with peptide 46 or 47. The phosphorylated bicyclic peptide 1 under similar testing conditions had an $IC_{50}$ value of 1.8 μM.

Finally, to ascertain that Pin1 is the molecular target of peptide 37 in vivo, the intracellular protein level of a well-established Pin1 substrate, promyeloretinoic leukemia protein (PML), was examined by western blot analysis. Pin1 negatively regulates the PML level in a phosphorylation-dependent manner and inhibition of Pin1 activity is expected to stabilize PML and increase its intracellular level. Indeed, treatment of HeLa cells with peptide 37 (0.2-5 μM) resulted in concentration-dependent increases in the PML level (FIG. 38*c,d*). The effect was already significant at 0.2 μM inhibitor (1.8-fold increase in the PML level) and plateaued at ~1 μM (3.3-fold increase). Again, bicyclic peptide 47 had no effect under the same conditions, while peptide 1 (the positive control, at 5 μM) increased the PML level by 3.1-fold.

By screening a peptide library followed by conventional medicinal chemistry approaches, the first potent, selective, metabolically stable, and cell-permeable peptidyl inhibitor against human Pin1 has been disclosed. Its high potency and selectivity should make it a useful chemical probe for exploring the cellular functions of Pin1.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A cyclic peptide of Formula Ia:

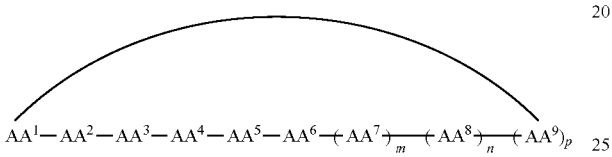

Ia or a pharmaceutically acceptable salt thereof,
wherein m, n and p are independently selected from 0 and 1,
$AA^1, AA^2, AA^3, AA^4, AA^5, AA^6, AA^7, AA^8$, and $AA^9$ are each independently an amino acid, wherein four or more of the amino acids are arginine, at least four arginines are consecutive, and at least four consecutive amino acids have alternating chirality.

2. The cyclic peptide of claim 1, wherein the at least four consecutive arginines have alternating chirality.

3. The cyclic peptide of claim 1, wherein at least one amino acid comprises a hydrophobic aromatic residue.

4. The cyclic peptide of claim 3, wherein the at least one amino acid comprising the hydrophobic aromatic residue is selected from the group consisting of naphthylalanine, phenylalanine, tryptophan, and tyrosine.

5. The cyclic peptide of claim 4, wherein the at least one amino acid comprising the hydrophobic aromatic residue is selected from the group consisting of naphthylalanine and phenylalanine.

6. The cyclic peptide of claim 5, wherein the at least one amino acid comprising the hydrophobic aromatic residue is naphthylalanine.

7. The cyclic peptide of claim 5, wherein the at least one amino acid comprising the hydrophobic aromatic residue is phenylalanine.

8. The cyclic peptide of claim 1, wherein the peptide comprises naphthylalanine or phenylalanine.

9. The cyclic peptide of claim 1, wherein the peptide comprises naphthylalanine and phenylalanine.

10. The cyclic peptide of claim 1 wherein the peptide has a cellular uptake efficiency which is at least about 1.5-fold higher than c(FΦRRRRQ).

11. The cyclic peptide of claim 1 having a structure of:
c(FfΦRrRrQ);
c(fΦRrRrQ);
c(fΦRrRrRQ);
c(FφrRrRq); or
c(FφrRrRQ).

12. A cyclic peptide of claim 1, wherein:
$AA^1$ is phenylalanine;
$AA^2$ is naphthylalanine;
$AA^3$ is arginine;
$AA^4$ is arginine;
$AA^5$ is arginine; and
$AA^6$ is arginine.

13. The cyclic peptide according to claim 12, wherein:
m and n are each 0;
p is 1; and
$AA^9$ is glutamine.

14. The cyclic peptide according to claim 12, wherein:
m is 0;
n and p are each 1;
$AA^8$ is arginine; and
$AA^9$ is glutamine.

15. The cyclic peptide according to claim 12, wherein:
m is 0;
n and p are each 1;
$AA^8$ is glutamine; and
$AA^9$ is phenylalanine.

16. A cyclic peptide comprising formula IIa, IIb, or IIc:

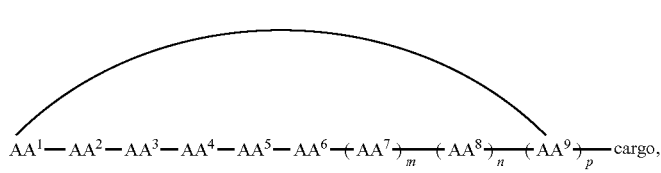

IIa

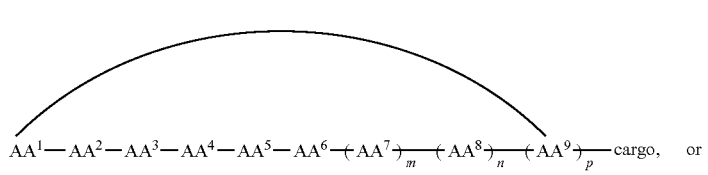

IIb or

-continued

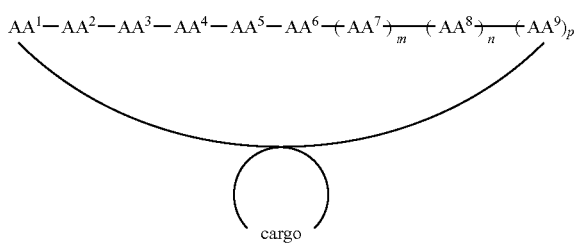

IIc or a pharmaceutically acceptable salt thereof,
wherein m, n and p are independently selected from 0 and 1,
$AA^1$, $AA^2$, $AA^3$, $AA^4$, $AA^S$, $AA^6$, $AA^7$, $AA^8$, and $AA^9$ are each independently an amino acid, wherein three or more of the amino acids are arginine, and
at least four consecutive amino acids have alternating chirality; and
wherein the cargo moiety comprises a detectable moiety, a therapeutic moiety, a targeting moiety or a combination thereof.

17. The cyclic peptide of claim 16, wherein at least four of the amino acids are arginine.

18. The cyclic peptide of claim 17, wherein the at least four arginines are consecutive.

19. The cyclic peptide of claim 18, wherein the at least four consecutive arginines have alternating chirality.

20. The cyclic peptide of claim 16, wherein at least one amino acid comprises a hydrophobic aromatic residue.

21. The cyclic peptide of claim 20, wherein the at least one amino acid comprising the hydrophobic aromatic residue is selected from the group consisting of naphthylalanine, phenylalanine, tryptophan, and tyrosine.

22. The cyclic peptide of claim 21, wherein the at least one amino acid comprising the hydrophobic aromatic residue is selected from the group consisting of naphthylalanine and phenylalanine.

23. The cyclic peptide of claim 22, wherein the at least one amino acid comprising the hydrophobic aromatic residue is naphthylalanine.

24. The cyclic peptide of claim 22, wherein the at least one amino acid comprising the hydrophobic aromatic residue is phenylalanine.

25. The cyclic peptide of claim 16, wherein the peptide comprises naphthylalanine or phenylalanine.

26. The cyclic peptide of claim 16, wherein the peptide comprises naphthylalanine and phenylalanine.

27. The cyclic peptide of claim 16 wherein the peptide has a cellular uptake efficiency which is at least about 1.5-fold higher than c(FΦRRRRQ) (SEQ ID NO: 186).

28. A cyclic peptide of claim 16, wherein
$AA^1$ is phenylalanine;
$AA^2$ is naphthylalanine;
$AA^3$ is arginine;
$AA^4$ is arginine;
$AA^S$ is arginine; and
$AA^6$ is arginine.

29. The cyclic peptide according to claim 28, wherein:
m and n are each 0;
p is 1; and
$AA^9$ is glutamine.

30. The cyclic peptide according to claim 28, wherein:
m is 0;
n and p are each 1;
$AA^8$ is arginine; and
$AA^9$ is glutamine.

31. A method for delivering a therapeutic agent to cytoplasm of a cell, comprising administering at least one cyclic peptide of claim 16, thereby delivering the therapeutic agent to the cytoplasm of the cell.

32. The method of claim 31, wherein:
$AA^1$ is phenylalanine;
$AA^2$ is naphthylalanine;
$AA^3$ is arginine;
$AA^4$ is arginine;
$AA^S$ is arginine; and
$AA^6$ is arginine.

33. The method of claim 32, wherein:
m and n are each 0;
p is 1; and
$AA^9$ is glutamine.

34. The method of claim 32, wherein:
m is 0;
n and p are each 1;
$AA^1$ is arginine; and
$AA^9$ is glutamine.

35. The method of claim 32, wherein:
m is 0;
n and p are each 1;
$AA^8$ is arginine; and
$AA^9$ is glutamine.

36. The method of claim 31, wherein the therapeutic agent is an inhibitor against Ras, PTP1B, Pin1, Grb2, SH2, or combinations thereof.

37. The method of claim 31, wherein the cyclic peptide further comprises a detectable moiety, a targeting moiety, or a combination thereof.

38. The cyclic peptide of claim 16, wherein the cargo moiety comprises a therapeutic moiety.

39. The cyclic peptide of claim 16, wherein
$AA^1$ is phenylalanine,
$AA^2$ is phenylalanine;
$AA^3$ is naphthylalanine;
$AA^4$ is arginine;
$AA^S$ is arginine; and
$AA^6$ is arginine.

40. The cyclic peptide according to claim 39, wherein:
m is 0;
n and p are each 1;
$AA^8$ is arginine; and
$AA^9$ is glutamine.

* * * * *